US008921376B2

(12) United States Patent
Ledeboer et al.

(10) Patent No.: US 8,921,376 B2
(45) Date of Patent: Dec. 30, 2014

(54) PYRROLOPYRIDINES USEFUL AS INHIBITORS OF PROTEIN KINASE

(75) Inventors: Mark Ledeboer, Acton, MA (US); Marion Wannamaker, Stow, MA (US); Luc Farmer, Foxboro, MA (US); Tiansheng Wang, Concord, MA (US); Albert Pierce, Cambridge, MA (US); Gabriel Martinez-Botella, West Roxbury, MA (US); Randy Bethiel, Lexington, MA (US); Guy Bemis, Arlington, MA (US); Jian Wang, Newton, MA (US); Francesco Salituro, Marlboro, MA (US); Michael Arnost, North Andover, MA (US); Jon Come, Cambridge, MA (US); Jeremy Green, Waltham, MA (US); Michelle Stewart, Somerville, MA (US); Craig Marhefka, Rockville, MD (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1862 days.

(21) Appl. No.: 11/438,748

(22) Filed: May 22, 2006

(65) Prior Publication Data

US 2007/0135466 A1    Jun. 14, 2007

Related U.S. Application Data

(60) Provisional application No. 60/683,554, filed on May 20, 2005.

(51) Int. Cl.
*C07D 471/04* (2006.01)
*A61K 31/437* (2006.01)
*C07D 487/04* (2006.01)

(52) U.S. Cl.
CPC ............ *C07D 471/04* (2013.01); *C07D 487/04* (2013.01)
USPC .......................................... 514/256; 544/328

(58) Field of Classification Search
CPC ........................... C07D 471/04; A61K 31/437
USPC .......................................... 544/328; 514/256
See application file for complete search history.

(56) References Cited

U.S. PATENT DOCUMENTS

| 7,226,919 | B2 | 6/2007 | Ledeboer et al. |
| 7,407,962 | B2 | 8/2008 | Aronov et al. |
| 7,446,199 | B2 | 11/2008 | Aronov et al. |
| 7,507,826 | B2 | 3/2009 | Salituro et al. |
| 7,514,448 | B2 | 4/2009 | Green et al. |
| 7,528,138 | B2 | 5/2009 | Knegtel et al. |
| 7,767,816 | B2 | 8/2010 | Farmer et al. |
| 8,163,917 | B2 | 4/2012 | Farmer et al. |
| 8,188,281 | B2 | 5/2012 | Salituro et al. |
| 8,247,421 | B2 | 8/2012 | Mortimore et al. |
| 8,450,489 | B2 | 5/2013 | Farmer et al. |
| 8,501,446 | B2 | 8/2013 | Salituro et al. |
| 8,530,489 | B2 | 9/2013 | Mortimore et al. |
| 8,580,802 | B2 | 11/2013 | Salituro et al. |
| 8,633,205 | B2 | 1/2014 | Ledeboer et al. |
| 8,722,889 | B2 | 5/2014 | Salituro et al. |
| 8,741,912 | B2 | 6/2014 | Ledeboer et al. |
| 2005/0137201 | A1 | 6/2005 | Aronov et al. |
| 2006/0003968 | A1 | 1/2006 | Green et al. |
| 2006/0084650 | A1 | 4/2006 | Dong et al. |
| 2006/0122185 | A1 | 6/2006 | Green et al. |
| 2006/0122213 | A1 | 6/2006 | Pierard et al. |
| 2006/0183761 | A1 | 8/2006 | Ledeboer et al. |
| 2007/0135466 | A1 | 6/2007 | Ledeboer et al. |
| 2007/0207995 | A1 | 9/2007 | Salituro et al. |
| 2012/0316186 | A1 | 12/2012 | Ledeboer et al. |
| 2013/0237516 | A1 | 9/2013 | Farmer et al. |
| 2013/0345218 | A1 | 12/2013 | Charifson et al. |
| 2014/0045812 | A1 | 2/2014 | Mortimore et al. |
| 2014/0094473 | A1 | 4/2014 | Charifson et al. |
| 2014/0142119 | A1 | 5/2014 | Charifson et al. |
| 2014/0171454 | A1 | 6/2014 | Ledeboer et al. |

FOREIGN PATENT DOCUMENTS

| WO | 01/02369 | | 1/2001 |
| WO | 01/02369 | A2 | 1/2001 |
| WO | 01/81345 | | 1/2001 |
| WO | 01/47922 | A2 | 7/2001 |
| WO | 02/32872 | A1 | 4/2002 |
| WO | 03/000688 | | 1/2003 |
| WO | 03/066632 | A1 | 8/2003 |
| WO | 2004/039796 | A1 | 5/2004 |
| WO | 2004/046124 | A1 | 6/2004 |
| WO | 2004/085425 | A1 | 10/2004 |
| WO | 2004/099205 | | 11/2004 |
| WO | 2004/099205 | A1 | 11/2004 |
| WO | 2005/013986 | | 2/2005 |
| WO | 2005/013986 | A1 | 2/2005 |

(Continued)

OTHER PUBLICATIONS

Tawara et al., PubMed Abstract (Yakugaku Zasshi, 127(3):501-14) Mar. 2007.*
Hu et al., Rho kinase as potential therapeutic target for cardiovascular diseases: opportunities and challenges, Expert Opin. Ther. Targets, 9(4):715-736, 2005.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20$^{th}$ Edition, vol. 1, pp. 1004-1010, 1995.*
Traxler, Protein Tyrosine Kinase inhibitors in cancer treatment, Expert Opinion on Therapeutic Patents 7(6), pp. 571-588 (1997).*

(Continued)

*Primary Examiner* — Deepak Rao
(74) *Attorney, Agent, or Firm* — Booyong S. Lim

(57) ABSTRACT

The present invention relates to compounds useful as inhibitors of protein kinases, particularly of JAK family and ROCK family kinases. The invention also provides pharmaceutically acceptable compositions comprising said compounds and methods of using the compositions in the treatment of various disease, conditions, or disorders.

19 Claims, No Drawings

(56) References Cited

FOREIGN PATENT DOCUMENTS

| WO | 2005/051304 | | 6/2005 |
|---|---|---|---|
| WO | 2005/062795 | | 7/2005 |
| WO | 2005/108397 | | 11/2005 |
| WO | 2005/108397 | A1 | 11/2005 |
| WO | 2005/113494 | | 12/2005 |
| WO | 2006/017443 | A2 | 2/2006 |
| WO | 2006/026754 | | 3/2006 |
| WO | 2006/026754 | A2 | 3/2006 |
| WO | 2006/032631 | A1 | 3/2006 |
| WO | 2006/046023 | | 5/2006 |
| WO | 2006/046024 | | 5/2006 |
| WO | 2006/052568 | | 5/2006 |
| WO | 2006/069080 | | 6/2006 |
| WO | 2006/071548 | | 7/2006 |
| WO | WO 2006/124863 | * | 11/2006 |
| WO | 2007/117494 | | 10/2007 |

OTHER PUBLICATIONS

Damasio, Alzheimer's Disease and Related Dementias, Cecil Textbook of Medicine, 20th Edition, vol. 2, pp. 1992-1996, 1996.*

Layzer, Degenerative Diseases of the Nervous System, Cecil Textbook of Medicine, 20th Edition, vol. 2, pp. 2050-2057, 1996.*

Thutewohl, Michael; Schirok, Hartmut; Bennabi, Samir; Figueroa-Perez, Santiago: "Synthesis of 4-substituted 7-azaindole derivatives via Pd-catalyzed C-N and C-O coupling" Synthesis, vol. 4, 2006, pp. 629-632, XP002399436 Compounds 3 and 8 and Table 1 (pp. 630-631).

Allegretti, M., et al., "Palladium-catalysed functionalisation at 4- and 6- position of the 7-azaindole system", Synlett (2001) (5), pp. 609-612.

Girgis, N.S., et al., "The synthesis of 5-azaindoles by substitution-rearrangement of 7-azaindoles upon treatment iwth certain primary amines", J. Heterocycl Chem (1989) 26(2), pp. 317-325.

* cited by examiner

PYRROLOPYRIDINES USEFUL AS INHIBITORS OF PROTEIN KINASE

This application claims the benefit of U.S. Provisional Application 60/683,554, filed May 20, 2005, which is herein incorporated by reference in its entirety.

TECHNICAL FIELD OF THE INVENTION

The present invention relates to compounds useful as inhibitors of Janus kinases (JAK) and Rho-associated coiled-coil forming protein serine/threonine kinases (ROCK). The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK3 has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

The Rho-associated coiled-coil forming protein serine/threonine kinase (ROCK) family are effectors of Ras-related small GTPase Rho. The ROCK family includes p160ROCK (ROCK-1), ROKα/Rho-kinase/ROCK-II, protein kinase PKN, and citron and citron kinase. ROCK has been implicated in various diseases and disorders including hypertension, cerebral vasospasm, coronary vasospasm, bronchial asthma, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, atherosclerosis, and cardiac hypertrophy and perivascular fibrosis.

Accordingly, there is a great need to develop compounds useful as inhibitors of protein kinases. In particular, it would be desirable to develop compounds that are useful as inhibitors of JAK family kinases and ROCK family kinases.

SUMMARY OF THE INVENTION

It has now been found that compounds of this invention, and pharmaceutically acceptable compositions thereof, are effective as inhibitors of protein kinases, particularly the JAK family kinases and ROCK family kinases. These compounds have the general formula I:

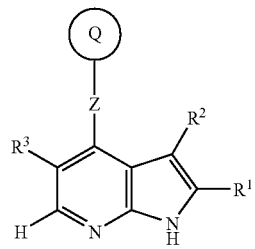

I or a pharmaceutically acceptable salt thereof, wherein $R^1$, $R^2$, $R^3$, Z and Q are as defined below.

These compounds, and pharmaceutically acceptable compositions thereof, are useful for treating or lessening the severity of a variety of disorders, including allergies, asthma, autoimmune diseases such as transplant rejection, rheumatoid arthritis, amyotrophic lateral sclerosis, multiple sclerosis, solid and hematologic malignancies such as leukemias and lymphomas, myeloproliferative disorders, hypertension, cerebral vasospasm, coronary vasospasm, bronchial asthma, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, atherosclerosis, and cardiac hypertrophy and perivascular fibrosis.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and In yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "cycloalkyl") refers to a monocyclic $C_3$-$C_8$ hydrocarbon or bicyclic $C_9$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle", "heterocyclyl", "heterocycloaliphatic", or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $J^Q$, $J^R$, $J^V$, $J^U$ and $J^X$ below. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)$_2$; —OC(O)N(R°)$_2$; —OC(O)R°; —C(O)N(OR°) R°; —C(NOR°) R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$ aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$ (alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O) CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$ (Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_4$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of

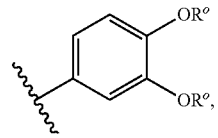

these two occurrences of R° are taken together with the oxygen atoms to which they are bound to form a fused 6-membered oxygen containing ring:

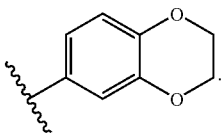 [SMILES: *c1ccc2c(c1)OCCO2]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O) CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

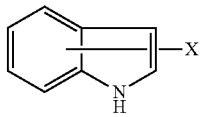

Figure a

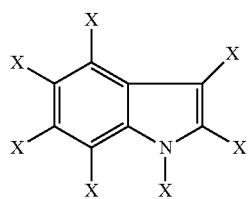

Figure b

This also applies to multiple ring systems fused to optional ring systems (which would be represented by dotted lines). For example, in Figure c, X is an optional substituent both for ring A and ring B.

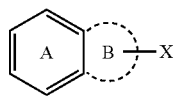

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

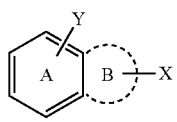

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Description of Compounds of the Invention

The present invention relates to a compound of formula I:

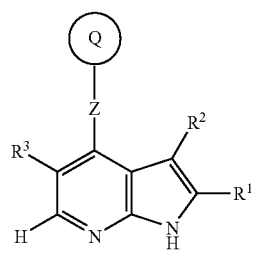

I or a pharmaceutically acceptable salt thereof
wherein
Q is a 3-8 membered saturated, partially saturated, or unsaturated monocyclic ring having 0-3 heteroatoms selected from nitrogen, oxygen, or sulfur; or an 8-12 membered bicyclic ring having 0-6 heteroatoms selected from nitrogen, oxygen, or sulfur; wherein Q is optionally substituted with 1-10 occurrences of $J^Q$;

Z is a bond, NH, N(C$_{1-3}$aliphatic) or C=CH$_2$;

$R^1$ is —(C$_{1-2}$ aliphatic)$_p$-$R^4$ wherein each $R^1$ is optionally substituted with 1-3 occurrences of J;

$R^2$ is —(C$_{1-2}$ aliphatic)$_d$-$R^5$ wherein each $R^1$ is optionally substituted with 1-3 occurrences of J;

$R^3$ is halogen, —CN, —NO$_2$ or —(U)$_m$—X, wherein
U is a C$_{1-6}$ aliphatic, wherein up to two methylene units are optionally and independently replaced by $G^U$ and wherein U is optionally substituted with 1-4 $J^U$;
X is H, halogen, CN, NO$_2$, S(O)R, SO$_2$R, C$_{1-4}$ haloaliphatic, or a group selected from C$_{1-6}$ aliphatic, a C$_{3-10}$ cycloaliphatic, C$_{6-10}$ aryl, 5-10 membered heteroaryl, 5-10 membered heterocyclyl; wherein said group is optionally substituted with 1-4 $J^X$;
$G^U$ is —NH—, —NR—, —O—, —S—, —CO$_2$—, —OC(O)—, —C(O)CO—, —C(O)—, —C(O)NH—, —C(O)NR—, —C(=N—CN)—, —NHCO—, —NRCO—, —NHC(O)O—, —NRC(O)O—, —SO$_2$NH—, —SO$_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO—, or —SO$_2$—;

$R^4$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NC(=O)CH$_3$, or OH;

$R^5$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NC(=O)CH$_3$, or OH;

$J^Q$ is halogen, $OCF_3$, —$(V_n)$—R", —$(V_n)$—CN, —$(V_n)$—$NO_2$, or —$(V_n)$—($C_{1-4}$ haloaliphatic), wherein $J^Q$ is not H;

V is a $C_{1-10}$ aliphatic, wherein up to three methylene units are replaced by $G^V$, wherein $G^V$ is selected from —NH—, —NR—, —O—, —S—, —$CO_2$—, —OC(O)—, —C(O)CO—, —C(O)—, —C(O)NH—, —C(O)NR—, —C(=N—CN), —NHCO—, —NRCO—, —NHC(O)O—, —NRC(O)O—, —$SO_2$NH—, —$SO_2$NR—, —$NHSO_2$—, —$NRSO_2$—, —NHC(O)NH—, —NRC(O)NH—, —NHC(O)NR—, —NRC(O)NR, —OC(O)NH—, —OC(O)NR—, —$NHSO_2$NH—, —$NRSO_2$NH—, —$NHSO_2$NR—, —$NRSO_2$NR—, —SO—, or —$SO_2$—; and wherein V is optionally substituted with 1-6 occurrences of $J^V$;

R" is H, or is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R" groups, on the same substituent or different substituents, together with the atom(s) to which each R" group is bound, form an optionally substituted 3-8 membered heterocyclyl; wherein each optionally substituted R" group is independently and optionally substituted with 1-6 occurrences of $J^R$;

R is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of $J^R$;

$J^V$, $J^U$, $J^X$, and $J^R$ are each independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-$NO_2$, -($L_n$)-CN, -($L_n$)-OH, -($L_n$)-$CF_3$, —$CO_2$R', —$CO_2$H, —COR', —COH, —OC(O)R', or —NC(O)R'; or two $J^V$, $J^U$, $J^X$, or $J^R$ groups, on the same substituent or different substituents, together with the atom(s) to which each $J^V$, $J^U$, $J^X$, and $J^R$ group is bound, form a 5-7 membered saturated, unsaturated, or partially saturated ring;

R' is H or $C_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —$NO_2$, —$CF_3$, —CN, —$CO_2$R*, —COR*, OCOR*, NHCOR*, wherein R* is H or $C_{1-6}$ aliphatic;

L is a $C_{1-6}$ aliphatic wherein up to three methylene units are replaced by —NH—, —$NR^6$—, —O—, —S—, —$CO_2$—, —OC(O)—, —C(O)CO—, —C(O)—, —C(O)NH—, —C(O)$NR^6$—, —C(=N—CN), —NHCO—, —$NR^6$CO—, —NHC(O)O—, —$NR^6$C(O)O—, —$SO_2$NH—, —$SO_2NR^6$, —$NHSO_2$—, —$NR^6SO_2$—, —NHC(O)NH—, —$NR^6$C(O)NH—, —NHC(O)$NR^6$—, —$NR^6$C(O)$NR^6$, —OC(O)NH—, —OC(O)$NR^6$—, —$NHSO_2$NH—, —$NR^6SO_2$NH—, —$NHSO_2NR^6$, —$NR^6SO_2NR^6$—, —SO—, or —$SO_2$—;

$R^6$ is selected from $C_{1-6}$ aliphatic, $C_{3-10}$ cycloaliphatic, $C_{6-10}$ aryl, 5-10 membered heteroaryl, or 5-10 membered heterocyclyl; or two $R^6$ groups, on the same substituent or different substituents, together with the atom(s) to which each $R^6$ group is bound, form a 3-8 membered heterocyclyl;

J is halogen, $OCH_3$, OH, $NO_2$, $NH_2$, $SCH_3$, $NCH_3$, CN, unsubstituted $C_{1-2}$aliphatic; two J's, together with the carbon to which they are attached, form a cyclopropyl ring or C=O;

m, n, d, and p are each independently 0 or 1; provided that when $R^1$, $R^2$, and $R^3$ are H and Z is a bond, then Q is not

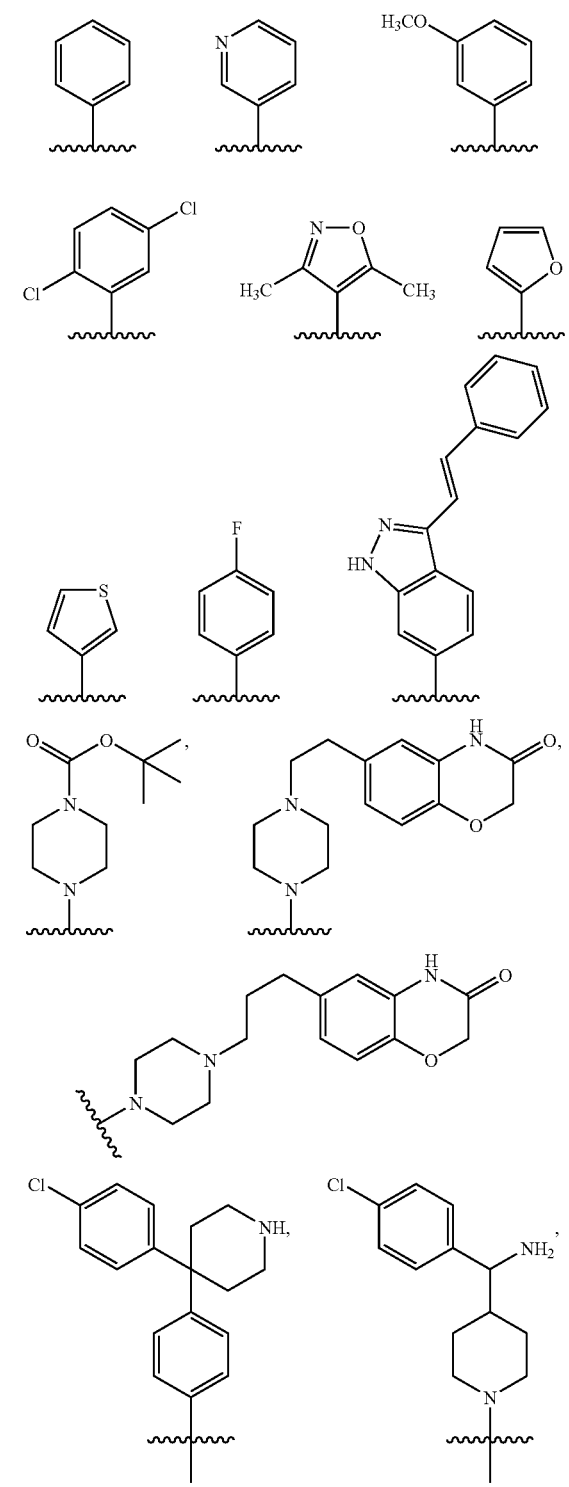

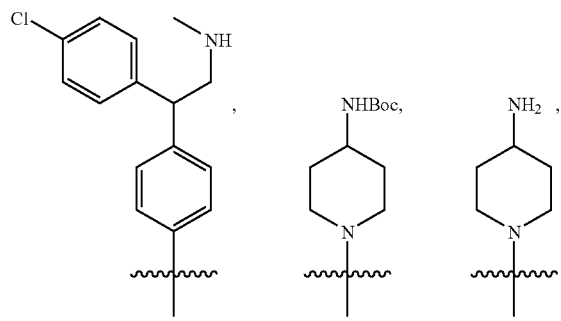
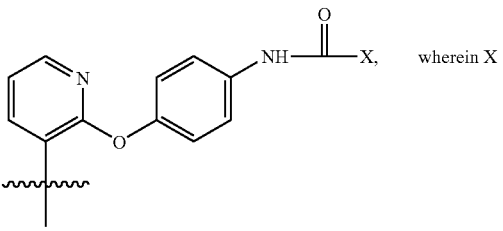
is —NH-tBu, —NH-phenyl or phenyl;
when $R^1$ and $R^2$ are H, $R^3$ is H, COOEt or COOH, and Z is a bond, then Q is not
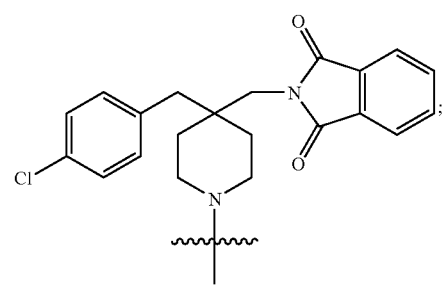 [SMILES: *N1CCC(Cc2ccc(Cl)cc2)(CN2C(=O)c3ccccc3C2=O)CC1]
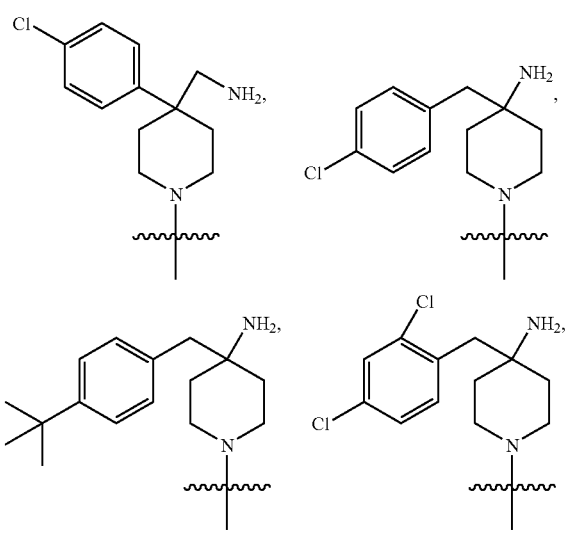
when $R^1$ is I, $R^2$ is H, $R^3$ is Br and Z is NH, then Q is not
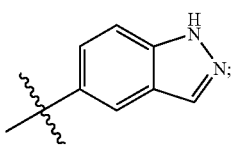 [SMILES: *c1ccc2[nH]ncc2c1]
when $R^1$ and $R^3$ are H, $R^2$ is H, Cl, F, Me or $CF_3$, and Z is NH; then Q is not 2-fluoro-4-amino phenyl, 2-fluoro-4-nitro phenyl or
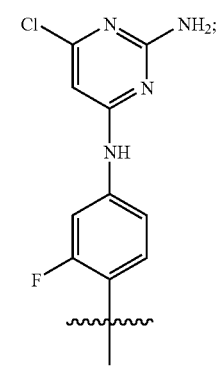
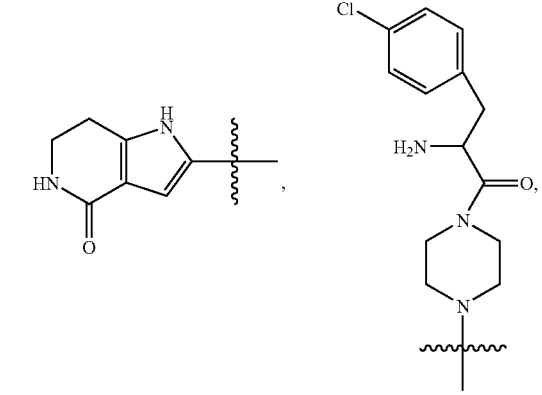
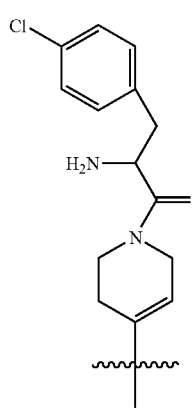
or
when $R^1$ and $R^3$ are H, $R^2$ is H or Me, and Z is NH, then Q is not 2,6-fluoro-4-amino phenyl,

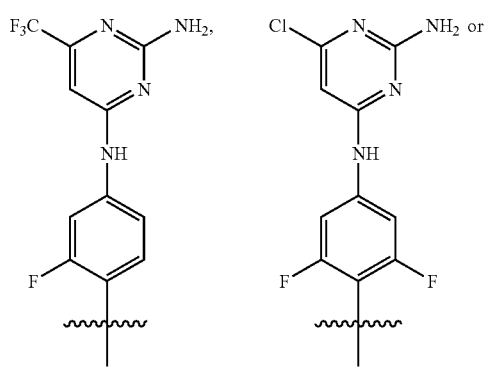

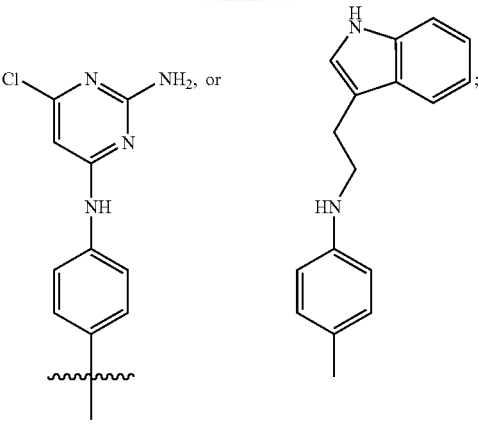

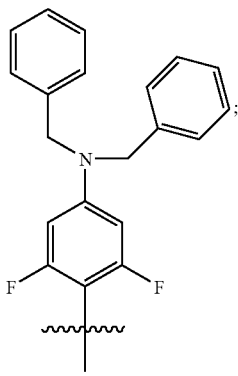 [SMILES: *c1c(F)cc(N(Cc2ccccc2)Cc2ccccc2)cc1F]

when $R^1$ and $R^3$ are H, $R^2$ is Me, and Z is NH, then Q is not

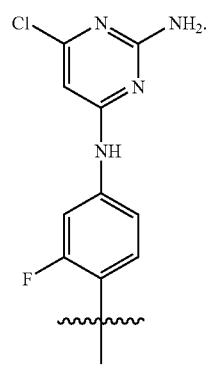 [SMILES: *c1ccc(Nc2cc(Cl)nc(N)n2)cc1F]

when $R^1$, $R^2$ and $R^3$ are H, and Z is NH; then Q is not 3,5-difluoro phenyl, 4-amino phenyl, 4-nitro phenyl, 2-chloro-4-amino phenyl, 2-chloro-4-nitro phenyl, 3,4-methoxyphenyl,

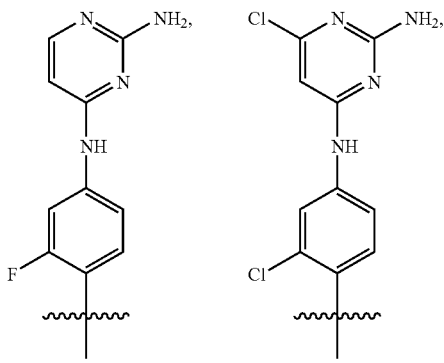

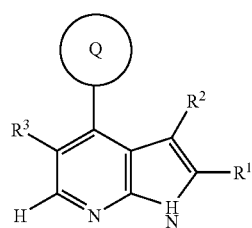

when $R^1$ and $R^2$ are H, $R^3$ is C(=O)NH$_2$ and Z is NH, then Q is not 2-ethylphenyl; and when $R^1$, $R^2$, and $R^3$ are H and Z is NCH$_3$; then Q is not unsubstituted phenyl, 2-fluoro-4-amino phenyl, 2-fluoro-4-nitro phenyl or In another embodiment, the invention provides a compound of formula I-a I-a or a pharmaceutically acceptable salt thereof,
wherein Q, $R^1$, $R^2$ and $R^3$ are as defined for formula I above,
when $R^1$, $R^2$, and $R^3$ are H, then Q is not

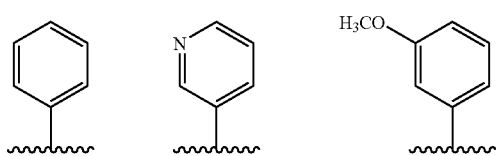

-continued
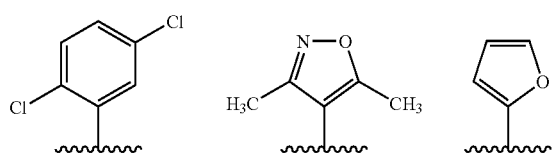
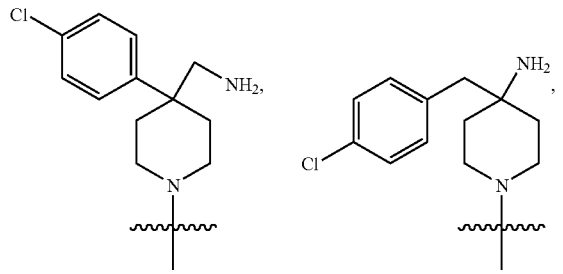
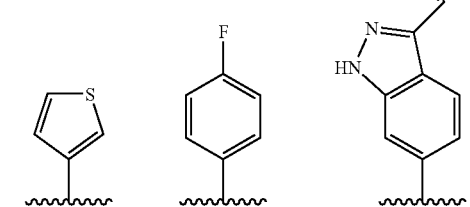
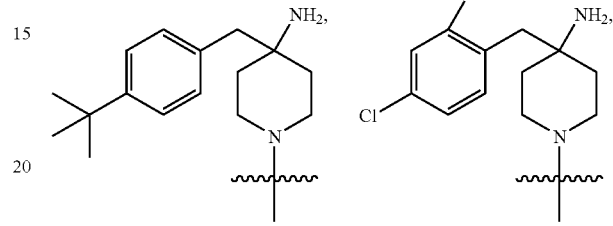
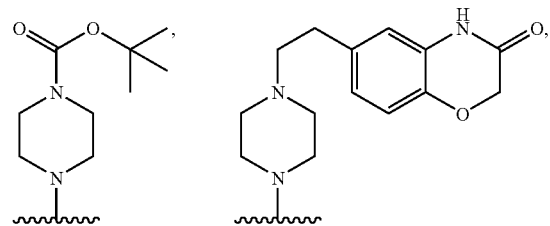
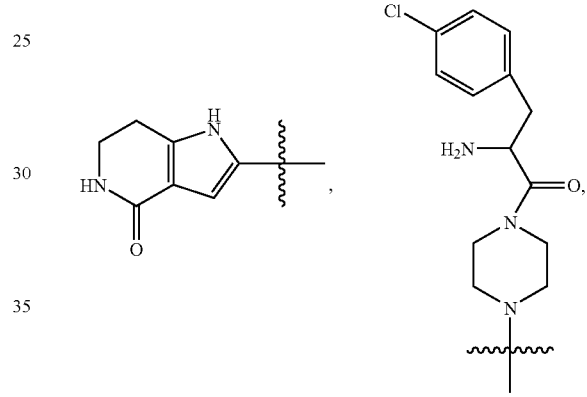
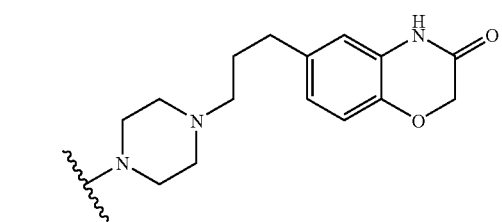
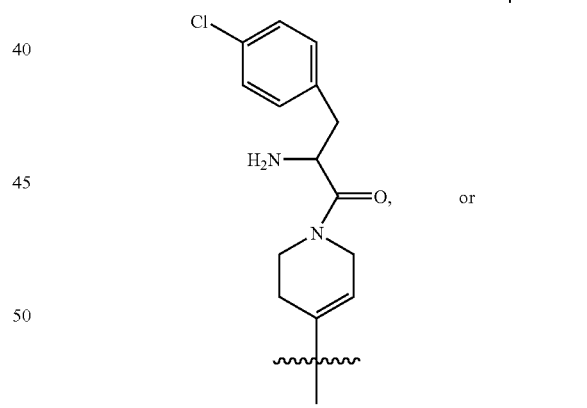
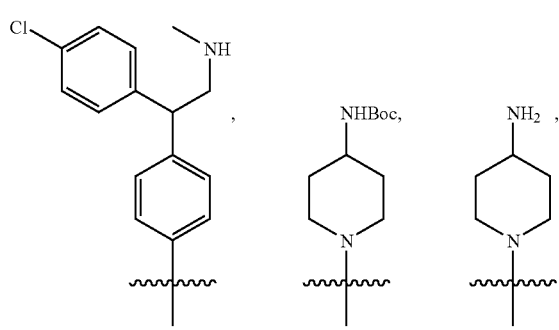
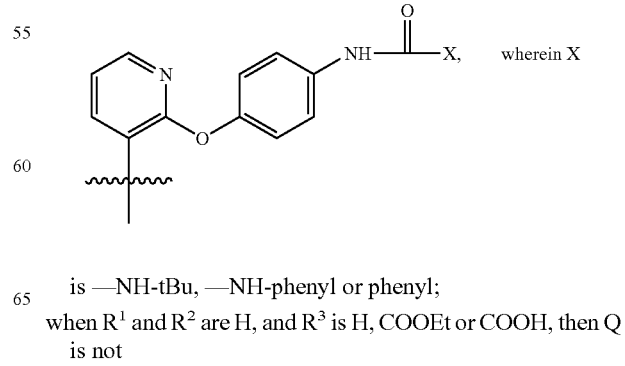
is —NH-tBu, —NH-phenyl or phenyl;
when $R^1$ and $R^2$ are H, and $R^3$ is H, COOEt or COOH, then Q is not

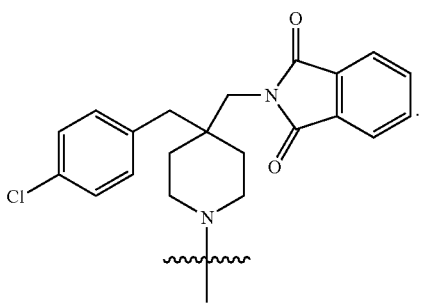 [SMILES: *N1CCC(Cc2ccc(Cl)cc2)(CN2C(=O)c3ccccc3C2=O)CC1]

In another embodiment, the invention provides a compound of formula I-b

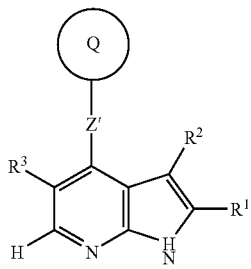

I-b or a pharmaceutically acceptable salt thereof,
wherein Q, $R^1$, $R^2$ and $R^3$ are as defined above,
and Z' is NH, N($C_{1-3}$aliphatic) or C=$CH_2$;
provided that
when $R^1$ is I, $R^2$ is H, $R^3$ is Br and Z' is NH, then Q is not

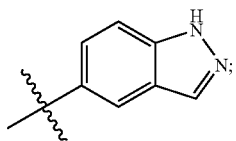 [SMILES: *c1ccc2[nH]ncc2c1]

when $R^1$ and $R^3$ are H, $R^2$ is H, Cl, F, Me or $CF_3$, and Z' is NH; then Q is not 2-fluoro-4-amino phenyl, 2-fluoro-4-nitro phenyl or

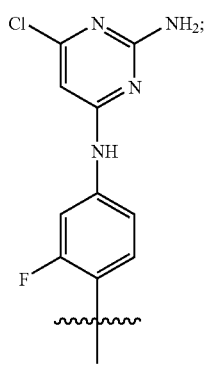 [SMILES: *c1ccc(Nc2cc(Cl)nc(N)n2)cc1F]

when $R^1$ and $R^3$ are H, $R^2$ is H or Me, and Z' is NH, then Q is not 2,6-fluoro-4-amino phenyl,

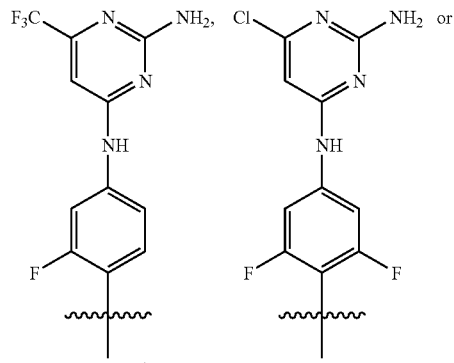

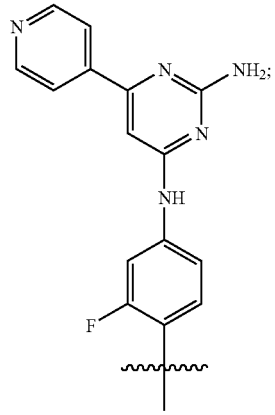

when $R^1$ and $R^3$ are H, $R^2$ is Me, and Z' is NH, then Q is not

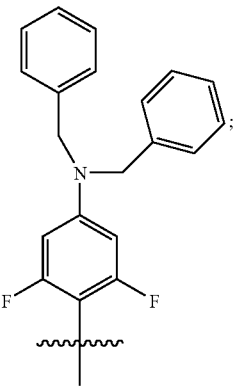 [SMILES: *c1c(F)cc(N(Cc2ccccc2)Cc2ccccc2)cc1F]

when $R^1$, $R^2$ and $R^3$ are H, and Z' is NH; then Q is not 3,5-difluoro phenyl, 4-amino phenyl, 4-nitro phenyl, 2-chloro-4-amino phenyl, 2-chloro-4-nitro phenyl, 3,4-methoxyphenyl,

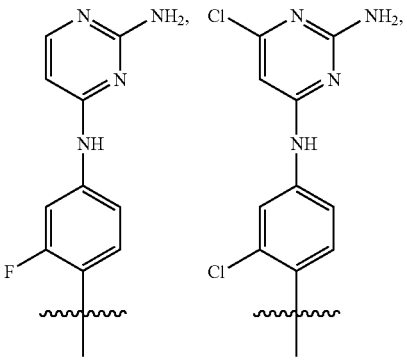

when $R^1$ and $R^2$ are H, $R^3$ is C(=O)NH$_2$ and Z' is NH, then Q is not 2-ethylphenyl;

and when $R^1$, $R^2$, and $R^3$ are H and Z' is NCH$_3$; then Q is not unsubstituted phenyl, 2-fluoro-4-amino phenyl, 2-fluoro-4-nitro phenyl or In one embodiment of the invention, p is 0. In a further embodiment, $R^1$ is H, halogen, CN, NH$_2$, NO$_2$, CF$_3$, CH$_3$, NCH$_3$, OCH$_3$, or OH. In yet another embodiment, $R^1$ is H, halogen, or CF$_3$. In another embodiment, $R^1$ is H.

In one embodiment, d is 0. In a further embodiment, $R^2$ is H, halogen, CN, NH$_2$, NO$_2$, CF$_3$, CH$_3$, NCH$_3$, OCH$_3$, or OH. In another embodiment, $R^2$ is H, halogen, or CF$_3$. In yet another embodiment, $R^2$ is H.

In another embodiment, both $R^1$ and $R^2$ are H.

In another embodiment, m is 0 and $R^3$ is H, halogen, —CN, —NO$_2$ or X. In yet another embodiment, $R^3$ is H, halogen or $C_{1-3}$ aliphatic. In another embodiment, $R^3$ is H or Cl.

In a different embodiment, m is 1 and U is an optionally substituted $C_{1-3}$ aliphatic, wherein up to two methylene units are optionally replaced with 0-2 $G^U$ groups. In another embodiment, $G^U$ is selected from —NH—, —NR—, —O—, —CO$_2$—, —OC(O)— or —C(O)—. In a further embodiment, X is selected from H, $C_{1-6}$aliphatic, halogen, CN, NO$_2$, S(O)$_{0-2}$R, or $C_{1-4}$haloalkyl. In yet a further embodiment, X is H, $C_{1-6}$alkyl or halogen. In another embodiment, X is H or Cl. In a further embodiment, $R^1$ and $R^2$ are H and $R^3$ is H or Cl.

In one embodiment, Z is a bond and $R^3$ is selected from H, Cl, Br, F, —CN, —COOH, —COOMe, —NH$_2$, —N(R')$_2$, —NO$_2$, —OR', —CON(R')$_2$, —COOR', —OH, —SR', —C(R')$_2$OR', —N(R')COR', —N(R')C(O)OR', —SO$_2$NH$_2$, —SO$_2$N(R')$_2$, or an optionally substituted group selected from $C_1$-$C_4$ aliphatic, $C_1$-$C_4$ alkyloxy or —C≡C—$C_1$-$C_4$ aliphatic. In a further embodiment, $R^3$ is selected from H, Cl, —Br, —CN, —COOH, —COOMe, —CONHR', —CON(Me)$_2$, —CH$_2$OH, —NO$_2$, —NH$_2$ or an optionally substituted $C_1$-$C_4$ aliphatic. In yet a further embodiment, $R^3$ is selected from Cl, —Br, —CN or an optionally substituted $C_1$-$C_4$ aliphatic. Yet further, $R^3$ is Cl.

In another embodiment, $J^U$ is selected from halogen, CN, NO$_2$, $C_{1-2}$haloalkyl, OH, $C_{1-3}$alkyl, —O—($C_{1-2}$alkyl), NH$_2$, —NH—($C_{1-2}$alkyl), —N($C_{1-2}$alkyl)$_2$, —O—($C_{1-2}$haloalkyl), or oxo.

In another embodiment, $J^X$ is selected from halogen, CN, NO$_2$, $C_{1-2}$haloalkyl, OH, $C_{1-3}$alkyl, —O—($C_{1-2}$alkyl), NH$_2$, —NH—($C_{1-2}$alkyl), —N($C_{1-2}$alkyl)$_2$, —O—($C_{1-2}$haloalkyl), or oxo.

In another embodiment, Q is a 5-10 membered aryl or heteroaryl ring optionally substituted with 1-5 $J^Q$ groups. In a further embodiment, Q is a 5-6 membered aryl or heteroaryl ring optionally substituted with 1-5 $J^Q$ groups.

In another embodiment, Q is a 5-6 membered ring selected from:

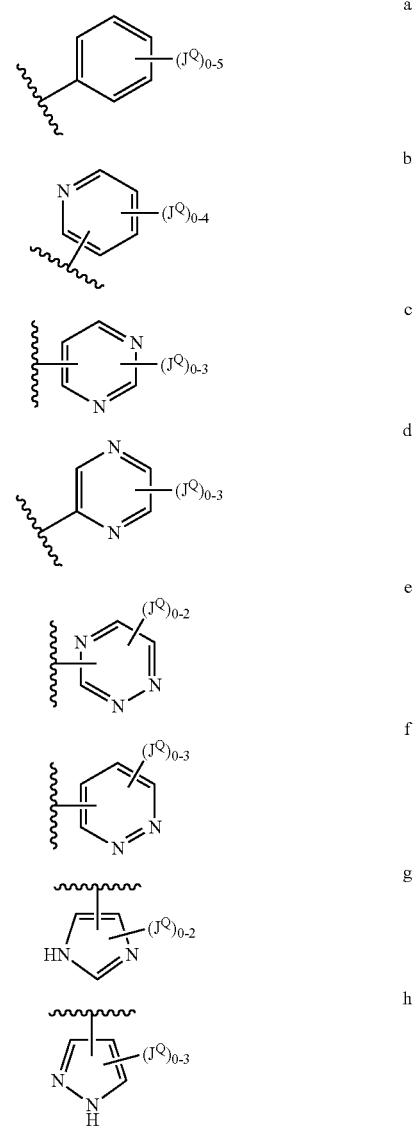

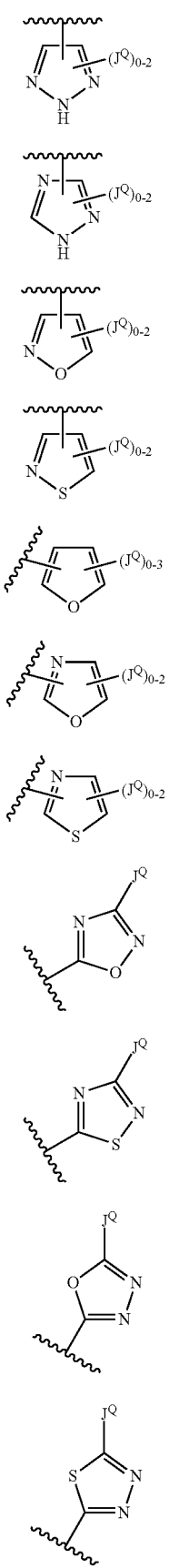

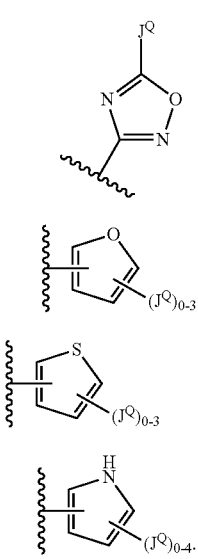

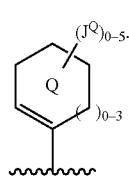

In a further embodiment, Q is a 6-membered ring selected from phenyl (a), pyridyl (b), pyrimidyl (c), pyrazinyl (d), triazinyl (e), or pyridazinyl (f). In a further embodiment, Q is phenyl (a), pyridyl (b), or pyrimidyl (c). In yet a further embodiment, Q is 2-pyridyl, 4-pyridyl, 2,6-pyrimidyl or phenyl. In a further embodiment, when Q is as described herein, $R^1$ and $R^2$ are H. In a further embodiment, when Q is as described herein, $R^3$ is H, halogen, or $C_{1-6}$ aliphatic. In yet a further embodiment, $R^3$ is H or Cl. In yet a further embodiment, when Q is as described herein, Z is a bond. In a different embodiment, when Q is as described herein, Z is NH.

In another embodiment, Q is a 5-membered ring selected from pyrazolyl (h), thiophenyl (v), furanyl (u) or pyrrolyl (w). In a further embodiment, pyrazolyl (h) or thiophenyl (v). In a further embodiment, when Q is as described herein, $R^1$ and $R^2$ are H. In a further embodiment, when Q is as described herein, $R^3$ is H, halogen, or $C_{1-6}$ aliphatic. In yet a further embodiment, $R^3$ is H or Cl. In yet a further embodiment, when Q is as described herein, Z is a bond. In a different embodiment, when Q is as described herein, Z is NH.

In another embodiment, Q is a 5-12 membered saturated or partially saturated monocyclic or bicyclic ring system optionally substituted with 1-5 $J^Q$ groups. In a further embodiment, Q is a 5-12 membered fully saturated or partially saturated monocyclic or bicyclic cycloaliphatic ring system.

In another embodiment, Q is a mono-unsaturated ring as represented by formula II:

$$\text{II}$$

In another embodiment, Q is a 5-6 membered fully saturated or partially saturated monocyclic cycloaliphatic ring system.

In another embodiment, Q is a 5-8 membered partially saturated heterocyclyl ring. In a further embodiment, Q is a 5-6 membered heterocyclyl containing 1-2 nitrogen atoms. In yet a further embodiment, Q contains 1 nitrogen atom. In yet a further embodiment, Q is the ring represented in formula III:

Formula III

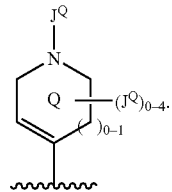

In another embodiment of the invention, Z is a bond or NH. In a further embodiment, $R^1$ and $R^2$ are H. In yet a further embodiment, $R^3$ is H, halogen, or $C_{1-6}$ aliphatic. In yet a further embodiment, $R^3$ is H or Cl. In another embodiment of the invention, the $J^Q$ substituent attached at the nitrogen atom of ring Q is —$(V_n)$—R", —$(V_n)$—CN, —$(V_n)$—$NO_2$, or —$(V_n)$—$(C_{1-4}$ haloaliphatic), wherein V is C(=O) or C(=O)O and n is 1.

In an embodiment of the invention, each occurrence of $J^Q$ is independently selected from R", —$CH_2R"$, halogen, CN, $NO_2$, —COR", —$COR^8R"$, —N(R')R", —$CH_2N(R')R"$, —OR", —$CH_2OR"$, —SR", —$CH_2SR"$, —C(O)OR", —NR'COR", —$NR'COR^8R"$, —NR'COOR", —$NR'COOR^8R"$, —CON(R')R", —$CON(R')R^8R"$, —$SO_2N(R')R"$, —$SO_2N(R')R^8R"$, —$CON(R')R^8N(R')R"$, —$OR^8OR"$, —$OR^8N(R')R"$, —$NR'CH(R^8)R"$, —$NR'CH(R^8)C(O)OR"$, —$N(R')R^8R"$, —$N(R')R^8R"$, —$N(R')R^8N(R')R"$, —$N(R')R^8OR"$, —$NR'CH(R^8)R"$, —$NR'CH_2C(O)N(R')R"$, or —$NR'CH(R^8)C(O)N(R')R"$, wherein $R^8$ is H or an $C_{1-6}$ alkyl optionally substituted with 1-4 occurrences of $J^V$.

In a further embodiment, each occurrence of $J^Q$ is independently selected from R", —$CH_2R"$, halogen, —CN, —$NO_2$, —N(R')R", —$CH_2N(R')R"$, —OR", —$CH_2OR"$, —SR", —$CH_2SR"$, —COOR", —NR'COR", —$NR'COCH_2R"$, —$NR'CO(CH_2)_2R"$, —NR'COOR", —CON(R')R", —$SO_2N(R')R"$, —$CONR'(CH_2)_2N(R')R"$, —$CONR'(CH_2)_3N(R')R"$, —$CONR'(CH_2)_4N(R')R"$, —$O(CH_2)_2OR"$, $O(CH_2)_3OR"$, $O(CH_2)_4OR"$, —$O(CH_2)_2N(R')R"$, —$O(CH_2)_3N(R')R"$, —$O(CH_2)_4N(R')R"$, —$NR'CH(CH_2OR^8)R"$, —$NR'CH(CH_2CH_2OR')R"$, —$NR'CH(CH_3)R"$, $NR'CH(CF_3)R"$, —$NR'CH(CH_3)C(O)OR"$, —$NR'CH(CF_3)C(O)OR"$, —$NR'(CH_2)R"$, —$NR'(CH_2)_2R"$, —$NR'(CH_2)_3R"$, —$NR'(CH_2)_4R"$, —$NR'(CH_2)N(R')R"$, —$NR'(CH_2)_2N(R')R"$, —$NR'(CH_2)_3N(R')R"$, —$NR'(CH_2)_4N(R')R"$, —$NR'(CH_2)OR"$, —$NR'(CH_2)_2OR"$, —$NR'(CH_2)_3OR"$, —$NR'(CH_2)_4OR"$, —$NR'CH(CH_2CH_3)R"$, —$NR'CH_2C(O)N(R')R"$, —$NR'CH(CH_3)C(O)N(R')R"$, $NR'CH(CF_3)C(O)N(R')R"$, —$NR'CH(CH_2CH_3)C(O)N(R')R"$, —$NR'CH(CH(CH_3)_2)C(O)N(R')R"$, —$NR'CH(C(CH_3)_3)C(O)N(R')R"$, —$NR'CH(CH_2CH(CH_3)_2)C(O)N(R')R"$, —$NR'CH(CH_2OR^8)C(O)N(R')R"$ or —$NR'CH(CH_2CH_2N(Me)_2)C(O)N(R')R"$.

In another further embodiment, R" is selected from hydrogen, a $C_1$-$C_6$ aliphatic group optionally substituted with up to six occurrences of $R^7$, or R" is a ring selected from:

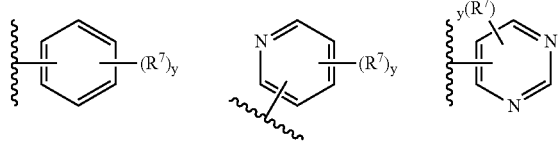

-continued

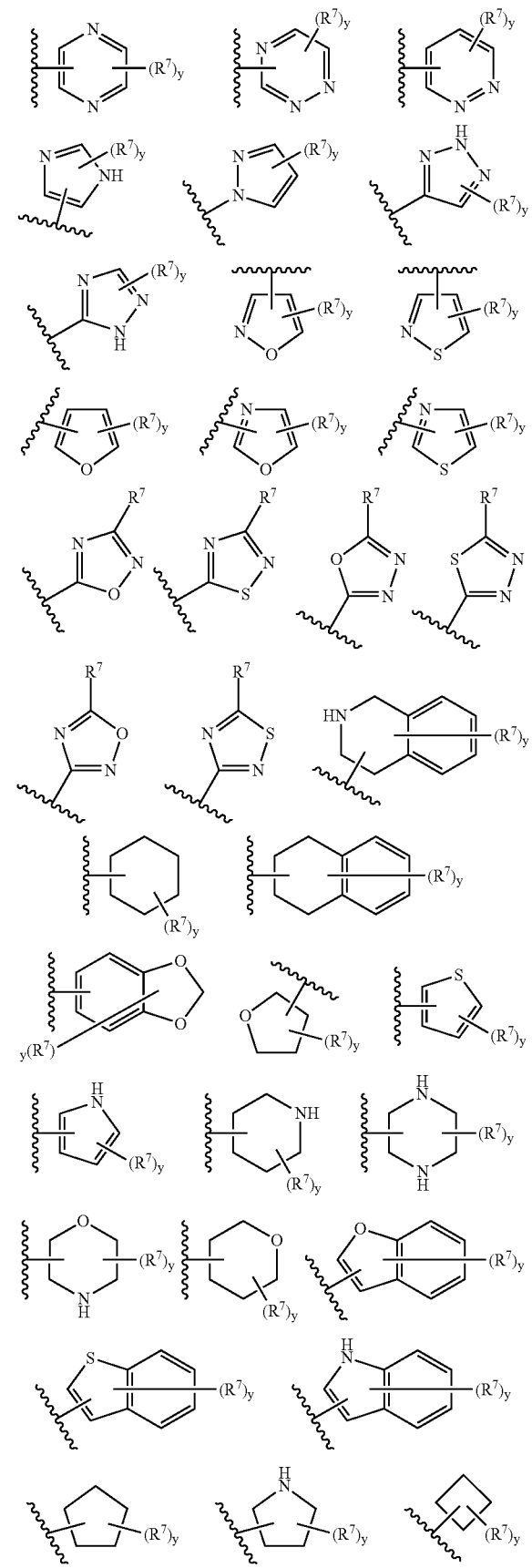

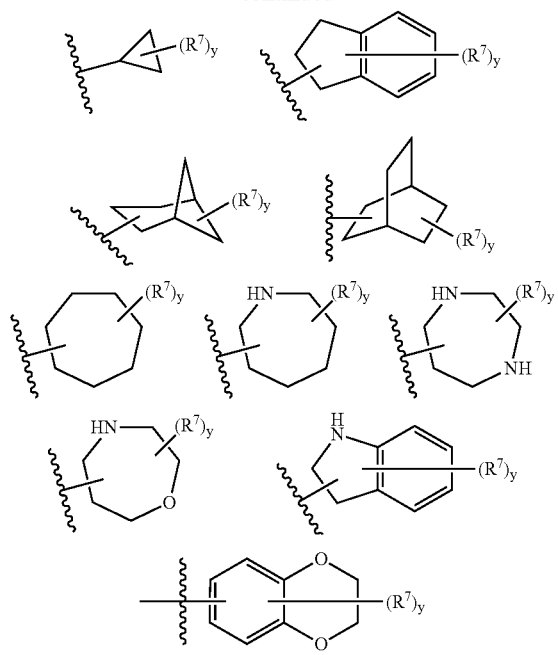

or two occurrences of R' are taken together with the nitrogen atom to which they are bound to form an optionally substituted 3-10-membered monocyclic or bicyclic heterocyclic ring selected from:

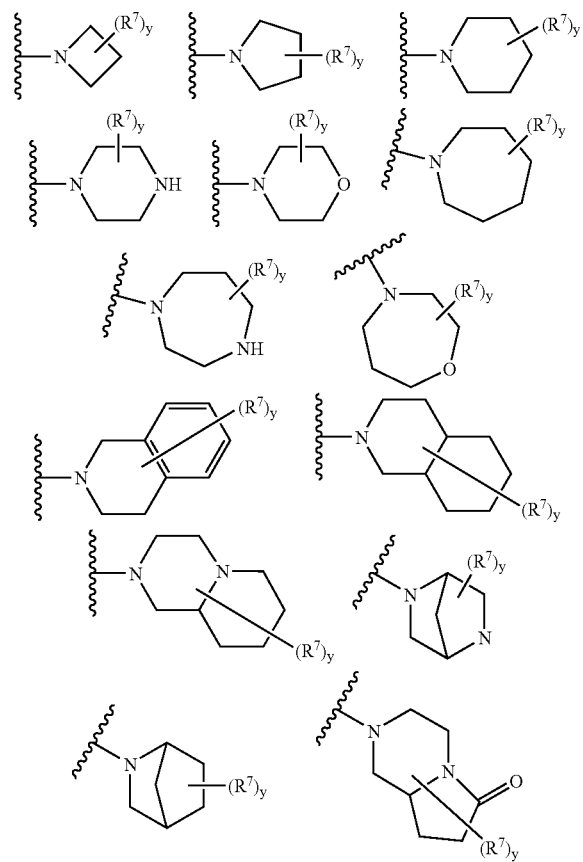

wherein y is 0, 1, 2, or 3, and each occurrence of $R^7$ is independently R', —CH$_2$R', halogen, CH$_2$CH, CN, NO$_2$, —N(R')$_2$, —CH$_2$N(R')$_2$, —OR', —CH$_2$OR', —SR', —CH$_2$SR', —COOR', —COR', —NR$^9$COR', —NR$^9$COOR', —CON(R')$_2$, —SO$_2$N(R')$_2$, —NR$^9$SO$_2$R', —CONR$^9$(CH$_2$)$_2$N(R$^9$)R', —CONR$^9$(CH$_2$)$_3$N(R$^9$)R', —CONR$^9$(CH$_2$)$_4$N(R$^9$)R', —O(CH$_2$)$_2$OR', O(CH$_2$)$_3$OR', O(CH$_2$)$_4$OR', —O(CH$_2$)$_2$N(R$^9$)R', —O(CH$_2$)$_3$N(R$^9$)R', —O(CH$_2$)$_4$N(R$^9$)R', —NR$^9$CH(CH$_2$OH)R', —NR$^9$CH(CH$_2$CH$_2$OH)R', —NR$^9$(CH$_2$)R', —NR$^9$(CH$_2$)$_2$R', —NR$^9$(CH$_2$)$_3$R', —NR$^9$(CH$_2$)$_4$R', —NR$^9$(CH$_2$)N(R$^9$)R', —NR$^9$(CH$_2$)$_2$N(R$^9$)R', —NR$^9$(CH$_2$)$_3$N(R$^9$)R', —NR$^9$(CH$_2$)$_4$N(R$^9$)R', —NR$^9$(CH$_2$)OR', —NR$^9$(CH$_2$)$_2$OR', —NR$^9$(CH$_2$)$_3$OR', or —NR$^9$(CH$_2$)$_4$OR'; wherein $R^9$ is H or $R^6$.

In another embodiment, $J^Q$ is H, halogen, OCF$_3$, R", CN, NO$_2$, or C$_{1-4}$haloaliphatic. In yet another embodiment, $J^Q$ is —V—R", —V—CN, —V—NO$_2$, or —V—(C$_{1-4}$haloaliphatic). In a further embodiment, V is C$_{1-6}$alkyl, wherein up to two methylene units are replaced by $G^V$ wherein $G^V$ is selected from —NH—, —NR—, —O—, —S—, —CO$_2$—, —OC(O)—, —C(O)—, —C(O)NH—, —C(O)NR—, —NHCO—, or —NRCO—. In yet a further embodiment, V is a C$_{1-6}$alkyl wherein zero methylene units are replaced by $G^V$. In yet a further embodiment, V is CH$_2$. In still a further embodiment, V is substituted with 2 $J^V$ groups; wherein $J^V$ is C$_{1-3}$alkyl or two $J^V$ groups, together with the methylene unit to which they are attached, form a 3-6 membered cycloalkyl ring.

In another embodiment, one methylene unit of V is replaced by $G^V$. In a further embodiment, V is a C$_1$alkyl, wherein one methylene unit is replaced by $G^V$. In another embodiment, $G^V$ is bonded directly to R".

In another embodiment, $J^V$ is selected from halogen, NH$_2$, NO$_2$, CN, OH, C$_{1-3}$alkyl, C$_{1-3}$haloalkyl, C$_{1-3}$haloalkoxy, —O—(C$_{1-3}$alkyl), —NH—(C$_{1-3}$alkyl), —N(C$_{1-3}$alkyl)$_2$, —C(=O)O(C$_{1-3}$alkyl), —C(=O)OH, —C(=O)(C$_{1-3}$alkyl), —C(=O)H, —OC(=O)(C$_{1-3}$alkyl), —NC(=O)(C$_{1-3}$ alkyl), or oxo.

In an embodiment of the invention, when Z is O, $R^1$ and $R^3$ are H and $R^2$ is H or CH$_3$, then Q is not an optionally substituted phenyl.

In another embodiment of the invention, Z is C=O.

In an embodiment of the invention, NH, C=O or O and Q is selected from an unsubstituted 5-7 membered cycloalkyl ring. In a further embodiment, Z is NH. In yet a further embodiment, Q is a cyclopentyl or cyclohexyl ring.

In another embodiment, Z is NH, C=O or O, and Q is a 5-8 membered saturated, partially saturated, or unsaturated monocycle optionally substituted with 0-4 occurrences of $J^Q$. In a further embodiment, Z is NH.

In another embodiment, Q is 5-10 membered aryl or heteroaryl optionally substituted with 0-4 occurrences of $J^Q$ and $J^Q$ is halogen, OCF$_3$, —(V$_n$)—CN, —(V$_n$)—NO$_2$, or —(V$_n$)—(C$_{1-4}$ haloaliphatic). In a further embodiment, $J^Q$ is —(V$_n$)—R" and V is a C$_{2-10}$ aliphatic, wherein up to three methylene units are replaced by $G^V$, wherein $G^V$ is selected from —NH—, —NR—, —O—, —S—, —CO$_2$—, —OC (O)—, —C(O)CO—, —C(O)—, —C(O)NH—, —C(O)NR—, —C(=N—CN), —NHCO—, —NRCO—, —NHC(O)O—, —NRC(O)O—, —SO₂NH—, —SO₂NR—, —NHSO₂—, —NRSO₂—, —NHC(O)NH—, —NRC(O)NH—, —NHC(O)NR—, —NRC(O)NR, —OC(O)NH—, —OC(O)NR—, —NHSO₂NH—, —NRSO₂NH—, —NHSO₂NR—, —NRSO₂NR—, —SO—, or —SO₂—; and wherein V is optionally substituted with 1-4 occurrences of J^V. In another embodiment, V is a Cl aliphatic, wherein up to one methylene unit is replaced by G^V, wherein G^V is selected from —O—, —S—, —CO₂—, —OC(O)—, —C(O)CO—, —C(O)—, —C(O)NH—, —C(O)NR—, —C(=N—CN), —NHCO—, —NRCO—, —NHC(O)O—, —NRC(O)O—, —SO₂NH—, —SO₂NR—, —NHSO₂—, —NRSO₂—, —NHC(O)NH—, —NRC(O)NH—, —NHC(O)NR—, —NRC(O)NR, —OC(O)NH—, —OC(O)NR—, —NHSO₂NH—, —NRSO₂NH—, —NHSO₂NR—, —NRSO₂NR—, —SO—, or —SO₂—.

In a further embodiment, R" is H, or is an optionally substituted group selected from $C_{1-6}$ aliphatic, $C_{3-10}$ cycloaliphatic, naphthyl, 5-membered heteroaryl, pyridinyl, pyridazinyl, pyrazinyl, 3,5-pyrimidinyl, triazinyl, 8-10 membered heteroaryl, or 5-10 membered heterocyclyl; or two R" groups, on the same substituent or different substituents, together with the atom(s) to which each R" group is bound, form an optionally substituted 3-8 membered heterocyclyl; wherein each optionally substituted R" group is independently and optionally substituted with 1-4 occurrences of $J^R$.

In another embodiment, Z is O, NH, N($C_{1-3}$aliphatic), S, CH₂, C=CH₂, or C=O; and Q is selected from a 3-8 membered saturated or partially saturated monocyclic ring having 0-3 heteroatoms selected from nitrogen, oxygen, or sulfur, wherein Q is optionally substituted with 1-5 $J^Q$.

In another embodiment, a compound of the invention is selected from Tables 1 or 2.

TABLE 1

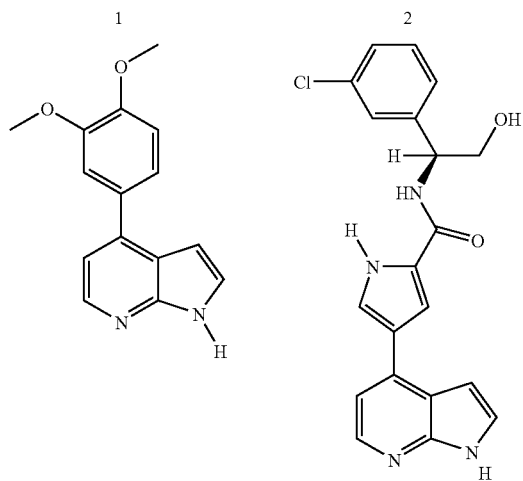

TABLE 1-continued

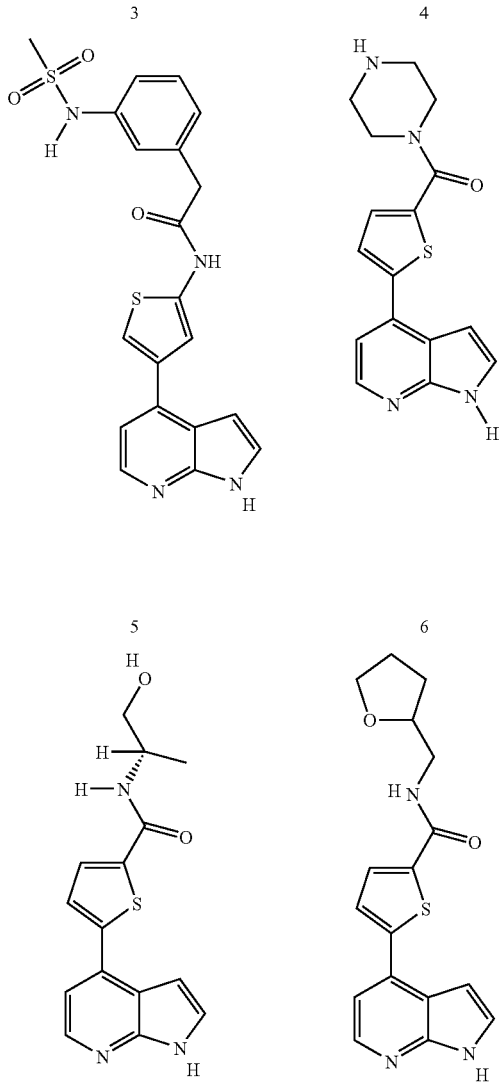

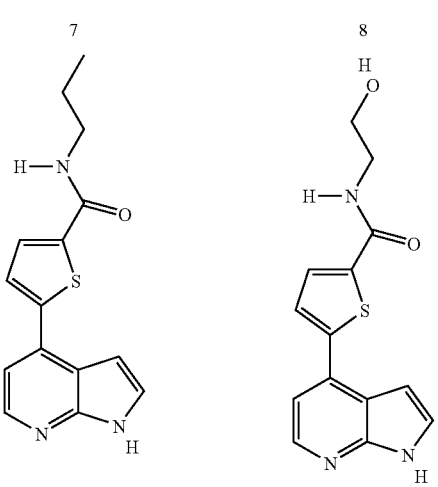

TABLE 1-continued
9 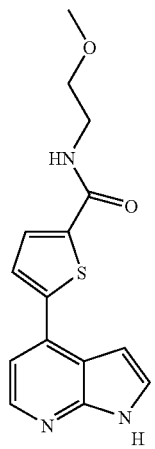 10 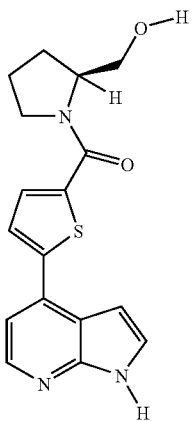 [SMILES: O=C(c1ccc(-c2ccnc3[nH]ccc23)s1)N1CCC[C@H]1CO]
11 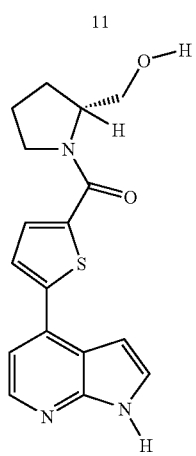 12 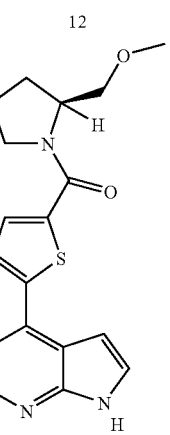
13 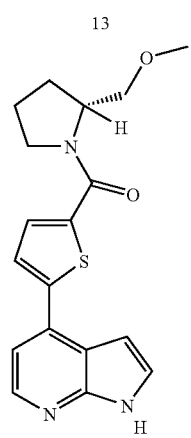 14 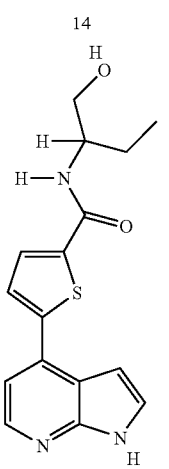
TABLE 1-continued
15 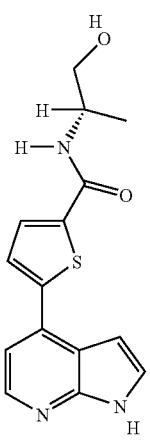 16 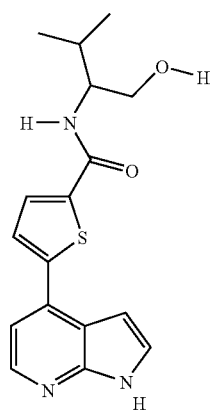
17 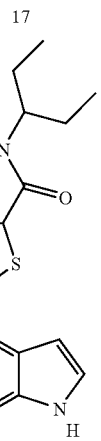 18 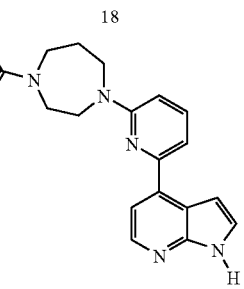
19 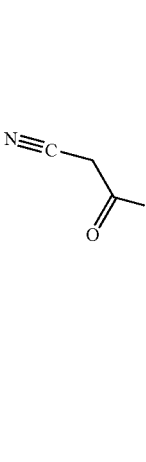

TABLE 1-continued
20 21
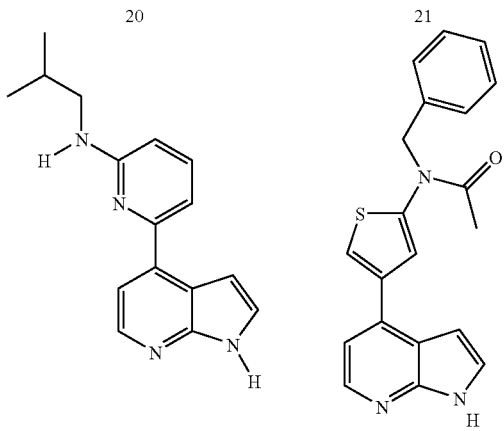
26
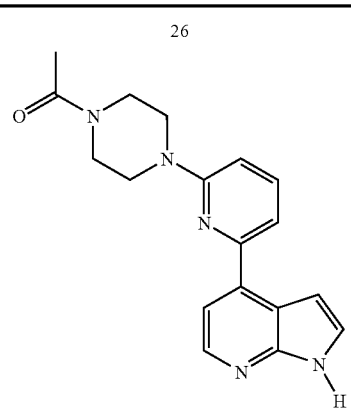
22
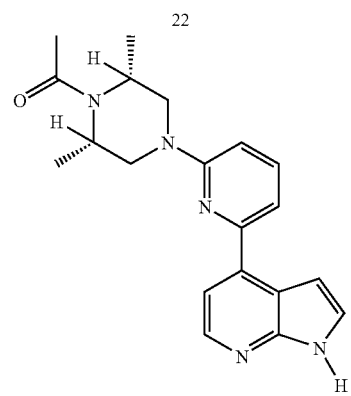
27 28
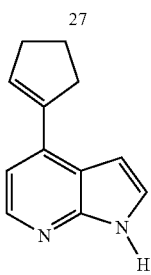 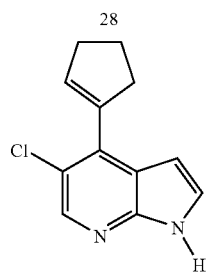
23 24
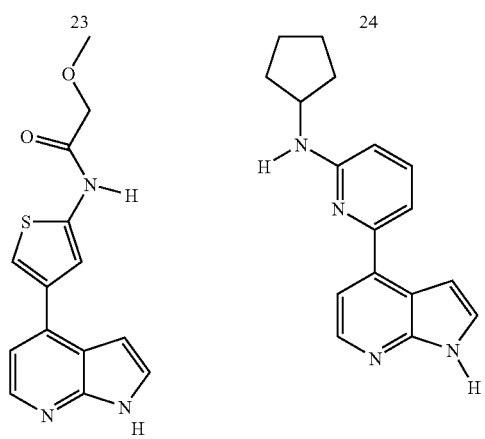
29 30
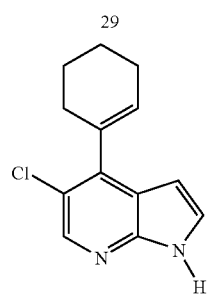 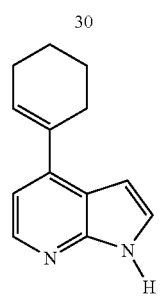
25
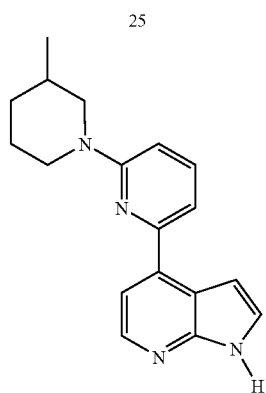 [SMILES: CCC(C)CNc1cccc(-c2ccnc3[nH]ccc23)n1]
31 32
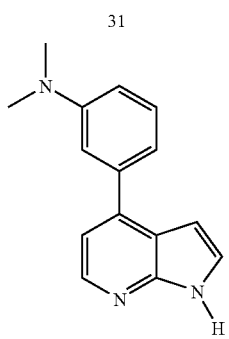 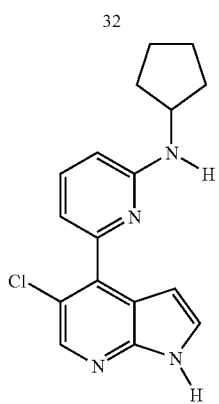

TABLE 1-continued
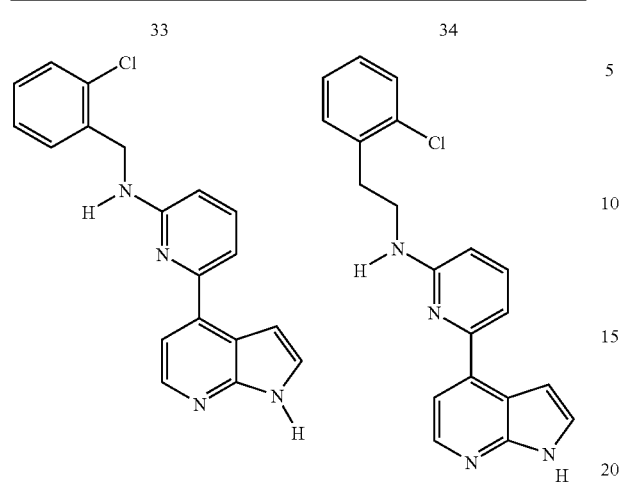
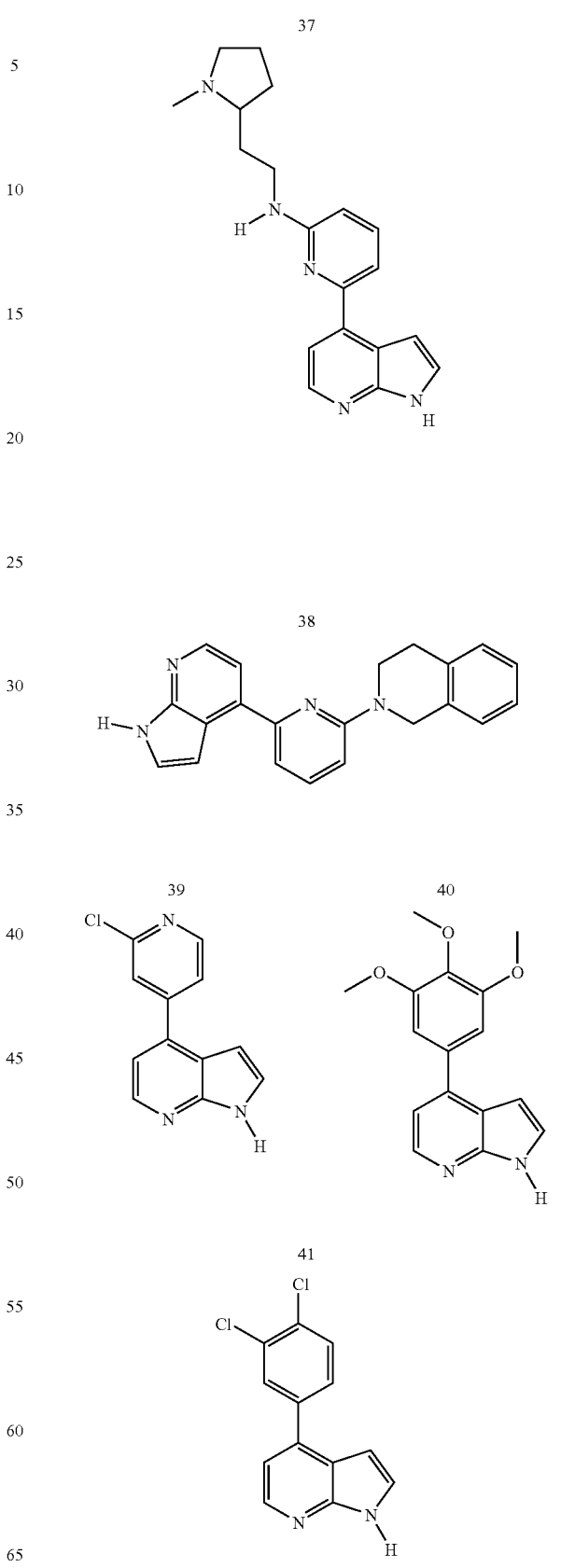

TABLE 1-continued
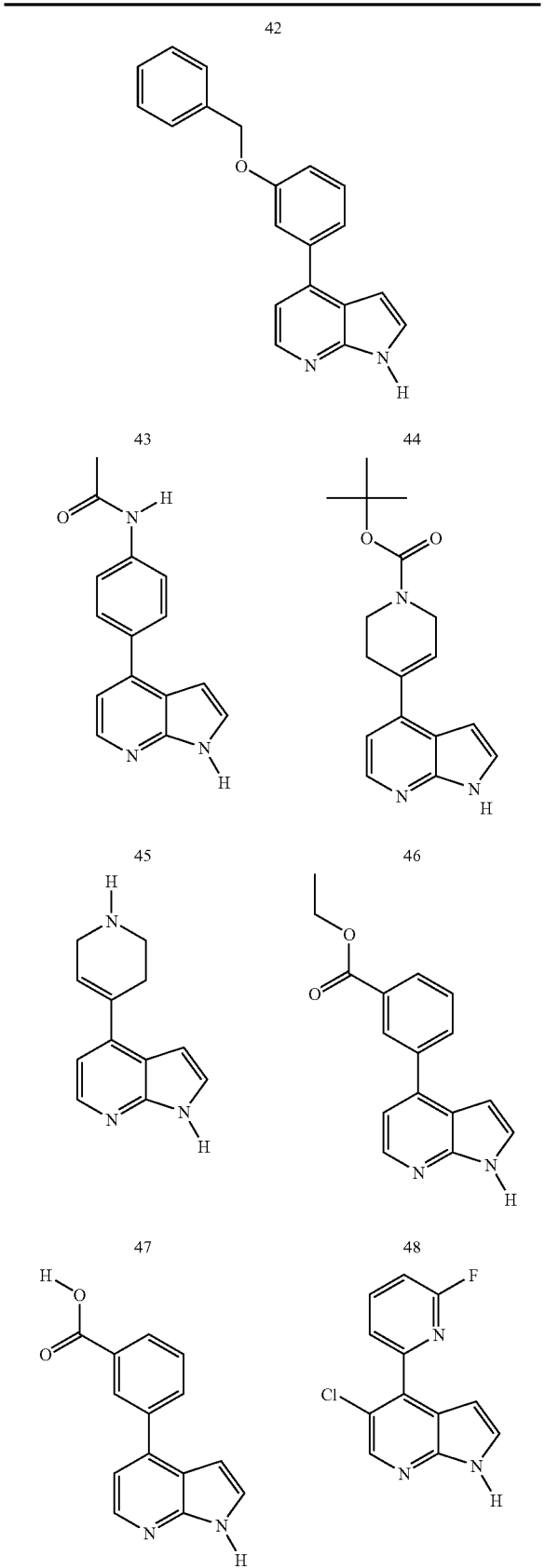
TABLE 1-continued
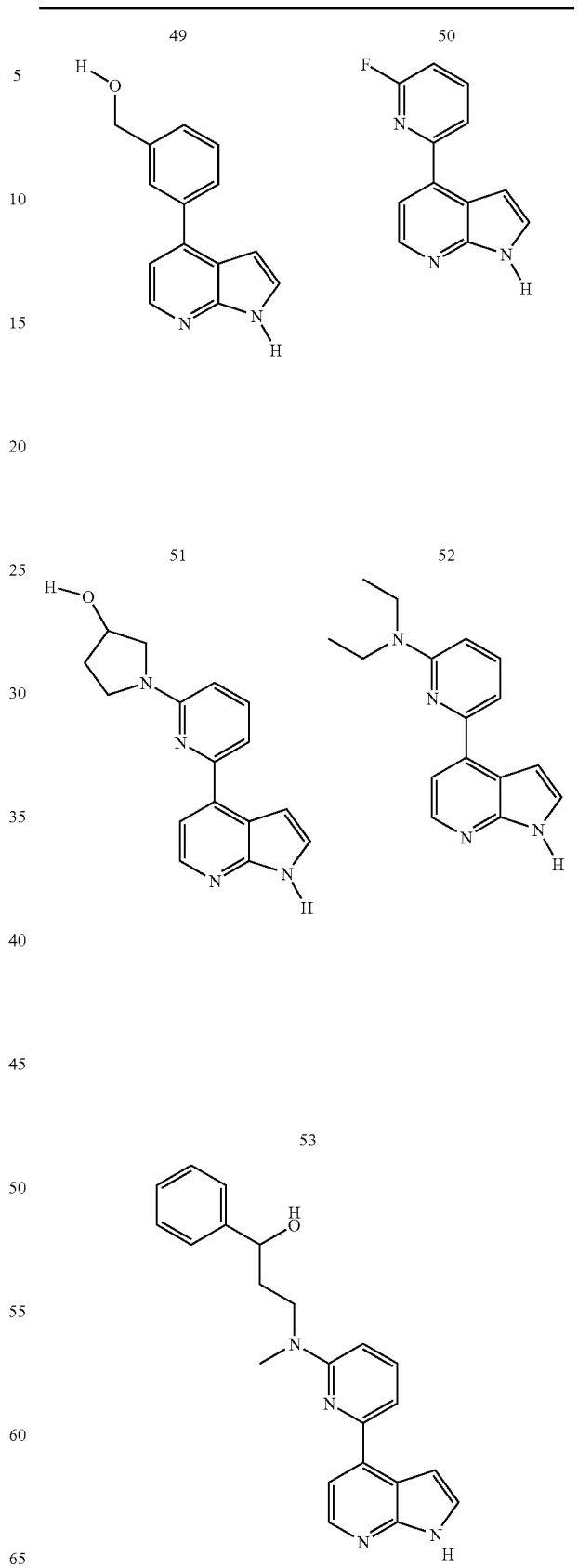

TABLE 1-continued
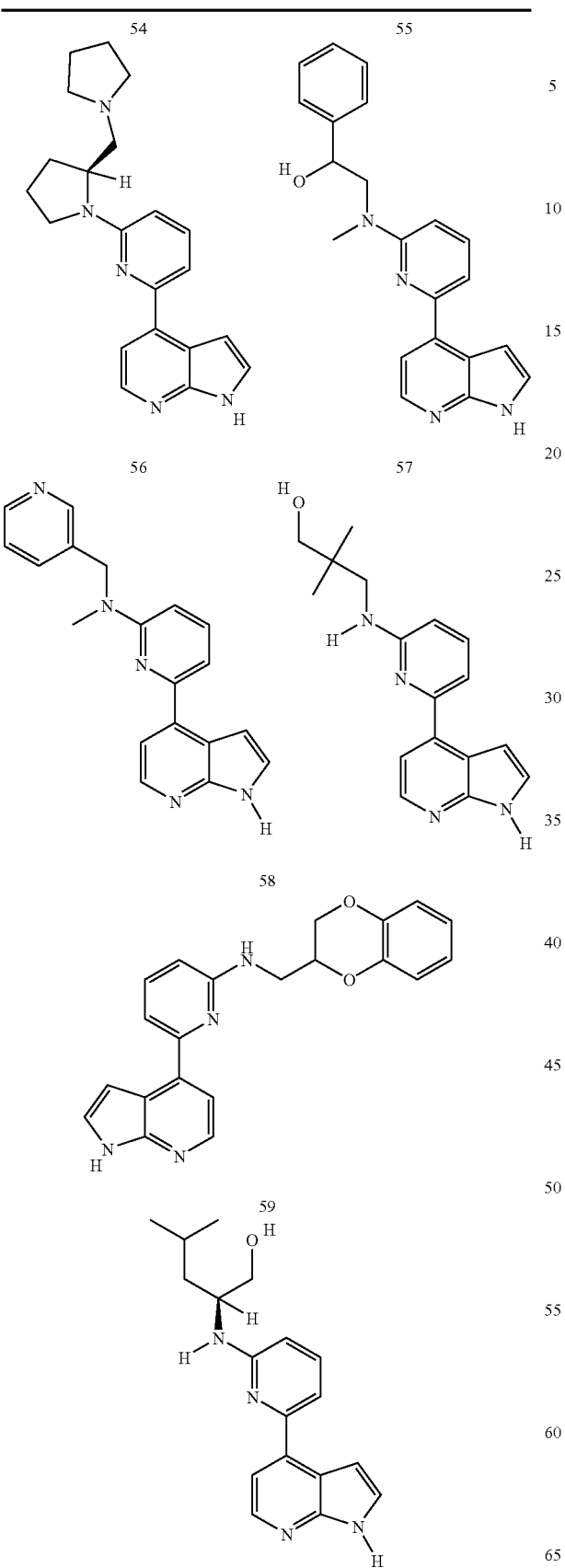
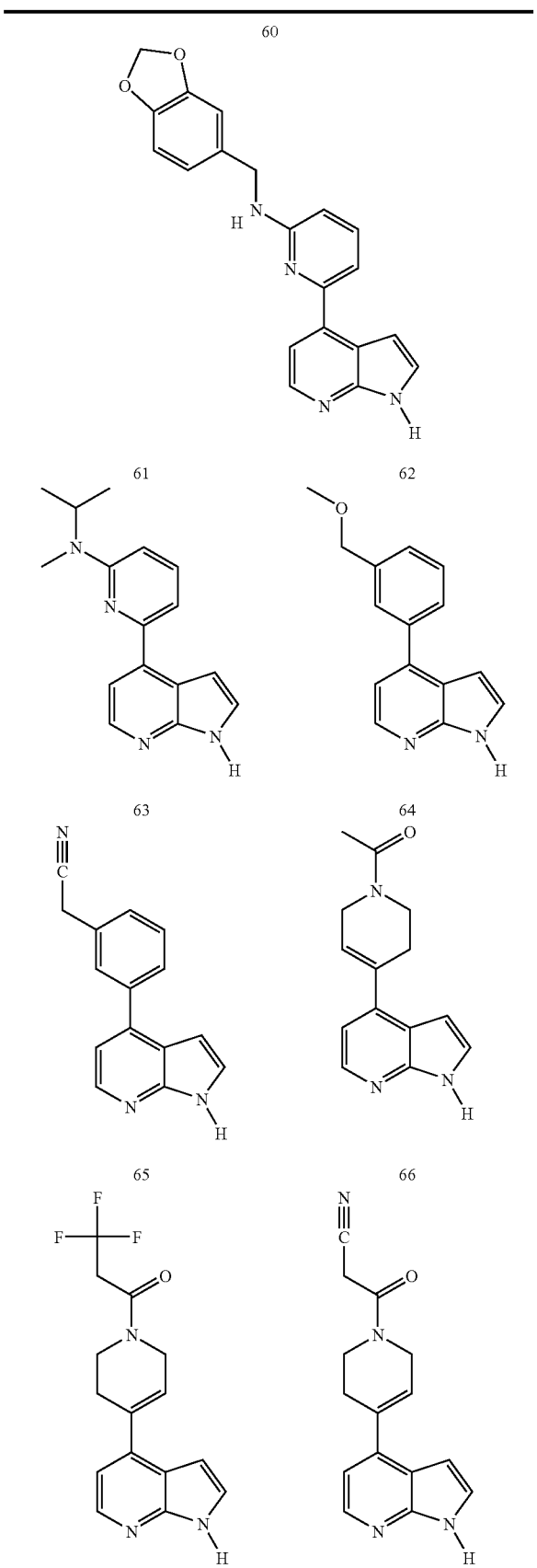

TABLE 1-continued
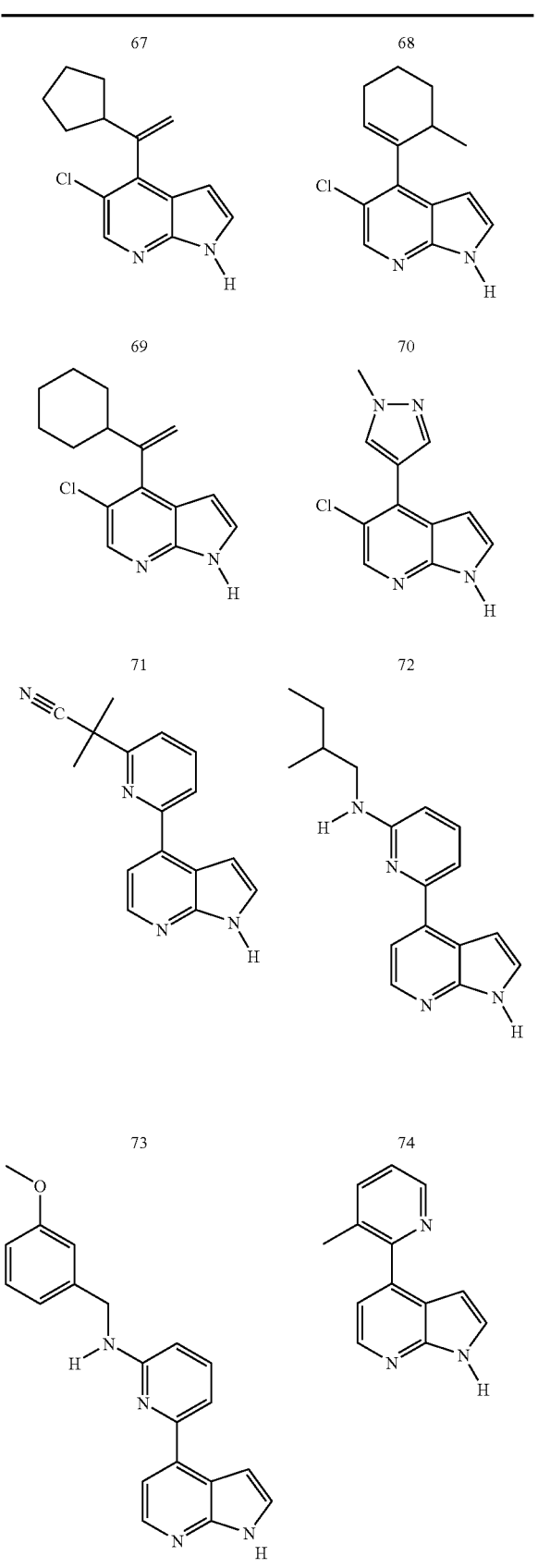
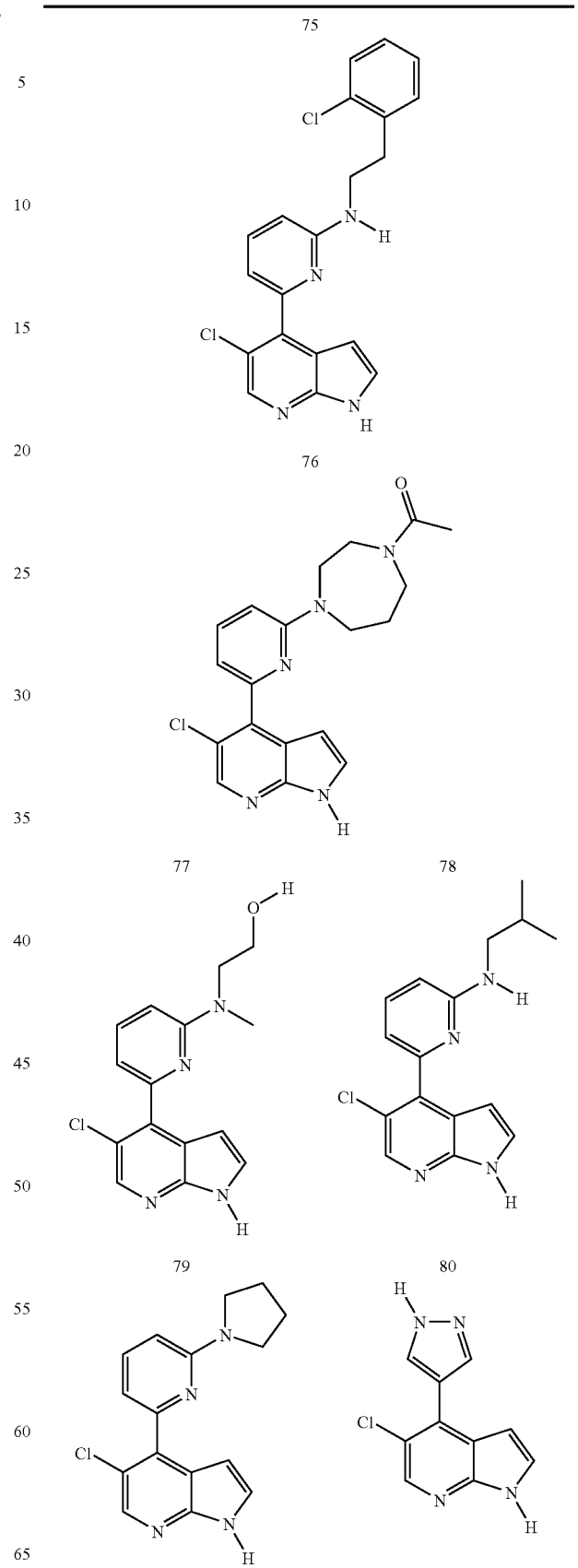

TABLE 1-continued
81
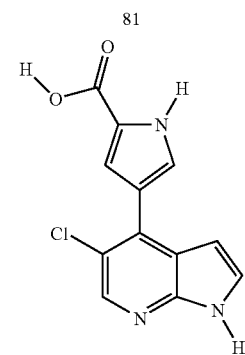
82
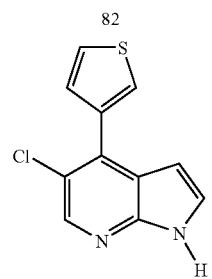
83
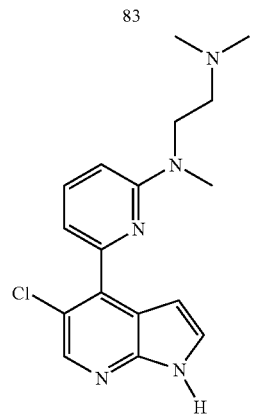
84
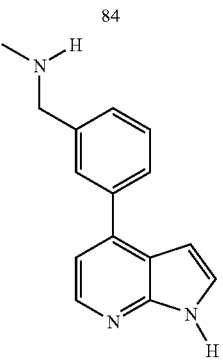
85
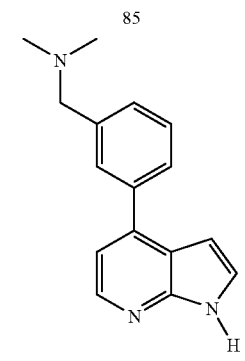
86
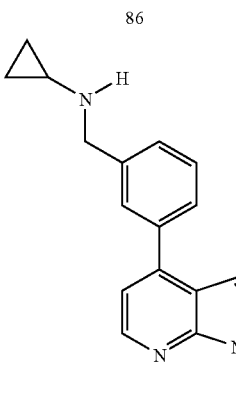
87
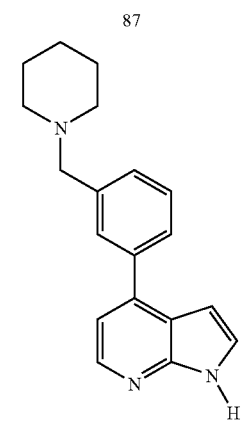
88
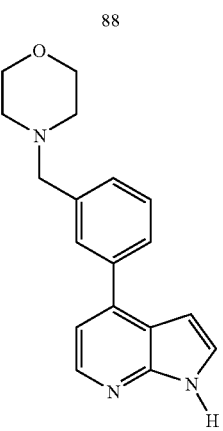
TABLE 1-continued
89
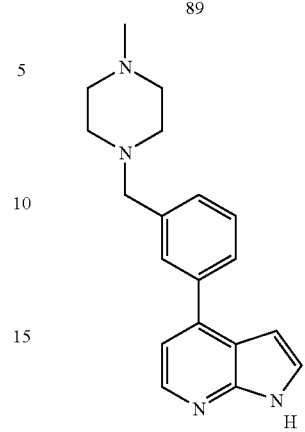
90
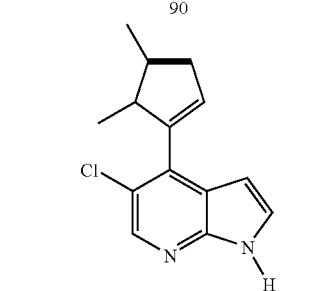
91
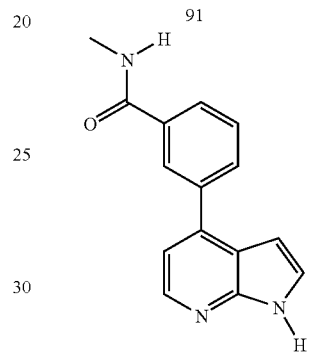
92
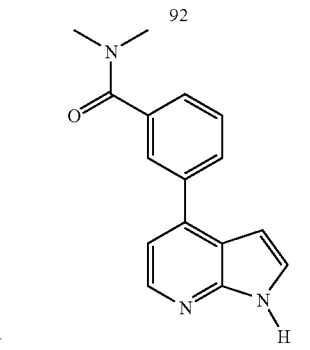
93
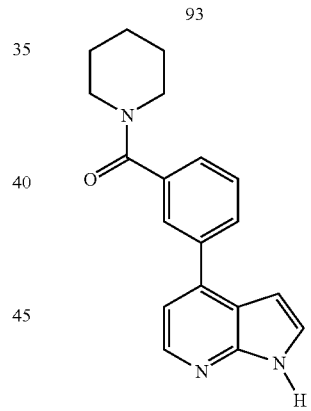
94
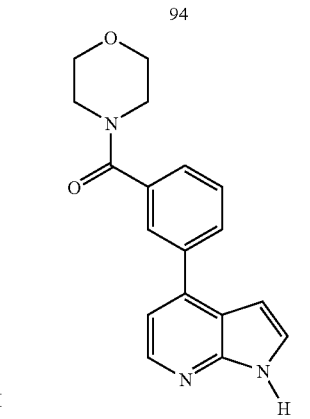
95
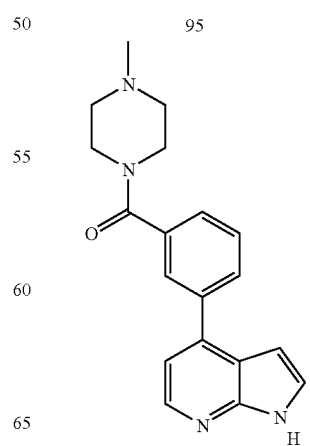
96
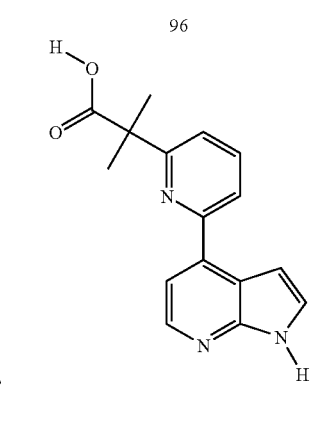

TABLE 1-continued
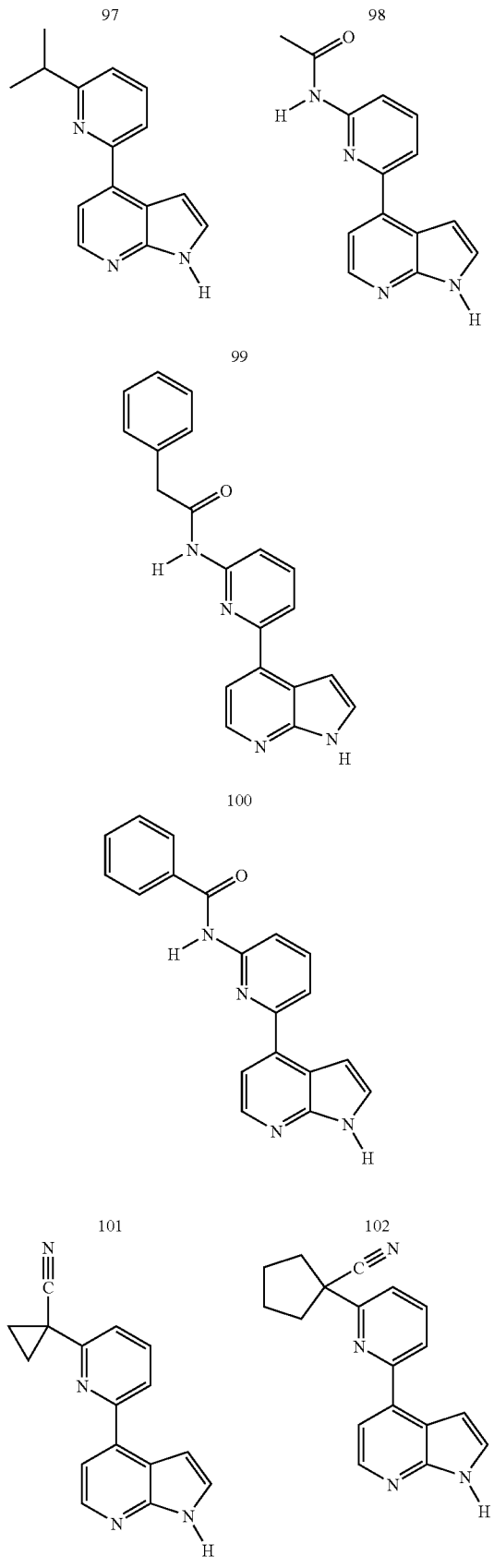
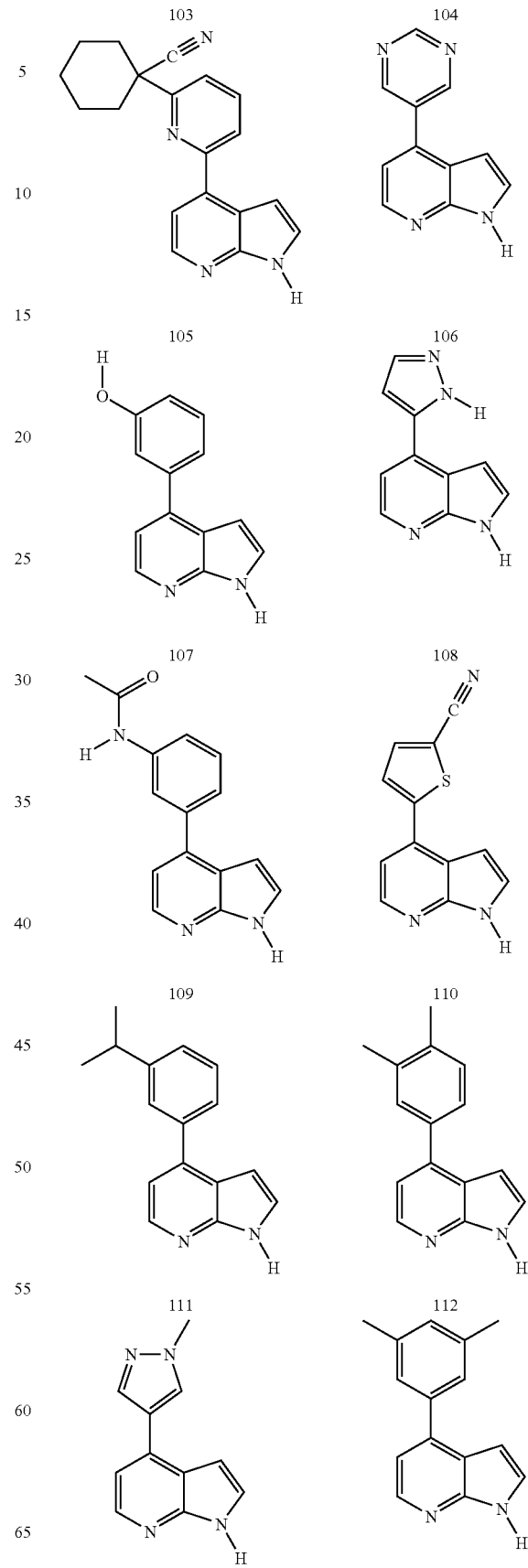

TABLE 1-continued
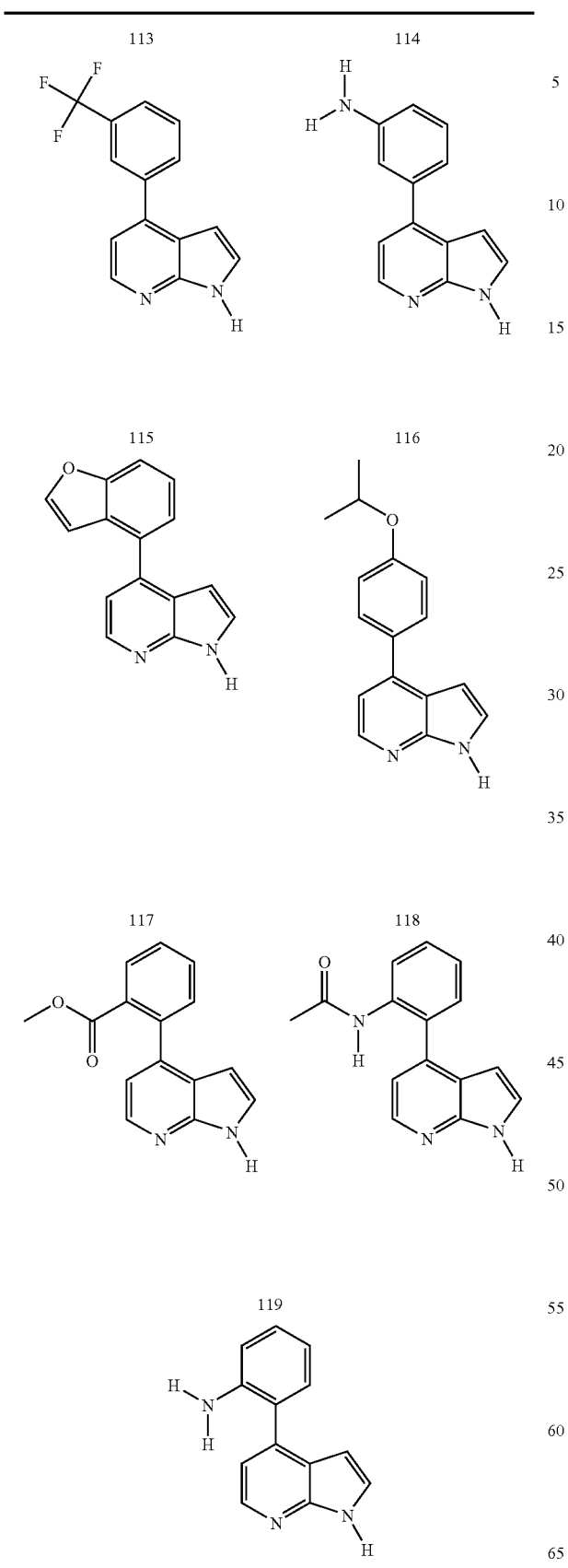

TABLE 1-continued
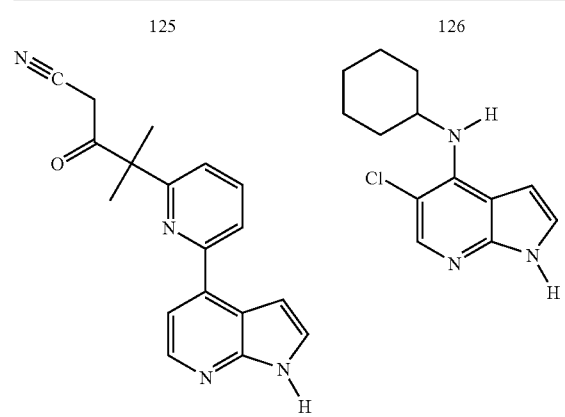
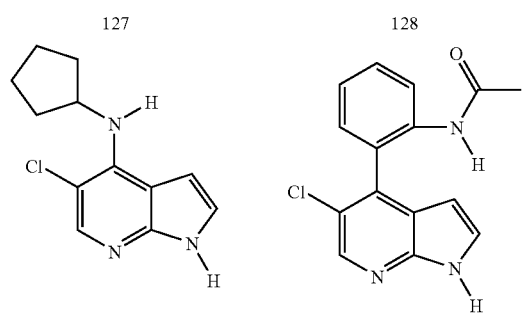
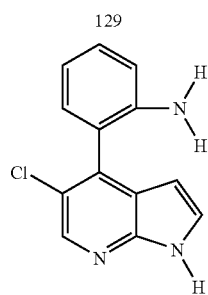
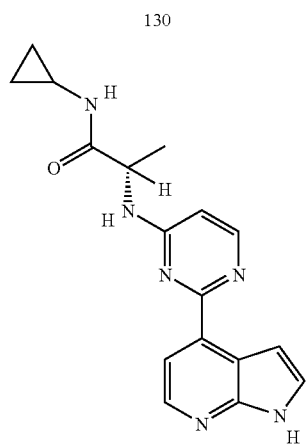
TABLE 1-continued
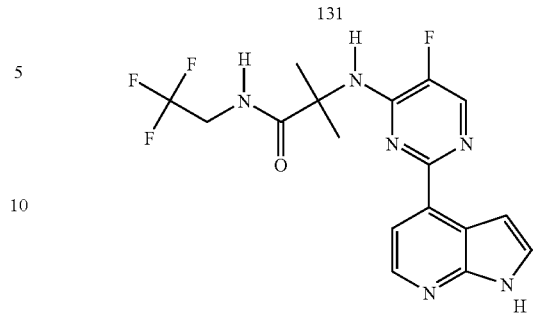
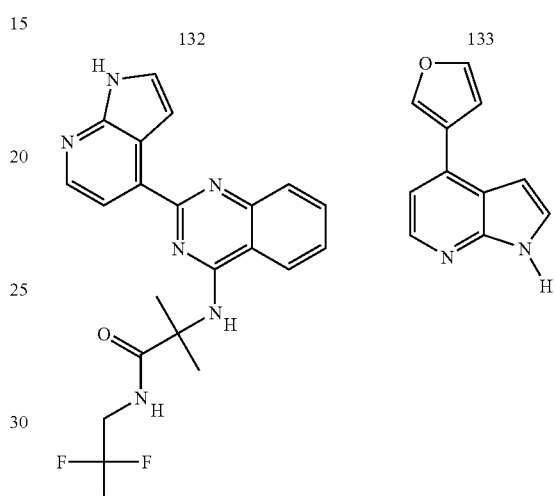
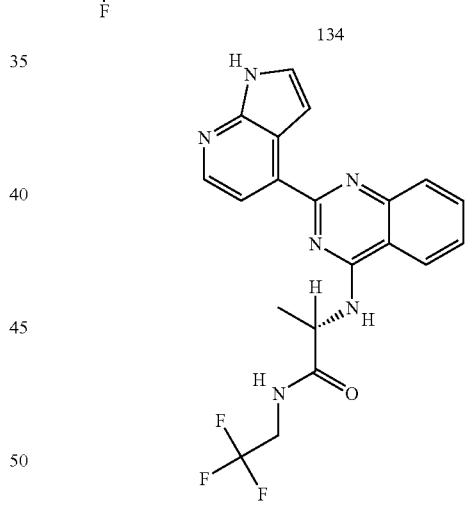
TABLE 2
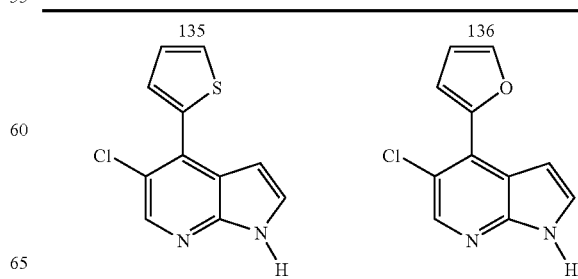

TABLE 2-continued
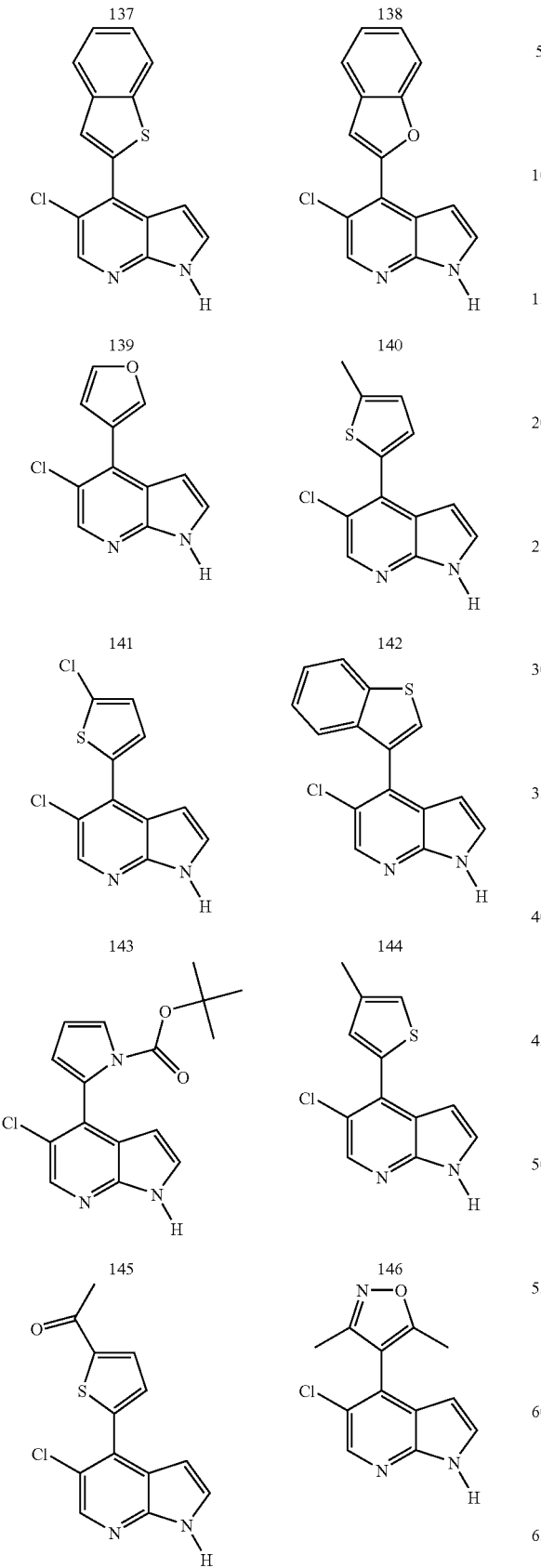
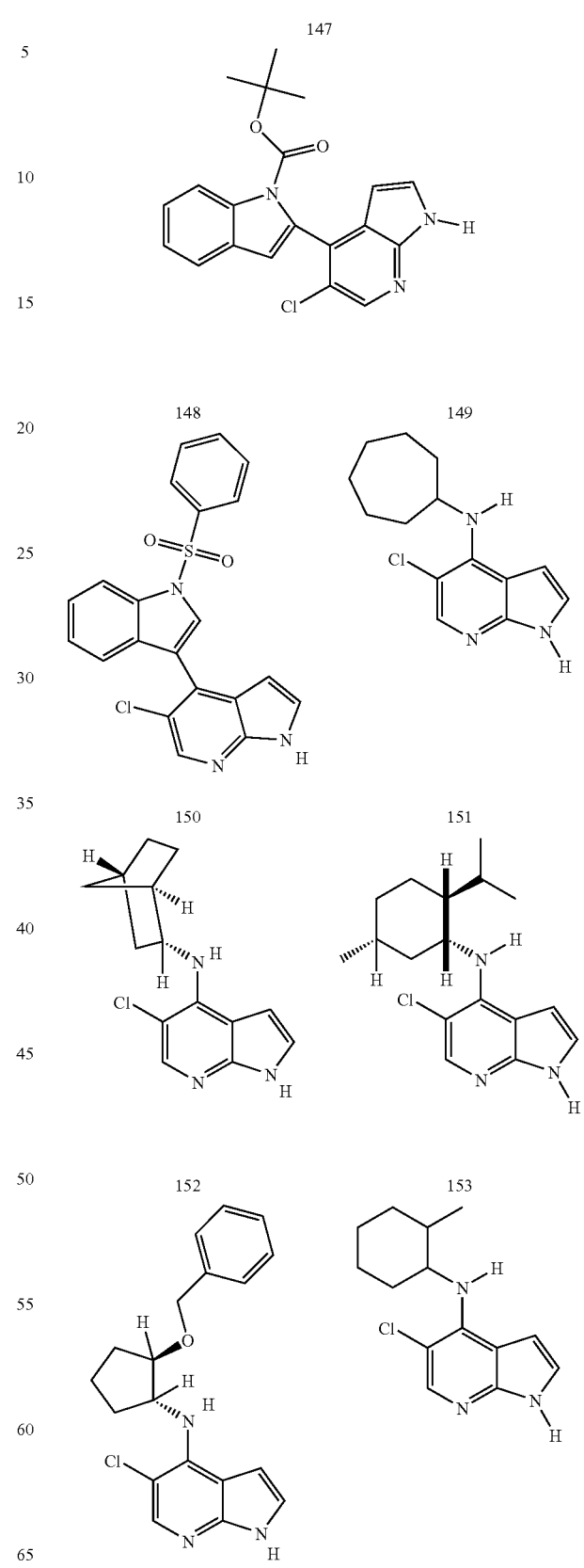

TABLE 2-continued
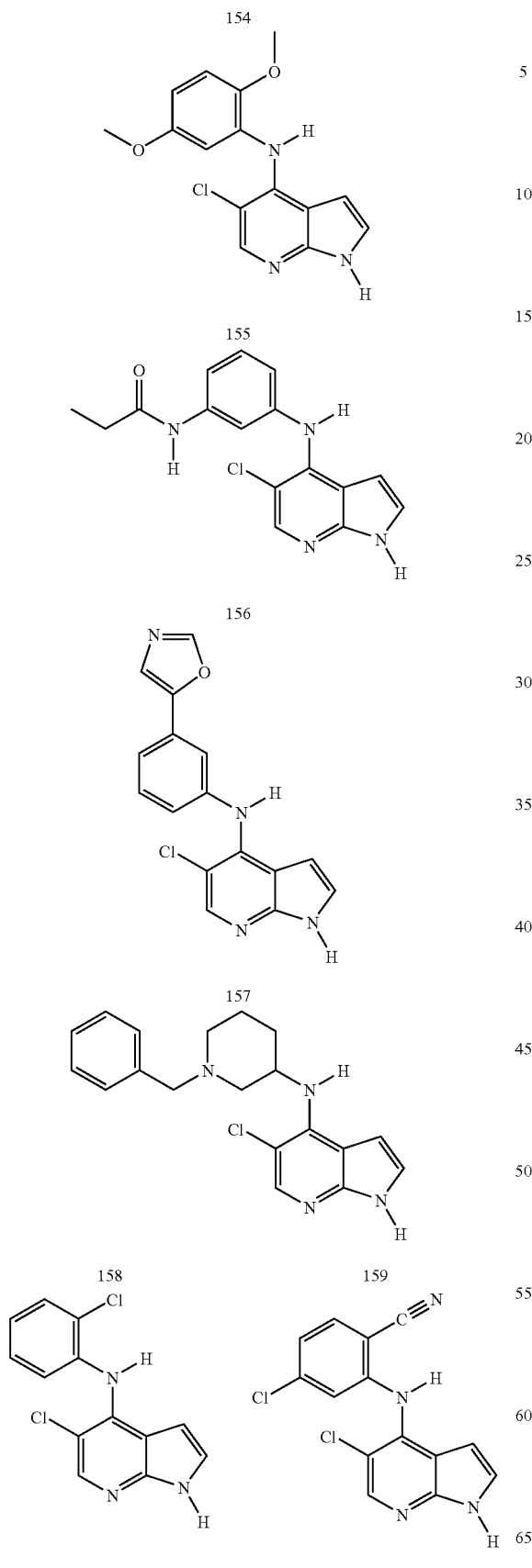
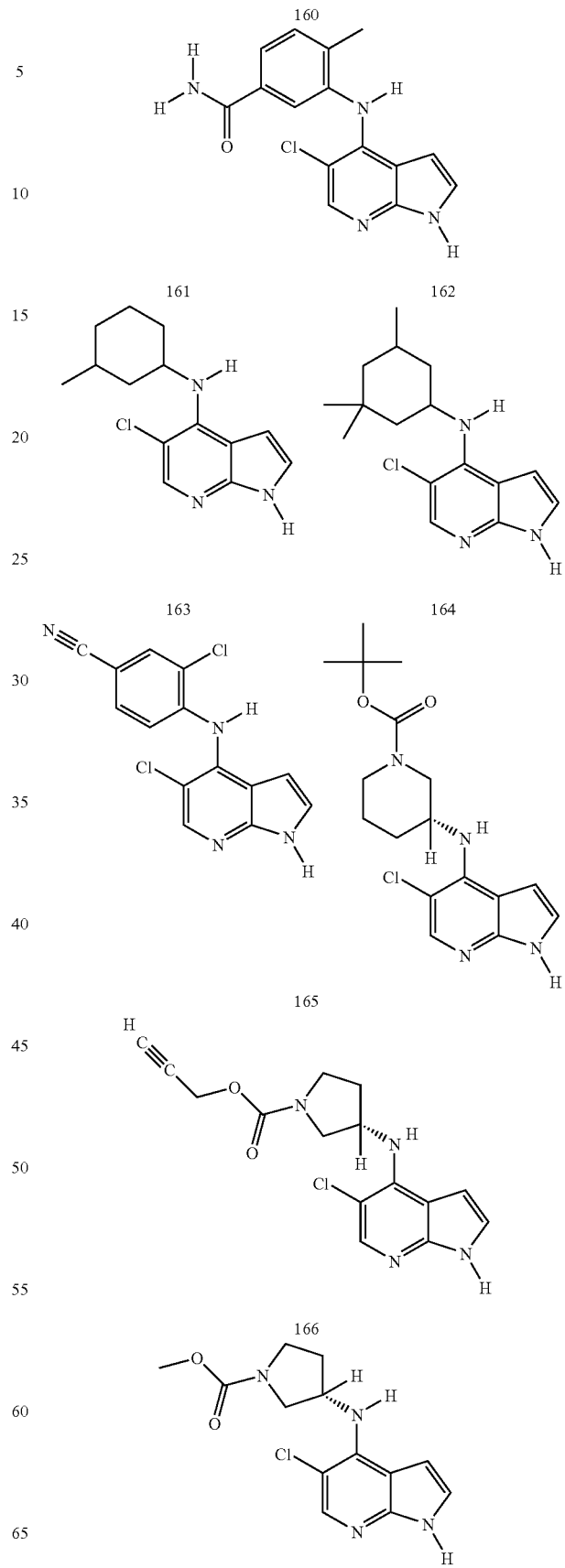

TABLE 2-continued
167
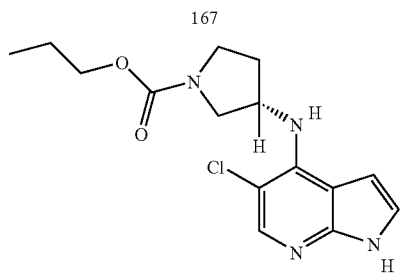
168
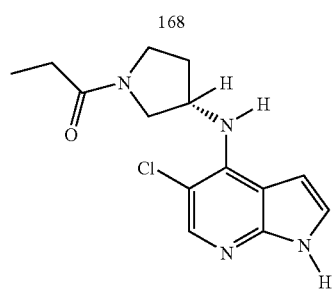
169
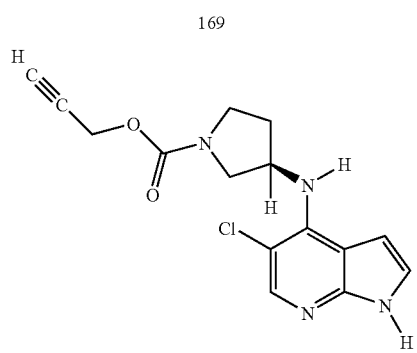
170
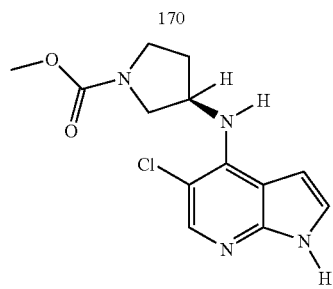
171
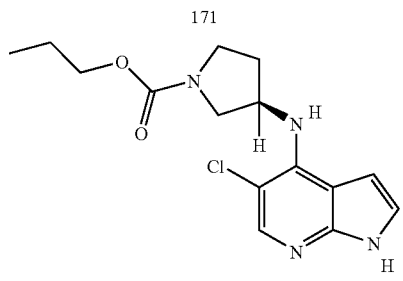
TABLE 2-continued
172
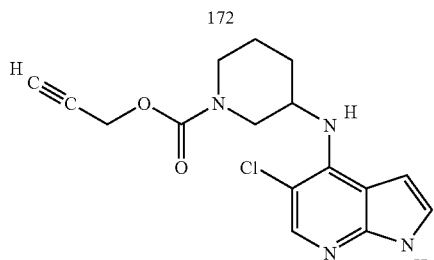
173 174
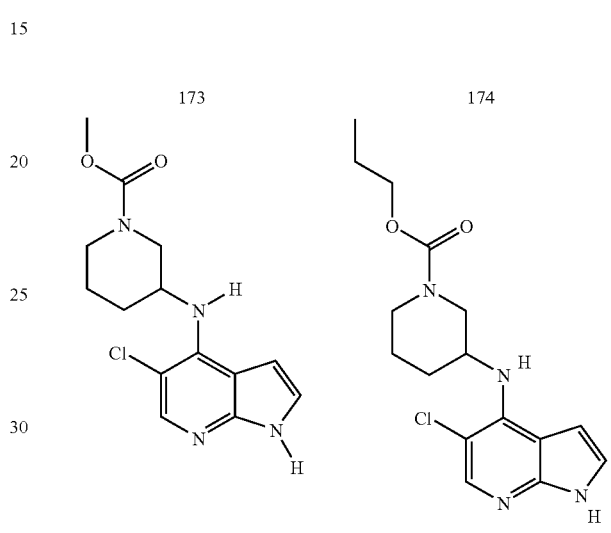
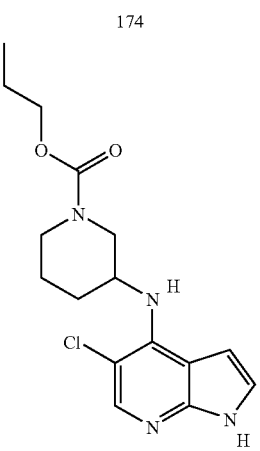
175
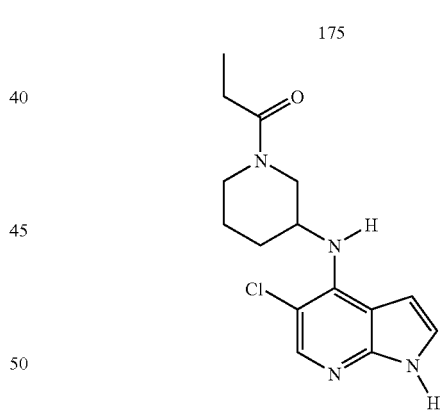
176
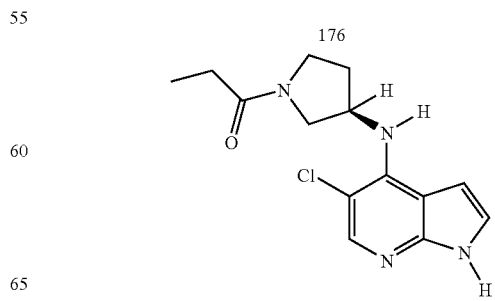

TABLE 2-continued
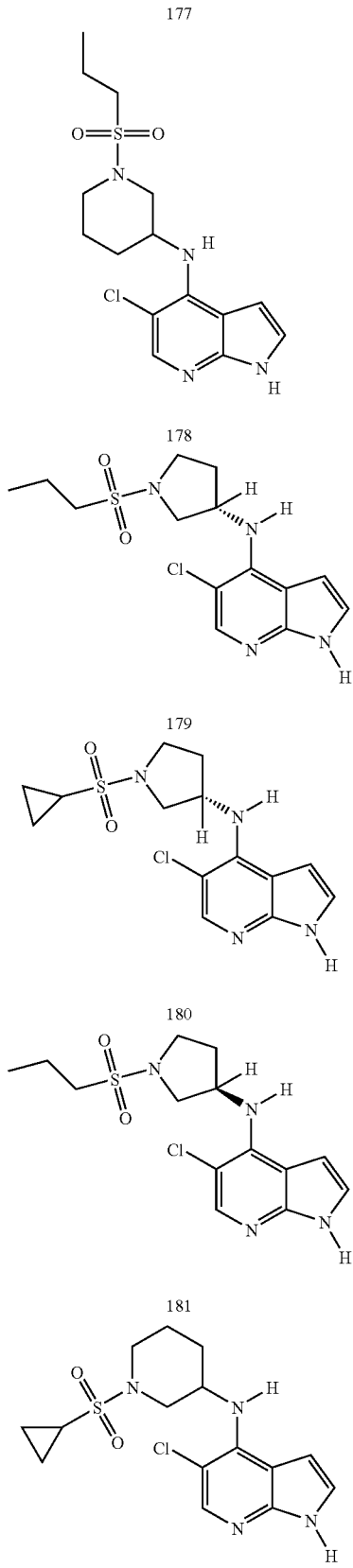
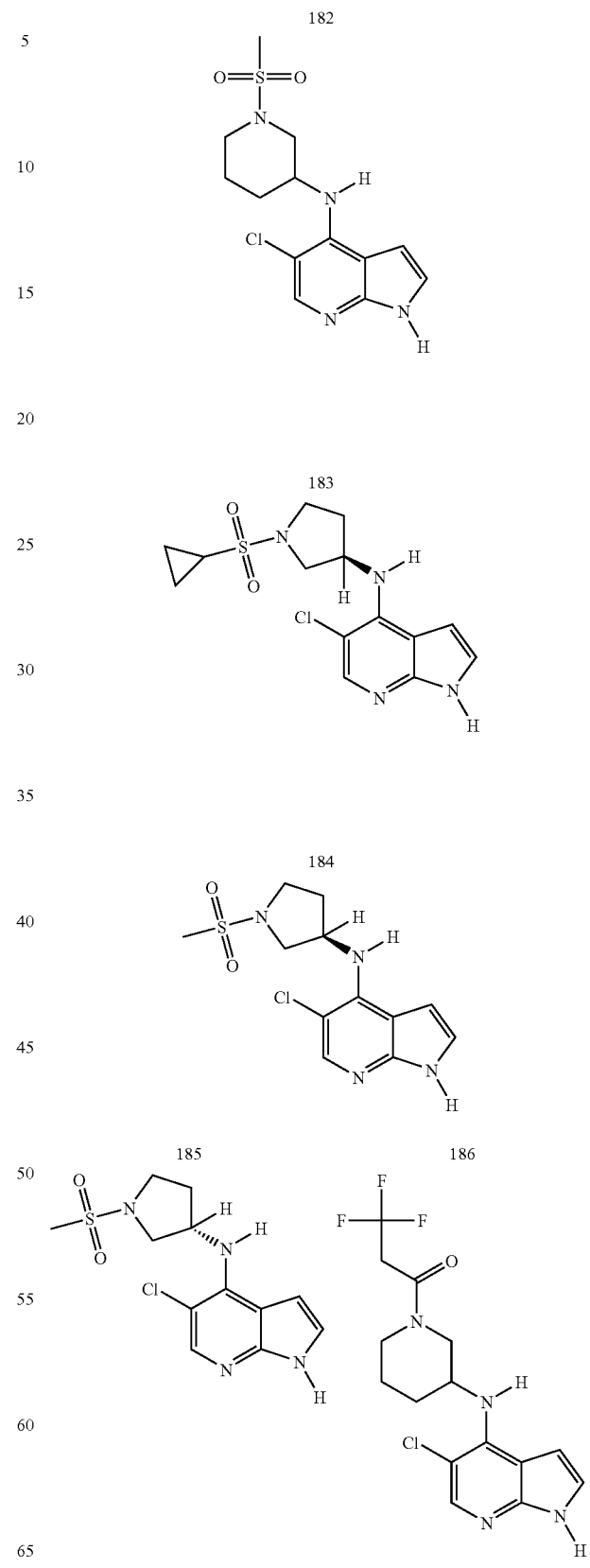

TABLE 2-continued
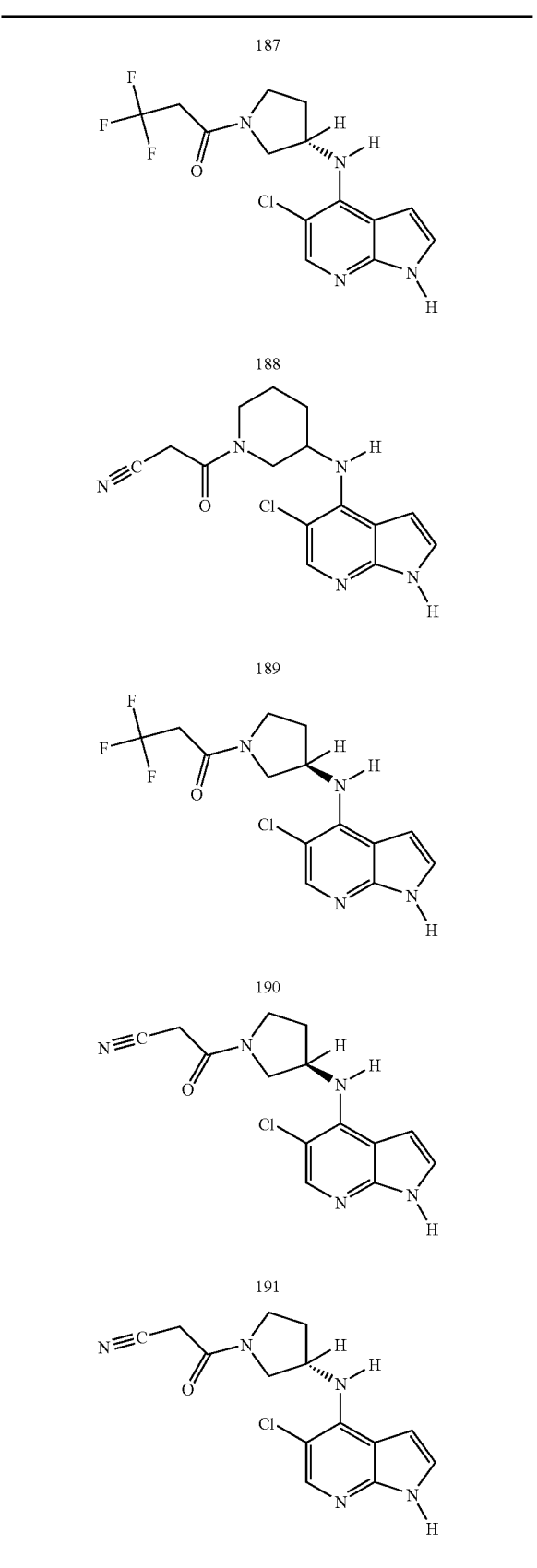
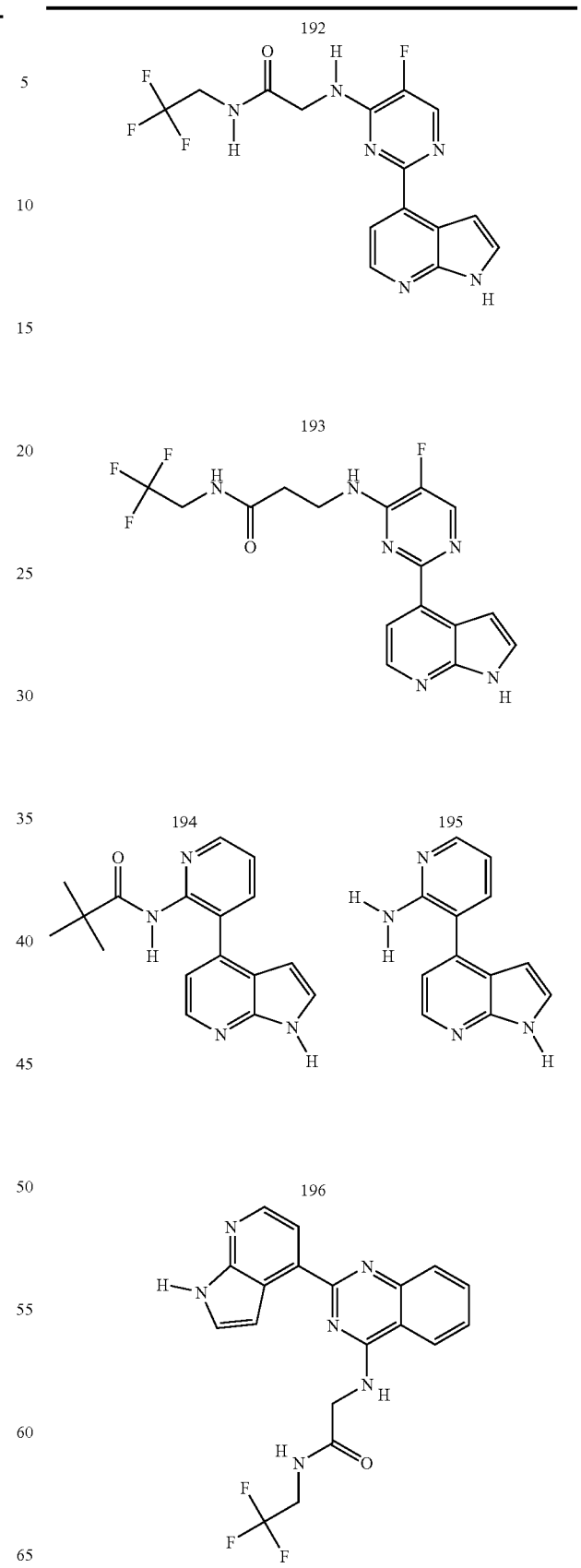

TABLE 2-continued
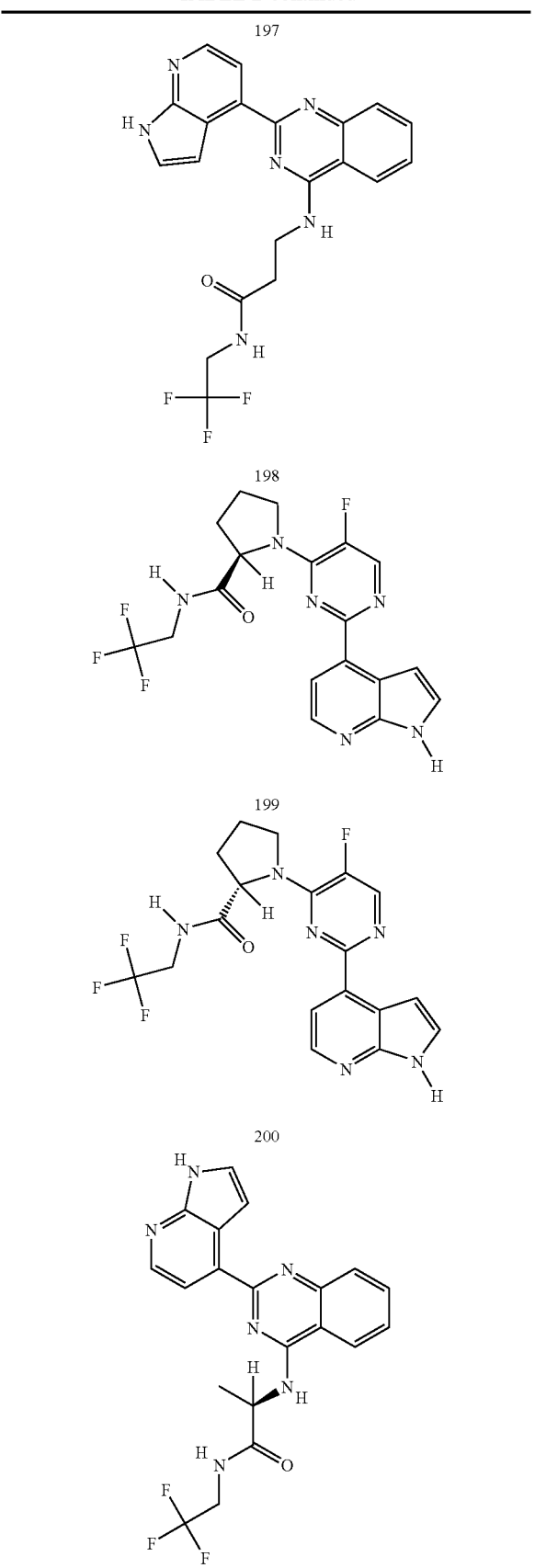
TABLE 2-continued
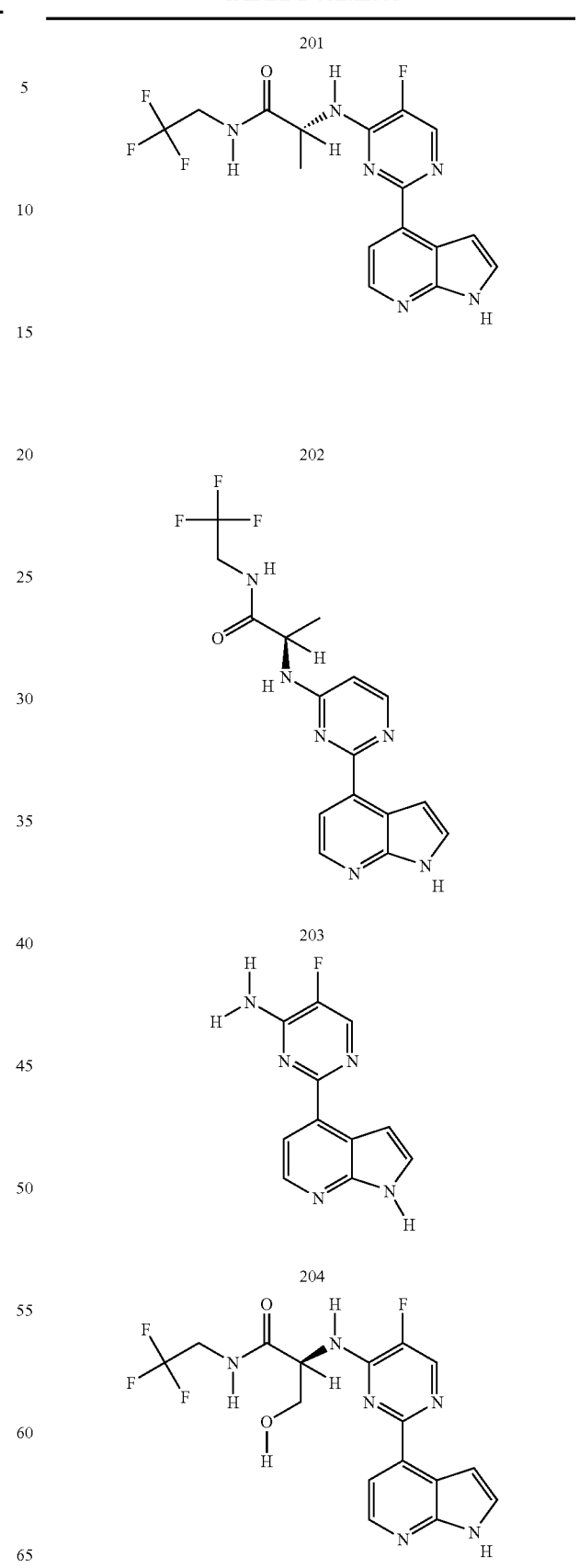

TABLE 2-continued
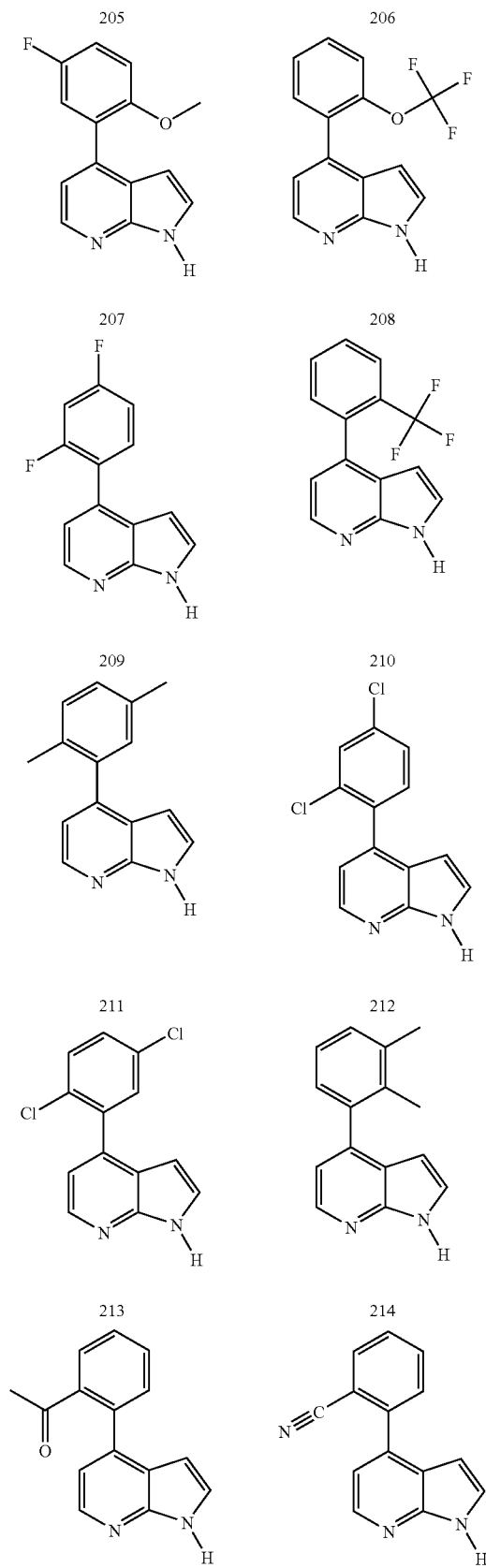
TABLE 2-continued
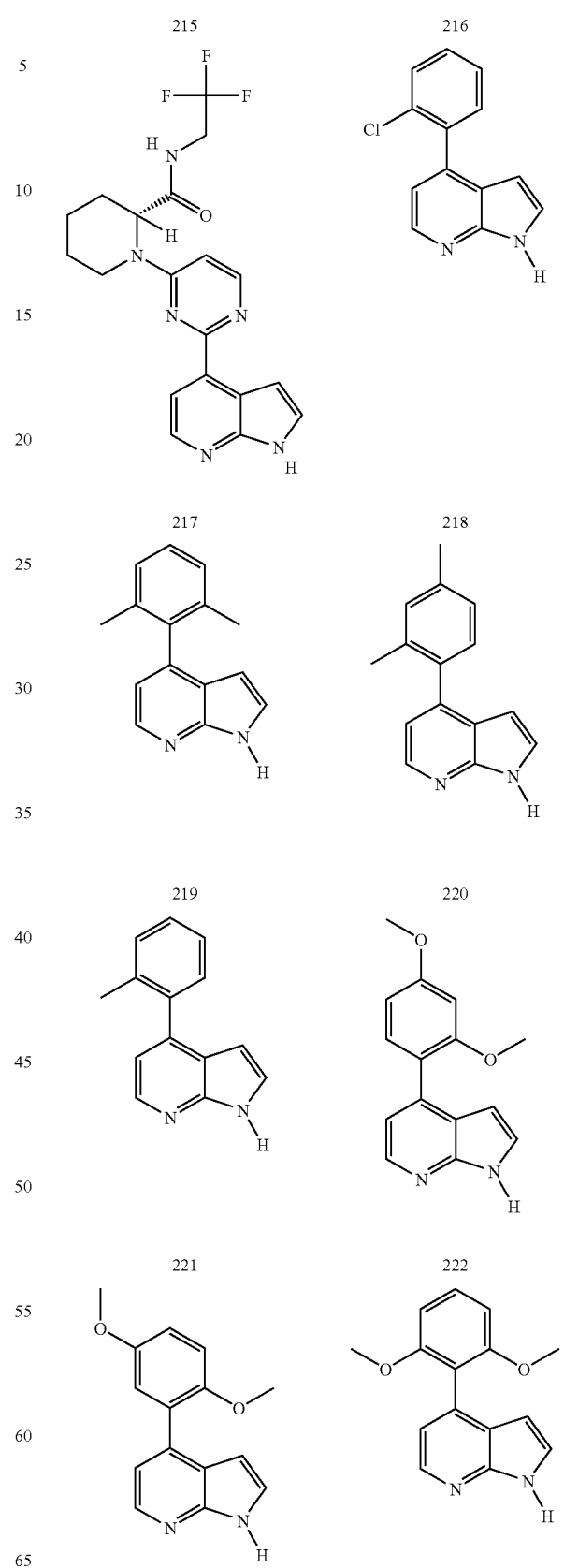

TABLE 2-continued
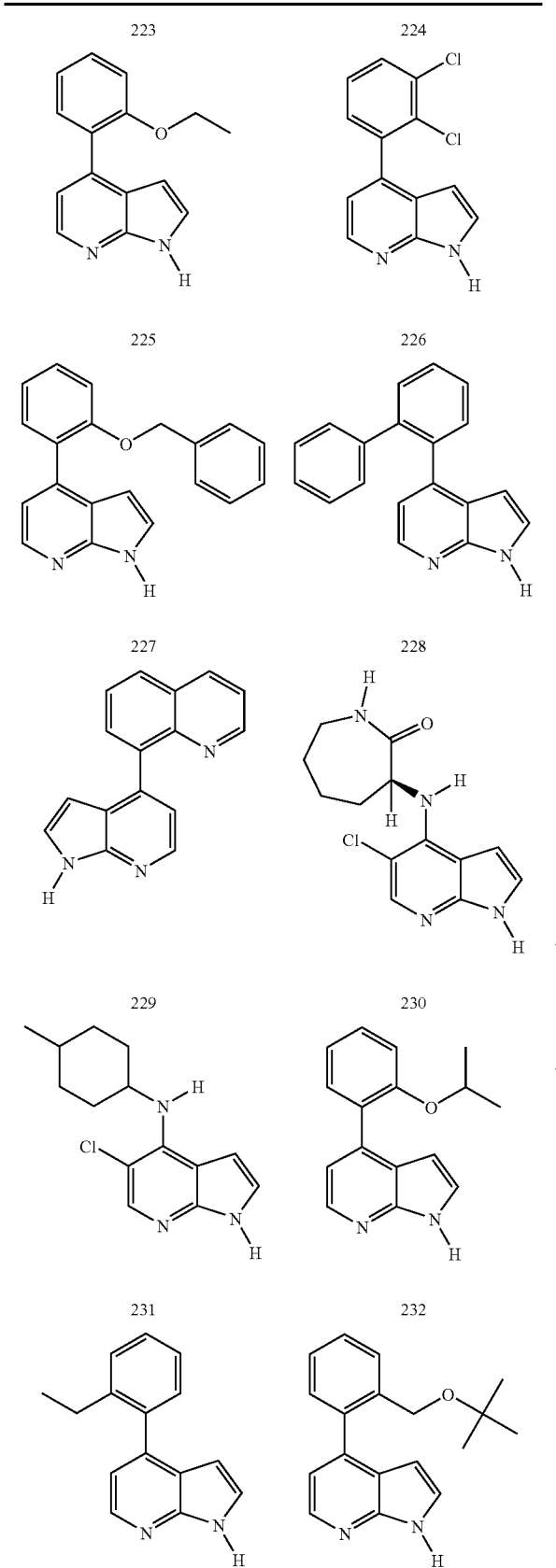
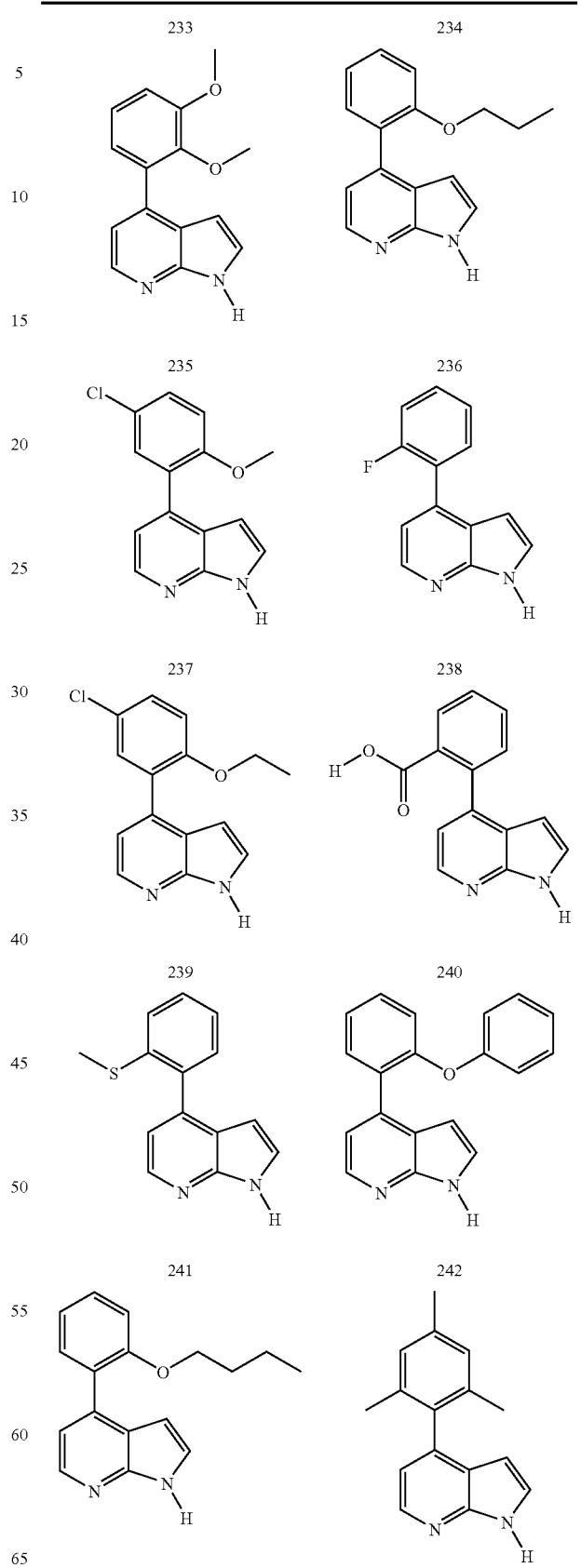

TABLE 2-continued
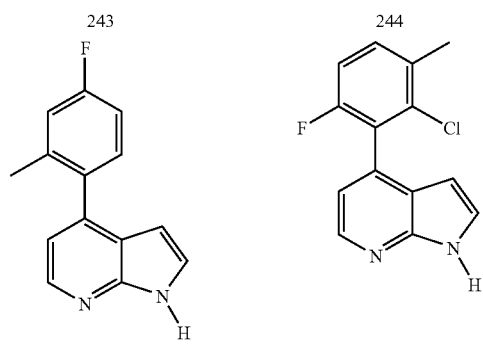
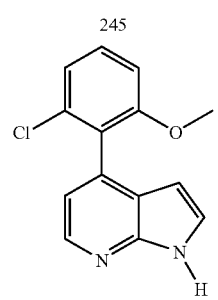
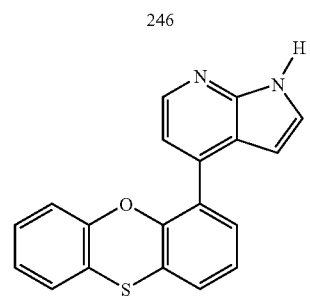
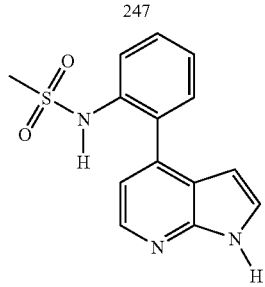
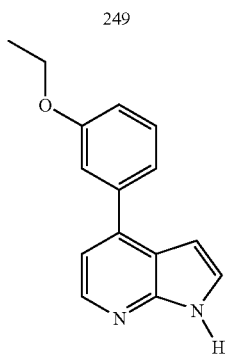
TABLE 2-continued
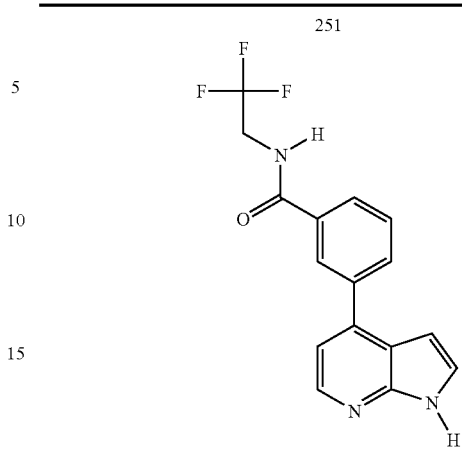
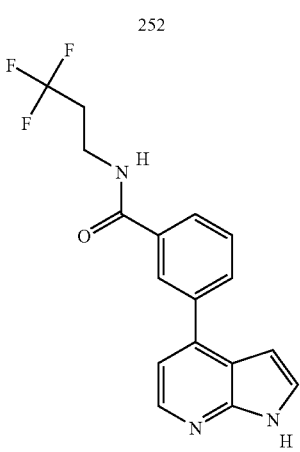
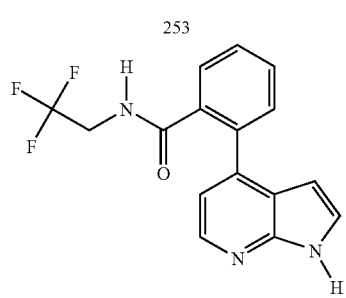
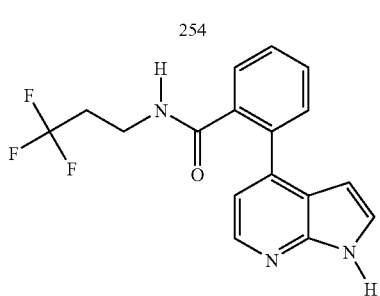

TABLE 2-continued
255 256
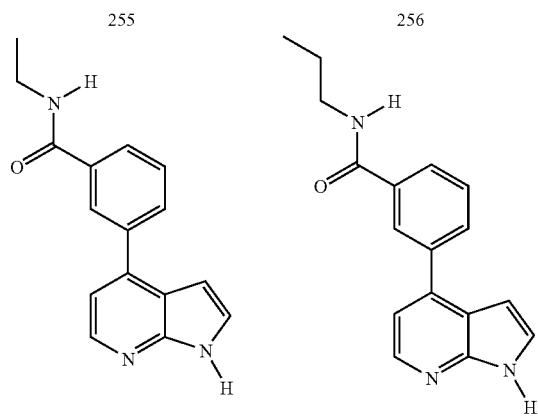
257
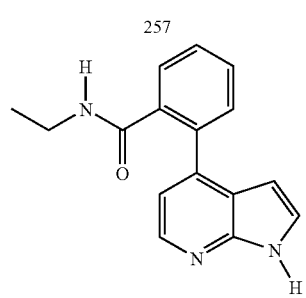
258
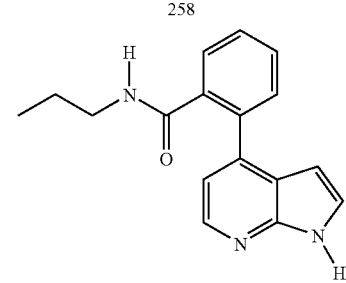
259 260
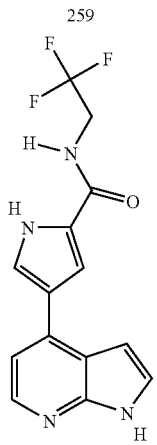
TABLE 2-continued
261 262
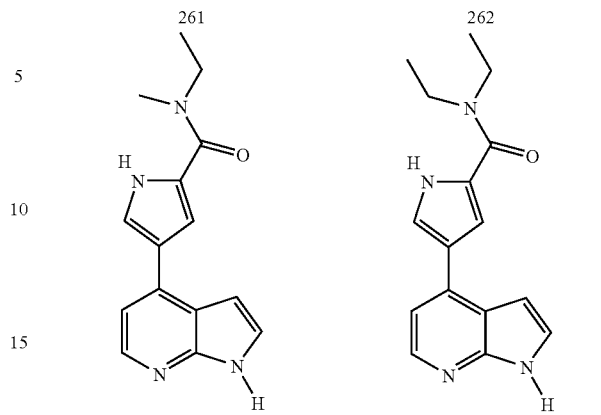
263 264
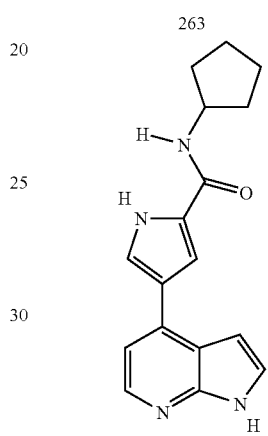
265
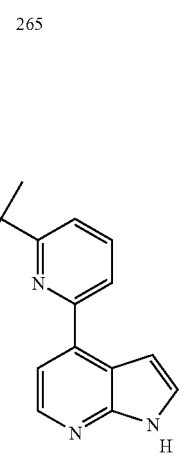
266
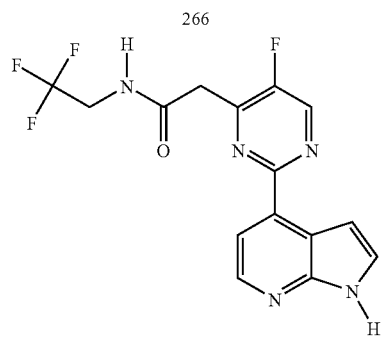

TABLE 2-continued
267 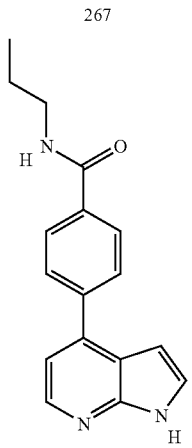
268 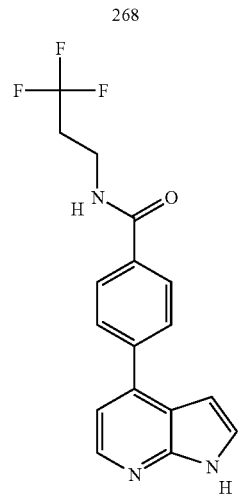
269 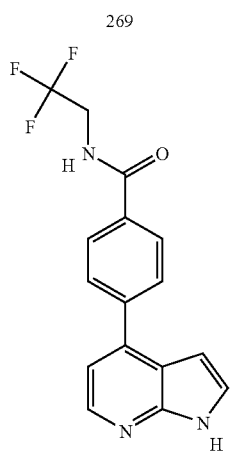
270 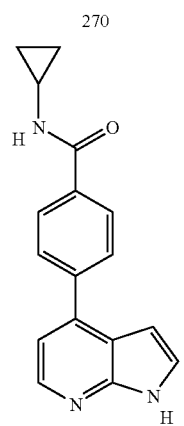
271 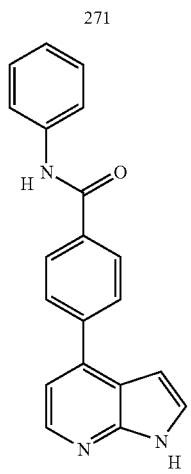
272 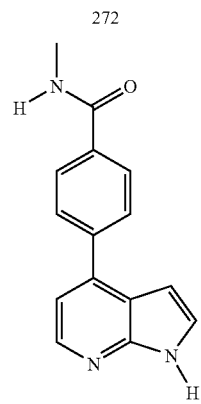
TABLE 2-continued
273 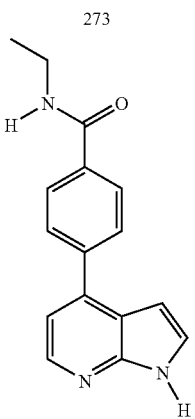
274 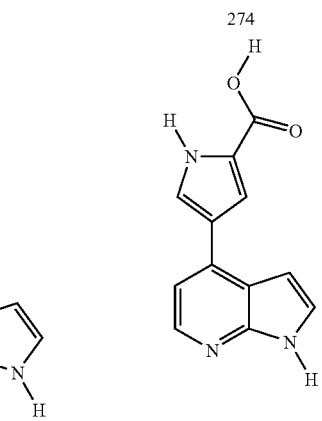
275 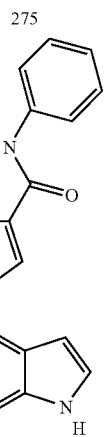
276 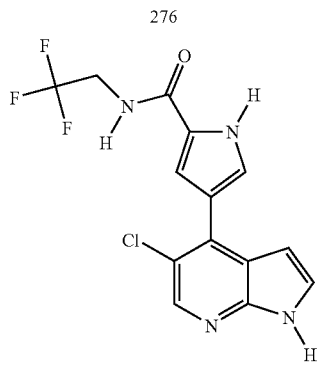
277 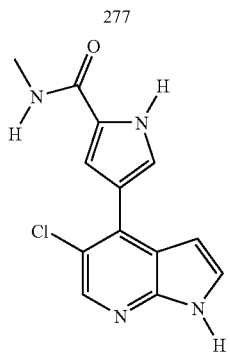
278 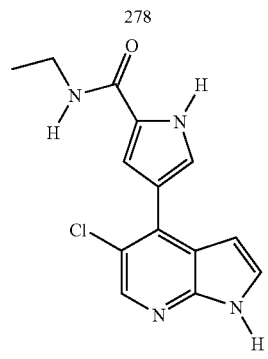

TABLE 2-continued
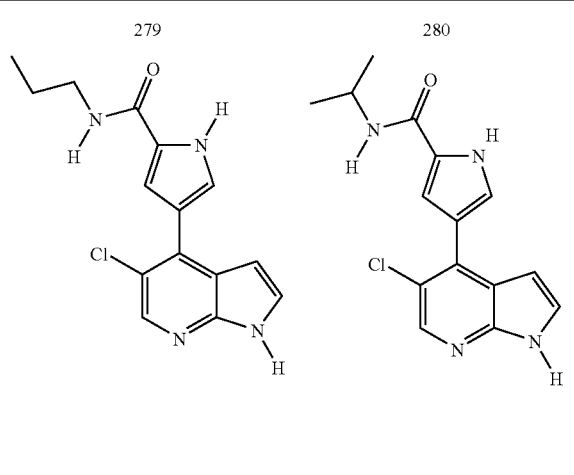
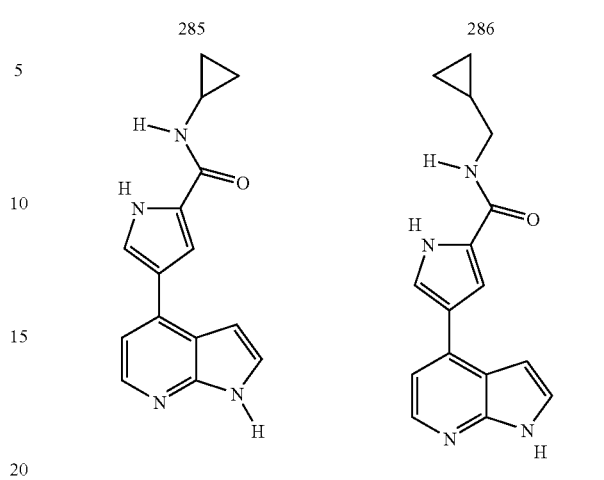
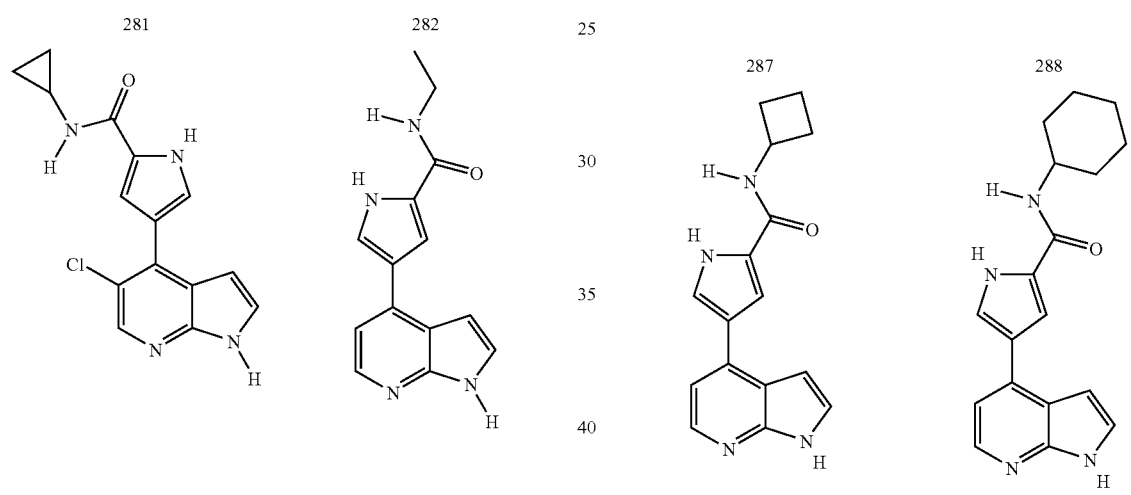
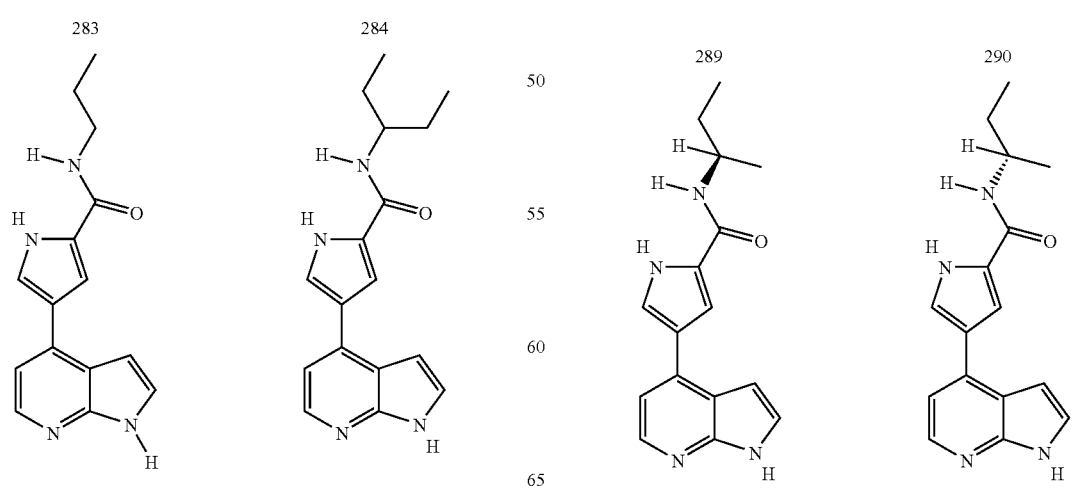

TABLE 2-continued
291 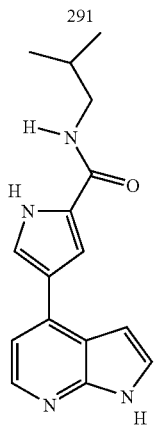
292 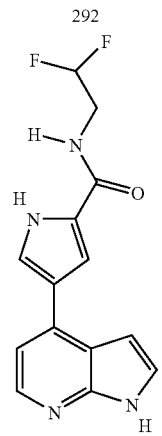
297 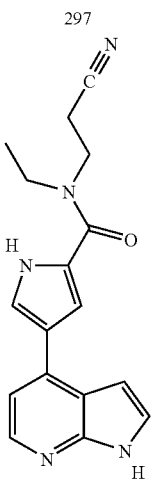
298 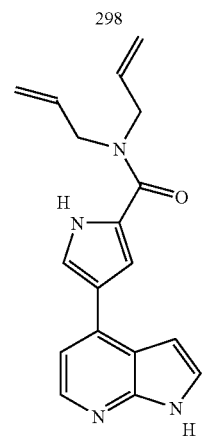
293 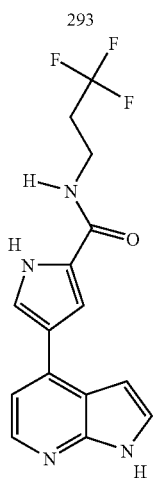
294 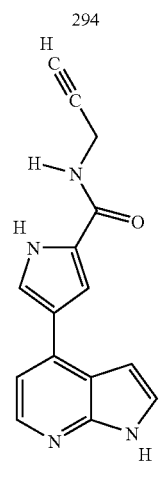
299 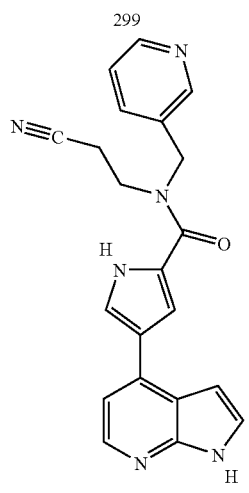
300 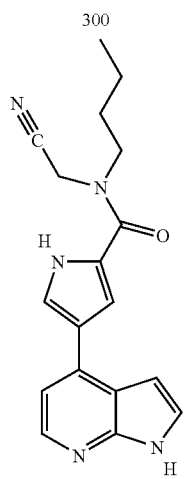
295 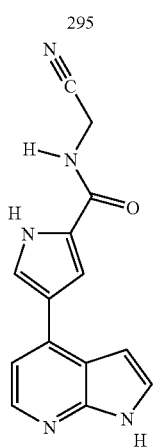
296 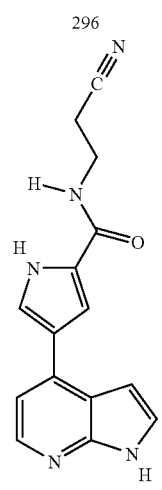
301 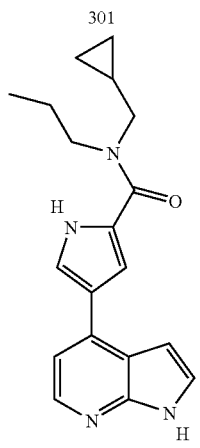
302 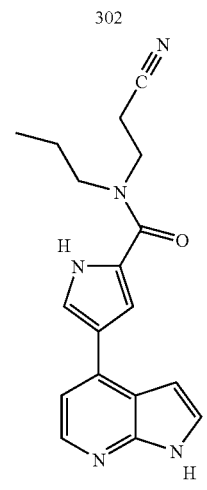

TABLE 2-continued
303
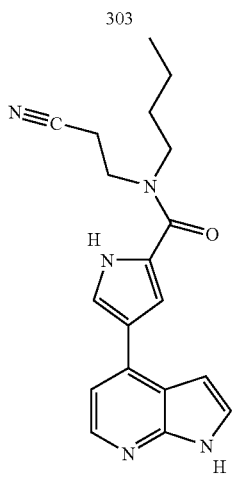
304
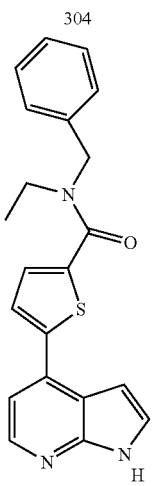
309
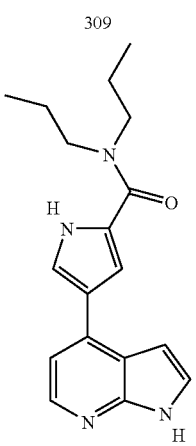
310
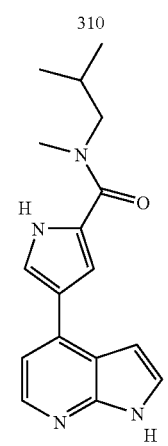
305
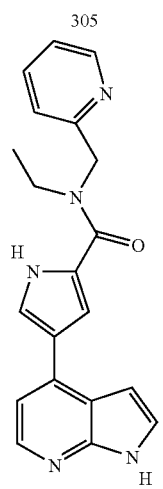
306
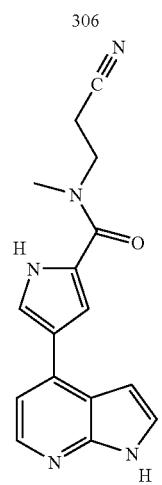
311
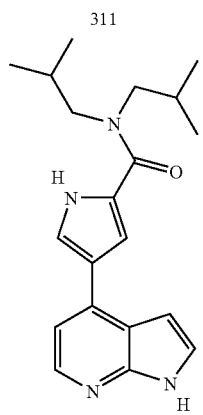
312
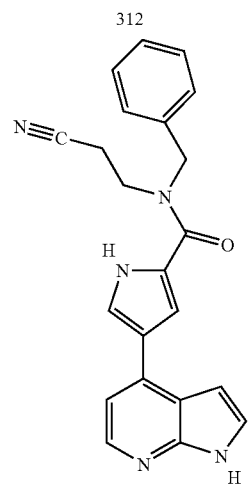
307
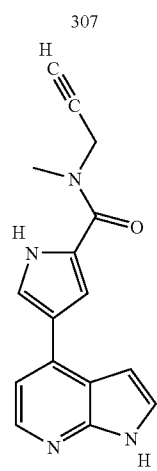
308
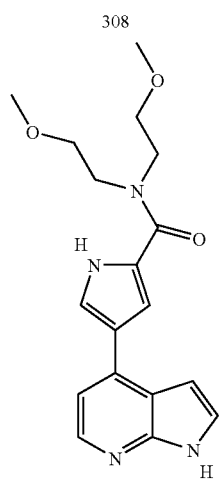
313
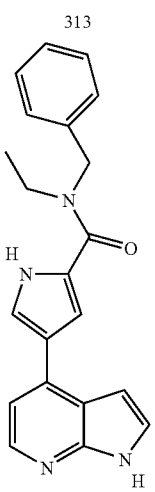
314
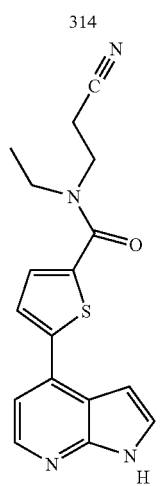

TABLE 2-continued
315
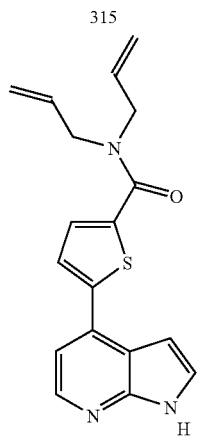
316
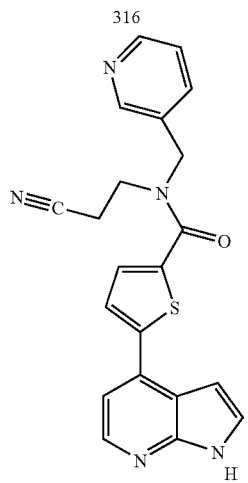
321
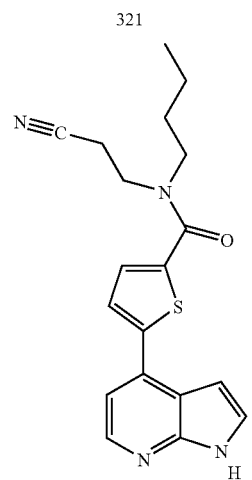
322
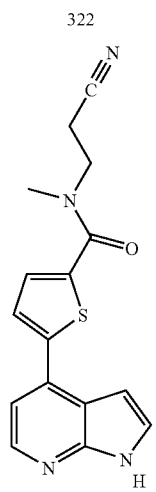
317
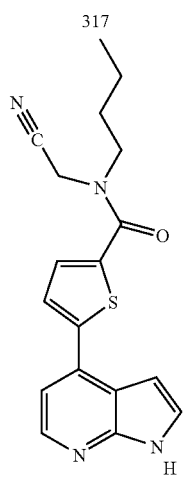
318
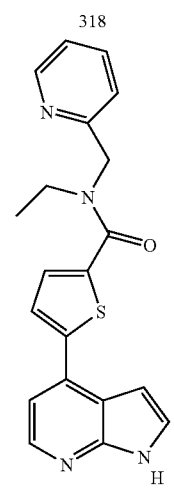
323
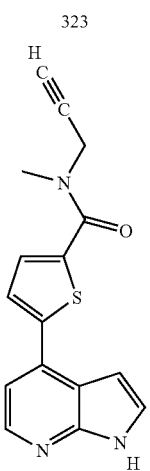
324
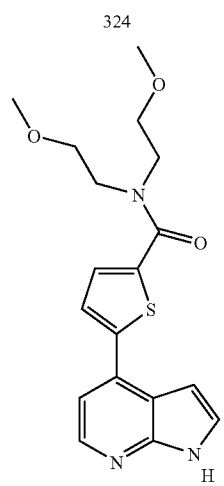
319
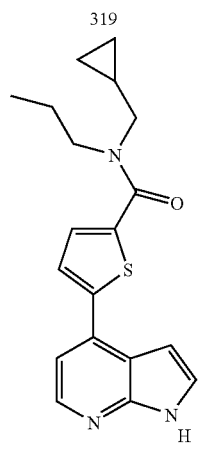
320
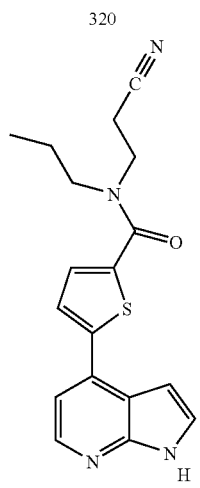
325
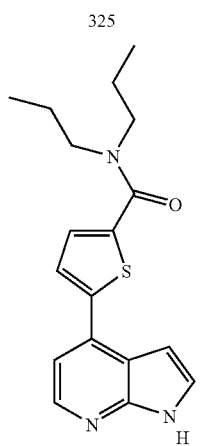
326
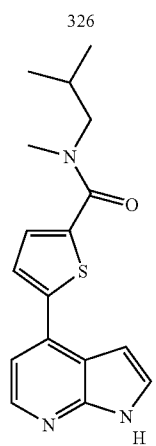

TABLE 2-continued
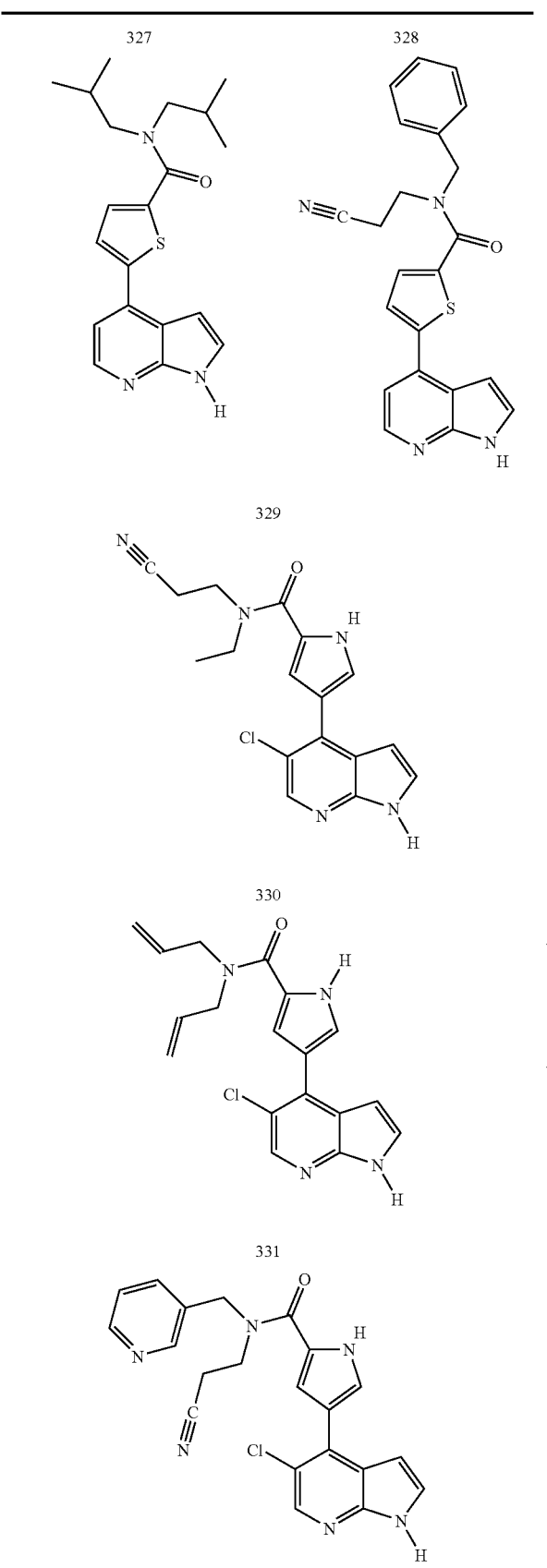
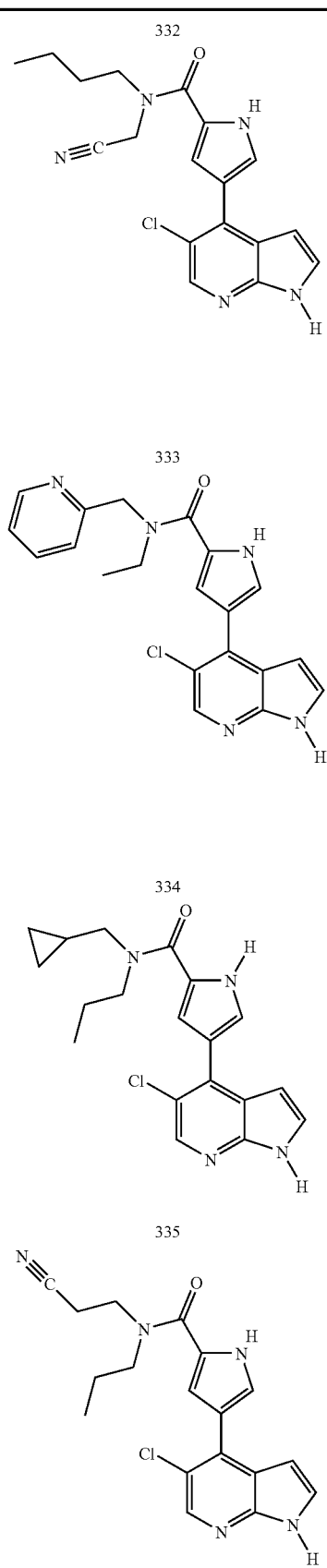

TABLE 2-continued
336
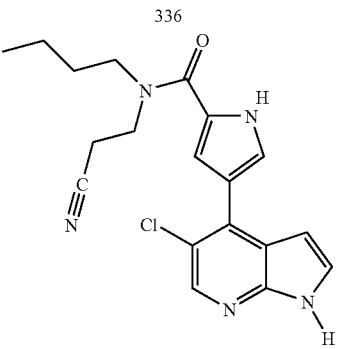
337
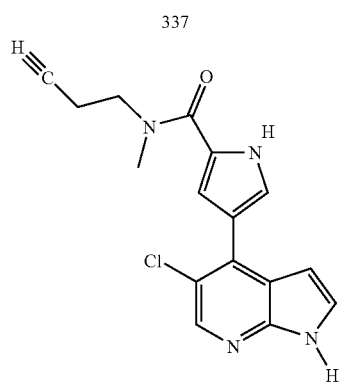
338
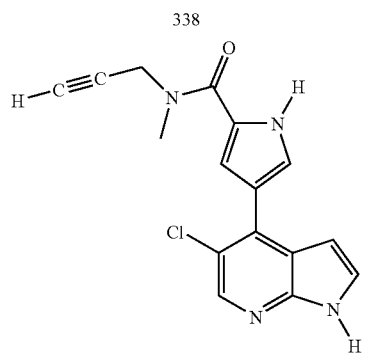
339
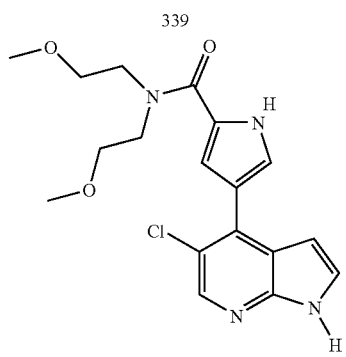
TABLE 2-continued
340
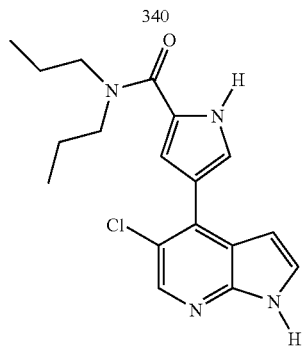
341
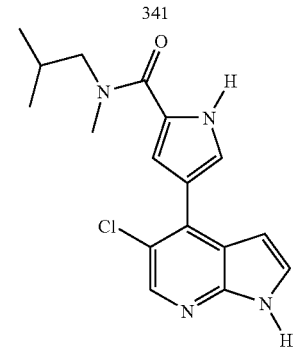
342
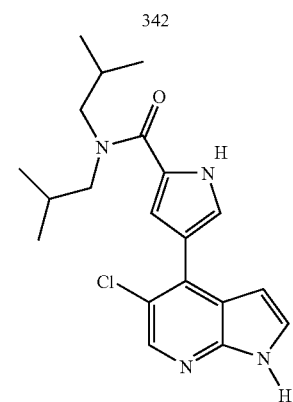
343
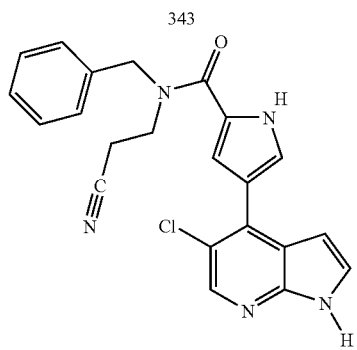

TABLE 2-continued
344
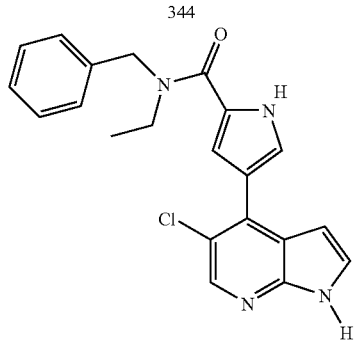
345
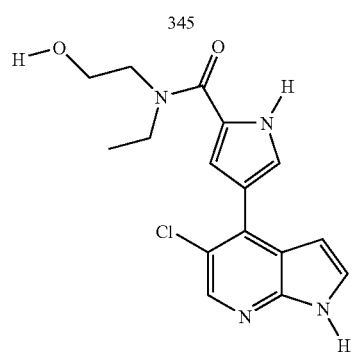
346
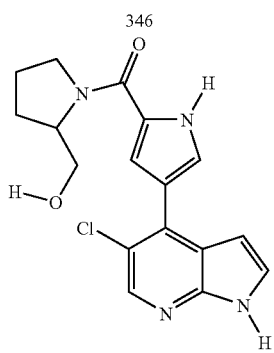
347
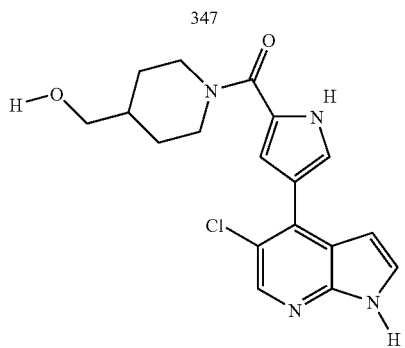
TABLE 2-continued
348
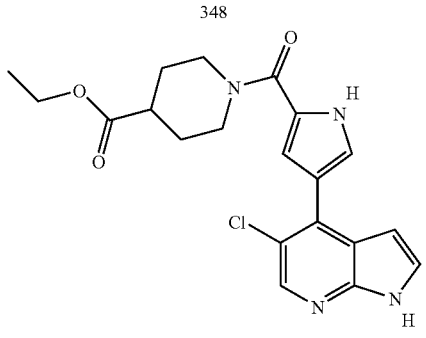
349
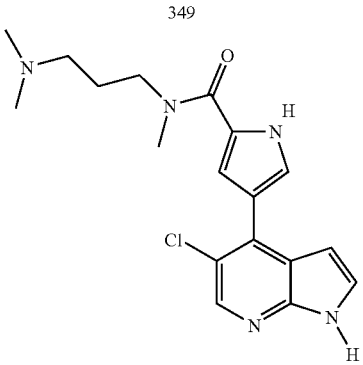
350
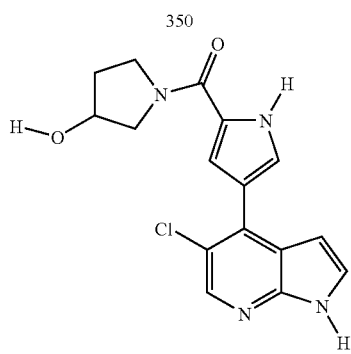
351
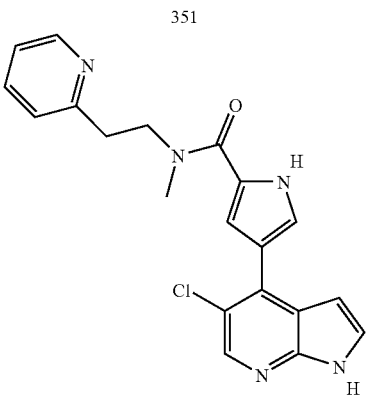

TABLE 2-continued
352
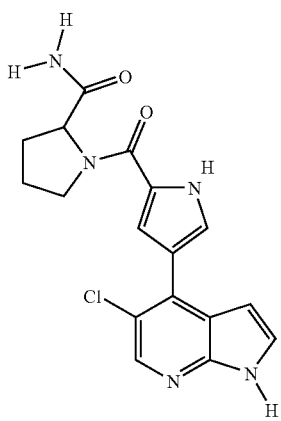
353
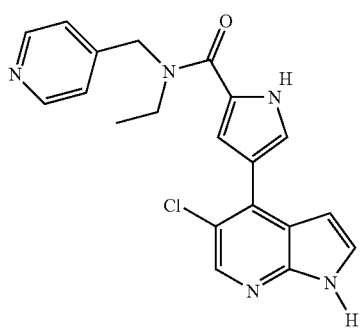
354
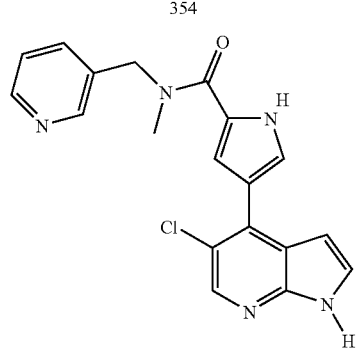
355
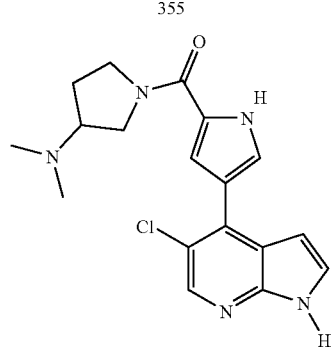
TABLE 2-continued
356
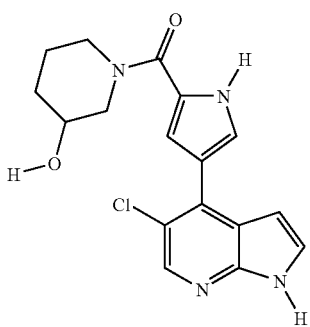 [SMILES: O=C(c1cc(-c2c(Cl)cnc3[nH]ccc23)c[nH]1)N1CCCC(O)C1]
357  358
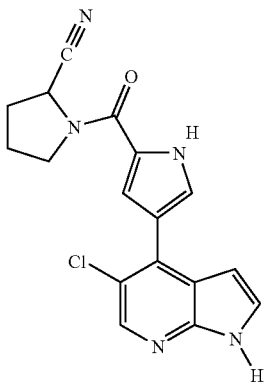 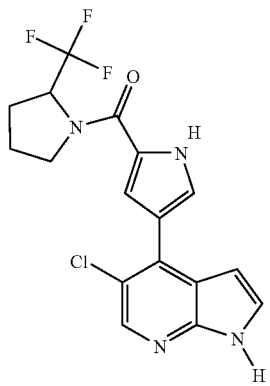
359
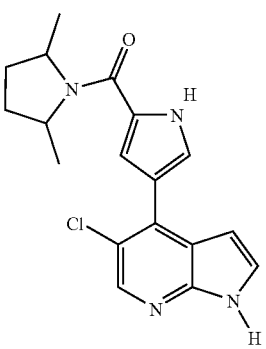
360
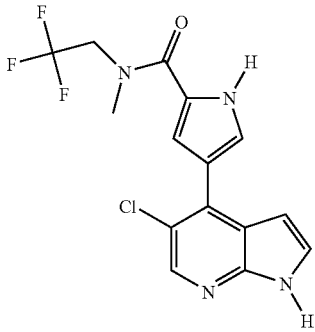 [SMILES: CN(CC(F)(F)F)C(=O)c1cc(-c2c(Cl)cnc3[nH]ccc23)c[nH]1]

TABLE 2-continued
361
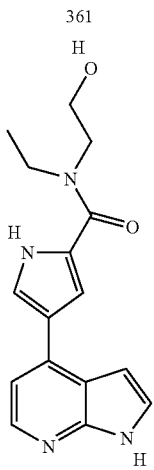
362
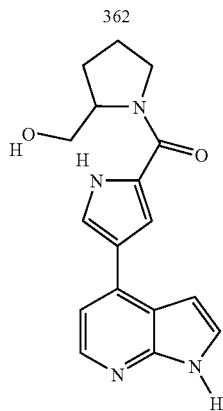
363
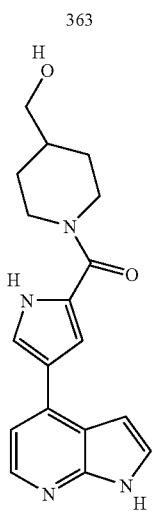
364
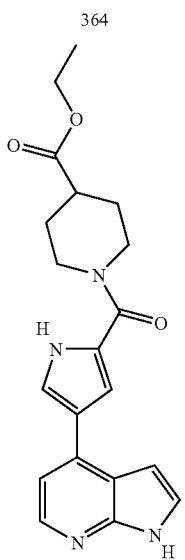
365
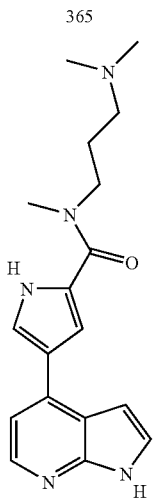
366
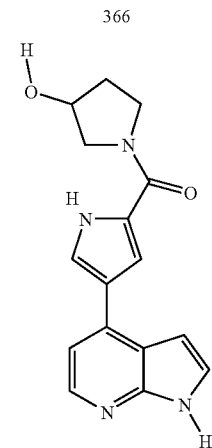
TABLE 2-continued
367
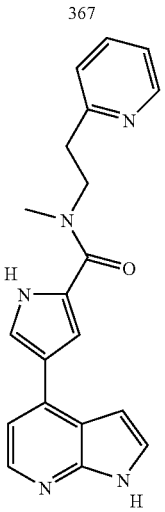
368
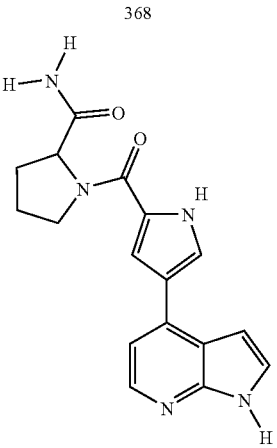
369
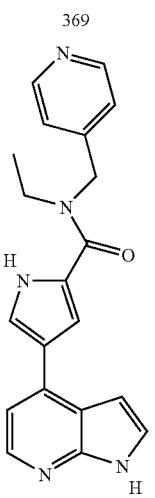
370
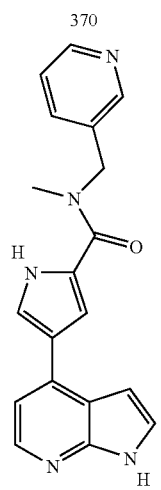
371
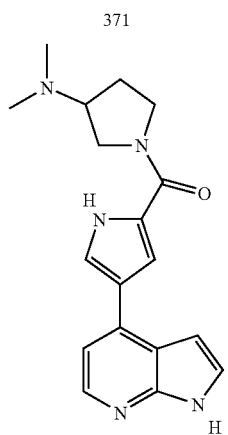
372
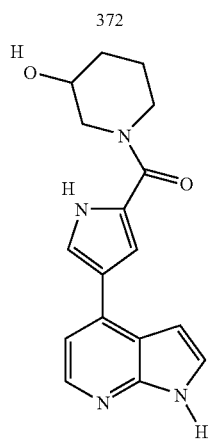

TABLE 2-continued
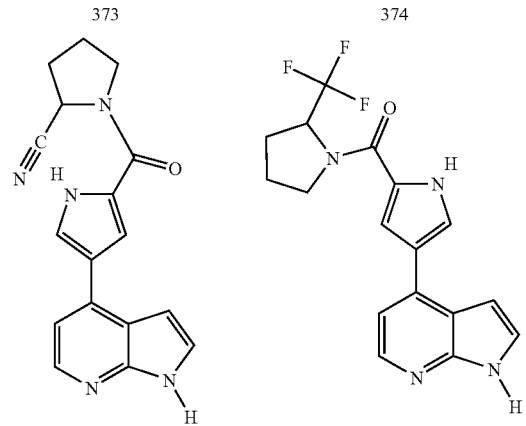
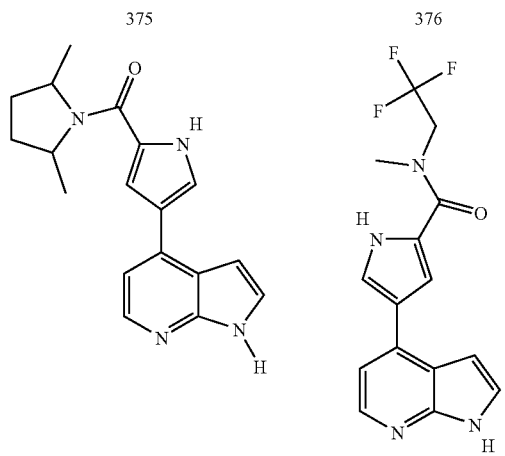
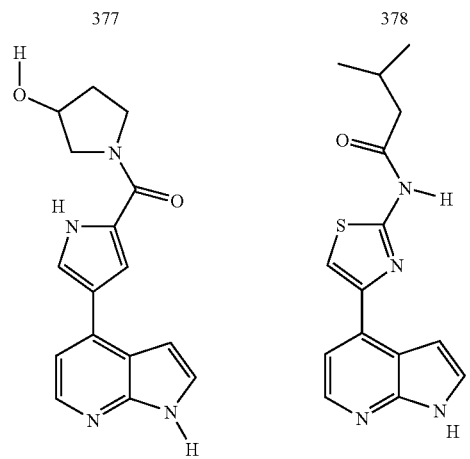
TABLE 2-continued
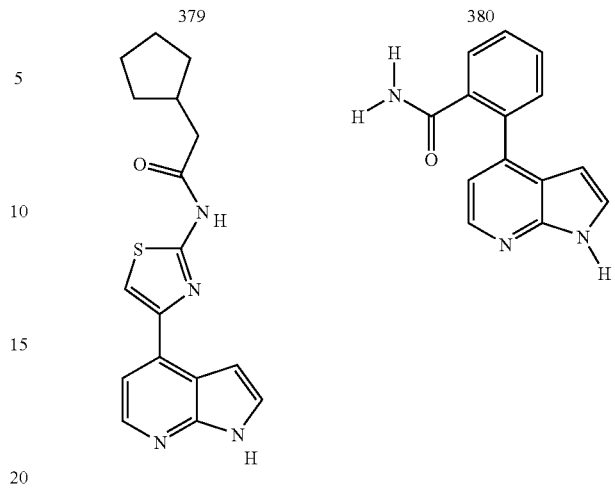
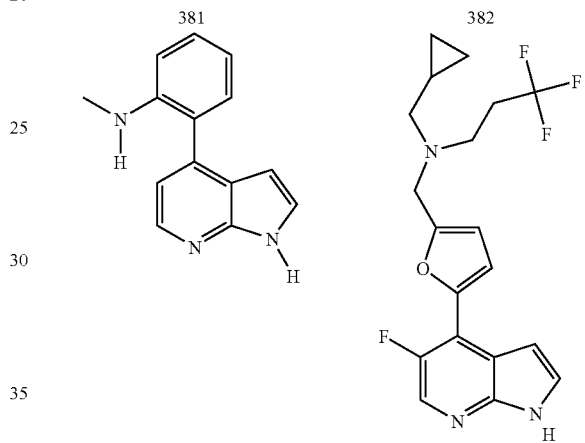
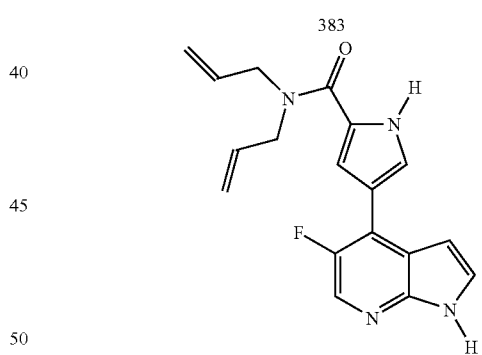
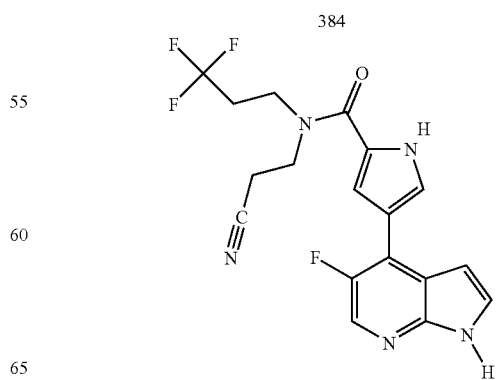

TABLE 2-continued
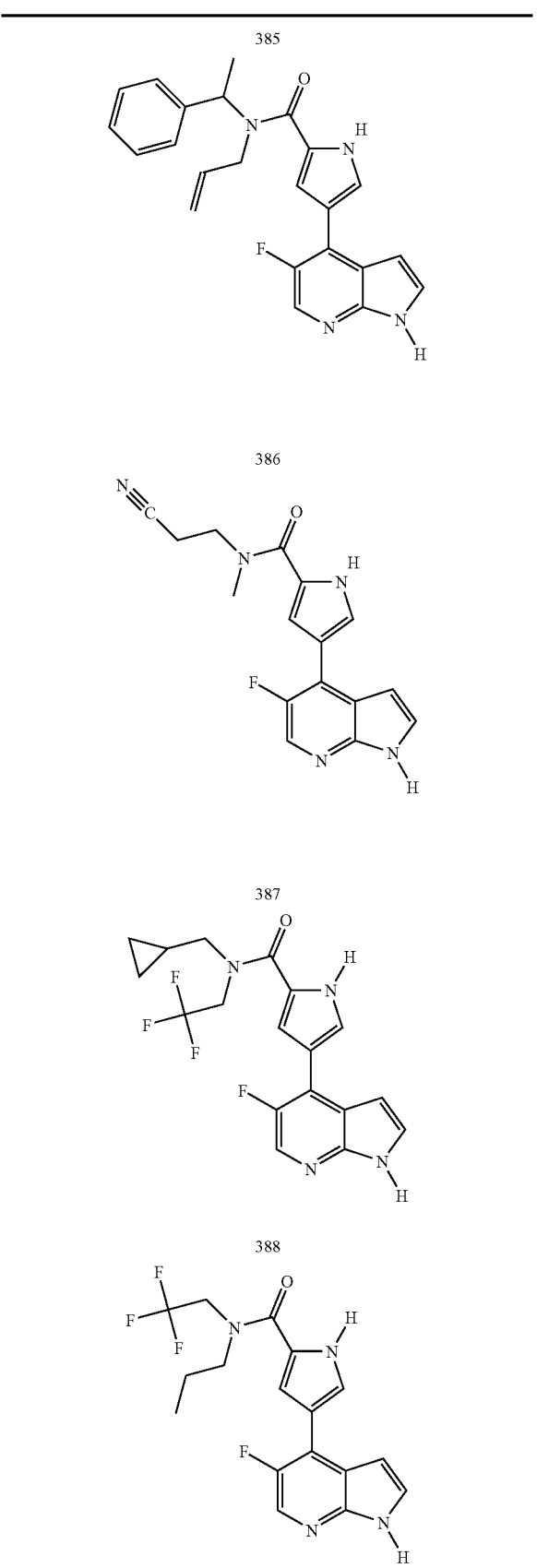
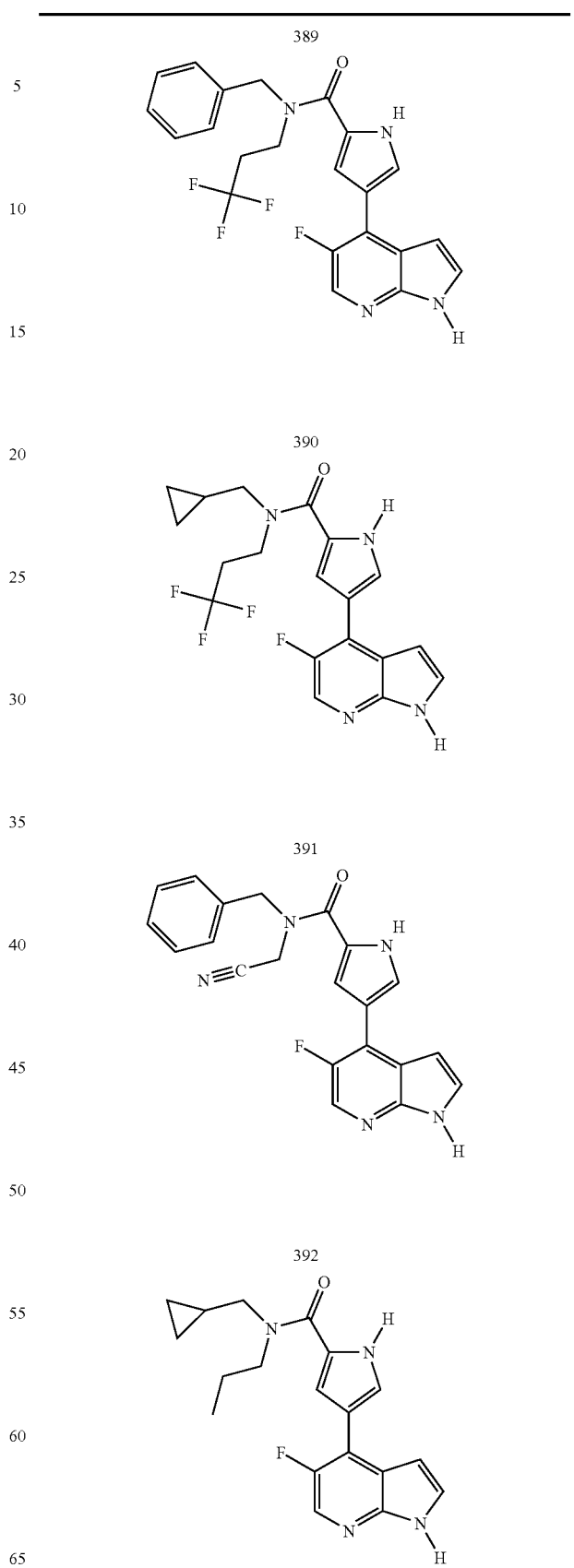

TABLE 2-continued
393
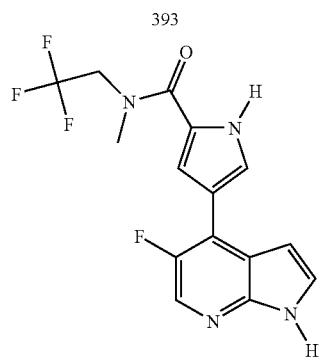
394
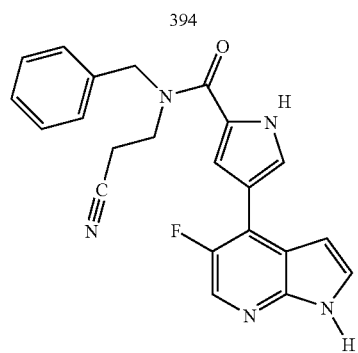
395
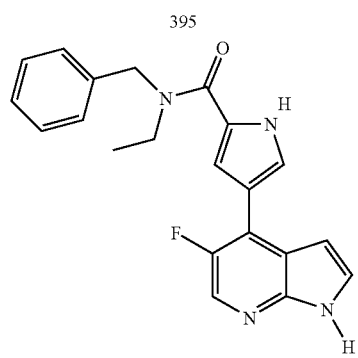
396
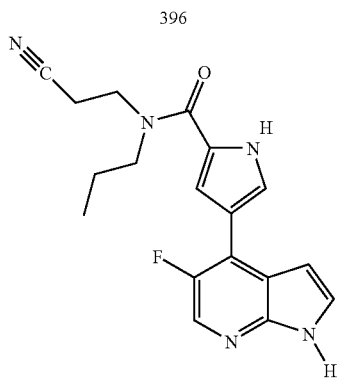
TABLE 2-continued
397
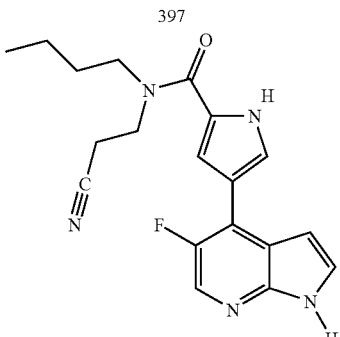
398
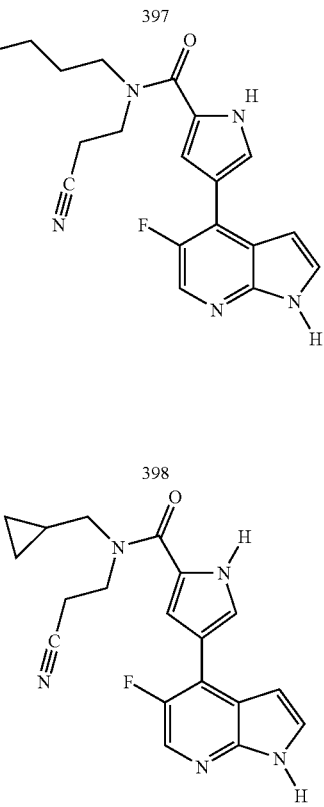
399
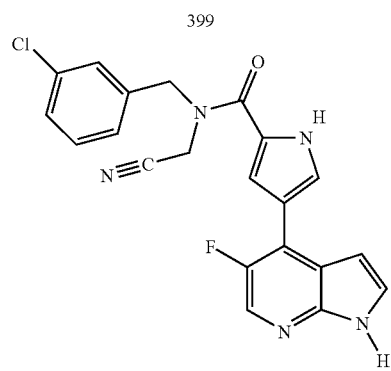
400
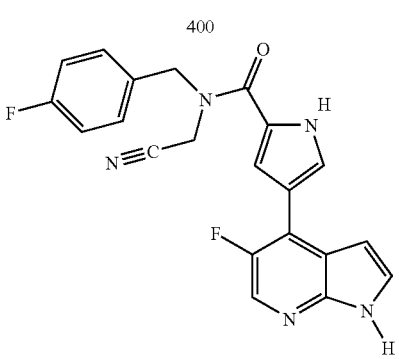

TABLE 2-continued
401 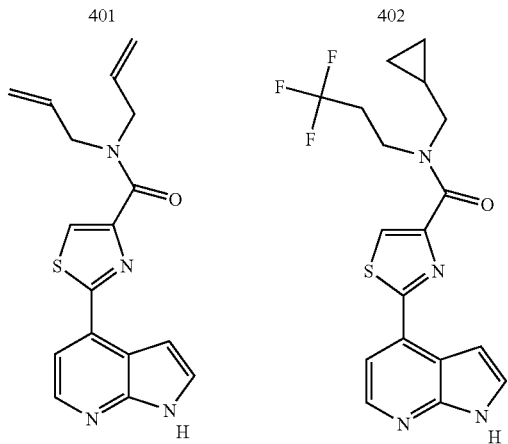
402 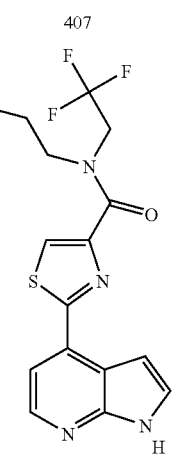
407 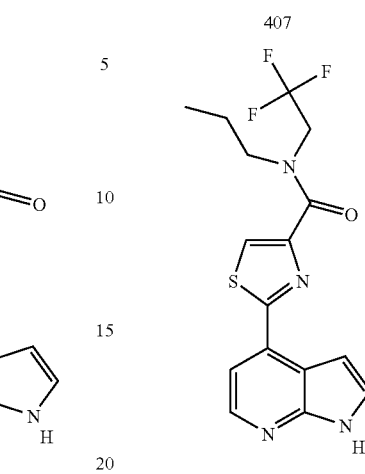
408 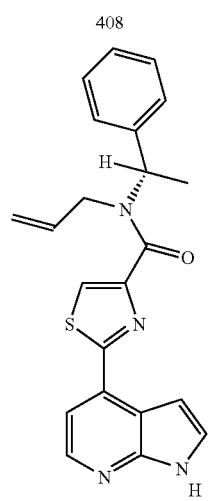
403 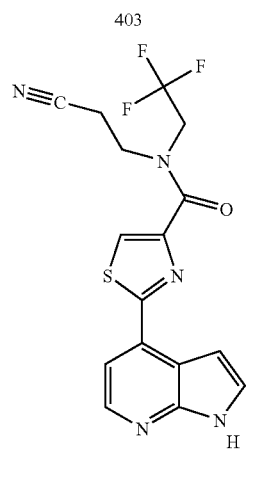
404 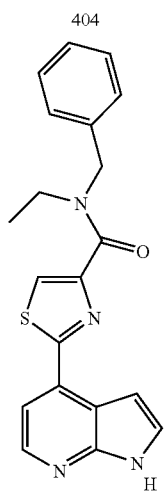
409 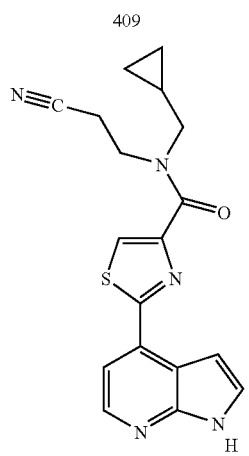
410 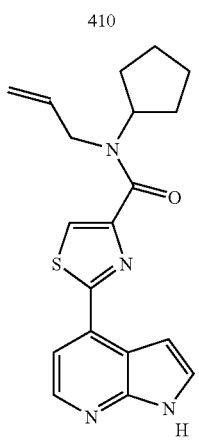
405 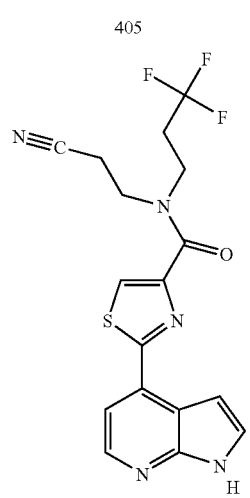
406 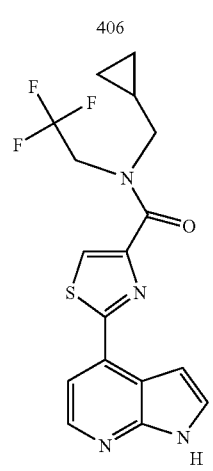
411 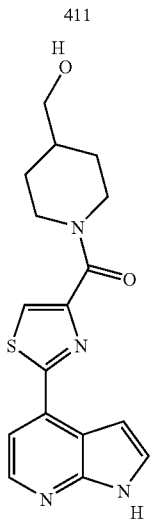
412 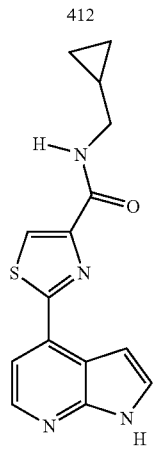

TABLE 2-continued
413 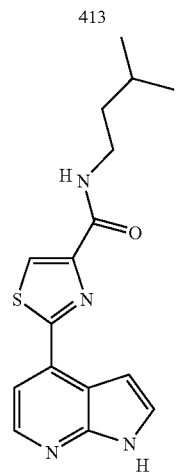
414 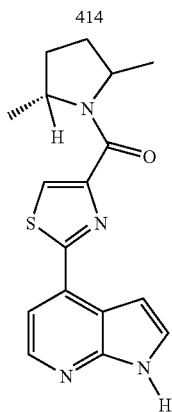
415 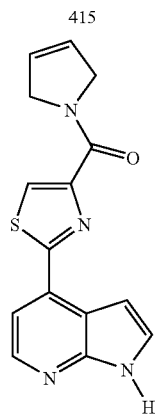
416 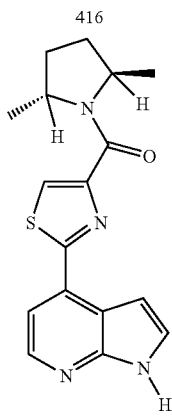
417 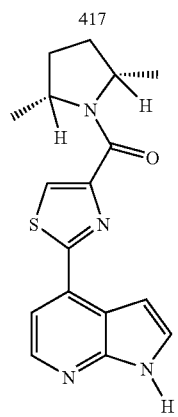
418 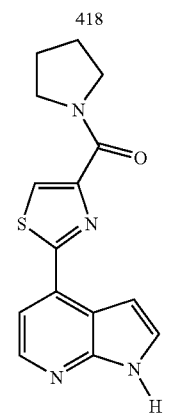
TABLE 2-continued
419 420 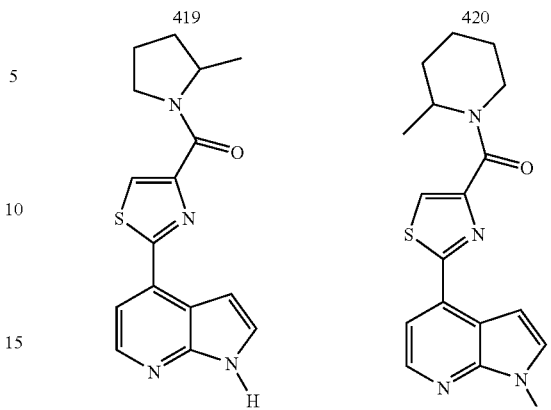
421 422 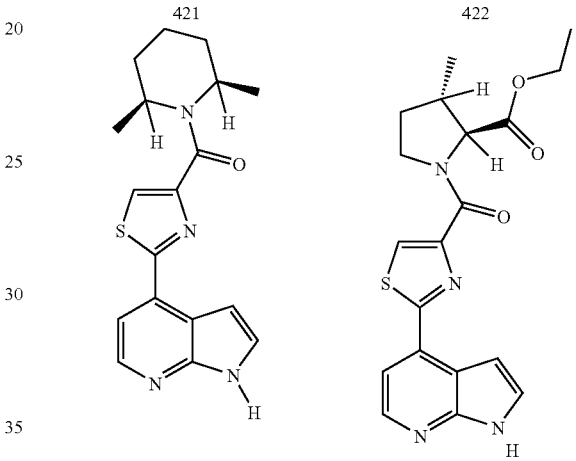
423
424 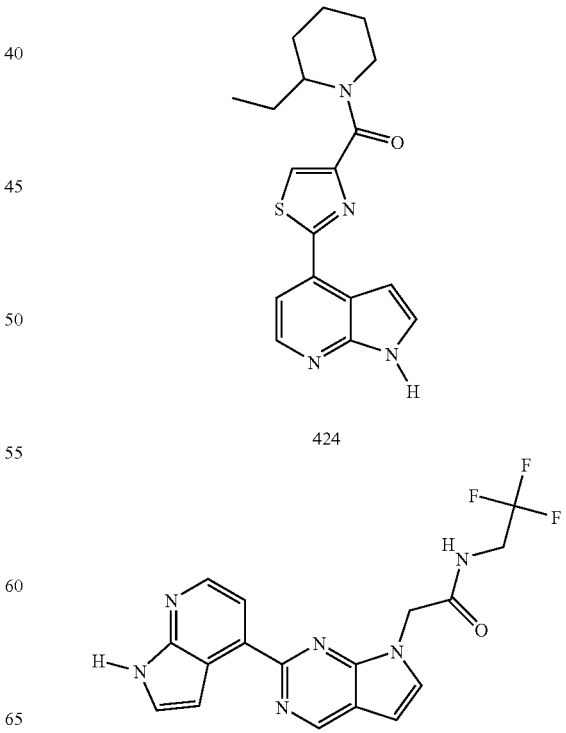

TABLE 2-continued

425

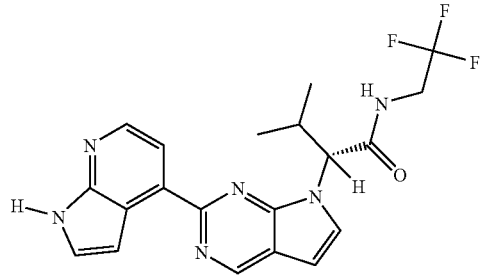

426

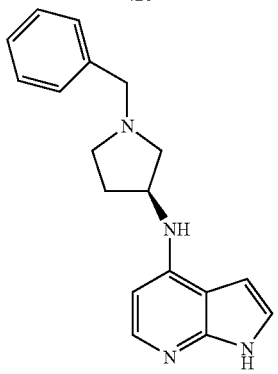

Uses, Formulation and Administration
Pharmaceutically Acceptable Compositions

In another embodiment, the invention provides A pharmaceutical composition comprising a compound of formula I

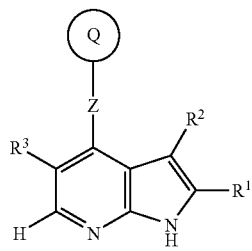

or a pharmaceutically acceptable salt thereof
wherein
Q is a 3-8 membered saturated, partially saturated, or unsaturated monocyclic ring having 0-3 heteroatoms selected from nitrogen, oxygen, or sulfur; or an 8-12 membered bicyclic ring having 0-6 heteroatoms selected from nitrogen, oxygen, or sulfur; wherein Q is optionally substituted with 1-10 occurrences of $J^Q$;

Z is a bond, O, NH, N($C_{1-3}$aliphatic), S, $CH_2$, C=$CH_2$, C=O, SO or $SO_2$;

$R^1$ is —($C_{1-2}$ aliphatic)$_p$-$R^4$ wherein each $R^1$ is optionally substituted with 1-3 occurrences of J;

$R^2$ is —($C_{1-2}$ aliphatic)$_d$-$R^5$ wherein each $R^1$ is optionally substituted with 1-3 occurrences of J;

$R^3$ is halogen, —CN, —$NO_2$ or —(U)$_m$—X, wherein
  U is a $C_{1-6}$ aliphatic, wherein up to two methylene units are optionally and independently replaced by $G^U$ and wherein U is optionally substituted with 1-4 $J^U$;
  X is H, halogen, CN, $NO_2$, S(O)R, $SO_2$R, $C_{1-4}$ haloaliphatic, or a group selected from $C_{1-6}$ aliphatic, a $C_{3-10}$ cycloaliphatic, $C_{6-10}$ aryl, 5-10 membered heteroaryl, 5-10 membered heterocyclyl; wherein said group is optionally substituted with 1-4 $J^X$;

$G^U$ is —NH—, —NR—, —O—, —S—, —$CO_2$—, —OC(O)—, —C(O)CO—, —C(O)—, —C(O)NH—, —C(O)NR—, —C(=N—CN)—, —NHCO—, —NRCO—, —NHC(O)O—, —NRC(O)O—, —$SO_2$NH—, —$SO_2$NR—, —$NHSO_2$—, —$NRSO_2$—, —NHC(O)NH—, —NRC(O)NH—, —NHC(O)NR—, —NRC(O)NR, —OC(O)NH—, —OC(O)NR—, —$NHSO_2$NH—, —$NRSO_2$NH—, —$NHSO_2$NR—, —$NRSO_2$NR—, —SO—, or —$SO_2$—;

$R^4$ is H, halogen, CN, $NH_2$, $NO_2$, $CF_3$, $C_{1-3}$ aliphatic, cyclopropyl, $NCH_3$, $OCH_3$, —C(=O)$NH_2$, —C(=O)$CH_3$, —NC(=O)$CH_3$, or OH;

$R^5$ is H, halogen, CN, $NH_2$, $NO_2$, $CF_3$, $C_{1-3}$ aliphatic, cyclopropyl, $NCH_3$, $OCH_3$, —C(=O)$NH_2$, —C(=O)$CH_3$, —NC(=O)$CH_3$, or OH;

$J^Q$ is halogen, $OCF_3$, —($V_n$)—R", —($V_n$)—CN, —($V_n$)—$NO_2$, or —($V_n$)—($C_{1-4}$haloaliphatic), wherein $J^Q$ is not H;

V is a $C_{10}$ aliphatic, wherein up to three methylene units are replaced by $G^V$, wherein $G^V$ is selected from —NH—, —NR—, —O—, —S—, —$CO_2$—, —OC(O)—, —C(O)CO—, —C(O)—, —C(O)NH—, —C(O)NR—, —C(=N—CN), —NHCO—, —NRCO—, —NHC(O)O—, —NRC(O)O—, —$SO_2$NH—, —$SO_2$NR—, —$NHSO_2$—, —$NRSO_2$—, —NHC(O)NH—, —NRC(O)NH—, —NHC(O)NR—, —NRC(O)NR, —OC(O)NH—, —OC(O)NR—, —$NHSO_2$NH—, —$NRSO_2$NH—, —$NHSO_2$NR—, —$NRSO_2$NR—, —SO—, or —$SO_2$—; and wherein V is optionally substituted with 1-6 occurrences of $J^V$;

R" is H, or is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R" groups, on the same substituent or different substituents, together with the atom(s) to which each R" group is bound, form an optionally substituted 3-8 membered heterocyclyl; wherein each optionally substituted R" group is independently and optionally substituted with 1-6 occurrences of JR;

R is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of JR;

$J^V$, $J^U$, $J^X$, and $J^R$ are each independently selected from halogen, L, -($L_n$)-R, -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-$NO_2$, -($L_n$)-CN, -($L_n$)-OH, -($L_n$)-$CF_3$, —$CO_2$R', —$CO_2$H, —COR', —COH, —OC(O)R', or —NC(O)R'; or two $J^V$, $J^U$, $J^X$, or $J^R$ groups, on the same substituent or different substituents, together with the atom(s) to which each $J^V$, $J^U$, $J^X$, and $J^R$ group is bound, form a 5-7 membered saturated, unsaturated, or partially saturated ring;

R' is H or $C_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —$NO_2$, —$CF_3$, —CN, —$CO_2$R*, —COR*, OCOR*, NHCOR*, wherein R* is H or $C_{1-6}$ aliphatic;

L is a $C_{1-6}$ aliphatic wherein up to three methylene units are replaced by —NH—, $NR^6$, —O—, —S—, —$CO_2$—, —OC(O)—, —C(O)CO—, —C(O)—, —C(O)NH—, —C(O)$NR^6$—, —C(=N—CN), —NHCO—, —$NR^6$CO—, —NHC(O)O—, —$NR^6$C(O)O—, —$SO_2$NH—, —$SO_2NR^6$—, —$NHSO_2$—, —$NR^6SO_2$—, —NHC(O)NH—, —$NR^6$C(O)NH—, —NHC(O)$NR^6$—, —$NR^6$C(O)$NR^6$, —OC(O)NH—, —OC(O)$NR^6$—, —$NHSO_2$NH—, —$NR^6SO_2$NH—, —$NHSO_2NR^6$—, —$NR^6SO_2NR^6$—, —SO—, or —$SO_2$—;

$R^6$ is selected from $C_{1-6}$ aliphatic, $C_{3-10}$ cycloaliphatic, $C_{6-10}$ aryl, 5-10 membered heteroaryl, or 5-10 membered heterocyclyl; or two $R^6$ groups, on the same substituent or different substituents, together with the atom(s) to which each $R^6$ group is bound, form a 3-8 membered heterocyclyl;

J is halogen, $OCH_3$, OH, $NO_2$, $NH_2$, $SCH_3$, $NCH_3$, CN, unsubstituted $C_{1-2}$ aliphatic; two J's, together with the carbon to which they are attached, form a cyclopropyl ring or C=O;

m, n, d, and p are each independently 0 or 1;

wherein when $R^1$ and $R^2$ are H, $R^3$ is C(=O)$NH_2$ and Z is NH, then Q is not 2-ethylphenyl;

and a pharmaceutically acceptable carrier, adjuvant, or vehicle.

In a further embodiment, the composition does not comprise a compound wherein when $R^1$, $R^2$, and $R^3$ are H and Z is a bond, then Q is not

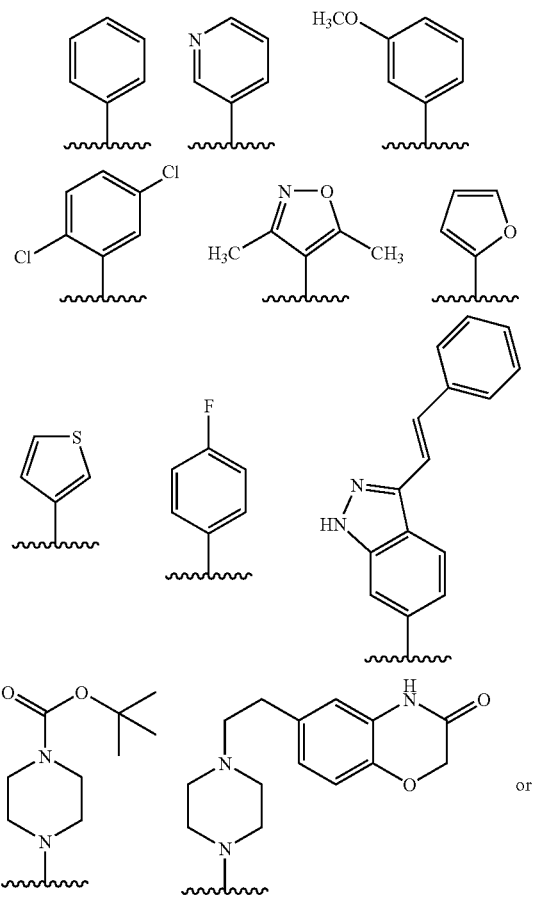

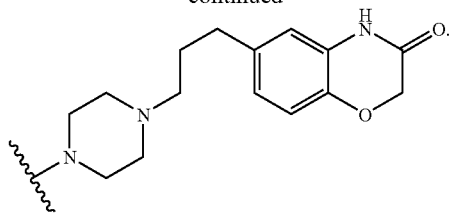

In a further embodiment, the composition does not comprise a compound wherein when $R^1$, $R^2$, and $R^3$ are H and Z is O; then Q is not 3,4-diaminophenyl, 4-benzyloxyphenyl, 3-amino-4-hydroxyphenyl, 4-hydroxyphenyl, 2-fluoro-4-aminophenyl, 3-fluoro-4-aminophenyl, 2,6-difluoro-4-aminophenyl, 4-nitrophenyl, 4-aminophenyl; an optionally substituted group selected from

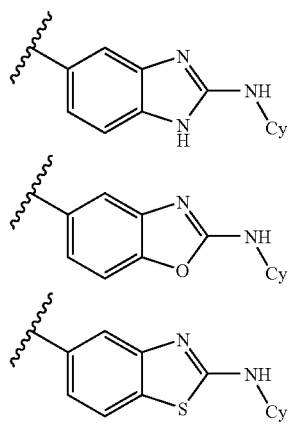

wherein Cy is an optionally substituted group selected from phenyl or piperidine; or a compound of formula X

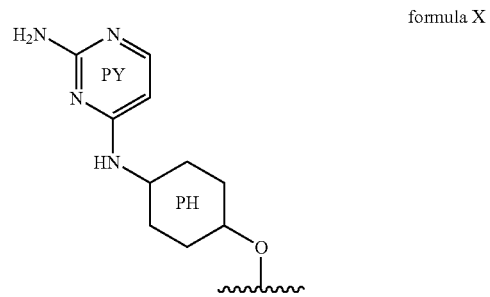

formula X wherein PY is an optionally substituted aminopyrimidine group and PH is phenyl mono- or disubstituted with fluoro.

In a further embodiment, the composition does not comprise a compound wherein when $R^1$ and $R^3$ are H, $R^2$ is methyl and Z is O, then Q is not 2-fluoro-4-aminophenyl.

In a further embodiment, the composition does not comprise a compound wherein when $R^1$, $R^2$, and $R^3$ are H and Z is $NCH_3$; then Q is not unsubstituted phenyl.

In a further embodiment, the composition additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly a JAK family or ROCK family kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof. As used herein, the term "inhibitory active metabolite or residue thereof" means that a metabolite or residue thereof is also an inhibitor of a JAK family or ROCK family kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly JAK family or ROCK family activity, between a sample comprising a compound of this invention and a JAK or ROCK kinase and an equivalent sample comprising JAK or ROCK kinase, respectively, in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Exelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In another embodiment, the invention comprises a method of inhibiting ROCK kinase activity in a biological sample, comprising contacting said biological sample with a compound or a composition of the invention.

In another embodiment, the invention comprises a method of inhibiting ROCK kinase activity in a patient, comprising administering to said patient a compound or a composition of the invention.

In another embodiment, the invention comprises a method of treating or lessening the severity of a ROCK kinase-mediated condition or disease in a patient. The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, preterm labor, cancer, erectile dysfunction, atherosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction. In another embodiment, the present invention relates to a method for treating or lessening the severity of benign prostatic hyperplasia or diabetes.

In another embodiment, the invention comprises a method of treating or lessening the severity of a disease, condition or disorder is selected from a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder, comprising the step of administering to said patient a compound or a composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an anti-psychotic agent, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In a further embodiment, said disease, condition, or disorder is allergy, asthma, chronic obstructive pulmonary disease (COPD), diabetes, Alzheimer's disease, Huntington's disease, Parkinson's disease, AIDS-associated dementia, amyotrophic lateral sclerosis (ALS), multiple sclerosis (MS), schizophrenia, cardiomyocyte hypertrophy, vascular smooth muscle cell proliferation, reperfusion/ischemia, stroke, baldness, cancer, hepatomegaly, hypertension, cardiovascular disease, cardiomegaly, cystic fibrosis, viral disease, autoimmune diseases, restenosis, psoriasis, inflammation, hypertension, angina pectoris, cerebrovascular contraction, peripheral circulation disorder, premature birth, atherosclerosis, vasospasm, cerebral vasospasm, coronary vasospasm, retinopathy, glaucoma, erectile dysfunction (ED), AIDS, osteoporosis, Crohn's Disease, colitis, neurite outgrowth, or Raynaud's Disease.

In another embodiment, said disease, condition, or disorder is hypertension, cerebral vasospasm, coronary vasospasm, bronchial asthma, preterm labor, erectile dysfunction, glaucoma, vascular smooth muscle cell proliferation, myocardial hypertrophy, malignoma, ischemia/reperfusion-induced injury, endothelial dysfunction, Crohn's Disease, colitis, neurite outgrowth, Raynaud's Disease, angina pectoris, Alzheimer's disease, benign prostatic hyperplasia, cardiac hypertrophy, perivascular fibrosis or atherosclerosis. In a further embodiment, said disease, condition, or disorder is atherosclerosis, hypertension, erectile dysfunction (ED), reperfusion/ischemia, stroke, cerebral vasospasm, coronary vasospasm, cardiac hypertrophy or glaucoma.

In another embodiment, the present invention relates to a method of treating hypertension. In another embodiment, the present invention relates to a method of treating chronic obstructive pulmonary disease (COPD). In another embodiment, the present invention relates to a method of treating glaucoma. In another embodiment, the present invention relates to a method of treating cardiac hypertrophy and/or perivascular fibrosis.

In some embodiments, the present invention relates to a method for treating or lessening the severity of a cancer. In further embodiments, the present invention relates to a method for treating or lessening the severity of a cancer selected from brain (gliomas), breast, colon, head and neck, kidney, lung, liver, melanoma, ovarian, pancreatic, prostate, sarcoma, or thyroid. In yet further embodiments, the present invention relates to a method for treating or lessening the severity of pancreatic, prostate, or ovarian cancer.

In another embodiment, the invention provides a method of inhibiting JAK kinase activity in a biological sample, comprising contacting said biological sample with a compound or composition of the invention.

In another embodiment, the invention provides a method of inhibiting JAK kinase activity in a patient, comprising administering to said patient a compound or composition of the invention.

In another embodiment, the invention comprises a method of treating or lessening the severity of a JAK-mediated condition or disease in a patient. The term "JAK-mediated disease", as used herein means any disease or other deleterious condition in which a JAK family kinase, in particular JAK2 or JAK3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas.

In another embodiment, the invention provides a method of treating or lessening the severity of a disease of condition selected from a proliferative disorder, a cardiac disorder, a neurodegenerative disorder, an autoimmune disorder, a condition associated with organ transplant, an inflammatory disorder, an immune disorder or an immunologically mediated disorder, comprising administering to said patient a compound or composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In one embodiment, the disease or disorder is allergic or type I hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection.

In another embodiment, a compound or composition of this invention may be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML or juvenile myelomonocytic leukemia.

The term "biological sample", as used herein, means an ex vivo sample, and includes, without limitation, cell cultures or extracts thereof; tissue or organ samples or extracts thereof, biopsied material obtained from a mammal or extracts thereof; and blood, saliva, urine, feces, semen, tears, or other body fluids or extracts thereof.

Inhibition of kinase activity, particularly JAK or ROCK kinase activity, in a biological sample is useful for a variety of purposes that are known to one of skill in the art. Examples of such purposes include, but are not limited to, biological assays and biological specimen preparation and storage.

In certain embodiments of the present invention an "effective amount" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like.

In an alternate embodiment, the methods of this invention comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

Methodology for Synthesis and Characterization of Compounds

The compounds of this invention may be prepared in general by methods known to those skilled in the art for analogous compounds or by those methods depicted in the Examples below. See, e.g., the examples described in WO 2005/095400, which is herein incorporated by reference in its entirety.

All references provided in the Examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

The following definitions describe certain of the terms and abbreviations used herein:
Ts-Cl p-toluenesulfonyl chloride (tosyl chloride)
DMF dimethylformamide
Tf triflate
dppf 1,1'-bis(diphenylphosphino)-ferrocene
Ac acetyl
DME 1,2-Dimethoxyethane
atm atmospheres
EDC 1-Ethyl-3-(3-dimethylaminopropy)carbodiimide Hydrochloride
DIPEA diisopropylethylamine
KHMDS Potassium Hexamethyldisilazane
THF tetrahydrofuran
HEPES 4-(2-hydroxyethyl)-1-piperazineethanesulfonic acid
Glu glutamate
Tyr tyrosine
ATP adenosine triphosphate
Ph phenyl
Me methyl
BSA bovine serum albumin
DTT dithiothreitol
DMF dimethylformamide
EtOAc ethyl acetate
HPLC high performance liquid chromatography
DMSO dimethyl sulfoxide
TFA trifluoacetic acid
NMP N-methylpyrrolidone
HOBT hydroxybenzotriazole
DCM dichloromethane
LC-MS liquid chromatography-mass spectrometry

EXAMPLES

Example 1

Synthesis of Compounds and Precursors Thereof

Synthesis of 4-Bromo-1-tosyl-1H[2,3-b]pyridine (A)

A

4-Bromo-1-tosyl-1H[2,3-b]pyridine (A) was prepared by modification of the procedure described by Thibault, C. *Org. Lett.* 5(26):5023-5025, 2003, using tosyl choloride. Specifically, a solution of 4-bromo-1H-pyrrolo[2,3-b]pyridine (2.7 g, 13.7 mmol) in DMF (40 mL) was treated with 60% NaH (0.55 g, 13.7 mmol) at 0° C. under nitrogen. After 10 min, tosyl choloride (2.61 g, 13.7 mmol) was added and the mixture warmed to room temperature and allowed to stir overnight. Methanol (10 mL) was added and the mixture diluted with ethylacetate (200 mL), washed with water (3×75 mL), brine, then dried over MgSO$_4$ and concentrated in vacuo. The resulting oil was purified via silica gel chromatography using a gradient of 10% to 15 ethylacetate:hexane to afford 3.66 g (76% yield) of (A) as a white foam. LC-MS 3.7 min, ES+ 352.6, $^1$H NMR (500 MHz, CDCl$_3$) d 8.22 (d, 1H), 8.10 (d, 2H), 7.80 (d, 1H), 7.38 (d, 1H), 7.28 (d, 2H), 6.65 (d, 1H), 2.42 (s, 3H).

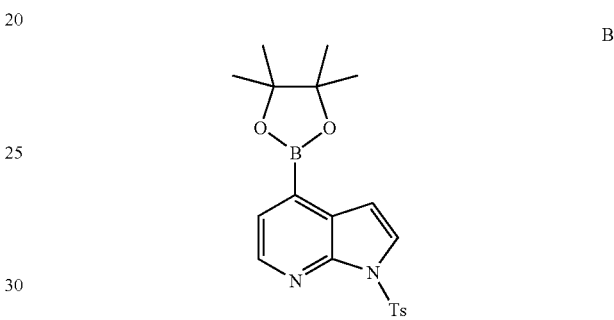

B

Synthesis of 4-(4,4,5,5-Tetramethyl-1,3,2-dioxaborolan-2-yl)-1-(toluene-4-sulfonyl)-1H-pyrrolo[2,3-b]pyridine (B)

A mixture of (A) (1.65 g, 4.7 mmol), 4,4,5,5-tetramethyl-2-(4,4,5,5-tetramethyl-1,3,2dioxaborolan-2-yl)-1,3,2-dioxaborolane (1.43 g, 5.64 mmol), potassium acetate (1.38 g, 14.1 mmol) and PdCl$_2$(dppf)$_2$ (195 mg, 0.24 mmol) was suspended in anhydrous DME (12 mL) in a 20 mL microwave vessel. The mixture was heated in the microwave at 160° C. for 20 minutes at which time HPLC analysis showed complete reaction. The resulting mixture was absorbed on celite and then applied to a pad of silica-gel (15 mL) and the product eluted using 30% ethylacetate:hexane (250 mL). Evaporation of the solvent and vacuum drying gave 1.83 g (97% yield) of a tan solid that was identified as the title compound B by LC-MS: 4.81 min, 398.92 ES+. The material was used without additional purification.

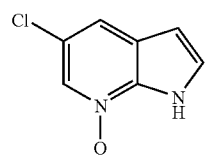

C 5-chloro-1H-pyrrolo[2,3-b]pyridine-N-oxide (C)

To 5-chloro-1H-pyrrolo[2,3-b]pyridine (10.0 g, 65.6 mmol) in EtOAc (70 mL) at 0° C. was added dropwise over 15 h a solution of m-chloroperbenzoic acid (57%, 17.9 g, 104 mmol) in EtOAc (80 mL). The reaction mixture was stirred for 20 h at RT. Then, the mixture was cooled to −40° C. and the solids were filtered off and rinsed with cold EtOAc. The solid was taken up in water (70 mL) and treated dropwise with 30% aq. K$_2$CO$_3$ until pH was 11. The solution was warmed for 30 min, cooled to 0° C., filtered and dried in vacuo. Analysis (NMR) indicated the presence of m-chloroperbenzoic acid. The solid was taken up in 10% MeOH in DCM and washed with 30% aq. K$_2$CO$_3$ until all m-chlorobenzoic acid was removed. The organic layer was dried over Na$_2$SO$_4$, filtered and concentrated to provide 2.61 g (24% yield) of 5-chloro-1H-pyrrolo[2,3-b]pyridine-N-oxide (C). The combined mother liquors were concentrated. Flash chromatography (5% MeOH-DCM) provided and additional 1.49 g (13% yield) contaminated with ~10% of the benzoic acid. LC/MS (M+H$^+$) 168.76.

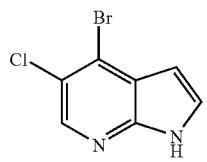

4-bromo-5-chloro-1H-pyrrolo[2,3-b]pyridine (D)

To 5-chloro-1H-pyrrolo[2,3-b]pyridine-N-oxide (C) (5.23 g, 31.0 mmol) and tetramethylammonium bromide (7.16 g, 46.5 mmol) in DMF (50 mL) at 0° C. was added portionwise methanesulfonic anhydride (10.8 g, 62.0 mmol). After stirring at RT for 3 h, the mixture was poured into water (100 mL), the pH was adjusted to 7 with saturated NaHCO$_3$. The solution was diluted with water (400 mL), cooled to 0° C. and filtered. The solid dried in a vac oven at 50° C. to provide 4.92 g of brown solid which was used without purification. The brown solid was dissolved in DMP (40 mL) cooled to 0° C. and treated with NaH (60% in oil, 750 mg) followed by addition of toluenesulfonyl chloride (3.92 g, 20.5 mmol). Additional portions of NaH (60% in oil, 2×750 mg) were added at 1 h intervals. After 4 h, EtOAc was added and the reaction was quenched with sat'd NaHCO$_3$. The mixture was separated and washed with water, and brine, dried over Na$_2$SO$_4$, filtered and concentrated. Flash chromatography (SiO$_2$, 20-50% EtOAc in hexanes, gradient elution) provided 4-bromo-5-chloro-1H-pyrrolo[2,3-b]pyridine (D) (1.89 g). LC/MS T$_{ret}$=3.3 min, (M+H$^+$) 232.7.

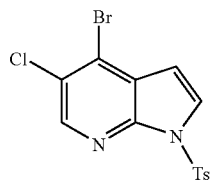

4-bromo-5-chloro-1-tosyl-1H-pyrrolo[2,3-b]pyridine (E)

To a solution of 4-bromo-5-chloro-1H-pyrrolo[2,3-b]pyridine (D) (1.89 g, 8.16 mmol) in DMF (15 mL) at 0° C. was added NaH (60% in oil, 328 mg) followed by toluenesulfo- nylchloride (1.72 g, 8.98 mmol). The reaction mixture was warmed to RT and additional NaH (60% in oil, 2×200 mg) was added at 1 h intervals. After a further 1 h, EtOAc was added and the reaction was quenched with sat'd NaHCO$_3$. The aqueous layer was extracted with EtOAc and the combined organic layer was washed with water, brine, dried over Na$_2$SO$_4$, filtered and concentrated. Flash chromatography (SiO$_2$, 7% EtOAc in hexanes) provided 4-bromo-5-chloro-1-tosyl-1H-pyrrolo[2,3-b]pyridine (E) (1.81 g, 58%) as an off white solid. LC/MS T$_{ret}$=4.8 min, (M+H$^+$) 386.6.

1-alkenyl boronates from corresponding 1-alkenyl triflates were prepared as described in (a) Takagi, J.; Ishiyama, T. T.; Miyaura, N. J. Am. Chem. Soc. 124:8001-8006, 2002, and (b) Comins, D. L.; Dehghani, A. Tetrahedron Let. 33:6299-6302, 1992.

Method A: Anhydrous Procedure for the Coupling of Aryl Boronic Acids with (A)

A mixture of (A) (70 mg, 0.2 mmol, 1 equivalent), aryl boronic acid (or pinacolborane) (1.2 equivalents), potassium acetate (3 equivalents) and Pd(PPh$_3$)$_4$ (0.1 equivalents) were suspended in anhydrous DME (2-3 mL) then heated in the microwave at 150-180° C. until complete by HPLC analysis (usually 20-30 minutes). The resulting mixture was filtered through a 4.5 □m filter and washed with methanol. Removal of the p-toluenesulfonyl group was performed as described for compound 47. The resulting products were then purified by preparative HPLC.

Method B: Procedure for the Coupling of Aryl Boronic Acids with (1) Under Heterogeneous Basic Conditions A mixture of (A) (70 mg, 0.2 mmol, 1 equivalent), aryl boronic acid (or pinacolborane) (1.2 equivalents) was dissolved in DME (2 mL) and 2M Na$_2$CO$_3$ (1 mL). To the mixture was added Pd(PPh$_3$)$_4$ (0.1 equivalents) and the resulting mixture heated in the microwave at 150-180° C. until complete by HPLC analysis (usually 20-30 minutes). The resulting mixture was filtered through a 4.5 □m filter and washed with methanol. Removal of the p-toluenesulfonyl group was performed as described for compound 47. The resulting products were then purified by preparative HPLC.

Dimethyl-[3-(1H-pyrrolo[2,3-b]pyridin-4-yl)-phenyl]-amine (compound 31)

The title compound (31) was prepared using method A to afford 41 mg (62% yield) of a yellow powder.

4-Cyclopentenyl-1H-pyrrolo[2,3b]pyridine (compound 27); 4-Cyclohexenyl-1H-pyrrolo[2,3b]pyridine (compound 30); 5-Chloro-4-cyclopentenyl-1H-pyrrolo[2,3b]pyridine (compound 28); 5-Chloro-4-cyclohexenyl-1H-pyrrolo[2,3b] pyridine (compound 29); 4-(5-Chloro-1H-pyrrolo[2,3b]pyridin-4-yl)-1H-pyrrole-2-carboxylic acid (compound 81); 5-Chloro-4-(1-methyl-1H-pyrazol-4-yl)-1H-pyrrolo[2,3b] pyridine (compound 70); 5-Chloro-4-(1H-pyrazol-4-yl)-1H-pyrrolo[2,3b]pyridine (compound 80); 4-(3-methylpyridin-2-yl)-1H-pyrrolo[2,3b]pyridine (compound 74); and 5-Chloro-4-(thiophen-3-yl)-1H-pyrrolo[2,3b]pyridine (compound 82) were prepared by method A.

4-(2-Chloro-pyridin-4-yl)-1H-pyrrolo[2,3-b]pyridine (compound 39)

The title compound (39) was prepared using method A to afford 1.1 mg of a yellow powder.

4-(3,4,5-Trimethoxy-phenyl)-1H-pyrrolo[2,3-b]pyridine (compound 40)

The title compound (40) was prepared using method A to afford 14.2 mg of a white solid.

4-(3,4-Dichloro-phenyl)-1H-pyrrolo[2,3-b]pyridine (compound 41)

The title compound (41) was prepared using method A to afford 6.6 mg of a solid.

4-(3-Benzyloxy-phenyl)-1H-pyrrolo[2,3-b]pyridine (compound 42)

The title compound (42) was prepared using method A to afford 18.8 mg of a white solid.

N-[4-(1H-Pyrrolo[2,3-b]pyridin-4-yl)-phenyl]-acetamide (compound 43)

The title compound (43) was prepared using method A to afford 1.1 mg of a white solid.

3-[1-(Toluene-4-sulfonyl)-1H-pyrrolo[2,3-b]pyridin-4-yl]-benzoic acid ethyl ester (compound F)

The title compound (F) was prepared using method A without removal of the tosyl group to afford 59 mg (70% yield) of a white solid.

3-(1H-Pyrrolo[2,3-b]pyridin-4-yl)-benzoic acid ethyl ester (compound 46) and 3-(1H-Pyrrolo[2,3-b]pyridin-4-yl)-benzoic acid (compound 47)

Sodium metal (50 mg, 2.2 mmol) was added to a solution of (F) (22 mg, 0.05 mmol) in ethanol (2 mL) and the mixture heated under nitrogen at 60° C. After 10 min, the reaction was subjected to acid-base isolation to afford 8.8 mg of ester (46). The aqueous layer contained 3.3 mg of acid (47) after adjusting to pH 5 and extraction with ethylacetate.

Synthesis of [3-(1H-Pyrrolo[2,3-b]pyridin-4-yl)-phenyl]-methanol (compound 49)

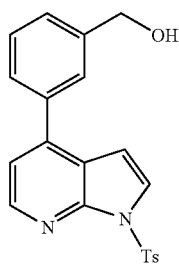

G

{3-[1-(Toluene-4-sulfonyl)-1H-pyrrolo[2,3-b]pyridin-4-yl]-phenyl}-methanol (G) was prepared as follows: Dibal-H (0.89 mL, 0.89 mmol, 1 M) was added to a solution of 37 mg (0.089 mmol) of (F) in anhydrous THF at −10° C. The solution was allowed to warm to RT and stir until complete as judged by HPLC and LC-MS (1.5 hours). The reaction was quenched with ethylacetate (30 mL) washed twice with 1 N NaOH, dried over MgSO₄ and concentrated in vacuo to afford an oil that was purified using silca-gel chromatography using ethylacetate:hexane (1:1) to afford 37 mg of {3-[1-(Toluene-4-sulfonyl)-1H-pyrrolo[2,3-b]pyridin-4-yl]-phenyl}-methanol (G) as a foam.

A 12 mg sample was treated with sodium metal in methanol at 60° C. After complete reaction, methanol was evaporated and the residue dissolved in water then extracted with ethylacetate and dried over Na₂SO₄. Concentration of the solvent in vacuo gave 7.4 mg of the title compound (49) as a light tan solid.

4-(3-Chloromethyl-phenyl)-1-(toluene-4-sulfonyl)-1H-pyrrolo[2,3-b]pyridine (H)

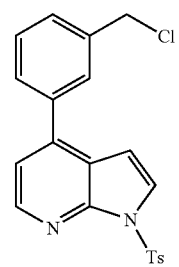

H

To a solution of (G) (0.25 g, 0.66 mmol) in dichloromethane (5 mL) was added thionyl chloride (0.5 mL, 6.9 mmol) at RT. The solution was allowed to stir until complete as judged by HPLC (1 hour). The solvent was removed under reduced pressure to afford 0.26 g of (H) (99% yield) as a white solid. FIA MS expected for $C_{21}H_{17}ClN_2O_2S$: m/e 396.07, found: 396.8 ES+. The material was used without further purification.

4-(3-Methoxymethyl-phenyl)-1H-pyrrolo[2,3-b]pyridine (compound 62)

Sodium metal was added to a solution of 35 mg (0.09 mmol) of (H) in methanol (2 mL) and the mixture heated under nitrogen at 60° C. After complete reaction, methanol was evaporated and the residue dissolved in water then extracted with ethylacetate and dried over Na₂SO₄. Concentration of the solvent in vacuo gave 16 mg (76% yield) of the title compound (62).

[3-(1H-Pyrrolo[2,3-b]pyridin-4-yl)-phenyl]-acetonitrile (compound 63)

A solution of 87 mg (0.22 mmol) of (51???) in anhydrous acetone was treated with KCN (71 mg, 1.1 mmol) and KI (1.0 mg) then refluxed under nitrogen overnight. The solvent was removed, methanol added and the tosyl group removed as previously described. After complete reaction, methanol was evaporated and the residue dissolved in water then extracted with ethylacetate and dried over Na₂SO₄. Concentration of the solvent in vacuo gave a residue that was purified by preparative HPLC chromatography to afford 23 mg (45% yield) of the title compound (63) as a white powder.

General Method for Preparation of Amines from 4-(3-Chloromethyl-phenyl)-1-(toluene-4-sulfonyl)-1H-pyrrolo[2,3-b]pyridine (H)

General Method for Preparation of Amides from 3-(1H-Pyrrolo[2,3-b]pyridin-4-yl)-benzoic acid (I)

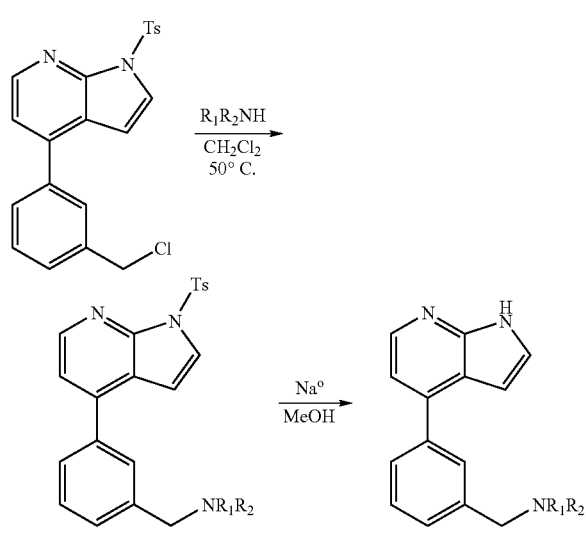

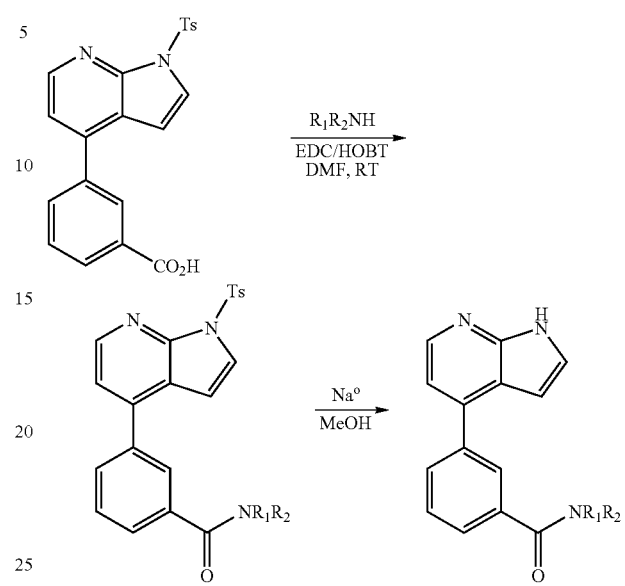

A solution of (H) (43 mg, 0.11 mmol) and amine (3 equivalents) in dichloromethane (2 mL) was heated at 50° C. overnight. The solvent was removed, methanol added and the tosyl group removed as previously described. After complete reaction, methanol was evaporated and the residue dissolved in water then extracted with ethylacetate and dried over Na$_2$SO$_4$. Concentration of the solvent in vacuo gave a residue that was purified by preparative HPLC chromatography.

Methyl-[3-(1H-pyrrolo[2,3-b]pyridin-4-yl)-benzyl]-amine (compound 84)

The above procedure using methylamine afforded 3.2 mg of the title compound (84).

Dimethyl-[3-(1H-pyrrolo[2,3-b]pyridin-4-yl)-benzyl]-amine (compound 85)

The above procedure using dimethylamine afforded 21.4 mg of the title compound (85).

Cyclopropyl-[3-(1H-pyrrolo[2,3-b]pyridin-4-yl)-benzyl]-amine (compound 86)

The above procedure using cyclopropylamine afforded 27.5 mg of the title compound (86).

4-(3-Piperidin-1-ylmethyl-phenyl)-1H-pyrrolo[2,3-b]pyridine (compound 87)

The above procedure using piperidine afforded 8.3 mg of the title compound (87).

4-(3-Morpholin-4-ylmethyl-phenyl)-1H-pyrrolo[2,3-b]pyridine (compound 88)

The above procedure using morpholine afforded 30.6 mg of the title compound (88).

4-[3-(4-Methyl-piperazin-1-ylmethyl)-phenyl]-1H-pyrrolo[2,3-b]pyridine (compound 89)

The above procedure using N-methylpiperazine afforded 15.7 mg of the title compound (89).

A solution of (I) (31 mg, 0.13 mmol) and amine (3 equivalents), HOBT (3 equivalents) and EDC (3 equivalents) in DMF (2 mL) was allowed to stir overnight at RT. Ethylacetate was added and the solution washed with water. The organic layer was dried over Na$_2$SO$_4$ then concentrated in vacuo. The resulting residue was dissolved in methanol and the tosyl group removed as previously described. After complete reaction, methanol was evaporated and the residue dissolved in water then extracted with ethylacetate and dried over Na$_2$SO$_4$. Concentration of the solvent in vacuo gave a residue that was purified by preparative HPLC chromatography.

N-Methyl-3-(1H-pyrrolo[2,3-b]pyridin-4-yl)-benzamide (compound 91)

The above procedure using methylamine afforded 1.1 mg of the title compound (91).

N,N-Dimethyl-3-(1H-pyrrolo[2,3-b]pyridin-4-yl)-benzamide (compound 92)

The above procedure using dimethylamine afforded 1.7 mg of the title compound (92).

Piperidin-1-yl-[3-(1H-pyrrolo[2,3-b]pyridin-4-yl)-phenyl]-methanone (compound 93)

The above procedure using piperazine afforded 2.6 mg of the title compound (93).

Morpholin-4-yl-[3-(1H-pyrrolo[2,3-b]pyridin-4-yl)-phenyl]-methanone (94)

The above procedure using morpholine afforded 0.9 mg of the title compound (94).

(4-Methyl-piperazin-1-yl)-[3-(1H-pyrrolo[2,3-b]pyridin-4-yl)-phenyl]-methanone (95)

The above procedure using N-methylpiperazine afforded 0.7 mg of the title compound (95).

4-Pyridin-3-yl-1H-pyrrolo[2,3-b]pyridine

The title compound was prepared using method A to afford 11.8 mg.

4-Pyrimidin-5-yl-1H-pyrrolo[2,3-b]pyridine (compound 104)

The title compound (104) was prepared using method A to afford 6.9 mg.

3-(1H-Pyrrolo[2,3-b]pyridin-4-yl)-phenol (compound 105)

The title compound (105) was prepared using method A to afford 18.9 mg.

4-(2H-Pyrazol-3-yl)-1H-pyrrolo[2,3-b]pyridine (compound 106)

The title compound (106) was prepared using method A to afford 2.8 mg.

N-[3-(1H-Pyrrolo[2,3-b]pyridin-4-yl)-phenyl]-acetamide (compound 107)

The title compound (107) was prepared using method A to afford 11.6 mg.

4-Furan-3-yl-1H-pyrrolo[2,3-b]pyridine (133) VRT-757779

The title compound (133) was prepared using method A to afford 12.8 mg.

5-(1H-Pyrrolo[2,3-b]pyridin-4-yl)-thiophene-2-carbonitrile (compound 108)

The title compound (108) was prepared using method A to afford 2 mg.

4-(3-Isopropyl-phenyl)-1H-pyrrolo[2,3-b]pyridine (compound 109)

The title compound (109) was prepared using method A to afford 10.3 mg.

4-(3,4-Dimethyl-phenyl)-1H-pyrrolo[2,3-b]pyridine (compound 110)

The title compound (110) was prepared using method A to afford 12.3 mg.

4-(1-Methyl-1H-pyrazol-4-yl)-1H-pyrrolo[2,3-b]pyridine (compound 111)

The title compound (111) was prepared using method B to afford 7.5 mg.

4-(3,5-Dimethyl-phenyl)-1H-pyrrolo[2,3-b]pyridine (compound 112)

The title compound (112) was prepared using method B to afford 2.9 mg as a white solid.

4-(3-Trifluoromethyl-phenyl)-1H-pyrrolo[2,3-b]pyridine (compound 113)

The title compound (113) was prepared using method B to afford 10.4 mg as a white solid.

3-(1H-Pyrrolo[2,3-b]pyridin-4-yl)-phenylamine (compound 114)

The title compound (114) was prepared using method B to afford 6.8 mg of an amber oil.

4-Benzofuran-4-yl-1H-pyrrolo[2,3-b]pyridine (compound 115)

The title compound (115) was prepared using method B to afford 5.5 mg as a yellow solid.

4-(4-Isopropoxy-phenyl)-1H-pyrrolo[2,3-b]pyridine (compound 116)

The title compound (116) was prepared using method B to afford 0.7 mg as an off-white solid.

4-Thiophen-3-yl-1H-pyrrolo[2,3-b]pyridine

The title compound was prepared using method B to afford 6.8 mg as a tan solid.

4-(3,5-Dimethyl-1H-pyrazol-4-yl)-1H-pyrrolo[2,3-b]pyridine (compound 124)

The title compound (124) was prepared using method B to afford 24 mg as a white solid.

General Procedure for Synthesis of 6-(1H-pyrrolo[2,3-b]pyridine-4-yl)pyridin-2-amine derivatives

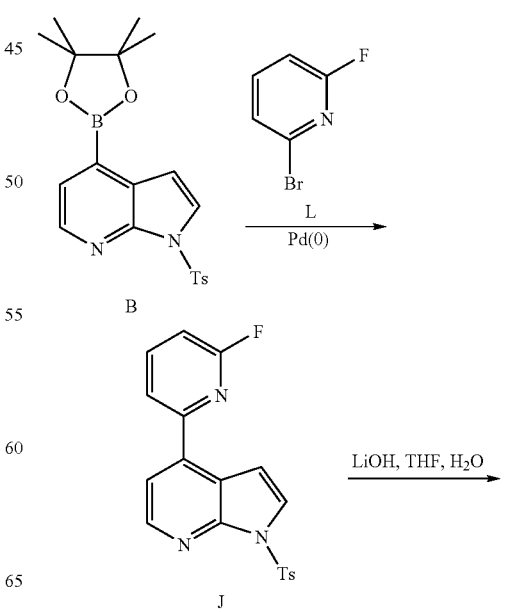

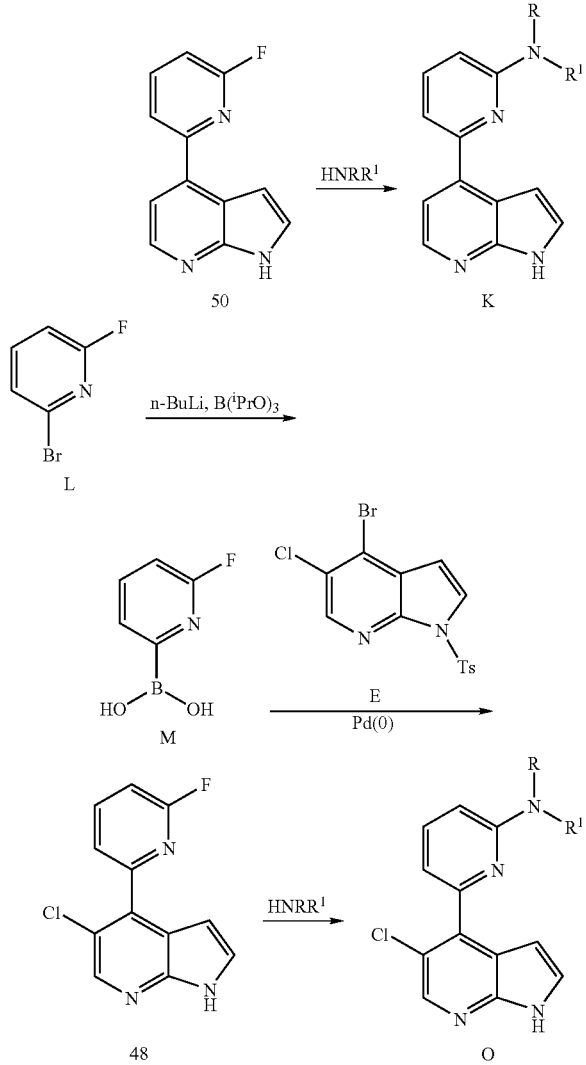

Synthesis of 4-(6-fluoropyridin-2-yl)-1-tosyl-1H-pyrrolo[2,3-b]pyridine (J)

In a 20 mL microwave tube, 2-Bromo-6-fluoropyridine (L) (682 mg, 3.3 mmol, 1.2 equiv.), 4-(4,4,5,5-tetramethyl-1,3,2-dioxaborolan-2-yl)-1-tosyl-1H-pyrrolo[2,3-b]pyridine (B)(1.1 g, 2.8 mmol, 1 equiv.) and Pd(PPh$_3$)$_4$ (323 mg, 0.28 mmol), 0.1 equiv.) were suspended in a mixture of DME (10 mL) and aqueous Na$_2$CO$_3$ 2M (3 mL). The container was sealed and the reaction mixture was exposed to microwave irradiation for 30 min at 160° C. The resulting mixture was diluted in ethyl acetate, washed with water and dried over anhydrous Na$_2$SO$_4$. The crude material was purified by flash chromatography on silica gel, eluting with hexanes/ethyl acetate mixtures (90:10 to 60:40). The title compound J was isolated as a pale yellow solid (2.1 g, 50%).

Synthesis of 4-(6-fluoropyridin-2-yl)-1H-pyrrolo[2,3-b]pyridine (compound 50)

To a solution of 4-(6-fluoropyridin-2-yl)-1-tosyl-1H-pyrrolo[2,3-b]pyridine (J) (700 mg, 1.9 mmol, 1 equiv.) in THF (6 mL), a solution of aqueous NaOH 1M (3 mL) was added. The resulting mixture was exposed to microwave irradiation for 15 min. at 170° C. The reaction crude was diluted in ethyl acetate, washed with water and dried over anhydrous Na$_2$SO$_4$. After removing the solvent under reduced pressure, the title compound (50) was isolated as a pale yellow solid (800 mg, 67%).

Synthesis of 6-fluoropyridin-2-yl-2-boronic acid (M)

Under a nitrogen atmosphere, 2-bromo-6-fluoropyridine (L) (2.5 g, 14.2 mmol, 1 equiv.) and B($^i$PrO)$_3$ (4 mL) were dissolved in a mixture of toluene (50 mL) and THF (12.5 mL) and cooled at −78° C. n-BuLi (10.8 mL, 1.6 M in hexanes) was added dropwise over 1.25 h. The resulting mixture was stirred for 30 min. at −78° C. and then was allowed to warm up to 0° C. over 2 h. The reaction mixture was quenched with a solution of aqueous HCl 2M (10 mL) and stirred at room temperature for 1 h. The organic layer was then separated, washed with aqueous HCl 0.5 M, dried over anhydrous Na$_2$SO$_4$ and the solvent removed under a stream of nitrogen. A second crop of desired product was obtained after neutralizing the aqueous layer with saturated solution of NaHCO$_3$ and extracting with ethyl acetate, followed by drying over anhydrous Na$_2$SO$_4$ and removing the organic solvent under a stream of nitrogen. The title compound (M) was isolated as a white solid (1.27 g, 64%).

Synthesis of 5-chloro-4-(6-fluoropyridin-2-yl)-1H-pyrrolo[2,3-b]pyridine (compound 48)

6-Fluoropyridin-2-yl-2-boronic acid (M) (91 mg, 0.62 mmol, 1.2 equiv.), 4-bromo-5-chloro-1-tosyl-1H-pyrrolo[2,3-b]pyridine (E) (200 mg, 0.5 mmol, 1 equiv.) and Pd(PPh$_3$)$_4$ (15 mg, 0.012 mmol, 0.025 equiv.) were suspended in a mixture of dioxane (2.5 mL) and aqueous Na$_2$CO$_3$ 2 M (1.25 mL). The resulting mixture was exposed to microwave irradiation for 30 min at 180° C. The crude reaction was filtered through celite and the residue was purified by flash chromatography on silica, eluting with mixtures of hexanes/ethyl acetate (65:35). The title compound (48) was isolated as a pale yellow solid (100 mg, 39%). LC/MS: 2.8 min; 247.8 ES+; 246.0 ES−. $^1$HNMR (500 MHz, DMSO-d$_6$) δ 6.31 (m, 1H), 7.32 (m, 1H), 7.61 (m, 1H), 7.67 (m, 1H), 8.20 (dt, 1H), 8.36 (s, 1H), 12.1 (s, 1H).

Synthesis of 6-(1H-pyrrolo[2,3-b]pyridine-4-yl)pyridin-2-amine derivatives (K and O)

To a solution of 4-(6-fluoropyridin-2-yl)-1H-pyrrolo[2,3-b]pyridine (50)(38 mg, 18 mmol, 1 equiv.) in NMP (1.5 mL), the desired amine (0.54 mmol, 3 equiv.) was added. The vessel was sealed and the resulting mixture was exposed to microwave irradiation for 15 min-3 h at 220° C.-250° C. The crude mixture was diluted in DMSO (1 mL) and purified by reversed phase HPLC, eluting with acetonitrile/water/1% TFA mixtures. After removing the solvent, the desire compound K or O was isolated.

Compounds prepared using the procedure described above include the following:

1-(4-(6-1H-Pyrrolo[2,3-b]pyridin-4-yl)pyridin-2-yl)-1,4-diazepan-1-yl)ethanone (compound 18).
3-(4-(6-1H-Pyrrolo[2,3-b]pyridin-4-yl)pyridin-2-yl)-1,4-diazepan-1-yl)-3-oxopropanenitrile (compound 19).
1-(6-(1H-Pyrrolo[2,3-b]pyridin-4-yl)pyridin-2-yl)pyrrolin-3-ol (compound 51).
N-Isobutyl-6-1H-Pyrrolo[2,3-b]pyridin-4-yl)pyridin-2-amine (compound 20).

1-((2R,6S)-4-(6-1H-Pyrrolo[2,3-b]pyridin-4-yl)pyridin-2-yl)-2,6-dimethylpiperazin-1-yl)ethanone (compound 22).

3-(N-(6-1H-Pyrrolo[2,3-b]pyridin-4-yl)pyridin-2-yl)-N-methylamino)-1-phenylpropan-1-ol (compound 53).

4-(6-((S)-2-(Pyrrolidin-1-yl)methyl)pyrrolidin-1-yl)pyridin-2-yl)-1H-pyrrolo[2,3-b]pyridine (compound 54).

N,N-Diethyl-6-(1H-pyrrolo[2,3-b]pyridin-4-yl)pyridin-2-amine (compound 52).

N-Cyclopentyl-6-(1H-pyrrolo[2,3-b]pyridin-4-yl)pyridin-2-amine (compound 24).

6-(5-Chloro-1H-pyrrolo[2,3-b]pyridin-4-yl)-N-cyclopentylpyrdin-2-anine (compound 32).

4-(6-(3-Methylpiperidin-1-yl)pyridin-2-yl)-1H-pyrrolo[2,3-b]pyridine (compound 25).

1-(4-(6-(1H-pyrrolo[2,3-b]pyridin-4-yl)pyridin-2-yl)piperazin-1-yl)ethanone (compound 26).

(S)-2-(6-(1H-Pyrrolo[2,3-b]pyridin-4-yl)pyridin-2-ylamino)-4-methylpentan-1-ol (compound 59).

N-((Benzo[d][1,3]dioxol-6-yl)methyl)-6-(1H-pyrrolo[2,3-b]pyridin-4-yl)pyridin-2-amine (compound 60).

N-(2-Chlorophenethyl)-6-(5-chloro-1H-pyrrolo[2,3-b]pyridin-4-yl)pyridin-1-amine (compound 75).

N-Isopropyl-N-methyl-6-(1H-pyrrolo[2,3-b]pyridin-4-yl)pyridin-2-amine (compound 61).

1-(4-(6-(5-Chloro-1H-pyrrolo[2,3-b]pyridin-4-yl)pyridin-2-yl)-1,4-diazepan-1-yl)ethanone (compound 76).

2-(N-(5-Chloro-1H-pyrrolo[2,3-b]pyridin-4-yl)pyridin-2-yl)-N-methylamino)ethanol (compound 77).

N-(3-Methoxybenzyl)-6-(1H-pyrrolo[2,3-b]pyridin-4-yl)pyridin-2-anine (compound 73).

6-(5-Chloro-1H-pyrrolo[2,3-b]pyridin-4-yl)-N-isobutylpyridin-2-anine (compound 78).

5-Chloro-4-(6-(pyrrolidin-1-yl)pyridine-2-yl)-1H-pyrrolo[2,3-b]pyridine (compound 79).

6-(5-Chloro-1H-pyrrolo[2,3-b]pyridin-4-yl)-N-(2-(dimethylamino)ethyl-N-methylpyridin-2-amine (compound 83).

N-(2-Methylbutyl)-6-(1H-pyrrolo[2,3-b]pyridin-4-yl)pyridin-2-amine (compound 72).

N-Methyl-N-((pyridin-3-yl)methyl)-6-(1H-pyrrolo[2,3-b]pyridin-4-yl)pyridin-2-amine (compound 56).

N-((2,3-Dihydrobenzo[b][1,4]dioxin-2-yl)methyl)-6-(1H-pyrrolo[2,3-b]pyridin-4-yl)pyridin-2-amine (compound 58).

N-(2-(1-Methylpyrrolidin-2-yl)ethyl)-6-(1H-pyrrolo[2,3-b]pyridin-4-yl)pyridin-2-amine (compound 37).

2-(6-(1H-Pyrrolo[2,3-b]pyridin-4-yl)pyridin-2-yl)-1,2,3,4-tetrahydroisoquinoline (compound 38).

3-(6-(1H-Pyrrolo[2,3-b]pyridin-4-yl)pyridin-2-ylamino)-2,2-dimethylpropan-1-ol (compound 57).

2-(N-(6-(1H-pyrrolo[2,3-b]pyridin-4-yl)pyridin-2-yl)-N-methylamino)1-phenylethanol (compound 55).

N-(2-Chlorobenzyl)-6-(1H-pyrrolo[2,3-b]pyridin-4-yl)pyridin-2-amine (compound 33).

N-(2-Chlorophenethyl)-6-(1H-pyrrolo[2,3-b]pyridin-4-yl)pyridin-2-amine (compound 34).

2-(N-(6-(1H-Pyrrolo[2,3-b]pyridin-4-yl)pyridin-2-yl)-N-methylamino)ethanol (compound 35).

N-((tetrahydrofuran-2-yl)methyl)-6-(1H-pyrrolo[2,3-b]pyridin-4-yl)pyridin-2-amine (compound 36).

General procedure for Synthesis of N-(6-(1H-pyrrolo[2,3-b]pyridine-4-yl)pyridin-2-yl)acetamine

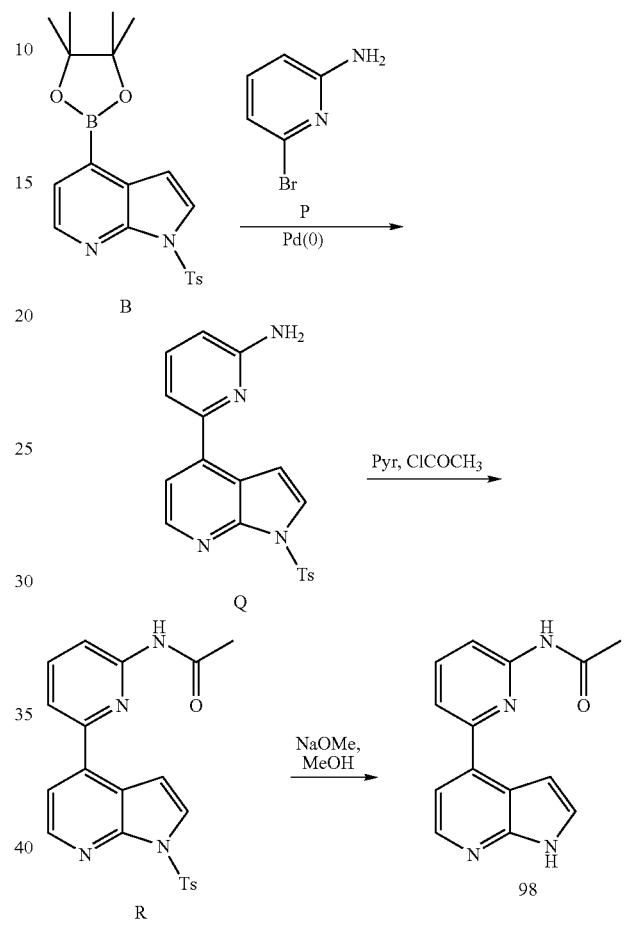

Synthesis of 6-(1-tosyl-1H-pyrrolo[2,3-b]pyridin-4-yl)pyridine-2-amine (Q). The title compound was synthesized following the procedure described for 4-(6-fluoropyridin-2-yl)-1-tosyl-1H-pyrrolo[2,3-b]pyridine (J) (162.5 mg, 55%).

Synthesis of N-(6-(1H-pyrrolo[2,3-b]pyridine-4-yl)pyridin-2-yl)acetamine (compound 98)

To a solution of 6-(1-tosyl-1H-pyrrolo[2,3-b]pyridin-4-yl)pyridine-2-amine (Q) (43 mg, 0.12 mmol, 1 equiv.) in pyridine (1.5 mL), acetyl chloride (47 mg, 0.6 mmol, 5 equiv.) was added. The mixture was then stirred at room temperature for 16 h. After diluting the reaction mixture in ethyl acetate, the mixture was washed with water, dried over anhydrous Na$_2$SO$_4$ and then, the solvent was removed under reduced pressure. The crude material was dissolved in DMSO and purified by reversed phase HPLC, eluting with Acetonitrile/water/1% TFA mixtures, yielding N-(6-(1-tosyl-(1H-pyrrolo[2,3-b]pyridine-4-yl)pyridin-2-yl)acetamine (R). R was dissolved in methanol and treated with NaOMe 0.5 M(1.5 mL). The resulting mixture was warmed at 60° C. for 30 min. The crude was diluted in ethyl acetate, washed with saturated aqueous NaHCO$_3$, dried over anhydrous Na$_2$SO$_4$, followed by removal of the solvent under reduced pressure. The crude oil was dissolved in DMSO (2 mL) and purified by reversed phase HPLC, eluting with acetonitrile/water/1% TFA mixtures. The title compound (98) was isolated after removing the solvents using a liophilizer (vacuum and heat lead to decomposition of the sample). (2.4 mg, 8%).

The following compounds were prepared following the procedure described above:

N-(6-(1H-pyrrolo[2,3-b]pyridine-4-yl)pyridin-2-yl)benzamide (compound 100)(3.5 mg, 9%).

N-(6-(1H-pyrrolo[2,3-b]pyridine-4-yl)pyridin-2-yl)phenylacetamide (compound 99)(1.4 mg, 3.5%).

General procedure for synthesis of 2-(6-chloropyridin-2-yl)-2-methylpropanenitrile (U)

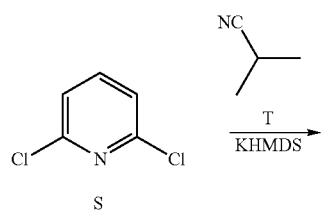

stirred for 15 min. This mixture was then added to a solution of 2,6-dichloropyridine (S)(4.39 g, 29.7 mmol, 2.5 equiv.) in toluene (10 mL) and the resulting solution was stirred at room temperature for 1 h. The reaction was quenched with a saturated solution of NH$_4$Cl, followed by aqueous NaHCO$_3$. The crude reaction was diluted in diethyl ether, washed with brine, dried over anhydrous Na$_2$SO$_4$ and the solvent was then removed under reduced pressure. The resulting material was purified by flash chromatography on silica gel, eluting with mixtures of dichloromethane/hexanes (2:1). The title compound U was isolated as a white solid (1.1 g, 51%). 1-(6-chloropyridin-2-yl)cyclopropanecarbonitrile (V), 1-(6-chloropyridin-2-yl)cyclopentanecarbonitrile (W), 1-(6-chloropyridin-2-yl)cyclohexanecarbonitrile (X), and ethyl 2-(6-chloropyridin-2-yl)-2-methylpropanoate (Y) were made following the procedure for 2-(6-chloropyridin-2-yl)-2-methylpropanenitrile (U).

General Procedure for Synthesis of 2-methyl-2-(6-(1-tosyl-1H-pyrrolo[2,3-b]pyridin-4-yl)pyridin-2-yl)propanetrile (Z)

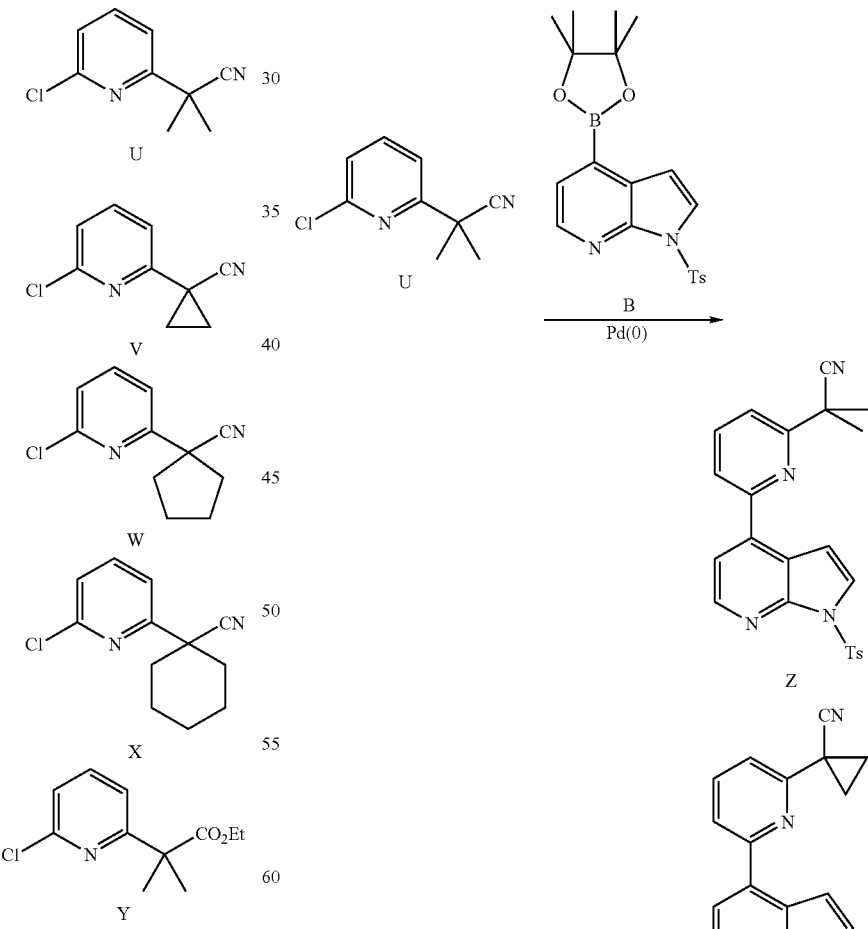

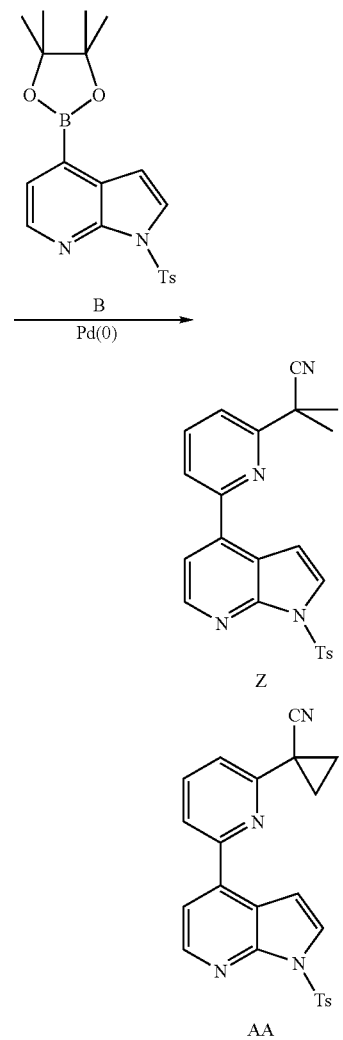

To a solution of isobutyronitrile (T) (830 mg, 12 mmol, 1 equiv.) in toluene (16 mL) at 0° C., a solution of KHMDS 0.5 M in toluene (26 mL, 13 mmol, 1.05 equiv.) was added. The resulting mixture was warmed to room temperature and cyclopentanecarbonitrile (BB), 1-(6-(1-tosyl-1H-pyrrolo[2,3-b]pyridin-4-yl)pyridin-2-yl)cyclohexanecarbonitrile (CC), ethyl 2-methyl-2-(6-(1-tosyl-1H-pyrrolo[2,3-b]pyridin-4-yl)pyridin-2-yl)propanoate (DD), and 2-(6-(1-tosyl-1H-pyrrolo[2,3-b]pyridin-4-yl)pyridin-2-yl)propan-2-ol (EE), were prepared as described for 2-methyl-2-(6-(1-tosyl-1H-pyrrolo[2,3-b]pyridin-4-yl)pyridin-2-yl)propanetrile (Z).

General Procedure for Synthesis of 2-(6-(1H-pyrrolo[2,3-b]pyridin-4-yl)pyridin-2-yl)-2-methylpropanetrile (compound 71)

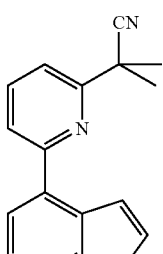
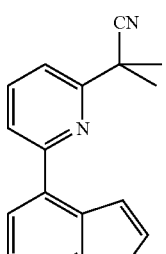

To a solution of 2-methyl-2-(6-(1-tosyl-1H-pyrrolo[2,3-b]pyridin-4-yl)pyridin-2-yl)propanetrile (Z) (29 mg, 0.07 mmol, 1 equiv) in methanol, sodium (20 mg) was added and the resulting mixture was warmed at 50° C. for 20 min. The mixture was quenched with TFA, the solvent was removed under reduced pressure, and the residue was dissolved in DMSO. The crude solution was then purified by reversed phase HPLC, eluting with acetonitrile/water/1% TFA mixtures, yielding the title compound 71 as a white solid (14.9 mg, 57%).

The following compounds were prepared following the procedure described above:

1-(6-(1H-pyrrolo[2,3-b]pyridin-4-yl)pyridin-2-yl)cyclopropanecarbonitrile (compound 101).

1-(6-(1H-pyrrolo[2,3-b]pyridin-4-yl)pyridin-2-yl)cyclopentanecarbonitrile (compound 102).

1-(6-(1H-pyrrolo[2,3-b]pyridin-4-yl)pyridin-2-yl)cyclohexanecarbonitrile (compound 103).

2-(6-(1H-pyrrolo[2,3-b]pyridin-4-yl)pyridin-2-yl)propan-2-ol (compound 123).

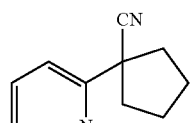
BB

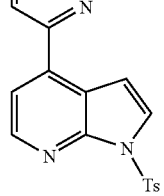
CC

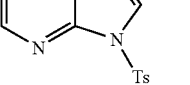
DD

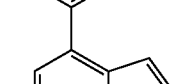
EE 2-(6-Chloropyridin-2-yl)-2-methylpropanenitrile (U) (45 mg, 0.25 mmol, 1 equiv.), 4-(4,4,5,5-tetramethyl-1,3,2-dioxaborolan-2-yl)-1-tosyl-1H-pyrrolo[2,3-b]pyridine (B) (100 mg, 0.25 mmol, 1 equiv.) and Pd(PPh$_3$)$_4$ (29 mg, 0.025 mmol), 0.1 equiv.) were suspended in a mixture of DME (2 mL) and aqueous Na$_2$CO$_3$ 2M (1 mL). The reaction mixture was exposed to microwave irradiation for 20 min at 160° C. The crude suspension was filtered, diluted in DMSO (1 mL) and purified by reversed phase HPLC, eluting with acetonitrile/water/1% TFA mixtures. After removing the solvent, the title compound Z was isolated as a white solid (29 mg, 28%). LC/MS: 3.7 min.; 416.9 ES+. 1-(6-(1-tosyl-1H-pyrrolo[2,3-b]pyridin-4-yl)pyridin-2-yl)cyclopropanecarbonitrile (AA), 1-(6-(1-tosyl-1H-pyrrolo[2,3-b]pyridin-4-yl)pyridin-2-yl)

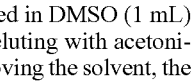
Z

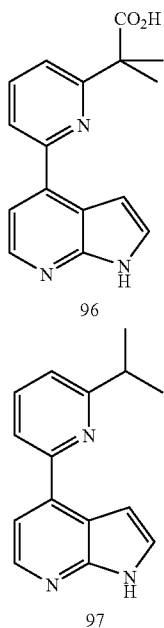

Synthesis of 2-(6-(1H-pyrrolo[2,3-b]pyridin-4-yl)pyridin-2-yl)-2-methylpropanoic acid (compound 96) and 4-(6-isopropylpyridin-2-yl)-1H-pyrrolo[2,3-b]pyridine (compound 97)

To a solution of 2-Methyl-2-(6-(1-tosyl-1H-pyrrolo[2,3-b]pyridin-4-yl)pyridin-2-yl)propanetrile (Z) (80 mg, 0.19 mmol, 1 equiv.) in THF (2 mL), a solution of aqueous HCl 6 M (5 mL) was added. The reaction mixture was then refluxed for 4 h. Concentrated $H_2SO_4$ (0.5 mL) was then added and the mixture was kept refluxing for 16 h. The solvent was the removed under reduced pressure and the crude oil was dissolved in DMSO and purified by reversed phase HPLC, eluting with acetonitrile/water/1% TFA mixtures, yielding acid 96 (5.4 mg, 10%) and 97 (9.3 mg, 20%).

Synthesis of 4-(6-(1H-pyrrolo[2,3-b]pyridin-4-yl)pyridin-2-yl)-4-methyl-3-oxopentanitrile (compound 125)

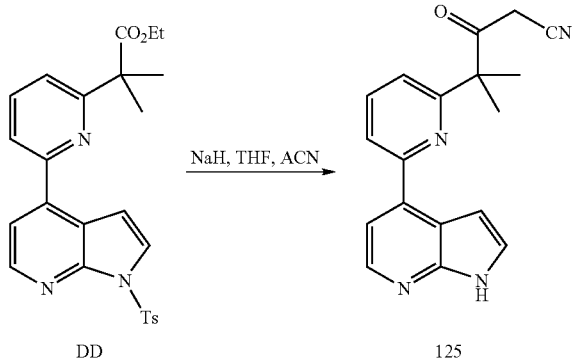 [SMILES: CCOC(=O)C(C)(C)c1cccc(-c2ccnc3c2ccn3S(=O)(=O)c2ccc(C)cc2)n1 ; CC(C)(C(=O)CC#N)c1cccc(-c2ccnc3[nH]ccc23)n1 ; "125" ; "DD"]

To a solution of ethyl 2-methyl-2-(6-(1-tosyl-1H-pyrrolo[2,3-b]pyridin-4-yl)pyridin-2-yl)propanoate (DD) (45 mg, 0.097 mmol, 1 equiv.) and acetonitrile (0.1 mL) in THF (5 mL) under an atmosphere of nitrogen, NaH 60% (15.6 mg, 0.39 mmol, 4 equiv.) was added. The resulting mixture was then warmed at 75° C. for 1.4 h. The reaction was quenched with methanol and the solvent was then removed under reduced pressure. The crude oil was dissolved in DMSO and purified by reversed phase HPLC, eluting with acetonitrile/water/1% TFA mixtures, yielding the title compound 125 as a white solid (10.5 mg, 34%).

Preparation of (S)-2-amino-N-(2,2,2-trifluoroethyl)propanamide hydrochloride (FF)

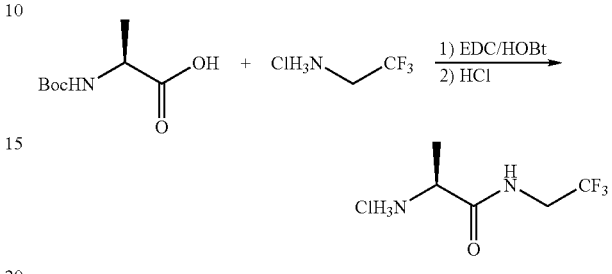

Boc-Ala-OH (14.24 g, 75.3 mmol), HOBT (1.35 g, 10 mmol), EDC (17.3 g, 90.4 mmol) and 2,2,2-trifluoroethylamine hydrochloride (10.2 g, 75.3 mmol) were dissolved in DMF (100 mL) using a water bath to maintain temperature. After the solids dissolved, triethylamine (20 mL, 150 mmol) was added and the resulting heterogeneous mixture stirred at room temperature overnight. The mixture was poured into ethylacetate (350 mL), washed with 1N HCl and brine then dried over $Na_2SO_4$. The solvent was removed under reduced pressure and the resulting oil dissolved in methanol (50 mL) and 2M HCl in ether (95 mL) then heated at 50° C. for 0.5 hours. The solvent was removed and the residue dried at 45° C. under vacuum to afford 12.2 g (78% yield) of the title compound (FF) as a white solid. FIA for $C_5H_9F_3N_2O$: 170.9 ES+.

Preparation of (S)-2-(6-bromopyridin-2-ylamino)-N-(2,2,2-trifluoroethyl)propanamide (GG)

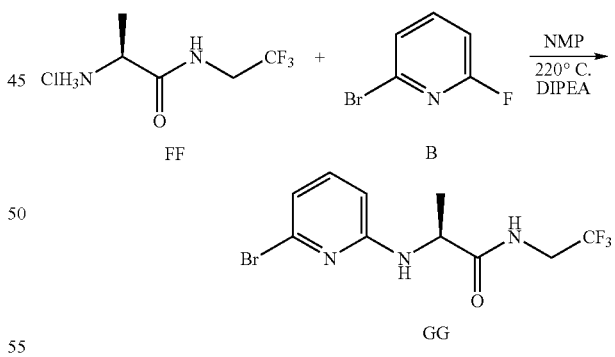

A solution of 2-bromo-6-fluoropyridine (1.23 g, 7 mmol) and (S)-2-amino-N-(2,2,2-trifluoroethyl)propanamide hydrochloride (FF) (1.44 g, 7 mmol) in NMP (10 mL) was treated with DIPEA (2.4 mL, 14 mmol) and heated at 220° C. for 40 min in the microwave. After complete reaction, the mixture was diluted with ethylacetate (100 mL) then washed with water (5×25 mL), brine (1×25 mL) then dried over $Na_2SO_4$. The solvent was removed and the residue purified with silica-gel chromatography using hexane:ethyl acetate (4:1) to afford 1.5 g (66% yield) of a white solid, GG. LC-MS: 2.8 min, 327.8 ES+; $^1$H NMR (500 MHz, dmso-d6) d 8.56 (m, 1H), 7.29 (t, 1H), 7.13 (d, 1H), 6.68 (d, 1H), 6.55 (d, 1H), 4.36 (m, 1H), 3.90 (m, 2H), 1.30 (d, 3H).

General Procedure for Synthesis of (S)-2-(2-chloropyrimidin-4-ylamino)-N-(2,2,2-trifluoroethyl)propanamide (HH)

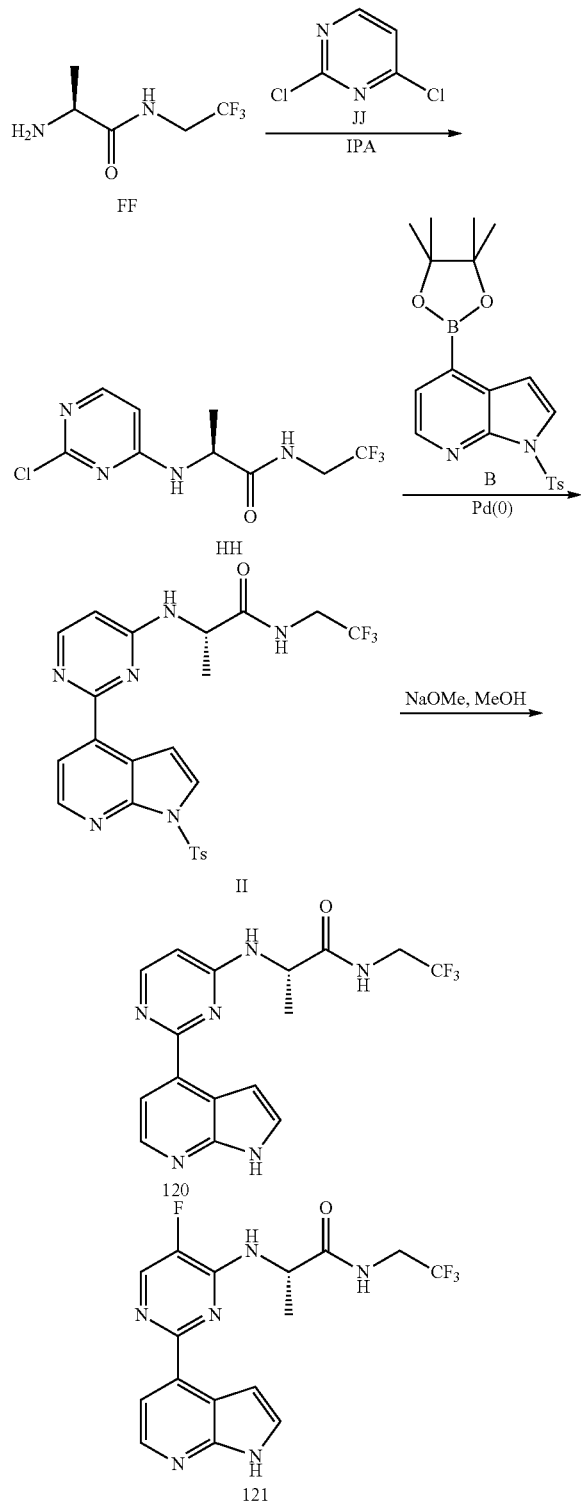

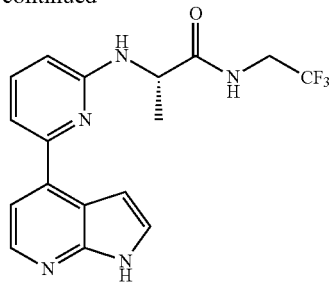

To a solution of (S)-2-amino-N-(2,2,2-trifluoroethyl)propanamide (FF) (1 g, 3.35 mol, 1 equiv.) in iso-propanol (10 mL), Huning's base (1.5 mL) was added, followed by 2,4-dichloropyrimidine (JJ). The resulting mixture was refluxed for 18 h. The reaction mixture was then diluted in ethyl acetate, washed with aqueous HCl 0.5 M and water, and dried over anhydrous $Na_2SO_4$. The crude oil was then purified by flash chromatography on silica gel, eluting with hexanes/ethyl acetate mixtures (100:0 to 0:100). The title compound HH was isolated as a white solid (600 mg, 63%).

General Procedure for Synthesis of (S)-2-(2-(1-tosyl-1H-pyrrolo[2,3b]pyridin-4-yl)pyrimidin-4-ylamino)-N-(2,2,2-trifluoroethyl)propanamide (II)

4-(4,4,5,5-tetramethyl-1,3,2-dioxaborolan-2-yl)-1-tosyl-1H-pyrrolo[2,3-b]pyridine (B) (72 mg, 0.18 mmol, 1 equiv.), S)-2-(2-chloropyrimidin-4-ylamino)-N-(2,2,2-trifluoroethyl)propanamide (HH)(50 mg, 0.18 mmol, 1 equiv.) and $Pd(PPh_3)_4$ (21 mg, 0.018 mmol), 0.1 equiv.) were suspended in a mixture of DME (2 mL) and aqueous $Na_2CO_3$ 2M (1 mL). The mixture was exposed to microwave irradiation for 20 min at 160° C. The resulting mixture was diluted in ethyl acetate and the solids removed by filtration. After removing the solvents under reduced pressure, the crude oil was purified by reversed phase HPLC, eluting with acetonitrile/water/1% TFA mixtures, yielding the title compound II (50 mg, 53%).

(S)-2-(5-fluoro-2-(1-tosyl-1H-pyrrolo[2,3b]pyridin-4-yl) pyrimidin-4-ylamino)-N-(2,2,2-trifluoroethyl)propanamide (LL) and (S)-2-(6-(1-tosyl-1H-pyrrolo[2,3b]pyridin-4-yl) pyridin-4-ylamino)-N-(2,2,2-trifluoroethyl)propanamide (MM) were synthesized using the procedure described above.

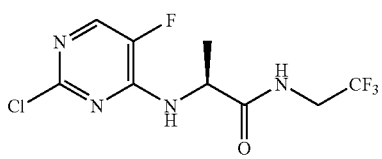

KK (S)-2-(2-chloro-5-fluoropyrimidin-4-ylamino)-N-(2,2,2-trifluoroethyl)propanamide (KK) was synthesized using the procedure above.

General Procedure for Synthesis of (S)-2-(2-(1H-pyrrolo[2,3b]pyridin-4-yl)pyrimidin-4-ylamino)-N-(2,2,2-trifluoroethyl)propanamide (compound 120)

(S)-2-(2-(1-tosyl-1H-pyrrolo[2,3b]pyridine-4-yl)pyrimidin-4-ylamino)-N-(2,2,2-trifluoroethyl)propanamide (50 mg, 0.096 mmol, 1 equiv.) was dissolved in methanol (2 mL). A solution of sodium methoxide 0.5 M in methanol (1 mL) was then added and the resulting mixture was heated at 70° C. for 30 min. The reaction mixture was quenched with TFA, the solvent was removed under reduced pressure and the oil crude was then dissolved in DMSO and purified by reversed phase HPLC, eluting with acetonitrile/water/1% TFA mixtures, yielding the title compound 120 (17.4 mg, 37%).

The following compounds were prepared following the procedure described above:
(S)-2-(5-fluoro-2-(1H-pyrrolo[2,3b]pyridin-4-yl)pyrimidin-4-ylamino)-N-(2,2,2-trifluoroethyl)propanamide (compound 121). 8.9 mg.
(S)-2-(6-(1H-pyrrolo[2,3b]pyridin-4-yl)pyridin-2-ylamino)-N-(2,2,2-trifluoroethyl)propanamide (compound 122). 27.8 mg.

General Procedure for Synthesis of 5-chloro-N-cyclopentyl-1H-pyrrolo[2,3-b]pyridin-4-amine (compound 127)

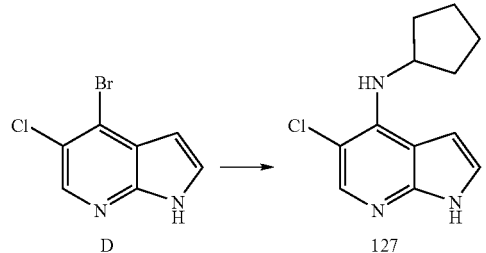

To 4-bromo-5-chloro-1H-pyrrolo[2,3-b]pyridine (D) was added cyclopentylamine (0.5 mL) in a sealed tube. The mixture was heated to 110° C. for 24-48 h. The mixture was concentrated. Preparative HPLC provided 5-chloro-N-cyclopentyl-1H-pyrrolo[2,3-b]pyridin-4-amine (127)(7.4 mg) as the TFA salt.

The following compounds were prepared following the procedure described above:

5-chloro-N-cyclohexyl-1H-pyrrolo[2,3-b]pyridin-4-amine (126) (3.8 mg).

4-(3,4-dimethoxyphenyl)-1H-pyrrolo[2,3-b]pyridine (compound 1)

4-choroazindole, (100 mg, 0.65 mmol), was dissolved in 1 mL DMF and 1 mL toluene. 3,4-dimethoxyphenylboronic acid, (130 mg, 0.71 mmol) and 65 μL of a 2M sodium carbonate solution were added. The solution was purged with nitrogen and tetrakis-triphenylphosphine palladium, (50 mg) was added. The mixture was heated to 100° C. under nitrogen for ~16 h. After cooling, the solvents were evaporated with a nitrogen stream and the residue purified by preparative thin layer chromatography (silica gel, eluent: 5% MeOH/DCM). The almost pure product was further purified by preparative HPLC affording 60 mg of 4-(3,4-dimethoxyphenyl)-1H-pyrrolo[2,3-b]pyridine, (TFA salt) as a pale yellow solid.

Compound A (2.0 g, 5.7 mmol), dipinacolborane (1.8 g, 7.125 mmol), potassium acetate (1.7 g, 17.1 mmol), and Pd(dppf)Cl$_2$ (0.142 g) were suspended in dioxane and flushed with nitrogen. The suspension was stirred at 90° C. under nitrogen overnight. The reaction was diluted with ethyl acetate and filtered over celite. The organic layer was washed with 10% citric acid, dried over MgSO$_4$, and concentrated. The product (compound B) was used as crude.

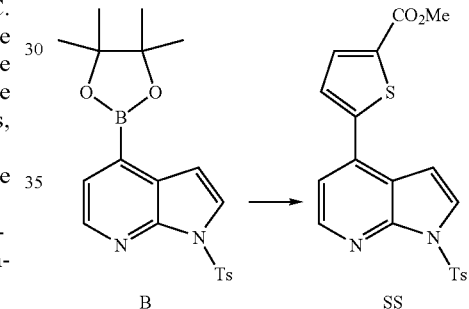

B (5.7 mmol), 2-bromo-5-methoxythiophene (1.8 g, 8.55 mmol), potassium carbonate (3.9 g, 28.5 mmol), and Pd(PPh$_3$)$_2$Cl$_2$ (0.200 g) were suspended in dioxane/water (1:1) and flushed with nitrogen. The suspension was stirred at 80° C. under nitrogen overnight. The reaction was diluted with ethyl acetate and filtered over celite. The organic layer was washed with saturated sodium bicarbonate, brine, dried over MgSO$_4$, and concentrated. Column chromatography (0-50% ethyl acetate/hexane) yielded a yellow solid, SS (0.570 g, 1.38 mmol, 24.3% yield).

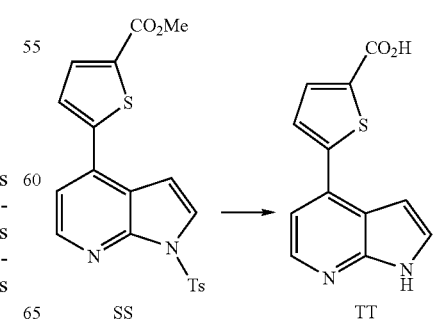

SS (0.57 g, 1.38 mmol) and lithium hydroxide (0.35 g, 8.29 mmol) were dissolved in THF:water (1:1) and microwaved for 10 minutes at 150° C. The reaction was concentrated, and the residue was diluted with water (20 mL) and acetic acid (2 mL). The precipitate was filtered and washed with water to yield TT (0.35 g, 1.43 mmol, >100% yield).

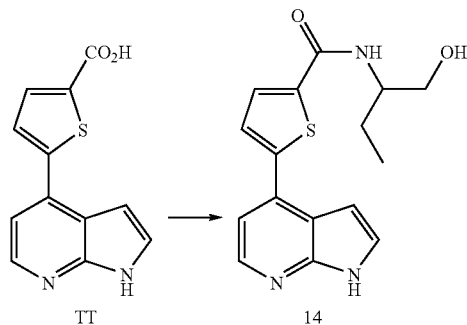

TT (0.030 g, 0.12 mmol), EDC (0.070 g, 0.37 mmol), HOBT (0.027 mg, 0.18 mmol), and (+/−) 2-amino-1-butanol (0.021 g, 0.24 mmol) were dissolved in DMF. The reaction was stirred for 2 hours under nitrogen at room temperature. Preparative HPLC afforded compound 14 (0.0315 g, 0.10 mmol, 83.3% yield).

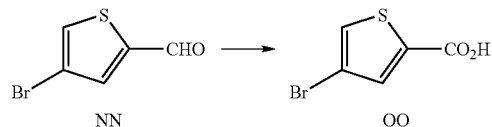

4-Bromothiophene-2-carboxylic acid

4-Bromothiophene-2-carbaldehyde (NN) (1.9 g, 10 mmol) was dissolved in 40 mL of t-BuOH and 4 mL of 2-methyl-2-butene. The reaction mixture was cooled to 0° C. and $NaClO_2$ (1.1 g, 12 mmol) dissolved in 12 mL of 1M $NaH_2PO_4$ was added. The reaction was let warm to room temperature and stirred for 5 hours. The reaction mixture was concentrated to about half the volume, and poured into 20 mL 1N NaOH and 50 mL $Et_2O$. The aqueous layer was made acidic with 6N HCl and extracted with EtOAc. This organic layer was dried over sodium sulfate and concentrated to obtain the product (OO) as a white solid, 1.75 g, 8.5 mmol, 85% yield. $^1H$ NMR 500 MHz (DMSO-$d_6$) 8.02 (1H, s), 7.78 (1H, s).

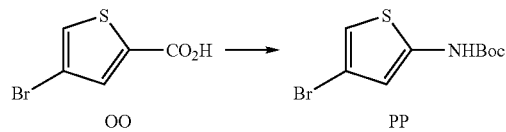

tert-Butyl 4-bromothiophen-2-ylcarbamate

4-Bromothiophene-2-carboxylic acid (O) (1.75 g, 8.5 mmol) was dissolved in 40 mL of t-BuOH. To this solution diphenylphosphoryl azide (2.8 g, 10.2 mmol) and triethylamine (1.4 mL, 10.1 mmol) were added. The reaction mixture was heated to reflux for 5 hours, cooled room temperature, and diluted with EtOAc. The organic layer was washed with 10% citric acid, saturated sodium bicarbonate and brine, and concentrated to an oil, which was purified by column chromatography on silica (0 to 25% EtOAc/hexanes) to give the product PP, 1.3 g, 4.7 mmol, 55%. $^1H$ NMR 500 MHz ($CDCl_3$) 6.96 (1H, br s), 6.83 (1H, s), 6.43 (1H, s), 1.54 (9H, s).

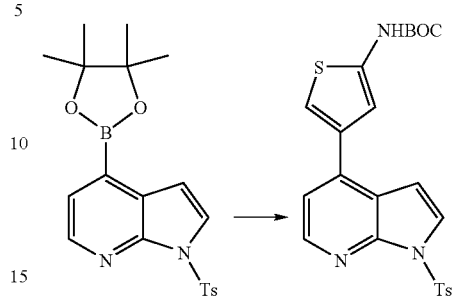

B (3.525 mmol), $Pd(Cl)_2(PPh_3)_2$ (0.12 g), $K_2CO_3$ (1.46 g, 10.6 mmol) and 3-bromo-5-(N—BOC)-aminothiophene (PP) (1.47 g, 5.29 mmol) were suspended in dioxane:water (1:1) and heated to 80° C. under nitrogen overnight. The reaction was diluted with ethyl acetate, and the organic layer was washed with saturated sodium bicarbonate, brine, dried over $Mg_2SO_4$, and concentrated. Column chromatography (0-50% ethyl acetate/hexane) afforded UU (0.697 g, 1.485 mmol, 42.1% yield).

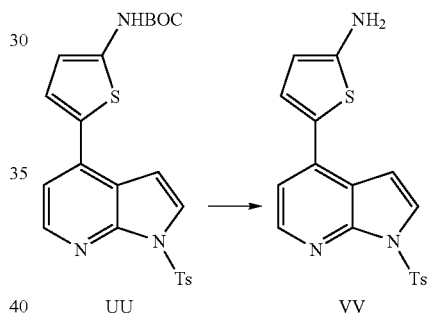

TFA (10 mL) was added slowly to a solution of UU (0.6965, 1.49 mmol) in methylene chloride. The reaction was stirred for 1.5 hours at room temperature. The solvent was evaporated, and the residue was dissolved in ethyl acetate. The organic layer was washed with saturated sodium bicarbonate, brine, dried over $MgSO_4$, and concentrated to yield VV (0.568 g, 1.5 mmol, 100% yield).

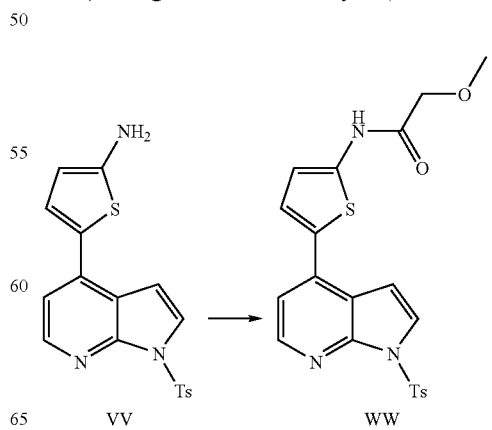

VV (0.050 g, 0.13 mmol), EDC (0.074 g, 0.39 mmol), HOBt (0.029 g, 0.195 mmol), and 2-methoxyacetic acid (0.023 g, 0.26 mmol) were dissolved in DMF and stirred under nitrogen overnight at room temperature. The reaction was diluted with ethyl acetate, washed with saturated sodium bicarbonate, brine, dried over MgSO$_4$, and concentrated. Column chromatography (0-20% methanol/methylene chloride) afforded WW (0.044 g, 0.10 mmol, 77% yield).

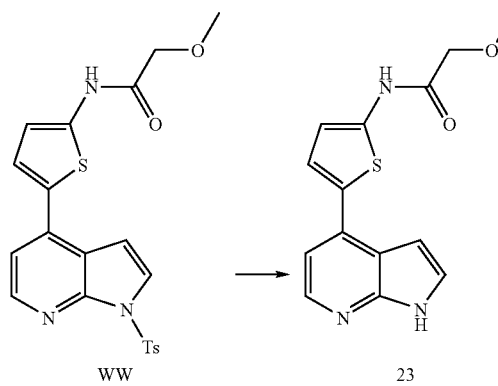

WW (0.044 g, 0.10 mmol) and lithium hydroxide (0.084 g, 0.40 mmol) were dissolved in THF:water (1:1) and microwaved at 150° C. for 10 minutes. The reaction was concentrated, and column chromatography (0-10% methanol/methylene chloride) afforded compound 23 (0.005 g, 0.02 mmol, 20% yield).

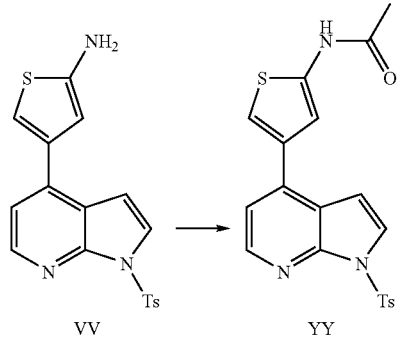 [SMILES: Cc1ccc(S(=O)(=O)n2ccc3c(-c4csc(N)c4)ccnc32)cc1 ; CC(=O)Nc1cc(-c2ccnc3c2ccn3S(=O)(=O)c2ccc(C)cc2)cs1 ; "VV" ; "YY"]

VV (0.075 g, 0.2 mmol) was dissolved in DMF under nitrogen. DIEA (0.003 mg, 0.02 mmol) and acetic anhydride (0.033 g, 0.3 mmol) were added, and the reaction was stirred overnight under nitrogen at room temperature. The reaction was diluted with ethyl acetate, and the organic layer was washed with saturated sodium bicarbonate, brine, dried over MgSO$_4$, and concentrated. Prep HPLC afforded YY (0.0104 g, 0.025 mmol, 12.6% yield).

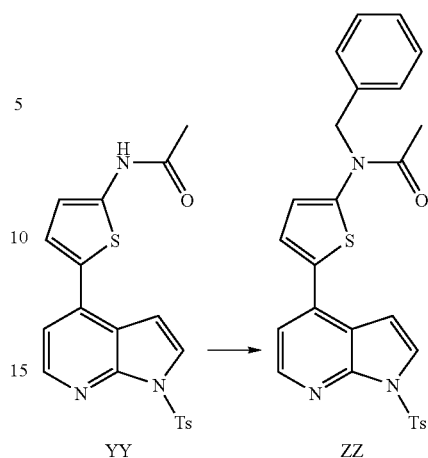

YY (0.067 g, 0.16 mmol) and potassium carbonate (0.044 g, 0.32 mmol) were suspended in DMF. Benzyl chloride (0.040 g, 0.32 mmol) was added to the suspension, and the reaction was stirred at 80° C. overnight. Sodium iodide (0.023 g, 0.16 mmol) was added to the reaction, and the reaction was stirred at 80° C. overnight or until completion. The reaction was diluted with ethyl acetate, and the organic layer was washed with water, brine, dried over MgSO$_4$, and concentrated. Column chromatography (0-35% ethyl acetate/hexane) afforded ZZ (0.043 g, 0.08 mmol, 50% yield).

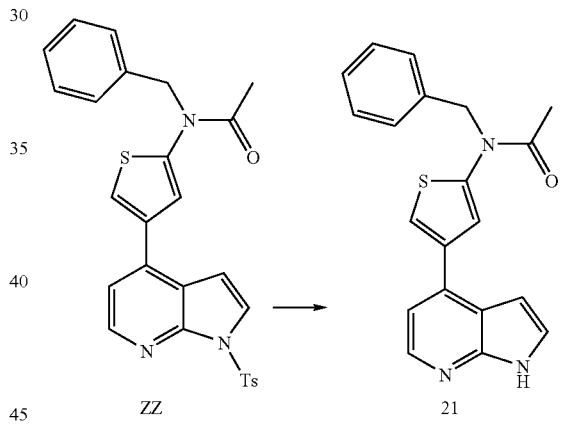

ZZ (0.043 g, 0.08 mmol) and lithium hydroxide (0.008 g, 0.32 mmol) was dissolved in THF:water (1:1). The reaction was microwaved at 150° C. for 10 minutes. The reaction was concentrated, and preparative HPLC afforded compound 21 (0.0058 g, 0.017 mmol, 20.9% yield).

General Procedure for Synthesis of 4-(7H-Pyrrolo[2,3-b]pyridin-4-yl)-1H-pyrrole-2-carboxylic acid amides (E')

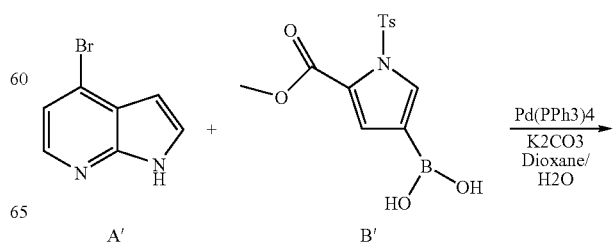

4-(7H-Pyrrolo[2,3-b]pyridin-4-yl)-1H-pyrrole-2-carboxylic acid amide (E')

To a vial with Compound D' (0.1 mmol) in DMF (1 mL), EDC (2 equivalent, 0.2 mmol) and HOBt (0.5 equivalent, 0.05 mmol) were added and the reaction mixture was stirred at room temperature for half an hour, amine (1.2 equivalent, 0.12 mmol) was added and the reaction mixture was stirred at room temperature for 2-3 hour. Reverse phase HPLC was used to purify the final compound.

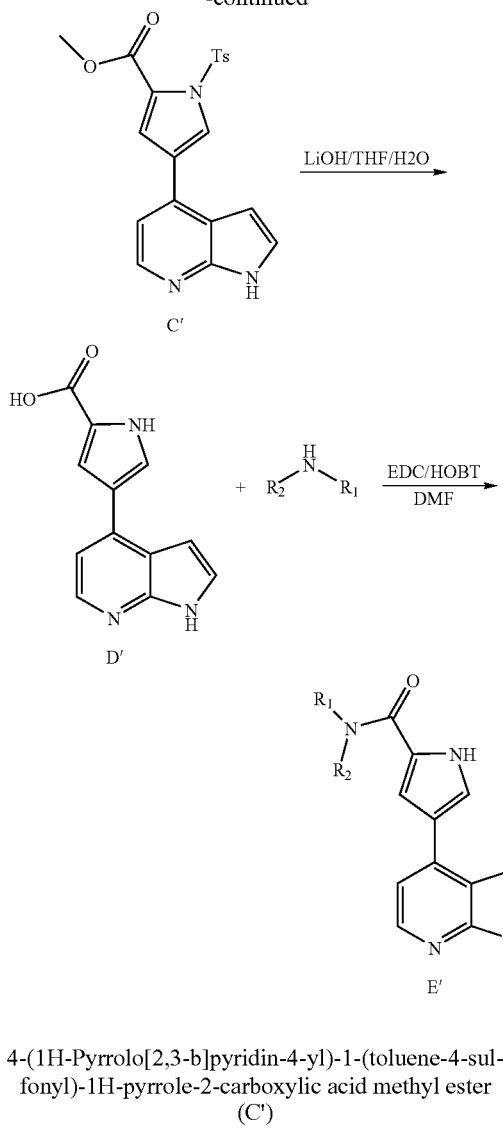
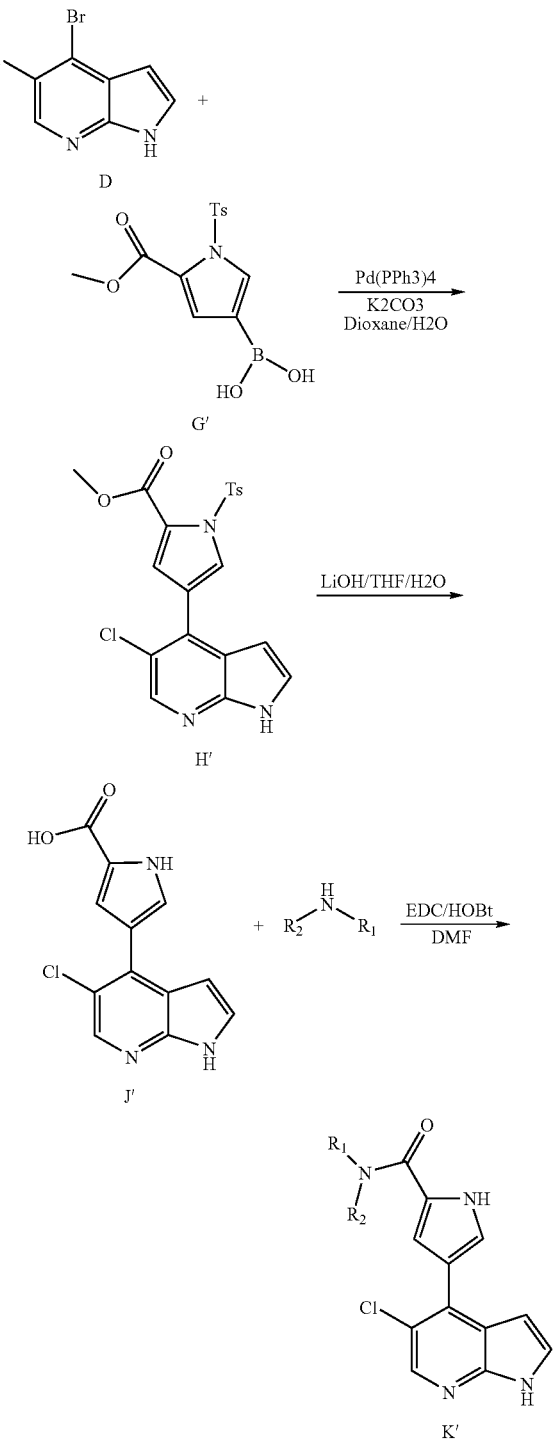

4-(1H-Pyrrolo[2,3-b]pyridin-4-yl)-1-(toluene-4-sulfonyl)-1H-pyrrole-2-carboxylic acid methyl ester (C')

Under $N_2$, Compound A' (1.65 g, 8.49 mmol) and compound B' (1.1 equivalent, 9.34 mmol) and $K_2CO_3$ (3.3 equivalent, 28 mmol) were dissolved into 9 mL of dioxane and 3 mL of $H_2O$ in a microwave, to this reaction mixture, catalytic amount of $Pd(Pph_3)_4$ was added and the tube was under microwave irradiation at 170° C. for 10 min. After cooled down the reaction mixture, the product crashed out and filtered off the solid, washed with $H_2O$ and $CH_3CN$ respectively to obtain title compound 3 quantitatively. MS+1=396.2.

4-(1H-Pyrrolo[2,3-b]pyridin-4-yl)-1H-pyrrole-2-carboxylic acid (D')

To a microwave tube with compound C' from previous step, LiOH (4 equivalent, 33.96 mmol) was added, followed by THF (8 mL) and $H_2O$ (4 mL), the reaction mixture was under microwave irradiation at 150° C. for 10 min. Poured reaction mixture into a beaker, and 2N HCl was added to the reaction mixture drop wise to adjust the pH of the solution to 4-5. In the process of acidify the solution, precipitation was formed, filtered off the solid and washed with $H_2O$ extensively and then small amount of $CH_3CN$. Dried to give title compound D' quantitatively. MS+1=228.1

4-(5-Chloro-1H-pyrrolo[2,3-b]pyridin-4-yl)-1-(toluene-4-sulfonyl)-1H-pyrrole-2-carboxylic acid methyl ester (H')

Under N$_2$, Compound D (1.95 g, 8.49 mmol) and compound G' (1.1 equivalent, 9.34 mmol) and K$_2$CO$_3$ (3.3 equivalent, 28 mmol) were dissolved into 9 mL of dioxane and 3 mL of H$_2$O in a microwave, to this reaction mixture, catalytic amount of Pd(Pph$_3$)$_4$ was added and the tube was under microwave irradiation at 170° C. for 10 min. After cooled down the reaction mixture, the product crashed out and filtered off the solid, washed with H$_2$O and CH$_3$CN respectively to obtain title compound H' quantitatively. MS+1=430.5.

4-(5-Chloro-1H-pyrrolo[2,3-b]pyridin-4-yl)-1H-pyrrole-2-carboxylic acid (J')

To a microwave tube with compound 9 from previous step, LiOH (4 equivalent, 33.96 mmol) was added, followed by THF (8 mL) and H$_2$O (4 mL), the reaction mixture was under microwave irradiation at 150° C. for 10 min. Poured reaction mixture into a beaker, and 2N HCl was added to the reaction mixture drop wise to adjust the PH of the solution to 4-5. In the process of acidify the solution, precipitation was formed, filtered off the solid and washed with H$_2$O extensively and then small amount of CH$_3$CN. Dried to give title compound J' quantitatively. MS+1=262.6

4-(5-Chloro-1H-Pyrrolo[2,3-b]pyridin-4-yl)-1H-pyrrole-2-carboxylic acid amide (K')

To a vial with Compound J' (0.1 mmol) in DMF (1 mL), EDC (2 equivalent, 0.2 mmol) and HOBt (0.5 equivalent, 0.05 mmol) were added and the reaction mixture was stirred at room temperature for half an hour, amine (1.2 equivalent, 0.12 mmol) was added and the reaction mixture was stirred at room temperature for 2-3 hour. Reverse phase HPLC was used to purify the final compound.

General procedure for synthesis 4-(5-Fluoro-1H-Pyrrolo[2,3-b]pyridin-4-yl)-1H-pyrrole-2-carboxylic acid amides (O')

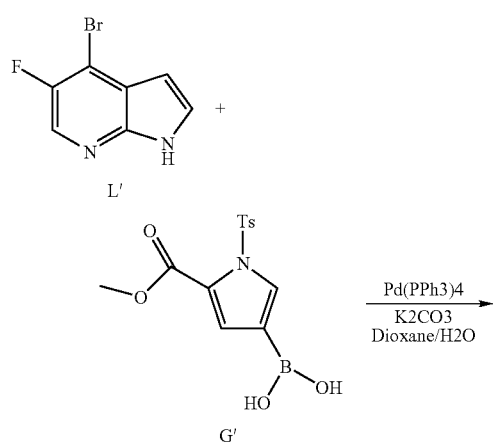

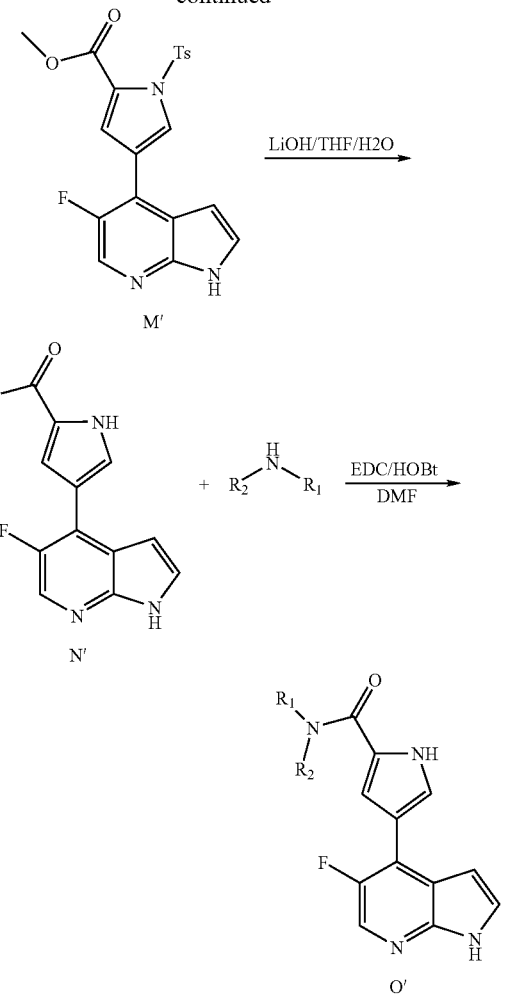

4-(5-Fluoro-1H-pyrrolo[2,3-b]pyridin-4-yl)-1-(toluene-4-sulfonyl)-1H-pyrrole-2-carboxylic acid methyl ester (M')

Under N$_2$, Compound L' (1.80 g, 8.49 mmol) and compound G' (1.1 equivalent, 9.34 mmol) and K$_2$CO$_3$ (3.3 equivalent, 28 mmol) were dissolved into 9 mL of dioxane and 3 mL of H$_2$O in a microwave, to this reaction mixture, catalytic amount of Pd(Pph$_3$)$_4$ was added and the tube was under microwave irradiation at 170° C. for 10 min. After cooled down the reaction mixture, the product crashed out and filtered off the solid, washed with H$_2$O and CH$_3$CN respectively to obtain title compound quantitatively. MS+1=414.2

4-(5-Fluoro-1H-pyrrolo[2,3-b]pyridin-4-yl)-1H-pyrrole-2-carboxylic acid (N')

To a microwave tube with compound M' from previous step, LiOH (4 equivalent, 33.96 mmol) was added, followed by THF (8 mL) and H$_2$O (4 mL), the reaction mixture was under microwave irradiation at 150° C. for 10 min. Poured reaction mixture into a beaker, and 2N HCl was added to the reaction mixture drop wise to adjust the pH of the solution to 4-5. In the process of acidifying the solution, precipitation was formed, filtered off the solid and washed with H$_2$O extensively and then small amount of CH₃CN. Dried to give title compound quantitatively. MS+1=246.2

4-(5-Fluoro-1H-Pyrrolo[2,3-b]pyridin-4-yl)-1H-pyrrole-2-carboxylic acid amide (O')

To a vial with Compound N' (0.1 mmol) in DMF (1 mL), EDC (2 equivalent, 0.2 mmol) and HOBt (0.5 equivalent, 0.05 mmol) were added and the reaction mixture was stirred at room temperature for half an hour, amine (1.2 equivalent, 0.12 mmol) was added and the reaction mixture was stirred at room temperature for 2-3 hour. Reverse phase HPLC was used to purify the final compound.

General Procedure for Synthesis of N-substituted-5-chloro-1H-pyrrolo[2,3-b]pyridin-4-amines Method C was used in the case of aliphatic and liquid amines (Scheme 3), while Pd-catalyzed coupling was used for solid and aromatic amines (Scheme 4).

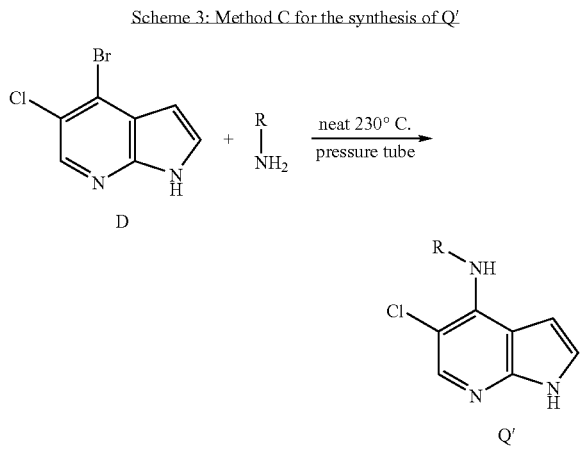

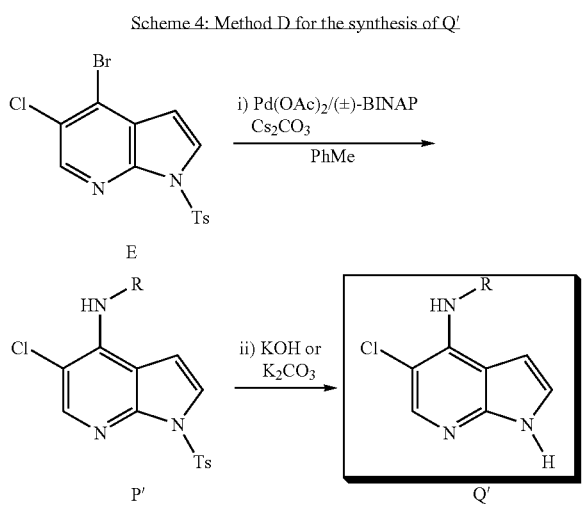

For the Pd coupling (Buchwald reaction) of E to P', various phosphines were employed, but the best results were obtained with (±)-BINAP and Cs₂CO₃ in toluene. The detosylated compounds Q' were obtained after treatment of compound P' with KOH or K₂CO₃ in MeOH.

Synthesis of S' from Chloroformates, Acid Chlorides and Sulfonyl Chlorides

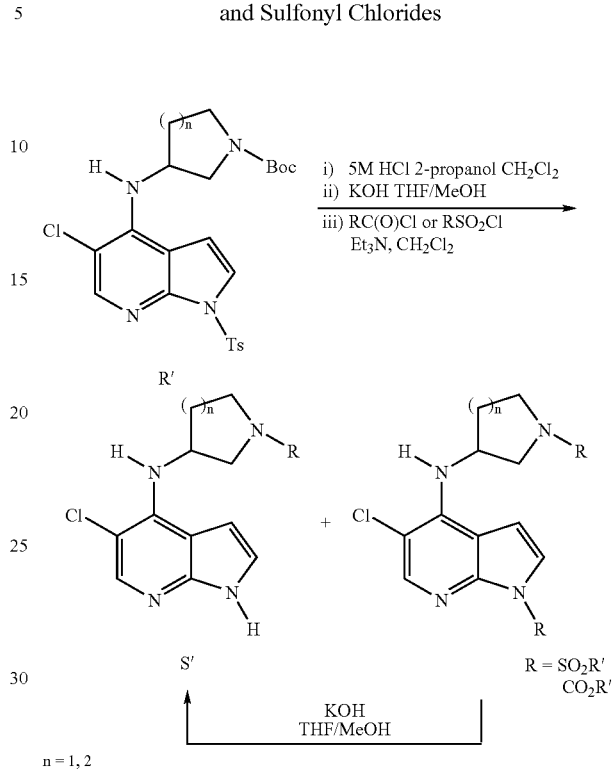

Amino piperidine and pyrrolidine derivatives (S') were obtained from the corresponding P' intermediate (R'), synthesized following the procedure described for Method B with 1-Boc-3-aminopiperidine or N-Boc-3-aminopyrrolidine and E. Successive deprotections of Tosyl and Boc groups were performed. If needed, the intermediate obtained after deprotection of Tosyl group could be purified by chromatography. Boc removal reaction was cleaner when the mixture was diluted in dichloromethane. Treatment with the corresponding acid chlorides gave then title compounds S' in mixture with disubstituted products. Those by-products were converted in S' by treatment with potassium hydroxide. The amide part on the indole nitrogen was hydrolysed selectively in presence of the amide on the piperidine/pyrrolidine nitrogen.

Due to this formation of disubstituted products, removal of the tosyl group after reaction with acid chlorides was preferred.

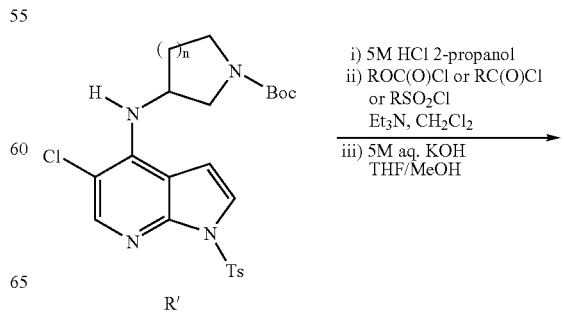

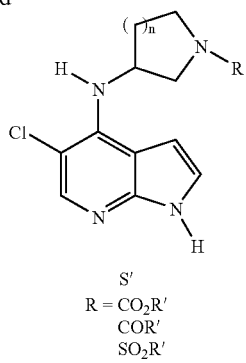

S'
R = CO$_2$R'
COR'
SO$_2$R' n = 1, 2

Synthesis of S' from Acids

Acids could be coupled after Boc deprotection in the presence of tosyl group on the indole nitrogen but attempts to remove this protecting group were unsuccessful. The newly introduced amides were hydrolyzed. Products from 3,3,3-trifluoropropionic acid and cyanoacetic acid were obtained after deprotection of tosyl and Boc protecting groups in this order and then using a coupling reagent.

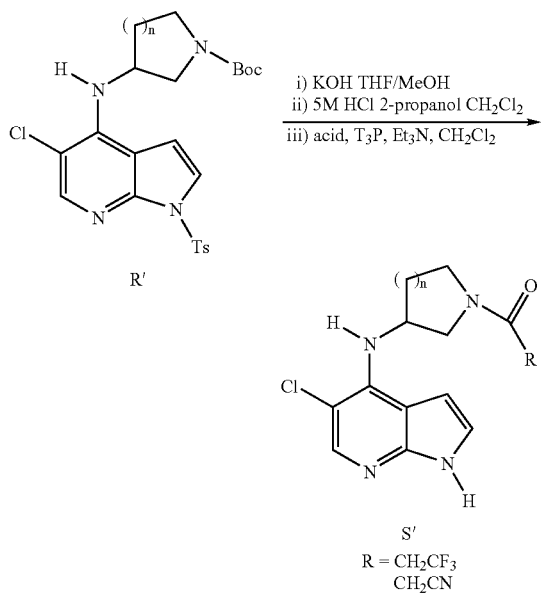

S'
R = CH$_2$CF$_3$
CH$_2$CN

Synthesis of 5-chloro-N-cyclopentyl-1H-pyrrolo[2,3-b]pyridin-4-amine (Compound 127)

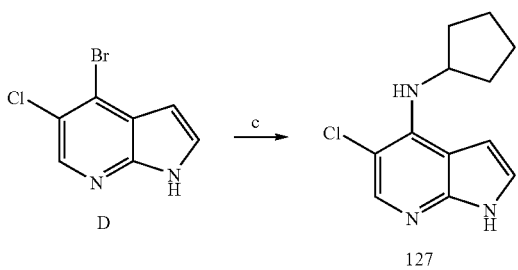

Method C: To D (20 mg, 0.086 mmol) was added amine (0.5 ml) in a pressure tube flushed with N$_2$. The mixture was heated to 230° C. (bath temperature) for 24 h. The mixture was concentrated. Preparative HPLC provided 5-chloro-N-cyclopentyl-1H-pyrrolo[2,3-b]pyridin-4-amine (7.4 mg) as the TFA salt.

Method D: Pd(OAc)$_2$ (3.9 mg, 0.015 mmol) and (±)-BINAP (20 mg, 0.052 mmol) were dissolved in nitrogen sparged toluene (0.5 mL) and stirred for 15 minutes under a nitrogen atmosphere. To this mixture were added in succession, toluene (1 mL), compound E (30 mg, 0.078 mmol), Cs$_2$CO$_3$ (127 mg, 0.39 mmol) and amine (5 eq; amino acid derivatives were added in solution of THF or Et$_2$O). The mixture was stirred at 70° C. for 24-48 h. After cooling to room temperature, celite was added and the solvent was removed in vacuo, the solid was poured on a column and the product obtained after elution with the appropriate solvent. The purification methods included a) Heptane:EtOAc 2:1 gradient pure EtOAc, b) 5% MeOH/CH$_2$Cl$_2$ and c) preparative HPLC.

Synthesis of Amino Acid Derivatives

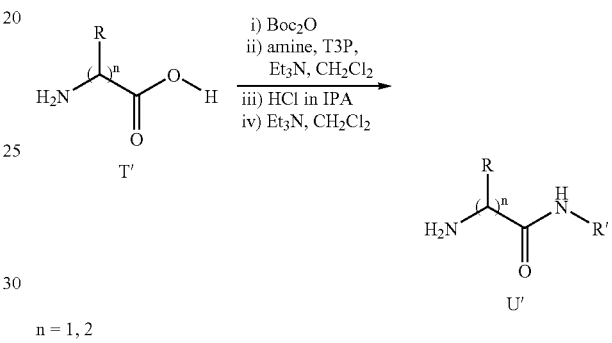

n = 1, 2

To a stirred solution of BocNH-acid (T', 1 eq) in CH$_2$Cl$_2$, (5 mL 1 mmol) at room temperature was added TBTU or T3P (1.3 eq) followed by Et$_3$N (2 eq) and the amine (1.2 eq). The solution was stirred at room temperature overnight then diluted with CH$_2$Cl$_2$ and H$_2$O. The layers were separated, and the organic layer washed with water, dried over sodium sulfate and the solvent removed in vacuo. The products (U') were purified by flash chromatography (CH$_2$Cl$_2$:MeOH 10:1 or Hept:EtOAc 1:1). Boc-NH—R compounds were treated with a standard solution 6N of HCl in IPA (1 mmol of compound in 4 mL), stirred 2 h at room temperature to remove Boc and isolated after the solvent was removed in vacuo. To a suspension of the amino acid salt in dichloromethane, was added triethylamine (3 eq) and the mixture was stirred for 10 min at room temperature. Water was added and the phases were separated. The organic layer was dried over sodium sulfate and the solvent was removed in vacuo. The amines were used without purification.

R' compounds were obtained in 90% yield from E with N-Boc-3-aminopyrrolidine or N-Boc-3-aminopiperidine using method D. If needed, compound R' could be separated from BINAP impurities by chromatography eluting with CH$_2$Cl$_2$:EtOAc 20:1.

Synthesis Using Acid Chlorides

A compound of formula S' (30 mg) was dissolved in 2 ml of 5 N HCl in 2-propanol at room temperature. After 1 hour the mixture was concentrated to dryness. The salts were then dissolved in dichloromethane (3 ml) and an excess of triethylamine (0.5 ml) was added. After 5 minutes the mixture was cooled to 0° C. and acid chloride (or chloroformate or sulfonyl chloride) was added (1.5 eq.). After 10 minutes at 0° C. the reaction was diluted with dichloromethane and saturated aq. NaHCO$_3$ solution was added. The organic layer was washed with brine, dried (Na$_2$SO$_4$), filtrated and concentrated. The crude mixture was dissolved in a 2:1 THF:MeOH mixture (3 ml) and 6N aq.KOH solution (0.6 ml) was added. After 1 h at room temperature, solvents were evaporated and the mixture was taken up in ethyl acetate, washed with brine, dried ($Na_2SO_4$), filtrated and concentrated. The products were purified with chromatography, eluting with a mixture of heptane:EtOAc to pure EtOAc, then washing the solid with EtOAc and methanol (2×).

added. After 40 minutes at 0° C. the reaction was diluted with dichloromethane and washed with brine, dried ($Na_2SO_4$), filtrated and concentrated. Compounds from trifluoropropionic acid were purified by chromatography eluting with pure EtOAc. Compounds from cyanoacetic acid were washed with EtOAc and methanol (3×).

General Procedure for Synthesis of 4-thiazole-1H-pyrrolo[2,3-b]pyridine derivatives

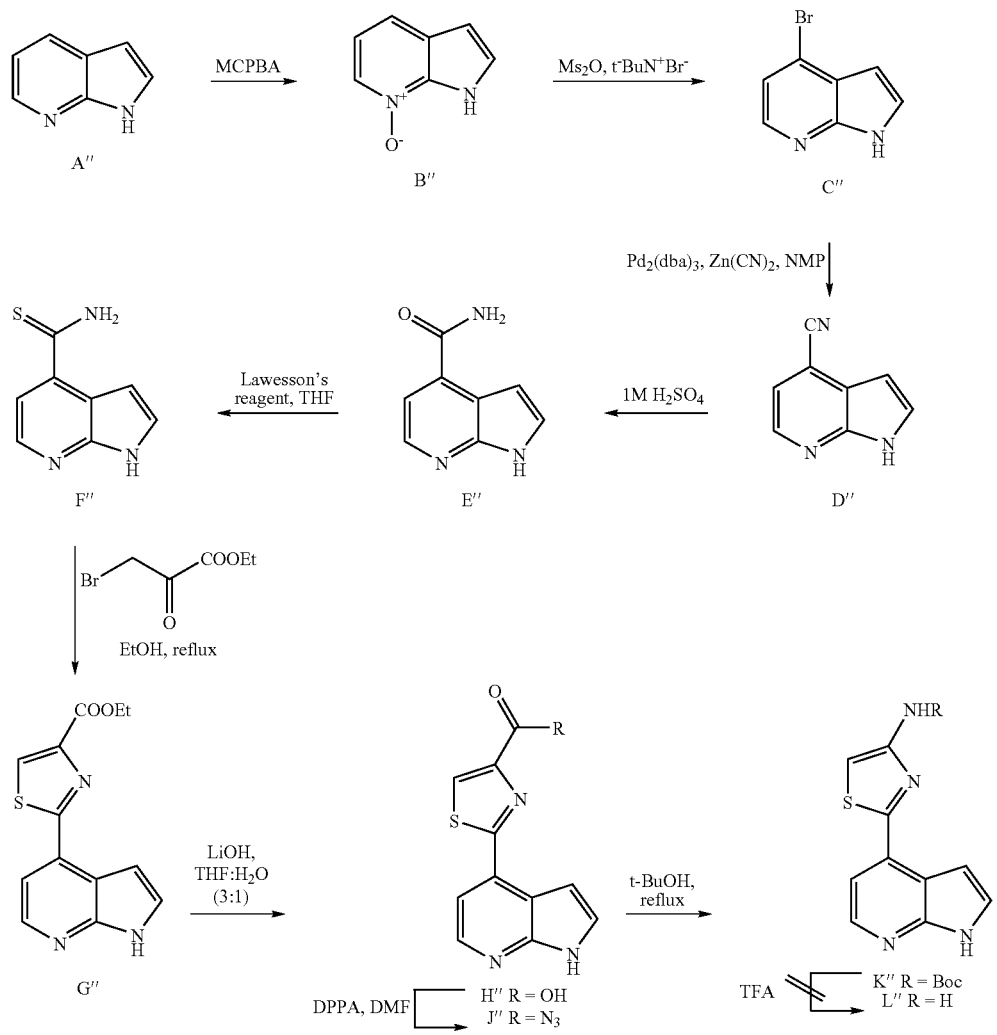

Synthesis Using Acids

A compound of formula S' (60 mg) was dissolved in a 2:1 THF:MeOH mixture (4 ml) and 6N aq KOH solution (0.8 ml) was added. After 1 h at room temperature, solvents were evaporated and the mixture taken up in ethyl acetate, washed with brine, dried ($Na_2SO_4$), filtrated and concentrated. The product could be purified by column chromatography (heptane:EtOAc 1:2 mixture). The product was then dissolved in dichloromethane (3 ml) and 5 N HCl in 2-propanol (0.7 ml) was added. After 1 h at room temperature the mixture was evaporated to dryness to give a white salt. The salt was then dissolved in dichloromethane (3 ml) and an excess of triethylamine (0.4 ml) was added. After 5 minutes the mixture was cooled to 0° C. and acid (1 eq) followed by T3P (propyl phosphonic acid anhydride, 50% in EtOAc, 1.3 eq) was A cold solution (0° C.) of compound A" (30 g, 0.253 mol) in DCM was added to 55% MCPBA in 800 mL DCM drop wise for 30 min, warmed to rt and stirred for 12 h. To the reaction mixture was added solid $NaHSO_3$, stirred at rt for 30 min, evaporated to dryness, diluted with water, adjusted to pH=8-9 by using sat aq. $Na_2CO_3$ solution and extracted with $CHCl_3$ (8×900 mL), dried ($Na_2SO_4$), filtered and concentrated to obtain compound B" as light pink solid. The crude compound B" was washed with 20% EtOAc in Hexane.

A cold solution (0° C.) of compound B" in DMF were added $Me_4NBr$ (92 g, 0.597 mol) and $Ms_2O$ (129.6 g, 0.745 mol) in DMF (100 mL) drop wise for 30 min, warmed to rt and stirred for 36 h. The reaction mixture was poured into water (200 ml), adjusted to pH=7 by using sat. aq. $NaHCO_3$ sol, the precipitated solid was filtered, washed with water and dried in vacuo to obtain compound C'''. The compound C''' was used as such for the next step without further purification.

A stirred solution of compound C''' (10 g, 0.507 mol) in NMP was added Zn(CN)$_2$ (35.7 g, 0.304 mol), purged with argon for 30 min, added dppf (7.04 g, 0.012 mol) and Pd$_2$(dba)$_3$ (9.28 g, 0.010 mol). The resulting mixture was again purged with argon for 30 min and heated at 140° C. for 2 h. The reaction mixture was cooled to 26° C., diluted with EtOAc and filtered through a celite bed. The filtrate was washed with water (3×500 ml) and NH$_4$Cl/aq. NH$_3$ soln./H$_2$O (1:2:1), brine solution, dried (Na$_2$SO$_4$), filtered and concentrated to obtain compound D'''. The compound D''' was purified by column chromatography (silica gel 60-120 mess silica gel, 60% EtOAc/Hexane).

The compound D''' was slowly treated with conc. H$_2$SO$_4$ and stirred for 4 h at rt. The reaction mixture was poured to ice cold water, adjusted to pH=7 (aq. NH$_3$ solution), extracted with acetone (6×500 ml) and co-evaporated with toluene to obtain compound E'''. The compound E''' was washed with hexanes several times and used as such for the next step.

To a stirred solution of compound E''' (14 g, 0.086 mol) in THF was added Lawesson's reagent at rt and heated at 50° C. for 2 h. The reaction mixture was poured to sat aq. Na$_2$CO$_3$ soln. (100 ml), extracted with EtOAc (3×300 ml), dried (Na$_2$SO$_4$), filtered and evaporated to obtain compound F''' as yellow solid. The crude F''' compound was washed with DCM and used as such for the next step.

A solution of F''' (8 g, 0.045 mol) in EtOH was treated with ethyl bromopyruvate (9.56 g, 0.049 mol) drop wise for 30 min and stirred at 70° C. for 2 h. The reaction mixture concentrated to half of its volume, solid precipitated out this time which was filtered, washed with EtOH and dried in vacuo to obtain compound G'''. The compound G''' was used as for the next step without further purification.

To a stirred solution of compound G''' in THF, water was added LiOH (3.68 g, 0.087 mol) at rt and stirred for 4 h at same temperature. The reaction mixture was concentrated to obtain residue which was diluted with water (50 ml), acidified with 2N aq. HCl solution, adjusted to pH=5-6, the precipitated solid was filtered, washed with water and dried (traces water were removed by co-evaporating with toluene) to obtain compound H'''. The compound H''' was washed with diethyl ether to obtain desired purity.

To a cold solution (0° C.) of H''' (5.2 g, 0.021 mol) in DMF were added Et$_3$N and DPPA over 30 min, warmed to rt and stirred for 1 h. The reaction mass was poured to water (100 ml), the precipitated solid was filtered was soluble in EtOAc organic layer was dried over sodium sulphate concentrated U/V. Purification was not considered necessary and directly used it for the next step.

A solution of J''' (5.2 g, 0.019 mol) in 'BuOH was stirred at 85° C. for 42 h. The crude compound K''' was purified by column chromatography (silica gel 100-200 mesh, MeOH/CHCl$_3$→1% MeOH/CHCl$_3$). The Boc group from K''' may be removed by standard procedures to obtain L'''.

2-(1H-Pyrrolo[2,3-b]pyridin-4-yl)-thiazole-4-carboxylic acid (2-cyano-ethyl)-(3,3,3-trifluoro-propyl)-amide (compound 405)

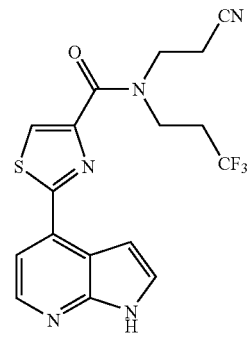 [SMILES: N#CCCN(CCC(F)(F)F)C(=O)c1csc(-c2ccnc3[nH]ccc23)n1]

Into 2 mL of dry pyridine was dissolved 60 mg (0.225 mMol) of 2-(1H-pyrrolo[2,3-b]pyridin-4-yl)-thiazole-4-carboxylic acid (H'''), along with 72 mg (0.367 mMol) of EDCI and 60 mg (0.367 mMol) of N(2-trifluoromethyl ethyl) amino-propronitrile. This reaction was heated in a microwave at 150° C. for 10 min at 300 W. The reaction was determined to be complete via LC and the solvent was evaporated under a stream of dry nitrogen. The crude residue was dissolved in 1 mL of DMSO and acidified with conc. HCl; the material was then purified on a Gilson liquid handler on C18 SiO$_2$ utilizing an eluent system of water, acetonitrile, and trifluoroacetic acid, 38 mg of a yellow solid was isolated after lyophilization of the collected fractions to give a 30% yield of the mono TFA salt.

Although certain exemplary embodiments are depicted and described above and herein, it will be appreciated that a compounds of the invention can be prepared according to the methods described generally above using appropriate starting materials by methods generally available to one of ordinary skill in the art.

Example 2

NMR and Mass Spectrometry of Compounds

Analytical data for certain compounds of the present invention was collected and recorded. For the compounds in Table 3, proton NMR was collected using a Bruker AMX 500 instrument and appropriate solvent. The LC/MS method used a Hypersil BDS C18 5 micron 2.1×50 mm column with a flow rate of 1.0 ml/min with an appropriate gradient. Mass spectrometer samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spectrometer analysis consisted of acetonitrile-water mixtures or TFA in some instances. Table 3 below depicts exemplary LC mass spectral data (LC/MS), retention time (RT) and $^1$H-NMR data for certain compounds of the present invention, wherein compound numbers in Table 3 correspond to the compounds depicted in Table 1 (empty cells indicate that the test was not performed):

TABLE 3

| Cmpd # | LC/MS | RT | NMR |
|---|---|---|---|
| 1 | 255.10 | 1.80 | CDCl3: 8.2(d, 1H), 7.5(m, 1H), 7.4(d, 1H), 7.3(d, 1H), 7.2(s, 1H), 7.0(d, 1H), 6.8(m, 1H), 3.93(s, 3H), 3.90(s, 3H). |

TABLE 3-continued

| Cmpd # | LC/MS | RT | NMR |
|---|---|---|---|
| 2 | 381.00 | 2.10 | 3.85(m, 2H), 5.15(t, 1H), 7.3(m, 4H), 7.4(s, 1H), 7.65(d, 1H), 7.7(d, 1H), 7.75(s, 1H), 7.9(s, 1H), 8.2(d, 1H) |
| 3 | 427.10 | 2.29 | H NMR(500MHz, CDCl3) 11.88(s, 1H), 11.49(s, 1H), 9.72(s, 1H), 8.25(d, 1H), 7.57(m, 2H), 7.25(m, 2H), 7.21(m, 2H) 7.12(m, 2H), 6.77(s, 1H), 3.70(s, 2H), 2.99(s, 3H). |
| 4 | 313.10 | 0.37 | H NMR(500MHz, DMSO-d6) 11.95(s, 1H), 8.86(s, 1H), 8.28(d, J=5.0Hz, 1H), 7.81(d, J=3.9Hz, 1H), 7.64(t, J=3.0Hz, 1H), 7.62(d, J=3.9Hz, 1H), 7.41(d, J=5.0Hz, 1H), 6.83(dd, J=3.5, 1.8Hz, 1H), 3.90(s, 4H), 3.23(s, 4H) |
| 5 | 301.90 | 1.60 | H NMR(500MHz, DMSO-d6) 11.8(s, 1H), 8.26(d, J=5.1Hz, 1H), 8.24(d, J=7.8Hz, 1H),, 7.86(dd, J=43.1, 2.0Hz, 1H),, 7.63(t, J=1.4Hz, 1H), 7.39(d, J=5.1Hz, 1H),, 6.86(dd, J=3.5, 1.7Hz, 1H), 4.00(m, 1H), 3.43(m, 2H),, 1.16(d, J=0.0Hz, 3H) |
| 6 | 327.90 | 1.99 | H NMR(500MHz, DMSO-d6) 11.95(s, 1H),, 8.69(t, J=5.8Hz, 1H), 8.27(d, J=5.1Hz, 1H), 7.91(d, J=3.9Hz, 1H), 7.82(d, J=3.9Hz, 1H), 7.63(t, J=2.9Hz, 1H), 7.40(d, J=5.1Hz, 1H), 6.87(s, 1H), 3.99(q, J=6.3Hz, 1H), 3.79(q, J=7.1Hz, 1H), 3.65(q, J=7.3Hz, 1H), 3.33(t, J=5.9Hz, 2H), 1.93(m, 1H), 1.83(m, 2H), 1.60(m, 1H) |
| 7 | 286.00 | 2.19 | H NMR(500MHz, DMSO-d6) 11.93(s, 1H), 8.57(s, 1H), 8.27(d, J=4.2Hz, 1H), 7.85(d, J=3.9Hz, 1H), 7.81(s, 1H), 7.62(s, 1H),, 7.39(s, 1H), 6.86(s, 1H), 3.23(q, J=6.6Hz, 2H), 1.55(q, J=7.2Hz, 2H), 0.91(t, J=7.4Hz, 3H) |
| 8 | 287.90 | 1.11 | H NMR(500MHz, DMSO-d6) 11.96(s, 1H), 8.60(t, J=5.5Hz, 1H), 8.28(d, J=5.1Hz, 1H), 7.87(d, J=3.9Hz, 1H), 7.82(d, J=3.9Hz, 1H), 7.64(t, J=1.5Hz, 1H), 7.41(d, J=5.1Hz, 1H), 6.87(dd, J=4.4, 0.9Hz, 1H), 3.53(t, J=6.2Hz, 2H), 3.34(q, J=6.0Hz, 2H) |
| 9 | 301.90 | 1.73 | H NMR(500MHz, DMSO-d6) 11.99(s, 1H), 8.68(t, J=5.4Hz, 1H), 8.28(d, J=5.1Hz, 1H), 7.88(d, J=4.0Hz, 1H), 7.84(d, J=0.0Hz, 1H), 7.64(t, J=3.0Hz, 1H), 7.42(d, J=5.1Hz, 1H), 6.88(dd, J=4.4, 0.9Hz, 1H), 3.48(m, 2H), 3.44(m, 2H), 3.29(s, 3H) |
| 10 | 327.90 | 1.91 | H NMR(500MHz, DMSO-d6) 12.00(s, 1H), 8.29(d, J=5.1Hz, 1H), 7.82(d, J=4.0Hz, 1H), 7.70(d, J=3.7Hz, 1H), 7.65(t, J=3.0Hz, 1H), 7.44(d, J=5.1Hz, 1H), 6.87(dd, J=3.5, 1.8Hz, 1H), 4.22(s, 1H), 3.81(s, 2H), 3.59(s, 1H), 3.48(s, 1H), 2.50(m, 4H) |
| 11 | 327.90 | 1.99 | H NMR(500MHz, DMSO-d6) 11.97(s, 1H), 8.28(d, J=5.1Hz, 1H), 7.81(d, J=4.0Hz, 1H), 7.70(d, J=3.7Hz, 1H), 7.64(t, J=3.0Hz, 1H), 7.43(d, J=5.1Hz, 1H), 6.86(dd, J=4.1, 0.8Hz, 1H), 4.22(s, 1H), 3.81(s, 2H), 3.59(s, 1H), 3.48(s, 1H), 1.90(m, 4H) |
| 12 | 341.90 | 2.46 | H NMR(500MHz, DMSO-d6) 11.99(s, 1H), 8.29(s, 1H), 7.82(s, 1H), 7.70(d, J=4.0Hz, 1H), 7.64(s, 1H), 7.44(s, 1H), 6.87(s, 1H), 4.34(s, 1H), 3.79(s, 2H),, 3.53(s, 1H), 3.41(s, 1H), 3.28(s, 3H) |
| 13 | 341.90 | 2.43 | H NMR(500MHz, DMSO-d6) 12.0(s, 1H), 8.29(d, J=5.1Hz, 1H), 7.82(d, J=4.0Hz, 1H), 7.70(d, J=4.0Hz, 1H), 7.65(t, J=3.0Hz, 1H), 7.44(d, J=5.2Hz, 1H), 6.87(dd, J=3.4, 1.8Hz, 1H), 4.34(s, 1H), 3.80(s, 2H), 3.54(s, 1H), 3.41(t, J=7.8Hz, 1H), 3.28(s, 3H) |
| 14 | 315.90 | 2.24 | H NMR(500MHz, DMSO-d6) 11.97(s, 1H), 8.28(d, J=5.1Hz, 1H), 8.16(d, J=8.5Hz, 1H), 7.93(d, J=3.9Hz, 1H), 7.82(d, J=3.8Hz, 1H), 7.64(s, 1H), 7.41(d, J=4.9Hz, 1H), 6.88(s, 1H), 3.46(ddd, J=15.9, 5.8Hz, 2H),, 1.68(m, 1H), 1.48(m, 1H), 0.90(t, J=7.4Hz, 3H) |
| 15 | 301.90 | 2.02 | H NMR(500MHz, DMSO-d6) 11.98(s, 1H), 8.29(d, J=12.6Hz, 1H), 8.25(d, J=8.0Hz, 1H), 7.91(d, J=4.0Hz, 1H), 7.83(d, J=3.8Hz, 1H), 7.64(s, 1H), 7.42(d, J=5.0Hz, 1H), 6.88(s, 1H), 4.01(m, 1H), 3.49(dd, J=7.8, 2.9Hz, 1H), 3.37(dd, J=10.7, 6.3Hz, 1H), 1.16(d, J=6.8Hz, 3H) |
| 16 | 329.90 | 2.15 | H NMR(500MHz, DMSO-d6) 11.94(s, 1H), 8.27(d, J=5.1Hz, 1H), 8.11(d, J=8.9Hz, 1H), 7.97(d, J=4.0Hz, 1H), 7.82(d, J=3.9Hz, 1H), 7.63(t, J=2.8Hz, 1H), 7.40(d, J=5.0Hz, 1H), 6.87(s, 1H), 3.78(m, 1H), 3.54(m, 2H), 1.94(m, 1H), 0.92(dd, J=12.4, 6.8Hz, 6H) |
| 17 | 314.00 | 2.76 | H NMR(500MHz, DMSO-d6) 11.92(s, 1H), 8.27(d, J=5.0Hz, 1H), 8.15(d, J=8.7Hz, 1H), 7.92(d, J=4.0Hz, 1H), 7.81(d, J=3.9Hz, 1H), 7.62(t, J=3.0Hz, |

TABLE 3-continued

| Cmpd # | LC/MS | RT | NMR |
|---|---|---|---|
| | | | 1H), 7.38(d, J=5.0Hz, 1H), 6.86(m, 1H), 3.77(m, 1H), 1.57(m, 2H), 1.49(m, 2H), 0.88(t, J=7.4Hz, 6H) |
| 18 | 335.90 | 1.76 | DMSOd6 12.2(bs, 1H); 8.3(m, 1H); 7.8(m, 3H); 7.3(dd, 1H); 7.1(d, 1H); 6.9(dd, 1H); 3.9(m, 1H); 3.8(m, 2H); 3.7(m, 1H); 3.6(m, 2H); 3.4(m, 2H); 1.9(m, 2H); 1.8(s, 3H) |
| 19 | 361.00 | 1.82 | DMSOd6 12.1(bs, 1H); 8.3(m, 1H); 7.8(m, 3H); 7.3(dd, 1H); 7.1(d, 1H); 6.9(dd, 1H); 4.1–3.7(m, 8H); 1.9(m, 2H) |
| 20 | 266.20 | 1.75 | DMSOd6 12.1(bs, 1H); 8.4(d, 1H); 7.7(bs, 3H); 7.65(bs, 1H); 7.5(d, 1H); 7.2(d, 1H); 7.0(bs, 1H); 6.9(bs, 1H); 3.1(d, 2H); 2.0(hept, 1H); 1.0(d, 6H) |
| 21 | 347.90 | 2.92 | |
| 22 | 350.00 | 1.97 | DMSOd6 12.1(bs, 1H); 8.4(d, 1H); 8.0(d, 1H): 7.8(dd, 1H); 7.6(m, 2H); 7.3(d, 1H); 7.0(m, 1H); 4.1(d, 4H); 3.2(bd, 2H); 2.1(s, 3H); 1.2(bs, 6H. |
| 23 | 287.90 | 1.84 | |
| 24 | 278.90 | 2.00 | (CD3OD) 1.7(m, 4H), 1.8(m, 2H), 2.1(m, 2H), 4.2(m, 1H), 6.8(d, 1H), 7.1(d, 1H), 7.3(d, 1H), 7.45(d, 1H), 7.65(d, 1H), 8(t, 1H), 8.4(d, 1H) |
| 25 | 292.90 | 3.80 | (CD3OD) 1.0(d, 3H), 1.2(m, 1H), 1.7(m, 3H), 1.9(m, 1H), 2.55(m, 1H), 2.9(m, 1H), 4.3(m, 2H), 6.8(d, 1H), 7(d, 1H), 7.2(d, 1H), 7.45(d, 1H), 7.55 9d, 1H), 7.6(t, 1H), 8.2(d, 1H) |
| 26 | 321.90 | 1.80 | H NMR(500MHz, DMSO-d6) d 11.93(s, 1H), 8.34(d, J=5.2Hz, 1H), 7.75(dd, J=8.4, 7.5Hz, 1H), 7.62–7.60(m, 2H), 7.38(d, J=7.4Hz, 1H), 7.00–6.96(m, 2H), 3.70(m, 2H), 3.60(s, 6H), 2.06(s, 3H) |
| 27 | 185.00 | 2.00 | (dmso-d6, 500MHz) 12.0(s, 1H), 8.24(d, 1H), 7.57(s, 1H), 7.14(d, 1H), 6.81(s, 1H), 6.75(s, 1H), 2.87(m, 2H), 2.61(m, 2H), 2.01(m, 2H) ppm |
| 28 | 219.00 | 3.50 | (dmso-d6, 500MHz) 11.9(s, 1H), 8.18(s, 1H), 7.50(m, 1H), 6.40(m, 1H), 6.10(m, 1H), 2.79(m, 2H), 2.57(m, 2H), 2.04(m, 2H) ppm |
| 29 | 233.00 | 3.70 | (dmso-d6, 500MHz) 11.8(s, 1H), 8.17(s, 1H), 7.48(m, 1H), 6.34(m, 1H), 5.76(m, 1H), 2.28(m, 2H), 2.23(m, 2H), 1.78(m, 2H), 1.71(m, 2H) ppm |
| 30 | 199.00 | 2.20 | (dmso-d6, 500MHz) 12.0(s, 1H), 8.23(d, 1H), 7.53(m, 1H), 7.11(d, 1H), 6.69(d, 1H), 6.43(m, 1H), 2.29(m, 2H), 1.78(m, 2H), 1.68(m, 2H) ppm |
| 31 | 237.90 | 1.90 | H NMR(500MHz, DMSO-d6) d 11.96(s, 1H), 8.32(d, J=5.1Hz, 1H), 7.58(t, J=2.9Hz, 1H), 7.39(t, J=8.0Hz, 1H), 7.28(d, J=5.1Hz, 1H), 7.10(s, 1H), 7.10(d, J=7.3Hz, 1H), 6.91(d, J=7.4Hz, 1H), 6.68(dd, J=3.4, 1.7Hz, 1H), 3.00(s, 6H) |
| 32 | 313.10 | 1.90 | |
| 33 | 335.10 | 2.30 | (DMSO-d6) 4.7(s, 2H), 6.7(d, 1H), 6.8(d, 1H), 7.2(d, 1H), 7.3(m, 2H), 7.45(m, 3H), 7.5(d, 1H), 7.6(t, 1H), 8.3(d, 1H) |
| 34 | 349.10 | 2.20 | (DMSO-d6) 3.05(t, 2H), 3.6(t, 2H), 6.7(bs, 1H), 6.95(bs, 1H), 7.3(m, 4H), 7.35(d, 1H), 7.4(d, 1H), 7.6(m, 2H), 8.4(d, 1H) |
| 35 | 269.20 | 1.40 | (DMSO-d6) 3.1(s, 3H), 3.6(t, 2H), 3.7(t, 2H), 6.7(d, 1H), 7.0(bs, 1H), 7.25(d, 1H), 7.6(m, 2H), 7.7(t, 1H), 8.35(s, 1H) |
| 36 | 295.20 | 1.40 | (DMSO-d6) 1.6(m, 1H), 1.8(m, 2H), 2.0(m, 1H), 3.5(m, 2H), 3.65(q, 1H), 3.7(q, 1H), 4.1(quintet, 1H), 6.8(bs, 1H), 7.0(bs, 1H), 7.2(d, 1H), 7.5(bs, 1H), 7.6(bs, 2H), 8.3(d, 1H) |
| 37 | 322.20 | 1.10 | (dmso-d6) 1.7(m, 1H), 1.9(2 × m, 3H), 2.2(m, 1H), 2.3(m, 1H), 2.7(d, 3H), 3.1(m, 1H), 3.3(m, 1H), 3.5(m, 3H), 6.6(d, 1H), 6.9(bs, 1H), 7.2(d, 1H), 7.5(m, 3H), 8.25(d, 1H) |
| 38 | 327.10 | 2.80 | (dmso-d6) 2.9(t, 2H), 3.95(t, 2H), 4.8(s, 2H), 6.9(d, 1H), 7.0(bs, 1H), 7.2(m, 4H), 7.4(d, 1H), 7.6(m, 2H), 7.75(t, 1H), 8.31(d, 1H) |
| 39 | 230.10 | 2.40 | |
| 40 | 285.20, 285.20 | 2.40, 2.00 | H NMR(500MHz, DMSO-d6) 11.90(s, 1H), 8.30(d, J=5.1Hz 1H), 7.57(t, J=2.9Hz, 1H), 7.29(d, J=5.1Hz, 1H), 7.03(s, 2H), 6.74(t, J=1.6Hz, 1H), 2.50(s, 9H), H NMR(500MHz, DMSO-d6) d 11.90(s, 1H), 8.30(d, J=5.1Hz 1H), 7.57(t, J=2.9Hz, 1H), 7.29(d, J=5.1Hz, 1H), 7.03(s, 2H), 6.74(t, J=1.6Hz, 1H), 2.50(s, 9H) |

TABLE 3-continued

| Cmpd # | LC/MS | RT | NMR |
|---|---|---|---|
| 41 | 263.00, 263.10 | 3.10, 2.50 | H NMR(500MHz, DMSO-d6) d 11.92(s, 1H), 8.32(d, J=5.0Hz, 1H), 7.98(d, J=2.0Hz, 1H), 7.83–7.77(m, 2H), 7.60(t, J=3.0Hz, 1H), 7.26(d, J=5.0Hz, 1H), 6.62(dd, J=3.5, 1.8Hz, 1H), H NMR(500MHz, DMSO-d6) d 11.92(s, 1H), 8.32(d, J=5.0Hz, 1H), 7.98(d, J=2.0Hz, 1H), 7.83–7.77(m, 2H), 7.60(t, J=3.0Hz, 1H), 7.26(d, J=5.0Hz, 1H), 6.62(dd, J=3.5, 1.8Hz, 1H) |
| 42 | 301.20, 301.20 | 2.90, 2.50 | H NMR(500MHz, DMSO-d6) d 11.92(s, 1H), 8.31(d, J=5.1Hz, 1H), 7.55(t, J=3.0Hz, 1H), 7.50–7.46(m, 3H), 7.43–7.40(m, 3H), 7.36–7.33(m, 3H), 7.25(d, J=5.1Hz, 1H), 6.55(dd, J=3.4, 1.8Hz, 1H), 5.23(s, 2H), H NMR(500MHz, DMSO-d6) d 11.92(s, 1H), 8.31(d, J=5.1Hz, 1H), 7.55(t, J=3.0Hz, 1H), 7.50–7.46(m, 3H), 7.43–7.40(m, 3H), 7.36–7.33(m, 3H), 7.25(d, J=5.1Hz, 1H), 6.55(dd, J=3.4, 1.8Hz, 1H), 5.23(s, 2H) |
| 43 | 252.10, 252.20 | 1.40, 1.60 | |
| 44 | 300.20 | 2.10 | (CDCl3) 10.21(s, 1H), 8.29(d, 1H), 7.36(d, 1H), 6.98(s, 1H), 6.64(s, 1H), 6.31(s, 1H), 4.17(br s, 2H), 3.71(br s, 2H), 2.67(br s, 2H), 1.52(s, 9H) |
| 45 | 200.00 | 0.35 | (d4-methanol) 8.42(d, 1H), 7.77(s, 1H), 7.56(d, 1H), 7.08(s, 1H), 6.64(br s, 1H), 4.04(br s, 2H), 3.59(dd, 2H), 3.01(br s, 2H) |
| 46 | 266.90 | 2.60 | H NMR(500MHz, DMSO-d6) d 11.85(s, 1H), 8.33–8.32(m, 2H), 8.06–8.05(m, 2H), 7.72(t, J=7.7Hz, 1H), 7.60–7.58(m, 1H), 7.24(d, J=4.9Hz, 1H), 6.59(dd, J=3.4, 1.9Hz, 1H), 4.37(q, J=7.1Hz, 2H), 1.35(t, J=7.1Hz, 3H) |
| 47 | 238.80 | 1.80 | H NMR(500MHz, DMSO-d6) d 13.10(s, 1H), 11.83(s, 1H), 8.31(d, J=4.8Hz, 2H), 8.04–8.01(m, 2H), 7.69(t, J=7.7Hz, 1H), 7.57(t, J=3.0Hz, 1H), 7.24(d, J=4.9Hz, 1H), 6.59(dd, J=3.4, 1.8Hz, 1H) |
| 48 | 248.00 | 2.80 | (500MHz, dmso-d6) 12.1(s, 1H), 8.36(s, 1H), 8.20(dt, 1H), 7.67(m, 1H), 7.61(m, 1H), 7.32(m, 1H), 6.31(m, 1H) ppm. |
| 49 | 224.80 | 1.60 | H NMR(500MHz, DMSO-d6) d 11.75(s, 1H), 8.28(d, J=4.9Hz, 1H), 7.73(s, 1H), 7.63(d, J=7.7Hz, 1H), 7.53(t, J=3.0Hz, 1H), 7.50(t, J=7.6Hz, 1H), 7.40(d, J=7.6Hz, 1H), 7.17(d, J=4.9Hz, 1H), 6.62(dd, J=3.4, 1.9Hz, 1H), 5.26(t, J=5.8Hz, 1H), 4.61(d, J=5.8Hz, 2H) |
| 50 | 213.10 | 1.80 | DMSO 7.0(t, 1H), 7.2(dd, 1H), 7.6(m, 2H), 8.1(dd, 1H), 8.2(q, 1H), 8.35(d, 1H) |
| 51 | 281.20 | 1.30 | DMSO 1.9(m, 1H), 2.1(m, 1H), 3.6(m, 2H), 4.4(m, 1H), 6.6(m, 1H), 7.1(m, 1H), 7.25(d, 1H), 7.65(m, 2H), 7.7(t, 1H), 8.3(d, 1H) |
| 52 | 267.20 | 2.00 | DMSO 1.2(t, 6H), 3.6(q, 4H), 6.6(d, 1H), 6.95(m, 1H), 7.25(d, 1H), 7.6(m, 3H), 8.35(d, 1H) |
| 53 | 359.10 | 2.01 | DMSO 1.9(dm, 2H), 3.1(s, 3H), 3.7(m, 2H), 4.65(m, 1H), 6.7(d, 1H), 7.0(bs, 1H), 7.15(t, 1H), 7.3(m, 5H), 7.7(bs, 2H), 7.8(t, 1H), 8.3(d, 1H) |
| 54 | 348.20 | 1.70 | DMSO 1.4(m, 2H), 1.8(m, 2H), 2.1(m, 2H), 3.05(m, 2H), 3.25(m, 1H), 3.3(m, 2H), 3.5(m, 1H), 3.6(m, 1H), 3.7(m, 1H), 4.6(m, 1H), 6.6(d, 1H), 6.75(m, 1H), 7.15(d, 1H), 7.45(d, 1H), 7.6(t, 1H), 7.8(t, 1H), 8.3(d, 1H), 9.75(bs, 1H) |
| 55 | 345.20 | 2.00 | DMSO 3.1(s, 3H), 3.6(m, 2H), 3.9(m, 2H), 4.95(m, 1H), 6.7(d, 1H), 7.0(m, 1H), 7.2(m, 2H), 7.3(t, 2H), 7.4(d, 2H), 7.55(t, 1H), 7.6(d, 1H), 7.7(t, 1H), 8.3(d, 1H) |
| 56 | 316.20 | 1.50 | DMSO 3.2(s, 3H), 5.0(s, 2H), 6.8(m, 2H), 7.3(d, 1H), 7.5(d, 2H), 7.7(m, 2H), 8.1(d, 1H), 8.2(d, 1H), 8.5(d, 1H), 8.7(s, 1H) |
| 57 | 297.20 | 1.50 | DMSO 1.1(s, 6H), 3.5(s, 2H), 4.3(s, 2H), 6.8(m, 1H), 6.9(m, 1H), 7.2(d, 1H), 7.65(m, 3H), 8.3(d, 1H) |
| 58 | 359.10 | 2.10 | DMSO 3.7(m, 1H), 4.1(dd, 1H), 4.4(dd, 2H), 4.5(m, 1H), 6.7(d, 1H), 6.85(m, 6H), 7.1(bs, 1H), 7.25(d, 1H), 7.6(2t, 3H), 8.3(d, 1H) |
| 59 | 311.10 | 1.60 | DMSO weak OK |
| 60 | 345.10 | 2.00 | DMSO 4.5(s, 2H), 5.9(s, 2H), 6.7(bs, 1H), 6.85(m, 4H), 7.2(d, 1H), 7.5(t, 2H), 7.6(bs, 1H), 8.2(d, 1H) |
| 61 | 267.20 | 1.90 | DMSO 1.2(d, 6H), 2.9(s, 3H), 5.0(m, 1H), 6.7(d, 1H), 6.9(m, 1H), 7.2(d, 1H), 7.5(m, 2H), 7.65(t, 1H), 8.3(d, 1H) |
| 62 | 238.90 | 2.00 | H NMR(500MHz, CDCl3) d 10.15(bs, 1H), 8.27(d, J=0.0Hz, 1H), 7.67(s, 1H), 7.62(d, J=6.4Hz, 1H), 7.46(t, J=7.6Hz, 1H), 7.40–7.36(m, 2H), 7.22(d, J=5.3Hz, |

TABLE 3-continued

| Cmpd # | LC/MS | RT | NMR |
|---|---|---|---|
| | | | 1H), 6.69(d, J=3.6Hz, 1H), 4.50(s, 2H), 3.39(s, 3H) |
| 63 | 233.90 | 2.00 | H NMR(500MHz, DMSO-d6) d 11.93(s, 1H), 8.33(d, J=5.0Hz, 1H), 7.78(s, 1H), 7.74(d, J=7.8Hz, 1H), 7.62–7.58(m, 2H), 7.47(d, J=7.6Hz, 1H), 7.25(d, J=5.0Hz, 1H), 6.67(dd, J=3.5, 1.8Hz, 1H), 4.17(s, 2H) |
| 64 | 241.90 | 1.39 | (d4-methanol) 8.36(d, 1H), 7.71(s, 1H), 7.53(d, 1H), 7.06(d, 1H), 6.68(m, 1H), 4.40–4.36(m, 2H), 3.89 and 3.84(2t, 2H), 2.84 and 2.75(2m, 2H), 2.22, 2.19(2s, 3H) |
| 65 | 309.90 | 2.10 | (d4-methanol) 8.31(d, 1H), 7.65(d, 1H), 7.42(d, 1H), 6.96(dd, 1H), 6.58(2m, 1H), 4.38(brs, 2H), 3.92 and 3.85(2t, 2H), 3.66–3.54(m, 2H), 2.84 and 2.76(2 br s, 2H) |
| 66 | | | (d4-methanol) 8.14(d, 1H), 7.40(d, 1H), 7.04(d, 1H), 6.66(d, 1H), 6.38 and 6.34(2 br s, 1H), 4.31 and 4.25(2m, 2H), 4.00 and 3.95(2s, 2H), 3.94–3.73(m, 4H) |
| 67 | 247.14 | 3.87 | (500MHz, CD3OD) 8.16(s, 1H), 7.38(d, 1H), 6.37(d, 1H), 5.49(br s, 1H), 5.05(br s, 1H), 3.01(m, 1H), 1.80(m, 2H), 1.73(m, 2H), 11.62–1.50(complex m, 4H) ppm. |
| 68 | 247.14 | 3.82 | (500MHz, CD3OD) 8.19(s, 1H), 7.42(d, 1H), 6.45(d, 1H), 5.77(m, 1H), 2.90(m, 1H), 2.25(m, 2H), 2.02(m, 1H), 1.89(m, 1H), 1.74(m, 1H), 1.54(m, 1H), 0.81(d, 3H) ppm. |
| 69 | 261.10 | 4.11 | (500MHz, CD3OD) 8.18(s, 1H), 7.40(d, 1H), 6.38(d, 1H), 5.44(br s, 1H), 5.05(br s, 1H), 2.45(m, 1H), 1.85(m, 2H), 1.77(d, 2H), 1.68(d, 1H), 1.28(m, 5H) ppm. |
| 70 | 232.05 | 2.05 | (DMSO) 3.95(s, 3H), 6.55(m, 1H), 7.5(m, 1H), 7.9(s, 1H), 8.2(s, 1H), 8.3(s, 1H) |
| 71 | 263.17 | 2.04 | (DMSO) 1.8(s, 6H), 7.2(bs, 1H), 7.6(m, 3H), 8.1(m, 2H), 8.4(d, 1H) |
| 72 | 281.20 | 2.00 | |
| 73 | 331.16 | 2.05 | (DMSO) 3.8(s, 3H), 4.6(s, 2H), 6.7(bs, 1H), 6.9(d, 1H), 7.0(m, 3H), 7.2(t, 1H), 7.3(d, 1H), 7.5(m, 2H), 7.9(t, 1H), 8.4(d, 1H) |
| 74 | 209.79 | 1.18 | (CD3OD) 2.2(s, 3H), 6.2(d, 1H), 7.1(d, 1H), 7.4(m, 2H), 7.85(d, 1H), 8.3(d, 1H), 8.45(d, 1H) |
| 75 | 383.00 | 2.45 | (500MHz, dmso-d6) 12.0(s, 1H), 8.31(s, 1H), 7.63(br s, 1H), 7.56(s, 1H), 7.40(dd, 1H), 7.32(dd, 1H), 7.24(m, 2H), 6.81(m, 1H), 6.66(br, 1H), 6.34(dd, 1H), 3.51(m, 2H), 3.02(t, 2H) ppm |
| 76 | 370.10 | 1.92 | (500MHz, dmso-d6) 11.9(s, 1H), 8.29(s, 1H), 7.67(m, 1H), 7.54(s, 1H), 6.82(m, 2H), 6.33(m, 0.5H), 6.28(m, 0.5H), 3.83(t, 1H), 3.70(m, 2H), 3.62(m, 3H), 3.42(m, 1H), 3.38(m, 2H), 1.87(m, 1H), 1.86(s, 3H), 1.79(m, 1H)ppm |
| 77 | 303.06 | 1.73 | |
| 78 | 301.00 | 2.14 | (500MHz, dmso-d6) 12.0(s, 1H), 8.33(s, 1H), 7.66(br, 1H), 7.59(s, 1H), 6.82(br, 2H), 6.35(s, 1H), 3.12(d, 2H), 1.88(m, 1H), 0.91(d, 6H) ppm |
| 79 | 299.00 | 1.94 | (500MHz, dmso-d6) 12.0(s, 1H), 8.32(s, 1H), 7.75(br, 1H), 7.55(s, 1H), 6.88(m, 1H), 6.70(br, 1H), 6.37(m, 1H), 3.46(m, 4H), 1.97(m, 4H) ppm |
| 80 | 219.10 | 2.00 | |
| 81 | 262.00 | 1.98 | |
| 82 | 235.00 | 3.06 | (500MHz, dmso-d6) 12.0(s, 1H), 8.30(s, 1H), 7.90(m, 1H), 7.74(m, 1H), 7.56(m, 1H), 7.45(m, 1H), 6.37(m, 1H) ppm |
| 83 | 330.05 | 2.00 | (500MHz, dmso-d6) 12.0(s, 1H), 8.31(s, 1H), 7.76(dd, 1H), 7.56(m, 1H), 6.93(d, 1H), 6.82(d, 1H), 6.32(m, 1H), 3.89(t, 2H), 3.31(m, 2H), 3.05(s, 3H), 2.75(s, 3H), 2.74(s, 3H) ppm |
| 84 | 238.17 | 1.39 | H NMR(500MHz, DMSO-d6) d 11.84(s, 1H), 8.79(s, 1H), 8.32(d, J=4.9Hz, 1H), 7.92(s, 1H), 7.83(d, J=7.7Hz, 1H), 7.64(t, J=7.7Hz, 1H), 7.60–7.55(m, 2H), 7.22(d, J=5.0Hz, 1H), 6.72(dd, J=3.4, 1.9Hz, 1H), 4.25(t, J=5.9Hz, 2H), 2.64(t, J=5.4Hz, 3H) |
| 85 | 252.13 | 1.40 | H NMR(500MHz, DMSO-d6) d 11.86(s, 1H), 9.68(s, 1H), 8.33(d, J=4.9Hz, 1H), 7.95(s, 1H), 7.88(d, J=7.8Hz, 1H), 7.67(t, J=7.7Hz, 1H), 7.61–7.58(m, 2H), 7.24(d, J=5.0Hz, 1H), 6.70(dd, J=3.4, 1.8Hz, 1H), 4.41(d, J=5.3Hz, 2H), 2.81(s, 3H), 2.80(s, 3H) |
| 86 | 264.13 | 1.50 | H NMR(500MHz, DMSO-d6) d 11.85(s, 1H), 8.98(s, 1H), 8.32(d, J=4.9Hz, 1H), 7.94(s, 1H), 7.83(d, J=7.6Hz, 1H), 7.65–7.57(m, 3H), 7.22(d, J=4.9Hz, 1H), 6.72(dd, J=3.4, 1.8Hz, 1H), 4.38(t, J=5.8Hz, 2H), 2.78(d, J=4.6Hz, 1H), 0.87–0.78(m, 4H) |

TABLE 3-continued

| Cmpd # | LC/MS | RT | NMR |
|---|---|---|---|
| 87 | 292.13 | 1.54 | H NMR(500MHz, DMSO-d6) d 11.85(s, 1H), 9.34(s, 1H), 8.32(d, J=4.9Hz, 1H), 7.94(s, 1H), 7.83(d, J=7.6Hz, 1H), 7.65–7.57(m, 3H), 7.22(d, J=4.9Hz, 1H), 6.72(dd, J=3.4, 1.8Hz, 1H), 4.42(d, J=5.2Hz, 2H), 3.39(d, J=11.9Hz, 2H), 2.95(q, J=10.5Hz, 2H), 1.85(d, J=14.4Hz, 2H), 1.71–1.59(m, 3H), 1.42–1.35(m, 1H) |
| 88 | 294.09 | 1.61 | H NMR(500MHz, DMSO-d6) d 11.85(s, 1H), 9.34(s, 1H), 8.32(d, J=4.9Hz, 1H), 7.94(s, 1H), 7.83(d, J=7.6Hz, 1H), 7.65–7.57(m, 3H), 7.22(d, J=4.9Hz, 1H), 6.72(dd, J=3.4, 1.8Hz, 1H), 4.42(d, J=5.2Hz, 2H), 3.98(bd, J=12.7Hz, 2H), 3.64(bt, J=12.0Hz, 2H), 3.34(bd, J=11.1Hz, 2H), 3.19(bs, 2H) |
| 89 | 307.11 | 1.38 | H NMR(500MHz, DMSO-d6) d 11.85(s, 1H), 8.32(d, J=4.9Hz, 1H), 7.94(s, 1H), 7.83(d, J=7.6Hz, 1H), 7.65–7.57(m, 3H), 7.22(d, J=4.9Hz, 1H), 6.72(dd, J=3.4, 1.8Hz, 1H), 4.0(bs, 2H), 3.30–2.95(bm, 8H), 2.8(s, 3H) |
| 90 | 247.14 | 3.87 | (500MHz, CD3OD) 8.14(s, 1H), 7.38(d, 1H), 6.43(d, 1H), 5.93(m, 1H), 3.03(m, 1H), 2.79(m, 1H), 2.17(m, 1H), 2.05(m, 1H), 1.23(d, 3H), 0.90(d, 3H)ppm. |
| 91 | 252.20 | 1.60 | |
| 92 | 266.20 | 1.70 | |
| 93 | 306.20 | 2.00 | |
| 94 | 308.20 | 1.70 | |
| 95 | 321.20 | 1.40 | |
| 96 | 281.90 | 2.00 | (CD3OD) 1.7(s, 6H), 7.4(d, 1H), 7.6(d, 1H), 7.7(d, 1H), 7.9(d, 1H), 8(t, 1H), 8.05(d, 1H), 8.45(d, 1H) |
| 97 | 237.90 | 2.30 | (CD3OD) 1.4(d, 6H), 3.2(m under methanol peak, 1H), 7.2(d, 1H), 7.55(d, 1H), 7.7(d, 1H), 7.8(d, 1H), 8(t, 1H), 8.1(d, 1H), 8.45(d, 1H) |
| 98 | 252.90 | 1.70 | (CD3OD) 2.2(s, 3H), 7.3(d, 1H), 7.6(d, 1H), 7.85(d, 2H), 7.9(t, 1H), 8.2(d, 1H), 8.4(d, 1H) |
| 99 | 328.90 | 2.50 | (CD3OD) 3.8(s, 2H), 7.2(t, 1H), 7.3(m, 3H), 7.35(m, 2H), 7.6(d, 1H), 7.8(m, 2H), 7.9(t, 1H), 8.2(d, 1H), 8.4(d, 1H) |
| 100 | 314.90 | 2.50 | (CD3OD) 7.4(d, 1H), 7.5(m, 2H), 7.6(m, 2H), 7.85(d, 1H), 7.9(m, 1H), 8(m, 3H), 8.35(d, 1H), 8.4(d, 1H) |
| 101 | 260.90 | 2.40 | (CD3OD) 1.8(m, 2H), 1.95(m, 2H), 6.9(d, 1H), 7.6(d, 1H), 7.75(d, 1H), 7.85(d, 1H), 8(m, 2H), 8.4(d, 1H) |
| 102 | 288.90 | 2.70 | (CD3OD) 2.0(m, 4H), 2.45(m, 4H), 7.35(d, 1H), 7.65(d, 1H), 7.75(d, 1H), 7.95(d, 1H), 8.1(t, 1H), 8.15(d, 1H), 8.45(d, 1H) |
| 103 | 302.90 | 2.80 | (CD3OD) 1.35(m, 1H), 1.8(m, 3H), 1.9(m, 2H), 2.1(td, 2H), 2.2(m, 2H), 7.4(d, 1H), 7.65(d, 1H), 7.7(d, 1H), 7.95(d, 1H), 8.05(t, 1H), 8.1(d, 1H), 8.4(d, 1H) |
| 104 | 197.20 | 1.30 | H NMR(500MHz, DMSO-d6) d 11.97(s, 1H), 9.30(s, 1H), 9.22(s, 2H), 8.36(d, J=4.9Hz, 1H), 7.63(t, J=3.0Hz, 1H), 7.36(d, J=4.9Hz, 1H), 6.69(dd, J=3.5, 1.8Hz, 1H) |
| 105 | 211.30 | 1.90 | H NMR(500MHz, DMSO-d6) d 11.88(s, 1H), 8.29(d, J=5.1Hz, 1H), 7.57(t, J=3.0Hz, 1H), 7.35(t, J=8.0Hz, 1H), 7.20–7.18(m, 3H), 6.88(dd, J=2.3, 0.7Hz, 1H), 6.87(t, J=1.7Hz, 1H) |
| 106 | 185.20 | 1.50 | |
| 107 | 252.20 | 1.70 | H NMR(500MHz, DMSO-d6) d 11.89(s, 1H), 10.09(s, 1H), 8.32(s, 8.31(s, 1H), 8.13(s, 1H), 7.64(s, 7.63(s, 1H), 7.58(s, 1H), 7.49(s, 7.43(s, 2H), 7.22(s, 7.21(s, 1H), 6.71(s, 6.70(s, 1H), 2.12(s, 3H) |
| 108 | 226.10 | 2.10 | |
| 109 | 237.20 | 2.50 | H NMR(500MHz, DMSO-d6) d 11.87(s, 1H), 8.31(d, J=5.0Hz, 1H), 7.63(s, 1H), 7.59(s, 1H), 7.57–7.56(m, 2H), 7.48(t, J=7.6Hz, 1H), 7.36(d, J=7.7Hz, 1H), 7.23(d, J=5.0Hz, 1H), 6.62(d d, J=3.4, 2.0Hz, 1H), 3.06–2.97(m, 1H), 1.28(d, J=6.9Hz, 6H) |
| 110 | 223.30 | 2.40 | H NMR(500MHz, DMSO-d6) d 11.87(s, 1H), 8.29(d, J=5.1Hz, 1H), 7.56(s, 2H), 7.50(d, J=7.7Hz, 1H), 7.32(d, J=7.7Hz, 1H), 7.21(d, J=5.1Hz, 1H), 6.65(dd, J=3.2, 1.8Hz, 1H), 2.36(s, 3H), 2.31(s, 3H) |
| 111 | 199.30 | 1.60 | H NMR(500MHz, DMSO-d6) d 12.01(s, 1H), 8.57(s, 1H), 8.24(d, J=5.4Hz, 1H), 8.20(s, 1H), 7.59(d, J=2.7Hz, 1H), 7.41(d, J=5.4Hz, 1H), 6.93(s, 1H), 3.95(s, 3H) |

TABLE 3-continued

| Cmpd # | LC/MS | RT | NMR |
|---|---|---|---|
| 112 | 223.20 | 2.30 | |
| 113 | 263.10 | 2.40 | H NMR(500MHz, DMSO-d6) d 11.92(s, 1H), 8.34(d, J=4.9Hz, 1H), 8.10(d, J=7.5Hz, 1H), 8.03(s, 1H), 7.86–7.80(m, 2H), 7.61(t, J=3.0Hz, 1H), 7.30(d, J=5.0Hz, 1H), 6.59(dd, J=3.5, 1.9Hz, 1H) |
| 114 | 210.20 | 1.30 | H NMR(500MHz, DMSO-d6) d 11.91(s, 1H), 8.32(s, 1H), 7.59(t, J=2.9Hz, 1H), 7.47(d, J=8.1Hz, 1H), 7.41(t, J=7.8Hz, 1H), 7.35(s, 1H), 7.30(d, J=6.1Hz, 1H), 7.20(d, J=5.1Hz, 1H), 7.10(d, J=7.9Hz, 1H), 7.02(d, J=6.9Hz, 1H), 6.67(dd, J=3.4, 1.6Hz, 1H) |
| 115 | 235.10 | 2.30 | |
| 116 | 253.20 | 2.30 | |
| 117 | 253.20 | 2.00 | (CDCl3) 10.48(br s, 1H), 9.00(br s, 1H), 7.99(d, 1H), 7.63(dd, 1H), 7.54(dd, 1H), 7.49(dd, 1H), 7.38(s, 1H), 6.41(s, 1H), 3.50(s, 3H) |
| 118 | 252.20 | 1.48 | (CDCl3) 10.76(br s, 1H), 8.49(s, 1H), 8.29(d, 1H), 7.48(dd, 1H), 7.46(s, 1H), 7.40(d, 1H), 7.20(s, 1H), 7.17(s, 1H), 6.41(s, 1H), 1.92(s, 3H) |
| 119 | 209.90 | 2.16 | (CDCl3) 10.43(br s, 1H), 8.37(s, 1H), 7.41(d, 1H), 7.28(dd, 1H), 7.26(d, 1H), 6.89(dd, 1H), 6.84(d, 1H), 6.53(s, 1H), 4.60(br s, 2H) |
| 120 | 365.00 | 1.80 | (CD3OD) 1.6(d, 3H), 3.9(m, 2H), 4.9(m, 1H), 6.9(d, 1H), 7.1(bs, 1H), 7.7(m, 2H), 8.25(d, 1H) |
| 121 | 383.00 | 1.80 | (CD3OD) 1.6(d, 3H), 3.9(m, 2H), 4.7(m, 1H), 7.5(d, 1H), 7.7(d, 1H), 7.7(d, 1H), 8.15(d, 1H), 8.35(m, 2H), 8.8(t, 1H) |
| 122 | 364.00 | 1.80 | (CD3OD) 1.5(d, 3H), 3.9(m, 2H), 4.5(q, 1H), 6.9(d, 1H), 7.2(d, 1H), 7.5(d, 1H), 7.7(m, 2H), 7.95(d, 1H), 8.4(d, 1H) |
| 123 | 253.90 | 1.60 | (CD3OD) 1.7(s, 6H), 7.4(d, 1H), 7.75(d, 1H), 7.9(d, 1H), 8.0(m, 3H), 8.5(d, 1H) |
| 124 | 212.90 | 1.90 | H NMR(500MHz, DMSO-d6) d 11.95(s, 1H), 8.28(d, J=5.4Hz, 1H), 7.54(t, J=3.15Hz, 1H), 7.05(d, J=5.4Hz, 1H), 6.36(m, 1H), 2.17(s, 6H) |
| 125 | 304.90 | 2.70 | (CDCl3) 1.7(s, 6H), 3.5(d, 2H), 7.1(bs, 1H), 7.5(d, 1H), 7.7(bs, 1H), 7.9(d, 1H), 8(d, 1H), 8.05(t, 1H), 8.3(d, 1H) |
| 126 | 250.10 | 1.90 | (500MHz, CD3OD) 8.13(s, 1H), 7.32(d, 1H), 6.80(d, 1H), 4.14(m, 1H), 2.15(m, 2H), 1.88(m, 2H), 1.75(m, 1H), 1.55(m, 4H), 1.34(m, 1H) |
| 127 | 236.10 | 1.80 | (500MHz, CD3OD) 8.12(s, 1H), 7.32(d, 1H), 6.96(d, 1H), 4.69(m, 1H), 2.20(m, 2H), 1.92–1.73(m, 6H) |
| 128 | 286.10 | 2.60 | (CDCl3) 10.55(br s, 1H), 8.30(d, 1H), 8.13(s, 1H), 7.87(s, 1H), 7.48(d, 2H), 7.13(s, 1H), 6.47(s, 1H), 1.95(s, 3H) |
| 129 | 244.10 | 2.50 | (d4-methanol) 8.34(s, 1H), 7.77(d, 1H), 7.67–7.59(m, 4H), 6.64(d, 1H) |
| 130 | 323.20 | 0.90 | H NMR(500MHz, DMSO-d6) d 11.67(s, 1H), 8.29–8.26(m, 2H), 8.16(d, J=4.1Hz, 1H), 7.96(d, J=5.0Hz, 1H), 7.59(d, J=6.1Hz, 1H), 7.50(t, J=2.9Hz, 1H), 7.28(s, 1H), 6.59(s, 1H), 4.54(s, 1H), 2.63(m, 1H), 1.36(d, J=7.0Hz, 3H), 0.58(m, 2H), 0.43(m, 2H) |
| 131 | 397.00 | 2.80 | (CD3OD) 1.7(s, 6H), 3.8(m, 2H), 7.6(m, 1H), 7.65(m, 1H), 8.2(d, 1H), 8.35(d, 1H), 8.4(m, 1H), 8.5(bt, 1H) |
| 132 | 429.00 | 1.90 | (CD3OD) 1.8(s, 6H), 3.8(m, 2H), 7.3(d, 1H), 7.7(d, 1H), 7.8(t, 1H), 7.95(d, 1H), 8.0(d, 1H), 8.05(t, 1H), 8.45(d, 1H), 8.6(d, 1H) |
| 133 | 185.20 | 1.80 | H NMR(500MHz, DMSO-d6) d 11.91(s, 1H), 8.52(s, 1H), 8.26(d, J=5.2Hz, 1H), 7.88(t, J=1.7Hz, 1H), 7.58(t, J=3.0Hz, 1H), 7.36(d, J=5.2Hz, 1H),, 7.18–7.18(m, 1H), 6.85(dd, J=3.4, 1.8Hz, 1H) |
| 134 | 415.00 | 1.70 | (CD3OD) 1.7(s, 3H), 3.9(2m, 2H), 5.2(q, 1H), 7.1(d, 1H), 7.7(d, 1H), 7.8(m, 2H), 7.9(d, 1H), 8.1(t, 1H), 8.45(d, 1H), 8.6(d, 1H) |

Table 4 below depicts exemplary LC/MS, RT and $^1$H-NMR data for certain compounds of the present invention, wherein compound numbers in Table 4 correspond to the compounds depicted in Table 2 (empty cells indicate that the test was not performed). For the compounds in Table 4, proton NMR was collected using as indicated.

TABLE 4

| Cmpd # | LC/MS | RT | NMR |
|---|---|---|---|
| 135 | 235.30 | 4.31 | (300MHz, CDCl3): 9.15(br. s, exchanged in D2O, 1H,), 8.39(s, 1H), 7.59–7.57(m, 2H), 7.38(dd, J=3.3, 2.4Hz, 1H), 7.25(m, 1H), 6.71(dd, J=3.3, 2.4Hz, 1H) |
| 136 | 219.30 | 6.01 | (300MHz, CDCl3): 9.20(br. s, exchanged with D2O, 1H), 8.34(s, 1H), 7.19(dd, J=1.8, 0.9Hz, 1H), 7.48(dd, J=3.6, 1Hz, 1H), 7.38(dd, J=3.6, 2.7Hz, 1H), 7.11(dd, J=3.6, 2.1Hz, 1H), 6.66(dd, J=3.3, 1.8Hz, 1H) |
| 137 | 285.20 | 6.75 | (300MHz, CDCl3): 9.15(br. s, exchanged with D2O, 1H), 8.42(br. s, 1H), 7.94–7.88(m, 2H), 7.71(s, 1H), 7.4–7.34(m, 3H), 6.74–6.72(m, 1H) |
| 138 | 269.20 | 6.12 | (300MHz, CDCl3): 8.95(br. s, exchanged with D2O, 1H), 8.39(s, 1H), 7.79(d, J=1Hz, 1H), 7.73–7.71(m, 1H), 7.65–7.62(m, 1H), 7.45–7.29(series of m, 3H), 7.20(dd, J=3.6, 2.1Hz, 1H) |
| 139 | 219.00 | 5.39 | (300MHz, CDCl3): 9.0(br. s, exchanged with D2O, 1H), 8.36(s, 1H), 7.71(dd, J=1.8, 0.6Hz, 1H), 7.46(br. d, J=4.2Hz, 1H), 7.37(dd, J=3.6, 2.4Hz, 1H), 7.10(dd, J=3.3, 1.8Hz, 1H), 6.65(dd, J=3.3, 1.8Hz, 1H) |
| 140 | 249.30 | 4.82 | (300MHz, CDCl3): 9.40(br. s, exchanged with D2O, 1H), 8.40(br. s, 1H), 7.39(d, J=3.3Hz, 1H), 7.37(dd, J=3.6, 2.7Hz, 1H), 6.90(dd, J=3.6, 0.9Hz, 1H), 6.75(dd, J=3.6, 1.8Hz, 1H), 1.47(s, 3H) |
| 141 | 269.10 | 4.80 | (300MHz, CDCl3): 9.70(br. s, exchanged with D2O, 1H), 8.40(s, 1H), 7.4(m, 1H), 7.35(d, J=3.9Hz, 1H), 7.05(d, J=3.9Hz, 1H), 6.69(dd, J=3.6, 1.5Hz, 1H) |
| 142 | 285.20 | 5.04 | (400MHz, CDCl3): 9.62(br. s, exchanged with D2O, 1H), 8.46(s, 1H), 7.97(d, J=8.2Hz, 1H), 7.64(s, 1H), 7.49(d, J=8.2Hz, 1H), 7.43–7.35(series of m, 3H), 6.23(dd, J=3.2, 1.9Hz, 1H) |
| 143 | 318.10 | 8.90 | (400MHz, CDCl3): 9.20(br. s, exchanged with D2O, 1H), 8.31(s, 1H), 7.52(dd, J=3.2, 2.0Hz, 1H), 7.33(dd, J=3.2, 2.4Hz, 1H), 6.40–6.37(m, 3H), 1.21(s, 9H) |
| 144 | 249.30 | 5.29 | (400MHz, CDCl3): 8.75(br. s, 1H), 8.35(s, 1H), 7.36(s, 1H), 7.34(t, J=3.2Hz, 1H), 7.14(s, 1H), 6.71(dd, J=3.2, 2.4Hz, 1H), 2.37(s, 3H) |
| 145 | 277.20 | 6.54 | (400MHz, CDCl3): 8.82(br. s, 1H), 8.40(s, 1H), 7.80(d, J=4.0Hz, 1H), 7.52(d, J=4.0Hz, 1H), 7.39(m, 1H), 6.68–6.66(m, 1H), 2.64(s, 3H) |
| 146 | 248.30 | 5.58 | (400MHz, CDCl3): 8.82(br. s, 1H), 8.39(s, 1H), 7.37(t, J=2.4Hz,, 1H), 6.21(dd, J=3.6, 2.0Hz, 1H), 2.31(s, 3H), 2.18(s, 3H) |
| 147 | 368.30 | 9.38 | (400MHz, CDCl3): 9.00(br. s, 1H), 8.34(d, J=8.0Hz, 1H), 8.33(s, 1H), 7.65(d, J=8.0Hz, 1H), 7.41(td, J=8.8, 1.6Hz, 1H), 7.35–7.33(m, 1H), 7.33(t, J=8.4Hz, 1H), 6.74(s, 1H), 6.39(dd, J=3.6, 2.0Hz, 1H), 1.15(s, 9H) |
| 148 | 408.00 | 3.77 | (400MHz, CDCl3): 8.92(br. s, 1H), 8.41(br. s, 1H), 8.09(d, J=9.6Hz, 1H), 7.96(br. dd, J=9.6, 1.2Hz, 2H), 7.89(s, 1H), 7.61(br. t, J=10.4Hz, 1H), 7.49(br. t, J=10.1Hz, 2H), 7.41–7.36(m, 2H), 7.32–7.31(m, 1H), 7.28–7.21(m, 1H), 6.25(dd, J=4.6, 2.5Hz, 1H) |
| 149 | 264.00 | 5.35 | 300MHz 1H NMR(CDCl3): δ 9.16(s, 1H); 8.00(s, 1H); 7.09(d, 1H); 6.54(d, 1H); 4.97(d, 1H); 4.16(m, 1H); 2.17(m, 2H); 1.58–1.69(m, 10H) |
| 150 | 262.00 | 4.70 | 300MHz 1H NMR(CDCl3): δ 9.05(s, 1H); 7.99(s, 1H); 7.08(d, 1H); 6.60(d, 1H); 4.80(d, 1H); 3.97(m, 1H); 2.40(m, 2H); 2.16(s, 1H); 1.96(m, 1H); 1.58(s, 2H); 1.23–1.37(m, 4H) |
| 151 | 306.00 | 7.07 | 300MHz 1H NMR(CDCl3): δ 7.99(s, 1H); 7.08(d, 1H); 6.51(d, 1H); 4.75(d, 1H); 3.86(dt, 1H); 2.16–2.26(m, 2H); 1.77–1.80(m, 2H); 1.17–1.30(m, 3H); 0.97(t, 9H); 0.75(d, 3H) |
| 152 | 342.00 | 4.93 | 300MHz 1H NMR(CDCl3): δ 8.89(s, 1H); 8.00(s, 1H); 7.34(s, 5H); 7.05(d, 1H); 6.78(d, 1H); 4.85(d, 1H); 4.57(m, 3H); 3.99(m, 1H); 2.35(m, 1H); 1.82–1.98(m, 5H) |
| 153 | 264.00 | 5.04 | 300MHz 1H NMR(CDCl3): δ 10.13(s, 1H); 8.01(s, 1H); 7.11(d, 1H); 6.51(d, 1H); 5.12 and 4.83(2 × d, 1H); 4.21 and 3.57(2 × m, 1H); 2.25 and 2.06(2 × m, 1H); 1.16–2.06(m, 8H); 0.97–1.06(2 × d, 3H) |
| 154 | 304.00 | 5.19 | 300MHz CDCl3-CD3OD: δ 8.02(s, 1H); 7.01(d, 1H); 6.90(d, 1H); 6.75(d, 1H); 6.64(dd, 1H); 5.80(d, 1H); 3.77(s, 3H); 3.71(s, 3H) |

TABLE 4-continued

| Cmpd # | LC/MS | RT | NMR |
|---|---|---|---|
| 155 | 315.00 | 1.72 | 300MHz CDCl3-CD3OD: δ 7.99(s, 1H); 7.45(m, 1H); 7.38(d, 1H); 7.27(t, 1H); 6.92(dd, 2H); 5.61(d, 1H); 2.34(q, 2H); 1.17(t, 3H) |
| 156 | 311.00 | 3.14 | 300MHz CDCl3-CD3OD: δ 8.05(m, 2H); 7.37–7.49(m, 3H); 7.33(, 1H); 7.16(dd, 1H); 6.98(d, 1H); 5.64(d, 1H) |
| 157 | 341.00 | 5.45 | 300MHz CDCl3: δ 10.91(s, 1H); 8.03(s, 1H); 7.23–7.40(m, 5H); 7.08(d, 1H); 6.44(d, 1H); 5.80(s, 2H); 4.24(m, 1H); 3.57(dd, 2H); 2.64(s, 3H); 2.35(m, 1H); 1.50–1.90(m, 1H) |
| 158 | 278.00 | 6.14 | 300MHz 1H NMR(CDCl3): δ 5.74(1H, dd, J=1.8, 3.3Hz), 6.74(1H, s), 7.10(2H, m), 7.23(2H, d, J=3.9Hz), 7.47(1H, dt, J=0.9, 7.8Hz), 8.24(1H, s), 10.26(1H, s). |
| 159 | 302.00 | 4.82 | 300MHz CDCl3: δ 8.80(s, 1H); 8.31(s, 1H); 7.57(d, 1H); 7.24(m, 1H); 7.05(m, 2H); 6.89(s, 1H); 5.95(d, 1H) |
| 160 | 301.00 | 5.79 | 300MHz CDCl3: δ 7.71(br s, 1H); 8.17(s, 1H); 7.67(d, 1H); 7.61(s, 1H); 7.39(d, 1H); 6.93(m, 1H); 6.43(s, 1H); 5.35(m, 1H); 2.35(s, 3H) |
| 161 | 264.00 | 7.71 | 300MHz 1H NMR(CDCl3): δ 0.97(9H, d, J=6.6), 1.06(2H, m), 1.45(2H, m), 1.67(12H, m), 2.22(2H, m), 3.94(1H, m), 4.40(1H, m), 4.88(1H, d, J=8.2), 5.23(1H, d, J=8.5), 6.49(1H, d, J=3.6), 6.51(1H, d, J=3.6), 7.14(1H, d, J=3.6), 7.15(1H, d, J=3.6), 8.04(2H, d, J=2.5), 11.70(2H, s). |
| 162 | 292.00 | 9.98 | 300MHz 1H NMR(CDCl3): δ 0.92(3H, m), 0.95(3H, d, J=6.6), 0.98(3H, s), 1.43(1H, m), 1.81(1H, m), 1.95(1H, m), 2.21(1H, m), 4.15(1H, m), 4.80(1H, d, J=8.5), 6.52(1H, d, J=3.6), 7.14(1H, d, J=3.6), 8.03(1H, s), 11.23(1H, s). |
| 163 |  | 5.33 | 300MHz 1H NMR(DMSO): δ 5.47(1H, d, J=3.6), 7.21(1H, d, J=3.6), 7.52(1H, d, J=1.9), 7.61(1H, dd, J=8.3, 1.9), 7.74(1H, d, J=8.2), 8.10(1H, s), 8.30(1H, s), 11.68(1H, s). |
| 164 | 351.00 | 2.03 | 300MHz 1H NMR(CDCl3): 1.43(9H, s), 1.69(3H, m), 2.06(1H, m), 3.29(2H, s), 3.61(1H, m), 4.00(1H, dd, J=13.2, 3.3), 4.12(1H, m), 5.06(1H, d, J=8.0), 6.57(1H, d, J=3.6), 7.17(1H, d, J=3.6), 8.05(1H, s), 11.40(1H, s). |
| 165 | 319.00 | 1.79 | 300MHz 1H NMR(CDCl3): δ 2.07(1H, m), 2.33(1H, m), 2.47(1H, m), 3.64(3H, m), 3.85(1H, m), 4.78(3H, m), 5.00(1H, d, J=7.4), 6.49(1H, d, J=3.6), 7.19(1H, s), 8.05(1H, s), 10.88(1H, s). |
| 166 | 295.00 | 1.41 | 300MHz 1H NMR(CDCl3): δ 2.09(1H, m), 2.30(1H, m), 3.64(4H, m), 3.71(3H, s), 4.76(1H, s), 5.00(1H, d, J=7.4), 6.49(1H, d, J=3.6), 7.18(1H, d, J=3.0), 8.05(1H, s), 11.14(1H, s). |
| 167 | 323.00 | 6.61 | 300MHz 1H NMR(CDCl3): δ 0.94(3H, m), 1.66(2H, m), 2.05(1H, m), 2.31(1H, m), 3.56(3H, m), 3.83(1H, m), 4.07(2H, m), 4.77(1H, s), 5.01(1H, d), 6.50(1H, d), 7.18(1H, s), 8.05(1H, s), 10.97(1H, s). |
| 168 | 293.00 | 5.53 | 300MHz 1H NMR(CDCl3): δ 1.14(3H, t), 1.18(3H, t), 2.06(2H, m), 2.27(6H, m), 3.67(6H, m), 3.86(2H, m), 4.76(1H, m), 4.83(1H, m), 4.97(1H, d), 5.02(1H, d), 6.48(1H, d), 6.50(1H, d), 7.17(1H, d), 7.22(1H, d), 8.02(1H, s), 8.05(1H, s), 11.02(1H, s), 11.16(1H, s). |
| 169 | 319.00 | 6.04 | 300MHz 1H NMR(CDCl3): δ 2.07(1H, m), 2.33(1H, m), 2.47(1H, m), 3.64(3H, m), 3.85(1H, m), 4.76(3H, m), 5.00(1H, d), 6.49(1H, d), 7.18(1H, s), 8.05(1H, s), 1074(1H, s). |
| 170 | 295.00 | 5.79 | 300MHz 1H NMR(CDCl3): δ 2.09(1H, m), 2.30(1H, m), 3.64(4H, m), 3.71(3H, s), 4.76(1H, s), 5.00(1H, d), 6.49(1H, d), 7.18(1H, s), 8.05(1H, s), 10.86(1H, s). |
| 171 | 323.00 | 6.50 | 300MHz 1H NMR(CDCl3): δ 0.94(3H, m), 1.65(2H, m), 2.05(1H, m), 2.29(1H, m), 3.56(3H, m), 3.83(1H, m), 4.07(2H, m), 4.76(1H, s), 5.02(1H, d), 6.49(1H, d), 7.18(1H, s), 8.05(1H, s), 11.49(1H, s). |
| 172 | 333.00 | 6.51 | 300MHz 1H NMR(CDCl3): δ 1.66(3H, m), 1.89(2H, m), 2.16(1H, m), 3.17(2H, m), 3.83(1H, m), 4.12(1H, m), 4.24(1H, m), 4.75(1H, d), 4.97(1H, d), 6.60(1H, s), 7.18(1H, d), 8.04(1H, s), 10.85(1H, s). |
| 173 | 309.00 | 6.41 | 300MHz 1H NMR(CDCl3): δ 1.66(2H, m), 1.81(1H, m), 2.14(1H, m), 2.16(1H, m), 3.18(2H, m), 3.72(3H, s), 3.77(1H, m), 4.13(2H, m), 4.99(1H, d), 6.58(1H, s), 7.17(1H, d), 8.05(1H, s), 10.98(1H, s). |

TABLE 4-continued

| Cmpd # | LC/MS | RT | NMR |
|---|---|---|---|
| 174 | 337.00 | 6.92 | 300MHz 1H NMR(CDCl3): δ 0.90(3H, m), 1.64(4H, m), 1.81(1H, m), 2.12(1H, m), 3.20(2H, m), 3.78(1H, m), 4.09(4H, m), 5.00(1H, d), 6.60(1H, s), 7.16(1H, d), 8.04(1H, s), 10.97(1H, s). |
| 175 | 307.00 | 6.12 | 300MHz 1H NMR(CDCl3): δ 1.09(3H, t), 1.20(3H, t), 1.75(6H, m), 2.27(6H, m), 3.30(5H, m), 3.63(1H, m), 3.85(2H, m), 4.19(1H, m), 4.43(1H, d), 5.00(1H, d), 6.47(1H, s), 6.65(1H, s), 7.18(2H, d), 8.02(1H, s), 8.07(1H, s), 10.91(1H, s), 11.35(1H, s). |
| 176 | 293.00 | 5.61 | 300MHz 1H NMR(CDCl3): δ 1.13(3H, t), 1.17(3H, t), 2.06(2H, m), 2.27(6H, m), 3.67(6H, m), 3.86(2H, m), 4.75(1H, m), 4.82(1H, m), 4.97(1H, d), 5.02(1H, d), 6.47(1H, d), 6.49(1H, d), 7.17(1H, d), 7.21(1H, d), 8.03(1H, s), 8.05(1H, s), 11.37(1H, s), 11.52(1H, s). |
| 177 | 357.00 | 6.53 | 300MHz 1H NMR(DMSO): δ 0.95(3H, t), 1.65(5H, m), 1.94(1H, m), 3.02(4H, m), 2.51(1H, m), 3.65(1H, m), 4.15(1H, m), 5.53(1H, d), 5.51(1H, dd), 7.24(1H, dd), 7.88(1H, s), 11.49(1H, s). |
| 178 | 343.00 | 6.21 | 300MHz 1H NMR(DMSO): δ 0.95(3H, t), 1.66(2H, sextuplet), 2.13(1H, m), 2.25(1H, m), 3.04(2H, m), 3.39(3H, m), 3.59(1H, dd), 4.77(1H, m), 5.77(1H, d), 6.55(1H, dd), 7.24(1H, dd), 7.87(1H, s), 11.49(1H, s). |
| 179 | 341.00 | 5.99 | 300MHz 1H NMR(DMSO): δ 0.94(4H, m), 2.14(1H, m), 2.28(1H, m), 2.66(1H, m), 3.50(3H, m), 3.65(1H, dd), 480(1H, m), 5.78(1H, d), 6.57(1H, dd), 7.25(1H, dd), 7.87(1H, s), 11.50(1H, s). |
| 180 | 343.00 | 6.20 | 300MHz 1H NMR(DMSO): δ 0.95(3H, t), 1.66(2H, sextuplet), 2.13(1H, m), 2.25(1H, m), 3.04(2H, m), 3.39(3H, m), 3.59(1H, dd), 4.78(1H, m), 5.77(1H, d), 6.56(1H, dd), 7.25(1H, dd), 7.87(1H, s), 11.50(1H, s). |
| 181 | 355.00 | 6.34 | 300MHz 1H NMR(DMSO): δ 0.94(4H, m), 1.71(3H, m), 1.90(1H, m), 2.63(1H, m), 3.03(2H, m), 3.39(1H, m), 3.66(1H, dd), 4.17(1H, m), 5.57(1H, d), 6.50(1H, dd), 7.24(1H, dd), 7.88(1H, s), 11.49(1H, s). |
| 182 | 329.00 | 5.86 | 300MHz 1H NMR(DMSO): δ 1.70(3H, m), 1.92(1H, m), 2.87(3H, s), 2.92(3H, m), 3.62(1H, dd), 4.18(1H, m), 5.54(1H, d), 6.50(1H, dd), 7.25(1H, dd), 7.88(1H, s), 11.49(1H, s). |
| 183 | 341.00 | 5.87 | 300MHz 1H NMR(DMSO): δ 0.94(4H, m), 2.14(1H, m), 2.28(1H, m), 2.66(1H, m), 3.50(3H, m), 3.65(1H, dd), 4.80(1H, m), 5.78(1H, d), 6.57(1H, s), 7.25(1H, dd), 7.87(1H, s), 11.50(1H, s). |
| 184 | 315.00 | 5.44 | 300MHz 1H NMR(DMSO): δ 2.11(1H, m), 2.25(1H, m), 2.90(3H, s), 3.14(3H, m), 3.59(1H, dd), 4.79(1H, m), 5.80(1H, d), 6.57(1H, dd), 7.25(1H, dd), 7.87(1H, s), 11.50(1H, s). |
| 185 | 315.00 | 5.44 | 300MHz 1H NMR(DMSO): δ 2.11(1H, m), 2.25(1H, m), 2.90(3H, s), 3.14(3H, m), 3.59(1H, dd), 4.79(1H, m), 5.80(1H, d), 6.57(1H, dd), 7.25(1H, dd), 7.87(1H, s), 11.50(1H, s). |
| 186 | 361.00 | 6.30 | 300MHz 1H NMR(CDCl3): δ 1.70(4H, m), 1.88(2H, m), 2.20(2H, m), 3.27(8H, m), 3.61(1H, m), 3.87(1H, dd), 3.96(1H, m), 4.18(2H, m), 4.47(1H, dd), 4.96(2H, d), 6.45(1H, d), 6.60(1H, d), 7.18(1H, d), 7.24(1H, d), 8.04(1H, s), 8.10(1H, s), 11.12(1H, s), 11.57(1H, s). |
| 187 | 347.00 | 5.95 | 300MHz 1H NMR(CD3OD): δ 2.20(2H, m), 2.37(2H, m), 3.41(4H, m), 3.69(4H, m), 3.87(1H, dd, J=12.7, 6.1), 3.97(1H, dd, J=11.0, 6.3), 4.92(2H, m), 6.65(2H, m), 7.20(2H, m), 7.88(2H, s). |
| 188 | 318.00 | 5.64 | 300MHz 1H NMR(CDCl3): δ 1.74(4H, m), 1.93(2H, m), 2.22(2H, m), 3.07(1H, dd, J=12.9, 8.8), 3.31(5H, m), 3.56(2H, s), 3.59(1H, m), 3.79(1H, d, J=12.9), 3.85(1H, m), 4.12(1H, m), 4.26(1H, m), 4.56(1H, d, J=11.8), 4.94(2H, m), 6.45(1H, d, J=3.0), 6.60(1H, d, J=3.0), 7.19(1H, d, J=2.5), 2.5(1H, d, J=2.8), 8.04(1H, s), 8.10(1H, s), 10.73(1H, s), 11.20(1H, s). |
| 189 | 347.00 | 5.95 | 300MHz 1H NMR(CDCl3): δ 2.13(1H, m), 2.26(1H, m), 2.42(2H, m), 3.15(2H, q, J=10.2), 3.2(2H, q, J=10.2), 3.54(1H, dd, J=10.7, 3.9), 3.74(2H, m), 3.91(1H, dd, J=5.8, 2.5), 3.94(1H, d, J=5.8), 4.85(2H, m), 4.95, (1H, d, J=7.2), 4.99(1H, d, |

TABLE 4-continued

| Cmpd # | LC/MS | RT | NMR |
|---|---|---|---|
| | | | J=8.0), 6.48(2H, m), 7.20(2H, m), 8.06(1H, s), 8.08(1H, s), 10.19(1H, s), 10.32(1H, s). |
| 190 | 304.00 | 4.36 | 300MHz 1H NMR(DMSO): 2.17(4H, m), 3.52(6H, m), 3.68(1H, dd, J=12.4, 6.3), 3.78(1H, dd, J=10.7, 6.3), 3.90(2H, s), 3.93(2H, s), 4.73(1H, m), 4.83(1H, m), 5.81(1H, d, J=7.4), 5.87(1H, d, J=7.9), 6.57(1H, dd, J=3.8, 2.2), 6.61(1H, dd, J=3.6, 1.9), 7.23(1H, d, J=2.8), 7.24(1H, d, J=3.5), 7.86(2H, s), 11.47(2H, s). |
| 191 | 304.00 | 4.47 | 300MHz 1H NMR(DMSO): 2.17(4H, m), 3.52(6H, m), 3.68(1H, dd, J=12.4, 6.3), 3.78(1H, dd, J=10.7, 6.3), 3.90(2H, s), 3.93(2H, s), 4.73(1H, m), 4.83(1H, m), 5.81(1H, d, J=7.4), 5.87(1H, d, J=7.9), 6.57(1H, dd, J=3.8, 2.2), 6.61(1H, dd, J=3.6, 1.9), 7.23(1H, d, J=2.8), 7.24(1H, d, J=3.5), 7.86(2H, s), 11.47(2H, s). |
| 192 | 369.10 | 1.70 | H NMR(500MHz, DMSO-d6) d 11.78(s, 1H), 8.75(t, J=6.4Hz, 1H), 8.42(d, J=3.5Hz, 1H), 8.29(d, J=5.1Hz, 1H), 8.08(t, J=5.8Hz, 1H), 7.88(d, J=5.1Hz, 1H), 7.53(t, J=2.9Hz, 1H), 7.18(dd, J=3.3, 2.0Hz, 1H), 4.18(d, J=6.0Hz, 2H), 3.93(m, 2H) |
| 193 | 383.10 | 1.90 | H NMR(500MHz, DMSO-d6) d 11.80(s, 1H), 8.57(t, J=6.1Hz, 1H), 8.35(d, J=3.6Hz, 1H), 8.33(d, J=5.1Hz, 1H), 7.95(d, J=5.1Hz, 1H), 7.83(d, J=5.3Hz, 1H), 7.55(t, J=2.9Hz, 1H), 7.29(dd, J=3.3, 2.0Hz, 1H), 3.94–3.87(m, 2H), 3.79(q, J=6.6Hz, 2H), 2.64(t, J=7.1Hz, 2H) |
| 194 | 295.30 | 1.30 | (CDCl3) 11.34(s, 1H), 8.60(d, 1H), 8.43(d, 1H), 7.96(s, 1H), 7.84(d, 1H), 7.46(d, 1H), 7.29(dd, 1H), 7.12(d, 1H), 6.38(d, 1H), 0.96(s, 9H) |
| 195 | 211.20 | 0.57 | (CDCl3)9.19(s, 1H), 8.41–6.44(m, 7H), 5.38(s, 2H) |
| 196 | 401.20 | 1.60 | H NMR(500MHz, DMSO-d6) d 11.89(s, 1H), 8.85(t, J=6.0Hz, 1H), 8.39(d, J=5.2Hz, 2H), 7.99–7.96(m, 2H), 7.69–7.62(m, 2H), 7.27(d, J=2.8Hz, 1H), 4.40(d, J=5.3Hz, 2H), 4.00–3.93(m, 2H) |
| 197 | 415.20 | 1.60 | H NMR(500MHz, DMSO-d6) d 12.03(s, 1H), 8.61(t, J=6.2Hz, 1H), 8.48(d, J=4.7Hz, 1H), 8.41(d, J=8.8Hz, 1H), 7.97(s, 3H), 7.70(s, 2H), 7.29(s, 1H), 4.03(d, J=6.0Hz, 2H), 3.94–3.87(m, 2H), 2.76(t, J=6.9Hz, 2H) |
| 198 | 409.30 | 14.20 | (DMSO) 1.95(m, 4H), 3.9(m, 4H), 4.05(m, 1H), 4.8(d, 1H), 7.2(bs, 1H), 7.5(bs, 1H), 7.9(bs, 1H), 8.25(d, 1H), 8.4(d, 1H), 8.75(t, 1H) |
| 199 | 409.30 | 1.90 | (DMSO) 1.95(m, 4H), 3.9(m, 5H),, 4.8(bd, 1H), 7.2(bs, 1H), 7.5(bs, 1H), 7.9(bs, 1H), 8.2(d, 1H), 8.45(d, 1H), 8.75(bt, 1H) |
| 200 | 415.30 | 1.70 | (DMSO) 1.5(d, 3H), 3.9(m, 2H), 5.0(m, 1H), 7.3(bs, 1H), 7.6(bs, 2H), 7.9(bs, 2H), 8.1(bs, 1H), 8.3(d, 1H), 8.6(d, 1H), 8.8(t, 1H) |
| 201 | 383.30 | 1.70 | (DMSO) 1.45(d, 3H), 3.9(m, 2H), 4.7(t, 1H), 7.15(bd, 1H), 7.55(t, 1H), 7.85(bs, 2H), 8.2(d, 1H), 8.4(d, 1H), 8.75(t, 1H) |
| 202 | 365.30 | 1.40 | (CD3OD) 1.6(d, 3H), 3.9(dm, 2H), 4.9(m, 1H), 6.9(bd, 1H), 7(bd, 1H), 7.7(bm, 2H), 8.25(d, 1H), 8.45(d, 1H), 8.9(bt, 1H) |
| 203 | 230.20 | 1.50 | (d4-Methanol) 8.25(d, 1H), 8.23(d, 1H), 7.87(d, 1H), 7.45(d, 1H), 7.34(d, 1H) |
| 204 | 399.10 | 1.60 | (d4-Methanol) 8.31(d, 1H), 8.24(d, 1H), 7.91(d, 1H), 7.46(d, 1H), 7.26(d, 1H), 4.91(dd, 1H), 4.04(d, 2H), 3.92(q, 2H) |
| 205 | 243.20 | 2.00 | H NMR(500MHz, DMSO-d6) 11.74(s,, 8.26(d, J=5.0Hz, 1H), 7.48(t, J=3.0Hz, 1H), 7.30–7.19(m, 3H), 7.10(d, J=4.9Hz, 1H), 6.27(dd, J=3.4, 1.9Hz, 1H), 3.73(s, 3H) |
| 206 | 279.20 | 2.20 | H NMR(500MHz, DMSO-d6) 11.84(s, 1H), 8.31(d, J=4.9Hz, 1H), 7.66–7.61(m, 2H), 7.58–7.52(m, 3H), 7.09(d, J=4.9Hz, 1H) |
| 207 | 230.10 | 2.00 | H NMR(500MHz, DMSO-d6) 11.84(s, 1H), 8.30(d, J=4.9Hz, 1H), 7.72–7.67(m, 1H), 7.54(t, J=3.0Hz, 1H), 7.47–7.42(m, 1H), 7.27(dt, J=12.1, 4.2Hz, 1H), 7.14–7.13(m, 1H), 6.36–6.34(m, 1H) |
| 208 | 263.20 | 2.20 | H NMR(500MHz, DMSO-d6) 11.82(s, 1H), 8.27(d, J=4.9Hz, 1H), 7.91(d, J=7.9Hz, 1H), 7.78(t, J=7.4Hz, 1H), 7.70(t, J=7.7Hz, 1H), 7.50–7.47(m, 2H), 6.97(d, J=4.8Hz, 1H), 6.05(dd, J=3.3, 1.9Hz, 1H) |
| 209 | 223.20 | 2.20 | H NMR(500MHz, DMSO-d6) 11.88(s, 1H), 8.28(d, J=4.9Hz, 1H), 7.49(t, J=2.9Hz, 1H), 7.25(d, J=7.8Hz, |

TABLE 4-continued

| Cmpd # | LC/MS | RT | NMR |
| --- | --- | --- | --- |
| | | | 1H), 7.17(d, J=7.8Hz, 1H), 7.11(s, 1H), 6.99(d, J=4.9Hz, 1H), 2.32(s, 3H), 2.11(s, 3H) |
| 210 | 263.10 | 2.40 | H NMR(500MHz, DMSO-d6) 11.84(s, 1H), 8.30(d, J=4.9Hz, 1H), 7.81(d, J=2.1Hz, 1H), 7.58(dd, J=8.3, 2.1Hz, 1H), 7.54–7.52(m, 2H), 7.06(d, J=4.9Hz, 1H), 6.20(dd, J=3.4, 1.9Hz, 1H) |
| 211 | 263.10 | 2.40 | H NMR(500MHz, DMSO-d6) 11.85(s, 1H), 8.31(d, J=4.8Hz, 1H), 7.68(d, J=8.4Hz, 1H), 7.59–7.52(m, 3H), 7.08(d, J=4.9Hz, 1H), 6.20(dd, J=3.4, 1.9Hz, 1H) |
| 212 | 223.20 | 2.10 | H NMR(500MHz, DMSO-d6) 11.82(s, 1H), 8.29(d, J=4.9Hz, 1H, 7.48(t, J=2.9Hz, 1H,) 7.26(d, J=7.3Hz, 1H), 7.20(t, J=7.5Hz, 1H), 7.12(d, J=7.1Hz, 1H), 6.97(d, J=4.9Hz, 1H), 6.13(dd, J=3.4, 1.9Hz, 1H), 2.33(s, 3H), 2.04(s, 3H) |
| 213 | 237.20 | 1.70 | H NMR(500MHz, DMSO-d6) 11.85(s, 1H), 8.27(d, J=4.9Hz, 1H), 7.78(dd, J=7.6, 1.1Hz, 1H), 7.67(dt, J=10.4, 3.7Hz, 1H), 7.59(dt, J=10.4, 3.8Hz, 1H), 7.53(d, J=1.0Hz, 1H), 7.51–7.50(m, 1H), 6.97(d, J=4.9Hz, 1H), 6.19(dd, J=3.4, 1.8Hz, 1H), 2.16(s, 3H) |
| 214 | 220.20 | 1.80 | |
| 215 | 405.20 | 1.70 | Major tautomer(67%), 1H NMR(CD3OD, 500MHz): 1.52–2.07(m, 6H), 2.38–2.49(m, 1H), 3.51–3.63(m, 1H), 3.90–4.05(m, 2H), 7.19–7.26(m, 1H), 7.67(d, 1H), 7.71(d, 1H), 8.38(d, 1H), 8.45(d, 1H) |
| 216 | 229.10 | 2.00 | H NMR(500MHz, DMSO-d6) d 11.85(s, 1H), 8.31(d, J=4.9Hz, 1H), 7.67–7.63(m, 1H), 7.53–7.48(m, 4H), 7.08(d, J=4.9Hz,, 1H), 6.19(dd, J=3.4, 1.8Hz, 1H) |
| 217 | 223.20 | 2.10 | H NMR(500MHz, DMSO-d6) d 11.86(s, 1H), 8.32(d, J=4.9Hz, 1H), 7.47(t, J=2.9Hz, 1H), 7.26–7.17(m, 3H), 6.92(d, J=4.9Hz, 1H), 5.97(dd, J=3.4, 1.8Hz, 1H), 1.91(s, 6H) |
| 218 | 223.20 | 2.20 | H NMR(500MHz, DMSO-d6) d 11.88(s, 1H), 8.29(d, J=5.0Hz, 1H), 7.50(t, J=2.9Hz, 1H), 7.21–7.19(m, 2H), 7.13(d, J=7.9Hz, 1H), 7.02(d, J=5.0Hz, 1H), 6.18(dd, J=3.4, 1.8Hz, 1H), 2.35(s, 3H), 2.14(s, 3H) |
| 219 | 209.20 | 2.00 | H NMR(500MHz, DMSO-d6) d 11.87(s,, 8.30(d, J=0.0Hz, 1H), 7.51(t, J=2.9Hz, 1H), 7.39–7.29(m, 2H), 7.03(d, J=5.0Hz, 1H), 6.16(dd, J=3.4, 1.8Hz, 1H), 2.17(s, 3H) |
| 220 | 255.20 | 1.90 | H NMR(500MHz, DMSO-d6) d 11.88(s, 1H), 8.26(d, J=5.2Hz, 1H), 7.50(t, J=2.9Hz, 1H), 7.37(d, J=8.4Hz, 1H), 7.17(d, J=5.2Hz, 1H), 6.75(d, J=2.3Hz, 1H), 6.69(dd, J=8.4, 2.3Hz, 1H), 6.34(dd, J=3.3, 1.7Hz, 1H), 3.85(s, 3H), 3.77(s, 3H) |
| 221 | 255.20 | 1.90 | H NMR(500MHz, DMSO-d6) d 11.82(s, 1H), 8.27(d, J=5.1Hz, 1H), 7.50(t, J=2.9Hz, 1H), 7.15–7.12(m, 2H), 7.03–6.96(m, 2H), 6.32(dd, J=3.2, 1.7Hz, 1H), 3.76(s, 3H), 3.69(s, 3H) |
| 222 | 255.20 | 1.90 | H NMR(500MHz, DMSO-d6) d 11.80(s, 1H), 8.25(d, J=5.1Hz, 1H), 7.45–7.40(m, 2H), 7.02(d, J=5.1Hz, 1H), 6.81(d, J=8.4Hz, 2H), 6.08(dd, J=3.3, 1.7Hz, 1H), 3.64(s, 6H) |
| 223 | 239.20 | 2.00 | H NMR(500MHz, DMSO-d6) d 11.83(s, 1H), 8.28(d, J=5.1Hz, 1H), 7.50(t, J=2.9Hz, 1H), 7.45–7.41(m, 2H), 7.20–7.18(m, 2H), 7.08(t, J=7.4Hz, 1H), 6.33(dd, J=3.3, 1.8Hz, 1H), 4.07(q, J=7.0Hz, 2H), 1.19(t, J 3H) |
| 224 | 263.10 | 2.30 | H NMR(500MHz, DMSO-d6) d 11.86(s, 1H), 8.31(d, J=4.9Hz, 1H), 7.76(dd, J=7.9, 1.7Hz, 1H), 7.53–7.45(m, 3H), 7.08(d, J=4.9Hz, 1H), 6.17(dd, J=3.4, 1.9Hz, 1H) |
| 225 | 301.30 | 2.30 | H NMR(500MHz, DMSO-d6) d 11.82(s, 1H), 8.27(d, J=5.1Hz, 1H), 7.50(t, J=2.9Hz, 1H), 7.46–7.43(m, 2H), 7.30–7.23(m, 6H), 7.22(d, J=5.1Hz, 1H), 7.12(dt, J=10.2, 3.7Hz, 1H), 6.36(dd, J=3.4, 1.8Hz, 1H) |
| 226 | 271.20 | 2.30 | H NMR(500MHz, DMSO-d6) d 11.69(s, 1H), 8.08(d, J=5.0Hz, 1H), 7.58–7.51(m, 4H), 7.38(t, J=2.9Hz, 1H), 7.16–7.09(m, 5H), 6.73(d, J=5.0Hz, 1H), 6.13(dd, J=3.3, 1.8Hz, 1H) |
| 227 | 246.20 | 1.50 | H NMR(500MHz, DMSO-d6) d 11.97(s, 1H), 8.86(dd, J=4.1, 1.8Hz, 1H), 8.53(dd, J=8.3, 1.5Hz, 1H), 8.37(d, J=5.1Hz, 1H), 8.15(dd, J=8.2, 1.2Hz, 1H), 7.93(dd, J=7.1, 1.3Hz, 1H), 7.78(t, J=7.6Hz, 1H), 7.63(dd, J=8.3, 4.2Hz, 1H), 7.52(t, J=2.9Hz, 1H), 7.36(d, J=5.1Hz, 1H), 6.18(dd, J=3.4, 1.8Hz, 1H) |
| 228 | 279.30 | 1.50 | (500MHz, CD3OD) 8.17(s, 1H), 7.39(s, 1H), 6.86(s, 1H), 5.07(d, 1H), 3.46(t, 1H), 2.27–1.22(m, 7H). |

TABLE 4-continued

| Cmpd # | LC/MS | RT | NMR |
|---|---|---|---|
| 229 | 264.30 | 2.10 | (500MHz, CD3OD) 8.09(s, 1H), 7.32(s, 1H), 6.78(s, 1H), 2.14(d, 1H), 2.22–0.84(m, 12H). |
| 230 | 253.30 | 2.10 | H NMR(500MHz, DMSO-d6) d 11.84(s, 1H),, 8.28(d, J=5.1Hz, 1H), 7.51(t, J=2.9Hz, 1H), 7.43–7.40(m, 3H), 7.20–7.18(m, 2H), 7.07(t, J=7.5Hz, 1H), 6.35(dd, J=3.3, 1.8Hz, 1H), 4.59(m, 1H), 1.16(d, J=6.0Hz, 6H) |
| 231 | 223.20 | 2.10 | H NMR(500MHz, DMSO-d6) d 11.85(s, 1H), 8.29(d, J=4.9Hz, 1H), 7.49(t, J=2.9Hz, 1H), 7.42–7.23(m, 5H), 7.00(d, J=4.9Hz, 1H), 6.12(dd, J=3.4, 1.9Hz, 1H), 2.51–2.49(m, 2H), 0.96(t, J=7.5Hz, 3H) |
| 232 | 281.30 | 2.20 | H NMR(500MHz, DMSO-d6) d 11.84(s, 1H), 8.29(d, J=5.0Hz, 1H), 7.56(d, J=7.4Hz, 1H), 7.50(t, J=2.9Hz, 1H), 7.47–7.40(m, 2H), 7.34(dd, J=7.4, 0.0Hz, 1H), 7.09(d, J=4.9Hz, 1H), 6.19(dd, J=3.4, 1.9Hz, 1H), 4.23(s, 2H), 0.98(s, 9H) |
| 233 | 255.30 | 1.80 | H NMR(500MHz, DMSO-d6) d d 11.84(s, 1H), 8.28(d, J=5.0Hz, 1H), 7.49(t, J=2.9Hz, 1H), 7.21–7.15(m, 2H), 7.12(d, J=5.0Hz, 1H), 7.00(dd, J=7.4, 1.8Hz, 1H), 6.30(dd, J=3.3, 1.8Hz, 1H), 3.88(s, 3H), 3.51(s, 3H) |
| 234 | 253.30 | 2.20 | H NMR(500MHz, DMSO-d6) d 11.81(s, 1H), 8.27(d, J=5.1Hz, 1H), 7.50(t, J=2.9Hz, 1H), 7.45–7.41(m, 2H), 7.20–7.17(m, 2H), 7.08(dt, J=10.1, 3.8Hz, 1H), 6.33(dd, J=3.4, 1.8Hz, 1H), 3.96(t, J=6.4Hz, 2H), 1.61–1.54(m, 2H), 0.81(t, J=7.4Hz, 3H) |
| 235 | 259.20 | 2.10 | H NMR(500MHz, DMSO-d6) d 11.79(s, 1H), 8.27(d, J=5.0Hz, 1H), 7.51–7.48(m, 2H), 7.40(d, J=2.6Hz, 1H), 7.23(d, J=8.9Hz, 1H), 7.11(d, J=5.0Hz, 1H), 6.26(dd, J=3.2, 1.8Hz, 1H), 3.80(s, 3H) |
| 236 | 213.20 | 1.90 | H NMR(500MHz, DMSO-d6) d 11.85(s, 1H), 8.31(d, J=5.0Hz, 1H), 7.64(dt, J=10.7, 3.8Hz, 1H), 7.56–7.52(m, 2H,) 7.42–7.37(m, 2H), 7.16(dd J=4.9, 1.3Hz, 1H), 6.37–6.35(m, 1H) |
| 237 | 273.20 | 2.30 | H NMR(500MHz, DMSO-d6) d 11.79(s, 1H), 8.27(d, J=5.0Hz, 1H), 7.50(t, J=2.9Hz, 1H), 7.47(dd, J=8.8, 2.7Hz, 1H), 7.40(d, J=2.7Hz, 1H), 7.21(d, J=8.9Hz, 1H), 7.14(d, J=5.0Hz, 1H), 6.29(dd, J=3.4, 1.8Hz, 1H), 4.07(q, J=7.0Hz, 2H), 1.17(t, J=6.9Hz, 3H) |
| 238 | 239.20 | 1.60 | H NMR(500MHz, DMSO-d6) d 11.77(s, 1H), 8.25(d, J=4.9Hz, 1H), 7.87(dd, J=7.7, 1.1Hz, 1H), 7.66(dt, J=10.5, 3.8Hz, 1H), 7.56(dt, J=10.5, 3.8Hz, 1H), 7.49–7.47(m, 2H), 7.00(d, J=4.9Hz, 1H), 6.20(dd, J=3.4, 1.8Hz, 1H) |
| 239 | 241.20 | 2.00 | (400MHz, DMSO-d6) 2.36(s, 3H), 6.15(d, 1H), 7.05(d, 1H), 7.30(m, 2H), 7.47(m, 3H), 8.27(d, 1H) |
| 240 | 287.20 | 2.30 | (400MHz, DMSO-d6) 6.42(s, 1H), 6.88(d, 2H), 7.05(m, 2H), 7.14(d, 1H), 7.28(m, 3H), 7.49(t, 2H), 7.59(d, 1H), 8.21(d, 1H) |
| 241 | 267.30 | 2.30 | H NMR(400MHz, DMSO-d6) 0.80(t, J=7.4Hz, 3H), 1.27(m, 2H), 1.54(m, 2H), 3.99(t, J=6.4Hz, 2H), 6.31(t, J=1.4Hz, 1H), 7.08(t, J=7.4Hz, 2H), 7.18(m, 2H), 7.42(m, 2H), 7.49(t, J=2.7Hz, 1H), 8.26(d, J=5.1Hz, 1H) |
| 242 | 237.10 | 2.30 | (400MHz, DMSO-d6) 1.85(s, 6H), 2.25(s, 3H), 5.95(d, 1H), 6.85(d, 1H), 7(s, 2H), 7.45(d, 1H), 8.3(d, 1H) |
| 243 | 227.20 | 2.10 | (400MHz, DMSO-d6) 2.15(s, 3H), 6.15(d, 1H), 6.95(d, !H), 7.15(t, 1H), 7.2(d, 1H), 7.3(t, 1H), 7.5(s, 1H), 8.3(d, 1H) |
| 244 | 261.20 | 2.40 | |
| 245 | 259.20 | 2.00 | (400MHz, DMSO-d6) 6(d, 1H), 6.9(d, 1H), 7.2(m, 2H), 7.4(m, 2H), 8.25(d, 1H) |
| 246 | 317.20 | 2.50 | |
| 247 | 288.20 | 1.60 | (400MHz, DMSO-d6) 2.8(s, 3H), 6.2(d, 1H), 7.15(d, 1H), 7.3(t, 1H), 7.5(m, 3H), 8.3(d, 1H), 8.85(s, 1H) |
| 248 | 211.20 | 1.60 | (400MHz, DMSO-d6) 6.3(d, 1H), 6.9(d, 1H), 7(d, 1H), 7.25(m, 2H), 7.35(d, 1H), 7.5(s, 1H), 8.2(d, 1H), 9.7(bs, 1H) |
| 249 | 238.10 | 2.10 | (400MHz, DMSO-d6) 1.3(t, 3H), 4.1(q, 2H), 6.6(d, 1H), 6.9(d, 1H), 7.2(m, 2H), 7.3(d, 1H), 7.4(t, 1H), 7.5(s, 1H), 8.3(d, 1H) |
| 250 | 185.20 | 1.40 | H NMR(500MHz, DMSO-d6) d 12.04(s, 1H), 8.43(s, 2H), 8.26(d, J=5.5Hz, 1H), 7.59(t, J=2.8Hz, 1H), 7.47(d, J=5.5Hz, 1H), 6.98(d, J=2.0Hz, 1H) |
| 251 | 320.30 | 1.90 | |
| 252 | 334.30 | 1.90 | H NMR(500MHz, DMSO-d6) 11.88(s, 1H), 8.8(t, J=5.4Hz, 1H), 8.34(d, J=5.0Hz, 1H), 8.21(t, J=1.6Hz, 1H), 7.95–7.92(m, 1H), 7.67(t, J=7.7Hz, 1H), |

TABLE 4-continued

| Cmpd # | LC/MS | RT | NMR |
|---|---|---|---|
| | | | 7.6–7.58(m, 1H), 7.27(d, J=5.0Hz, 1H), 6.64(q, J=1.8Hz, 1H), 3.54(dd, J=6.9, 12.7Hz, 2H), 2.61–2.54(m, 2H) |
| 253 | 320.20 | 1.70 | H NMR(500MHz, DMSO-d6) 11.74(s, 1H), 8.94(t, J=6.3Hz, 1H), 8.19(d, J=4.9Hz, 1H), 7.63–7.6(m, 1H), 7.57–7.54(m, 3H), 7.46(t, J=2.9Hz, 1H), 6.98(d, J=4.9Hz, 1H), 6.31(dd, J=1.9, 3.4Hz, 1H), 3.82 td, J=6.5, 9.8Hz, 2H) |
| 254 | 334.30 | 1.80 | H NMR(500MHz, DMSO-d6) 11.8(s, 1H), 8.43(t, J=5.7Hz, 1H), 8.24(d, J=5.0Hz, 1H), 7.61–7.52(m, 4H), 7.48(t, J=2.9Hz, 1H), 7.03(d, J=5.0Hz, 1H), 6.32(q, J=1.8Hz, 1H), 3.24–3.2(m, 2H), 2.21–2.15(m, 2H) |
| 255 | 266.30 | 1.60 | |
| 256 | 280.30 | 1.80 | H NMR(500MHz, DMSO-d6) 11.88(s, 1H), 8.57(t, J=5.4Hz, 1H), 8.33(d, J=5.0Hz, 1H), 8.21(t, J=1.5Hz, 1H), 7.94–7.91(m, 2H), 7.64(t, J=7.7Hz, 1H), 7.59–7.58(m, 1H), 7.28(d, J=5.0Hz, 1H), 6.64(q, J=1.8Hz, 1H), 3.28–3.24(m, 2H), 1.55(quin, J=7.2Hz, 2H), 0.91(t, J=7.4Hz, 3H) |
| 257 | 266.30 | 1.50 | H NMR(500MHz, DMSO-d6) 11.8(s, 1H), 8.24(d, J=5.0Hz, 1H), 8.12(t, J=5.5Hz, 1H), 7.58–7.48(m, 5H), 7.06(d, J=5.0Hz, 1H), 6.34(q, J=1.7Hz, 1H), 3.03–2.98(m, 2H), 0.82(t, J=7.2Hz, 3H) |
| 258 | 280.30 | 1.60 | H NMR(500MHz, DMSO-d6) 11.77(s, 1H), 8.23(d, J=5.0Hz, 1H), 8.12(t, J=5.5Hz, 1H), 7.58–7.47(m, 5H), 7.04(d, J=5.0Hz, 1H), 6.33(dd, J=1.8, 3.4Hz, 1H), 2.95–2.91(m, 2H), 1.22(q, J=7.1Hz, 2H), 0.65(t, J=7.4Hz, 3H) |
| 259 | 309.30 | 1.70 | |
| 260 | 326.20; Lot 2: 326.06 | 1.90; Lot 2: 2.27 | H NMR(500MHz, DMSO-d6) d 11.93(s, 1H), 9.22(t, J=6.4Hz, 1H), 8.28(d, J=5.0Hz, 1H), 7.98(d, J=4.0Hz, 1H), 7.85(d, J=4.0Hz, 1H), 7.64(t, J=3.0Hz, 1H), 7.4(d, J=5.0Hz, 1H), 6.86(q, J=1.8Hz, 1H), 4.11(m, 2H) |
| 261 | 269.30 | 1.60 | H NMR(500MHz, DMSO-d6) d 12.01(s, 2H), 8.23(d, J=5.6Hz, 1H), 7.72(s, 1H), 7.57(s, 1H), 7.47(d, J=5.4Hz, 1H), 7.17(s, 1H), 6.91(s, 1H), 3.58(d, J=4.3Hz, 2H), 3.19(t, 3H), 1.19(s, 3H) |
| 262 | 283.30 | 1.70 | H NMR(500MHz, DMSO-d6) d 12.0(s, 2H), 8.23(d, J=5.5Hz, 1H), 7.71(s, 1H), 7.57(t, J=2.7Hz, 1H), 7.46(d, J=5.3Hz, 1H), 7.08(s, 1H), 6.87(s, 1H), 3.58(d, 4H), 1.23(s, 6H) |
| 263 | 295.30; 295.15 | 1.80; 1.71 | H NMR(500MHz, DMSO-d6) d 12.02(s, 2H), 8.22(d, J=5.6Hz, 1H), 8.02(d, J=7.3Hz, 1H), 7.72(s, 1H), 7.6(s, 1H), 7.57(s, 1H), 7.41(d, J=5.4Hz, 1H), 7.02(s, 1H), 4.23(m, 1H), 1.93–1.91(m, 2H), 1.73–1.71(m, 2H), 1.58–1.52(m, 4H) |
| 264 | 269.30 | 1.60 | |
| 265 | 363.00 | 2.30 | (CD3OD, 500MHz) 1.7(s, 6H), 3.9(m, 2H), 7.3(d, 1H), 7.5(d, 1H), 7.65(d, 1H), 7.9(d, 1H), 8(t, 1H), 8.05(d, 1H), 8.15(t, 1H), 8.4(d, 1H) |
| 266 | 354.10 | 1.60 | H NMR(500MHz, DMSO-d6) 11.86(s, 1H), 9.01(s, 1H), 8.37(d, J=5.0Hz, 1H), 7.97(d, J=5.0Hz, 1H), 7.61(t, J=2.9Hz, 1H), 7.29(dd, J=3.2, 1.9Hz, 1H), 4.03–3.89(m, 4H). |
| 267 | 280.40 | 1.70 | H NMR(500MHz, DMSO-d6) 11.90(s, 1H), 8.54(t, J=5.3Hz, 1H), 8.33(d, J=4.9Hz, 1H), 8.02(d, J=7.5Hz, 2H), 7.86(d, J=7.8Hz, 2H), 7.59(bt, 1H), 7.27(d, J=4.9Hz, 1H), 6.65(t, J=1.6Hz, H), 3.26(q, J=6.5Hz, 2H), 1.57(q, J=7.3Hz, 2H), 0.92(t, J=7.4Hz, 3H), 0.00(TMS) |
| 268 | 334.30 | 1.90 | H NMR(500MHz, DMSO-d6) 11.88(s, 1H), 8.77(t, J=5.6Hz, 1H), 8.32(d, J=5.0Hz, 1H), 8.01(d, J=8.3Hz, 2H), 7.88(d, J=8.3Hz, 2H), 7.59(t, J=3.0Hz, 1H), 7.26(d, J=5.0Hz, 1H), 6.65(m, 1H), 3.54(dd, J=12.6, 6.8Hz, 2H), 2.63–2.49(m, 2H), 0.00(TMS) |
| 269 | 320.30 | 1.80 | H NMR(500MHz, DMSO-d6) 11.89(s, 1H), 9.19(t, J=6.2Hz, 1H), 8.33(d, J=5.0Hz, 1H), 8.07(d, J=8.3Hz, 2H), 7.91(d, J=8.3Hz, 2H), 7.60(t, J=3.0Hz, 1H), 7.27(d, J=5.0Hz, 1H), 6.65(m, 1H), 4.17–4.10(m, 2H), 0.00(TMS) |
| 270 | 278.30 | 1.60 | H NMR(500MHz, DMSO-d6) 11.87(s, 1H), 8.52(d, J=4.0Hz, 1H), 8.32(d, J=5.0Hz, 1H), 7.99(d, J=8.2Hz, 2H), 7.85(d, J=8.2Hz, 2H), 7.58(t, J=2.9Hz, 1H), 7.25(d, J=5.0Hz, 1H), 6.63(m, 1H), 2.89(m, 2H), 0.73–0.70(m, 2H), 0.62–0.59(m, 2H), 0.00(TMS) |

TABLE 4-continued

| Cmpd # | LC/MS | RT | NMR |
|---|---|---|---|
| 271 | 314.30 | 2.10 | H NMR(500MHz, DMSO-d6) 11.89(s, 1H), 10.34(s, 1H), 8.34(d, J=4.9Hz, 1H), 8.14(d, J=8.3Hz, 2H), 7.94(d, J=8.3Hz, 2H), 7.81(d, J=7.6Hz, 2H), 7.60(t, J=3.0Hz, 1H), 7.37(t, 2H), 7.29(d, J=5.0Hz, 1H), 7.12(t, J=7.4Hz, 1H), 6.67(m, 1H), 0.00(TMS) |
| 272 | 252.10 | 2.00 | H NMR(500MHz, Methanol-d4) 8.27(d, J=5.0Hz, 1H), 7.98(d, J=8.4Hz, 2H), 7.86(d, J=8.4Hz, 2H), 7.47(d, J=3.5Hz, 1H), 7.24(d, J=5.1Hz, 1H), 6.67(d, J=3.5Hz, 1H), 2.97(s, 3H) |
| 273 | 266.10 | 2.40 | H NMR(500MHz, Methanol-d4) 8.27(d, J=5.0Hz, 1H), 7.99–7.98(m, 2H), 7.87–7.85(m, 2H), 7.47(d, J=3.6Hz, 1H), 7.24(d, J=5.1Hz, 1H), 6.68(d, J=3.5Hz, 1H), 3.46(q, J=7.3Hz, 2H), 1.89(s, H), 1.26(t, J=7.3Hz, 3H) |
| 274 | 228.00 | 1.52 | H NMR(500MHz, DMSO-d6) d 12.26(s, 1H), 11.86(s, 1H), 8.19(d, J=5.3Hz, 1H), 7.74(s, 1H), 7.53(t, J=2.9Hz, 1H), 7.38(d, 1H), 7.35(t, 1H), 6.84(s, 1H) |
| 275 | 303.00 | 1.81 | H NMR(500MHz, DMSO-d6) d 12.55(s, 1H), 12.50(s, 1H), 10.10(s, 1H), 8.34(d, J=6.0Hz, 1H), 8.00(t, 1H), 7.95(d, J=1.9Hz, 1H), 7.79(d, J=7.6Hz, 2H), 7.75(t, 1H), 7.65(d, J=6.0Hz, 1H), 7.38(t, J=7.9Hz, 2H), 7.25(d, J=2.1Hz, 1H), 7.11(t, J=7.3Hz, 1H) |
| 276 | 343.30 | 2.19 | |
| 277 | 275.20 | 1.71 | |
| 278 | 289.30 | 1.89 | |
| 279 | 303.30 | 2.08 | |
| 280 | 303.30 | 2.07 | |
| 281 | 301.30 | 1.92 | |
| 282 | 255.30 | 1.49 | |
| 283 | 269.30 | 1.63 | |
| 284 | 297.40 | 1.88 | H NMR(500MHz, DMSO-d6) d 12.15(s, 1H), 12.05(s, 1H), 8.25(d, J=5.7Hz, 1H), 7.81(d, 1H), 7.77(s, 1H), 7.63–7.62(m, 2H), 7.46(d, J=5.6Hz, 1H), 7.07(s, 1H), 3.83–3.75(m, 1H), 1.61–1.55(m, 2H), 1.50–1.44(m, 2H), 0.89(t, J=7.4Hz, 6H) |
| 285 | 267.30 | 1.52 | |
| 286 | 281.30 | 1.71 | H NMR(500MHz, DMSO-d6) d 12.10(m, 2H), 8.33(t, J=5.8Hz, 1H), 8.25(d, J=5.7Hz, 1H), 7.77(s, 1H), 7.63(s, 1H), 7.59(s, 1H), 7.46(d, J=5.6Hz, 1H), 7.06(s, 1H), 3.16(t, J=6.2Hz, 2H), 1.06–1.03(m, 1H), 0.48–0.45(m, 2H), 0.27–0.24(m, 2H) |
| 287 | 281.30 | 1.71 | |
| 288 | 309.40 | 1.96 | H NMR(500MHz, DMSO-d6) d 12.01(m, 2H), 8.21(d, J=5.5Hz, 1H), 7.95(d, J=8.0Hz, 1H), 7.71(s, 1H), 7.61–7.58(m, 2H), 7.40(d, J=5.8Hz, 1H), 7.01(s, 1H), 3.76(s, 1H), 1.86(m, 2H), 1.75(m, 2H), 1.62(m, 1H), 1.34–1.29(m, 4H), 1.19(m, 1H) |
| 289 | 283.30 | 1.77 | H NMR(500MHz, DMSO-d6) d 12.13(s, 1H), 12.06(s, 1H), 8.24(d, J=5.6Hz, 1H), 7.91(d, J=8.2Hz, 1H), 7.76(s, 1H), 7.63(s, 1H), 7.60(s, 1H), 7.46(d, J=5.3Hz, 1H), 7.06(s, 1H), 3.95–3.90(m, 1H), 1.55–1.50(m, 2H), 1.16(d, J=6.6Hz, 3H), 0.90(t, J=7.4Hz, 3H) |
| 290 | 283.30 | 1.77 | H NMR(500MHz, DMSO-d6) d 12.13(s, 1H), 12.06(s, 1H), 8.24(d, J=5.6Hz, 1H), 7.91(d, J=8.2Hz, 1H), 7.76(s, 1H), 7.63(s, 1H), 7.60(s, 1H), 7.46(d, J=5.3Hz, 1H), 7.06(s, 1H), 3.95–3.90(m, 1H), 1.55–1.50(m, 2H), 1.16(d, J=6.6Hz, 3H), 0.90(t, J=7.4Hz, 3H) |
| 291 | 283.30 | 1.78 | H NMR(500MHz, DMSO-d6) d 12.00(s, 2H), 8.35(d, J=7.8Hz, 1H), 8.21(d, J=5.5Hz, 1H), 7.70(s, 1H), 7.60(s, 1H), 7.58(s, 1H), 7.39(m, 1H), 7.00(s, 1H), 4.43(m, 1H), 2.26–2.22(m, 2H), 2.09–2.04(m, 3H), 1.72–1.67(m, 3H) |
| 292 | 291.30 | 1.58 | |
| 293 | 323.30 | 1.78 | H NMR(500MHz, DMSO-d6) d 12.13(s, 1H), 12.06(s, 1H), 8.46(t, J=5.7Hz, 1H), 8.23(d, J=5.5Hz, 1H), 7.75(s, 1H), 7.62(s, 1H), 7.54(s, 1H), 7.42(d, J=5.4Hz, 1H), 6.99(s, 1H), 3.51(dd, J=6.7, 12.9Hz, 2H), 2.59–2.54(m, 2H) |
| 294 | 265.30 | 1.52 | |
| 295 | 266.30 | 1.41 | |
| 296 | 280.30 | 1.44 | |
| 297 | 308.40 | 1.50 | H NMR(500MHz, DMSO-d6) 11.88(s, 1H), 11.58(s, 1H), 8.15(d, J=4.8Hz, 1H), 7.58(s, 1H), 7.46(s, 1H), 7.26(d, J=4.7Hz, 1H), 7.08(s, 1H), 6.71(s, 1H), 3.79(s, 2H), 3.70(s, 2H), 2.91(s, 2H), 1.28(s, 3H), |
| 298 | 307.40 | 1.80 | H NMR(500MHz, DMSO-d6) 11.90(s, 1H), 11.57(s, 1H), 8.13(d, J=5.0Hz, 1H), 7.57(q, J=1.5Hz, 1H), 7.45–7.44(m, 1H), 7.19(d, J=5.0Hz, 1H), |

TABLE 4-continued

| Cmpd # | LC/MS | RT | NMR |
|---|---|---|---|
| | | | 7.07–7.06(m, 1H), 6.65(q, J=1.8Hz, 1H), 5.96(s, 2H), 5.26(s, 2H), 5.23(s, 2H), 4.16(s, 4H), 3.30(s, HOD??), 2.50(qn, J=1.8Hz, DMSO-d6), |
| 299 | 371.40 | 0.80 | H NMR(500MHz, DMSO-d6) 12.02(s, 1H), 11.56(s, 1H), 8.60(s, 1H), 8.53(d, J=3.9Hz, 1H), 8.14–8.11(m, 1H), 7.76(d, J=7.9Hz, 1H), 7.61(dd, J=1.3, 3.0Hz, 1H), 7.44–7.40(m, 2H), 7.21–7.17(m, 1H), 7.00(s, 1H), 6.51(s, 1H), 4.97(s, 2H), 3.87(s, 2H), 3.32(s, HOD??), 2.98(t, J=6.2Hz, 2H), 2.50(qn, J=1.7Hz, DMSO-d6), |
| 300 | 322.40 | 1.70 | H NMR(500MHz, DMSO-d6) 12.05(s, 1H), 11.60(s, 1H), 8.15(dd, J=5.1, 10.6Hz, 1H), 7.64(dd, J=1.3, 3.0Hz, 1H), 7.48–7.47(m, 1H), 7.25(d, J=5.0Hz, 1H), 7.16(s, 1H), 6.75(s, 1H), 4.62(s, 2H), 3.73(t, J=7.5Hz, 2H), 3.31(s, HOD??), 2.50(qn, J=1.8Hz, DMSO-d6), 1.75–1.67(m, 2H), 1.40(s, 2H), 0.95–0.86(m, 3H), 0.00(s, H), |
| 301 | 323.40 | 1.90 | H NMR(500MHz, DMSO-d6) 11.81(s, 1H), 11.58(s, 1H), 8.15(d, J=5.0Hz, 1H), 7.55(q, J=1.4Hz, 1H), 7.47–7.46(m, 1H), 7.23(d, J=5.0Hz, 1H), 7.03(s, 1H), 6.70(q, J=1.7Hz, 1H), 3.59(s, 2H), 3.47(s, 2H), 3.31(s, HOD??), 2.50(qn, J=1.8Hz, DMSO-d6), 1.70(d, J=7.0Hz, 2H), 1.14–1.07(m, 1H), 0.93(t, J=7.4Hz, 3H),, 0.53(d, J=7.4Hz, 2H), 0.31–0.26(m, 2H), |
| 302 | 322.40 | 1.60 | H NMR(500MHz, DMSO-d6) 11.88(s, 1H), 11.58(s, 1H), 8.15(d, J=5.0Hz, 1H), 7.57(dd, J=1.3, 2.9Hz, 1H), 7.46(t, J=3.0Hz, 1H), 7.23(d, J=5.0Hz, 1H), 7.05(s, 1H), 6.70(q, J=1.6Hz, 1H), 3.82(s, 2H), 3.64(s, 2H), 3.29(s, HOD??), 2.92–2.89(m, 2H), 2.50(qn, J=1.8Hz, DMSO-d6), 1.68(d, J=6.6Hz, 2H), 1.36(qn, J=7.4Hz, 2H), 0.95(t, J=7.4Hz, 3H), |
| 303 | 336.40 | 1.70 | H NMR(500MHz, DMSO-d6) 11.88(s, 1H), 11.58(s, 1H), 8.15(d, J=5.0Hz, 1H), 7.57(dd, J=1.3, 3.0Hz, 1H), 7.46–7.45(m, 1H), 7.24(d, J=5.0Hz, 1H), 7.03(s, 1H), 6.70(q, J=1.6Hz, 1H), 3.80(s, 2H), 3.60(s, 2H), 3.29(s, HOD??), 2.90(t, J=6.4Hz, 2H), 2.50(qn, J=1.8Hz, DMSO-d6), 1.71(t, J=7.4Hz, 2H), 0.94(t, J=7.4Hz, 3H), |
| 304 | 362.40 | 2.30 | |
| 305 | 346.30 | 1.30 | |
| 306 | 294.20 | 1.50 | |
| 307 | 279.20 | 1.60 | |
| 308 | 343.30 | 1.60 | |
| 309 | 311.30 | 2.00 | |
| 310 | 297.30 | 1.80 | |
| 311 | 339.30 | 2.10 | |
| 312 | 370.30 | 1.90 | |
| 313 | 345.30 | 2.00 | |
| 314 | 325.30 | 1.80 | |
| 315 | 324.10 | 2.20 | |
| 316 | 388.30 | 1.40 | |
| 317 | 339.40 | 2.20 | |
| 318 | 363.40 | 1.40 | |
| 319 | 340.40 | 1.40 | |
| 320 | 339.30 | 2.00 | |
| 321 | 353.40 | 2.10 | |
| 322 | 311.30 | 1.70 | |
| 323 | 296.30 | 1.90 | |
| 324 | 360.40 | 1.80 | |
| 325 | 328.40 | 2.30 | |
| 326 | 314.30 | 2.10 | |
| 327 | 356.40 | 2.50 | |
| 328 | 387.30 | 2.20 | |
| 329 | 342.10 | 2.00 | |
| 330 | 341.30 | 2.80 | |
| 331 | 405.20 | 1.50 | |
| 332 | 356.20 | 2.40 | |
| 333 | 380.20 | 1.50 | |
| 334 | 357.40 | 3.00 | |
| 335 | 356.40 | 2.50 | |
| 336 | 370.20 | 2.40 | |
| 337 | 328.10 | 1.90 | |
| 338 | 313.30 | 2.40 | |
| 339 | 377.40 | 2.40 | |
| 340 | 345.30 | 2.90 | |
| 341 | 331.10 | 2.40 | |
| 342 | 373.30 | 3.10 | |
| 343 | 404.30 | 2.70 | |

TABLE 4-continued

| Cmpd # | LC/MS | RT | NMR |
|---|---|---|---|
| 344 | 379.20 | 2.70 | |
| 345 | 333.10 | 2.00 | |
| 346 | 345.30 | 2.00 | |
| 347 | 359.30 | 1.90 | |
| 348 | 401.30 | 2.40 | |
| 349 | 360.40 | 1.60 | |
| 350 | 331.30 | 1.70 | |
| 351 | 380.30 | 1.60 | |
| 352 | 358.30 | 1.80 | |
| 353 | 380.30 | 1.70 | |
| 354 | 366.30 | 1.60 | |
| 355 | 358.40 | 1.60 | |
| 356 | 345.30 | 1.90 | |
| 357 | 340.30 | 2.20 | |
| 358 | 383.30 | 2.60 | |
| 359 | 343.30 | 2.50 | |
| 360 | 357.00 | 2.30 | |
| 361 | 299.00 | 1.40 | |
| 362 | 311.00 | 1.40 | |
| 363 | 325.10 | 1.40 | |
| 364 | 367.10 | 1.80 | |
| 365 | 326.10 | 1.20 | |
| 366 | 297.10 | 1.10 | |
| 367 | 346.10 | 1.30 | |
| 368 | 324.10 | 1.30 | |
| 369 | 346.10 | 1.30 | |
| 370 | 332.10 | 1.20 | |
| 371 | 324.20 | 1.10 | |
| 372 | 311.00 | 1.40 | |
| 373 | 306.10 | 1.60 | |
| 374 | 349.10 | 1.90 | |
| 375 | 309.10 | 1.80 | |
| 376 | 323.00 | 1.80 | |
| 377 | 297.10 | 1.30 | |
| 378 | 301.00 | 2.10 | 500MHz; DMSO-d6: 12.3(s, 1H), 11.9(s, 1H), 8.3(d, 1H), 8.0(s, 1H), 7.65(d, 1H), 7.60(t, 1H), 7.13(dd, 1H), 2.38(d, 2H), 2.15(sept, 1H), 0.95(d, 6H) |
| 379 | 327.00 | 2.40 | 500MHz; DMSO-d6: 12.3(s, 1H), 11.9(s, 1H), 8.3(d, 1H), 8.0(s, 1H), 7.65(d, 1H), 7.60(t, 1H), 7.13(dd, 1H), 2.27(m, 1H), 1.8(m, 2H). 1.6(m, 2H), 1.53(m, 2H), 1.2(m, 2H) |
| 380 | 237.80 | 0.26 | H NMR(500MHz, DMSO) 11.65(s, H), 8.20(d, J=4.8Hz, H), 7.66(s, H), 7.58–7.37(m, 5H), 7.20(s, H), 7.02(d, J=4.8Hz, H), 6.33(dd, J=1.9, 3.4Hz, H). |
| 381 | 224.20 | 2.00 | H NMR(500MHz, MeOD) 8.27(d, J=4.3Hz, H), 7.45–7.43(m, H), 7.34–7.30(m, H), 7.21–7.17(m, 2H), 6.81–6.77(m, 2H), 6.38(d, J=3.5Hz, H), 2.76(d, J=4.4Hz, 3H). |
| 382 | 382.20 | 1.91 | CD3CN(H) 10.3 s(1H), 8.3 s(1H), 7.6 s(1H), 7.3 s(1H), 7.2 s(1H), 7.1 s(1H), 4.7 s(2H), 3.5 t(2H), 3.2 m(2H), 3.0 m(2H), 1.5 m(2H), 1.3 m(1H), 0.8 m(2H), 0.5 m(2H) |
| 383 | 325.10 | 2.20 | DMSO(H) 12.2 s(1H), 11.7 s(1H), 8.2 s(1H), 7.5 d(2H), 7.1 s(1H), 6.7 s(1H), 6.0 s(2H), 5.3 d(4H), 4.2 s(4H). |
| 384 | 394.10 | 2.20 | DMSO(H) 12.2 s(1H), 11.7 s(1H), 8.2 s(1H), 7.5 d(2H), 7.1 s(1H), 6.8 s(1H), 3.9s(4H), 3.0 s(2H), 2.7 m(2H), |
| 385 | 389.10 | 2.60 | H NMR(500MHz, DMSO-d6) 12.06(s, 1H), 11.72(s, 1H), 8.16(d, J=3.7Hz, 1H), 7.51(s, 2H), 7.38(d, J=6.0Hz, 4H), 7.29(d, J=2.2Hz, 1H), 7.06(s, 1H), 6.57(s, 1H), 5.88(t, J=7.3Hz, 2H), 5.18(s, 1H), 5.13(d, J=12.3Hz, 1H), 4.29(d, J=1.3Hz, 1H), 3.85(s, 1H), 1.63(d, J=7.0Hz, 3H) |
| 386 | 312.00 | 1.70 | H NMR(500MHz, DMSO-d6) 12.04(s, 1H), 11.75(s, 1H), 8.19(d, J=3.7Hz, 1H), 7.55(t, J=2.9Hz, 1H), 7.52(s, 1H), 7.14(s, 1H), 6.76(d, J=1.9Hz, 1H), 3.81(s, 3H), 3.31(s, 2H), 2.89(t, J=6.4Hz, 2H), |
| 387 | 381.00 | 2.50 | |
| 388 | 369.10 | 2.50 | |
| 389 | 431.10 | 2.70 | H NMR(500MHz, DMSO-d6) 12.13(s, 1H), 11.69(s, 1H), 8.13(d, J=3.3Hz, 1H), 7.51(s, 1H), 7.45–7.42(m, 3H), 7.35–7.32(m, 3H), 6.9 s(1H), 6.3 s(1H), 4.96(s, 2H), 3.72(s, 2H), 2.73(s, 2H) |

TABLE 4-continued

| Cmpd # | LC/MS | RT | NMR |
|---|---|---|---|
| 390 | 395.20 | 2.50 | H NMR(500MHz, DMSO-d6) 12.03(s, 1H), 11.75(s, 1H), 8.19(d, J=3.7Hz, 1H), 7.56(t, J=2.9Hz, 1H), 7.52(s, 1H), 7.12(s, 1H), 6.72(dd, J=1.8, 3.2Hz, 1H), 3.83(s, 2H), 3.57(s, 2H), 2.71(d, J=6.6Hz, 2H), 1.13–1.11(m, 1H), 0.58(d, J=7.2Hz, 2H), 0.32(t, J=4.7Hz, 2H) |
| 391 | 374.10 | 2.30 | H NMR(500MHz, DMSO-d6) 12.30(s, 1H), 11.71(s, 1H), 8.14(d, J=3.4Hz, 1H), 7.57(s, 1H), 7.46–7.43(m, 6H), 7.36(t, J=7.4Hz, 1H), 6.99(s, 1H), 5.02(s, 2H), 4.62(s, 2H) |
| 392 | 341.10 | 2.40 | H NMR(500MHz, DMSO-d6) 11.96(s, 1H), 11.75(s, 1H), 8.19(d, J=3.7Hz, 1H), 7.56(t, J=2.9Hz, 1H), 7.49(s, 1H), 7.06(s, 1H), 6.71(dd, J=1.8, 3.2Hz, 1H), 3.58(s, 2H), 3.46(s, 2H), 1.71(d, J=5.9Hz, 2H), 1.11(s, 1H), 0.93(t, J=7.4Hz, 4H), 0.53(d, J=7.3Hz, 2H), 0.30(dd, J=5.1, 9.5Hz, 2H) |
| 393 | 341.00 | 2.10 | |
| 394 | 388.10 | 2.20 | |
| 395 | 363.10 | 2.40 | H NMR(500MHz, DMSO-d6) 12.06(s, 1H), 11.70(s, 1H), 8.14(s, 1H), 7.49(s, 1H), 7.46(s, 1H), 7.40(d, J=6.5Hz, 1H), 7.35–7.29(m, 6H), 4.85(s, 2H), 3.58(s, 2H), 1.23(s, 3H) |
| 396 | 340.10 | 2.00 | H NMR(500MHz, DMSO-d6) 12.03(s, H), 11.76(s, H), 8.20(d, J=3.7Hz, 1H), 7.56(t, J=2.8Hz, 1H), 7.52(s, 1H), 7.04(s, 1H), 6.72(s, 1H), 3.78(s, 2H), 3.59(s, 2H), 2.90(t, J=6.7Hz, 2H), 1.73(d, J=7.3Hz, 2H), 0.94(t, J=7.4Hz, 3H) |
| 397 | 354.10 | 2.20 | H NMR(500MHz, DMSO-d6) 12.03(s, 1H), 11.76(s, 1H), 8.20(d, J=3.7Hz, 1H), 7.56(t, J=2.9Hz, 1H), 7.52(s, 1H), 7.06(s, 1H), 6.72(s, 1H), 3.78(s, 2H), 3.63(s, 2H), 2.90(t, J=6.5Hz, 2H), 1.70(s, 2H), 1.36(q, J=7.4Hz, 2H),, 0.94(t, J=7.4Hz, 3H) |
| 398 | 352.10 | 2.00 | H NMR(500MHz, DMSO-d6) 12.06(s, 1H), 11.76(s, 1H), 8.19(d, J=3.7Hz, 1H), 7.56(t, J=2.9Hz, 1H), 7.52(s, 1H), 7.16(s, 1H), 6.74(s, 1H), 3.88(s, 2H), 3.58(d, J=4.9Hz, 2H), 2.92(t, J=6.6Hz, 2H), 1.15(t, J=12.4Hz, 1H), 0.56(d, J=7.3Hz, 2H), 0.35(t, J=4.7Hz, 2H), |
| 399 | 408.10 | 2.40 | |
| 400 | 392.10 | 2.30 | |
| 401 | 325.00 | 2.60 | 500MHz DMSO-d6: 12.03(s, 1H), 8.35(m, 2H), 7.82(m, 1H), 7.79(m, 1H)7.0(s, 1H), 5.9(m, 2H), 5.2(m, 4H), 4.3(s, 2H), 4.1(s, 2H) |
| 402 | 395.00 | 3.00 | 500MHz DMSO-d6: 12.03(s, 1H), 8.4(m, 2H), 7.82(m, 1H), 7.8(m, 2H) 7.0(d, 1H), 4.0(m, 1H), 3.7(m, 2H), 3.4(m, 1H), 2.97(m, 1H), 2.89(m, 1H) 1.67(m, 2H), 0.9(m, 1H), 0.78(m, 2H) |
| 403 | 380.00 | 2.60 | |
| 404 | 363.00 | 2.80 | 500MHz DMSO-d6: compound displaying two conformations 12.05(br d, 1H), 8.3(m, 2H), 7.8(m, 1H), 7.65(d, 1H), 7.35(m, 5H), 7.03(m, 1H), 6.87(m, 1H), 5.0(s, 1H), 4.85(s, 1H), 3.65(m, 1H), 3.4(m, 1H), 1.14(d m, 3H) |
| 405 | 394.00 | 2.60 | 500MHz DMSO-d6: 12.059s, 1H), 8.559s, 1H), 8.47(d, 1H), 7.73(s, 1H), 7.70(m, 1H), 7.01(s, 1H), 4.14(m, 1H), 4.03(m, 1H), 3.75(m, 2H), 3.0(m, 12H), 2.95(m, 1H), 2.78(m, 1H), 2.7(m, 2H) |
| 406 | 381.00 | 3.00 | 500MHz DMSO-d6: 12.059s, 1H), 8.5(m, 1H), 8.4(d, 1H), 7.73(s, 1H), 7.68(d, 1H), 6.97(m, 1H), 5.1(m, 1H), 4.45(m, 1H), 3.75(m, 1H), 3.5(m, 1H), 1.2(m, 1H), 0.5(m, 3H), 0.2(m, 1H) |
| 407 | 369.00 | 2.90 | 500MHz DMSO-d6: 12.1s, 1H), 8.5(m, 1H), 8.4(d, 1H), 7.73(s, 1H), 7.68(d, 1H), 7.0(m, 1H), 5.1(m, 1H), 4.45(m, 1H), 3.8(m, 1H), 3.55(m, 1H), 1.6(m, 2H), 0.9(m, 1H), 0.77(m, 2H) |
| 408 | 389.00 | 3.10 | 500MHz DMSO-d6: 12.1(m, 1H), 8.35(m, 1H), 7.7(m, 1H), 7.3(m, 6H), 6.9(m, 1H), 5.8(m, 1H), 5.6(m, 2H), 5.0)m, 2H), 3.6(d, 1H), 3.4(d, 1H), 3.1(m, 1H), 1.6(m, 1H), 1.4(m, 2H), 1.0(m, 2H) complexity due to rotormers |
| 409 | 352.00 | 2.40 | 500MHz DMSO-d6: 12.1(m, 1H), 8.42(m, 2H), 7.7(m, 2H), 7.1(m, 1H), 7.0(m, 1H), 4.13(m, 1H), 3.8(m, 1H), 3.64(m, 1h), |

TABLE 4-continued

| Cmpd # | LC/MS | RT | NMR |
|---|---|---|---|
| 410 | 353.00 | 2.30 | 3.45(m, 1H), 2.97(2H)1.15(m, 1H), 0.5(m, 2H), 0.36(m1H), 0.24(m, 1H) complexity due to rotomers 500MHz DMSO-d6: 12.0(s, 1H), 8.36(d, 1H), 8.25(s, 1H), 7.7(m, 1H), 7.67(d, 1H), 7.0(s, 1H), 5.90(m, 1H), 5.1(m, 2H), 4.6(m, 1H), 4.0(m, 1H), 1.9(m, 2H), 1.7(m, 5H), 1.4(m, 2H) |
| 411 | 343.00 | 1.50 | 500MHz DMSO-d6: 12.0(s, 1H), 8.32(d, 1H), 8.28(m, 1H), 7.69(m, 1H), 7.67(d, 1H), 7.0(s, 1H), 4.56(m, 1H), 4.3(d, 2H), 3.2(m, 1H), 2.85(m, 1H), 2.1(m, 2H), 1.76(m, 3H), 1.3(m, 3H) |
| 412 | 299.00 | 1.90 | 500MHz DMSO-d6: 12.0(s, 1H), 8.6(t, 1H), 8.45(s, 1H), 8.3(d, 1H), 7.77(d, 1H), 7.7ds, 1H), 7.2(s, 1H), 3.2(t, 2H), 1.1(m, 1H), 0.5(m, 2H), 0.31(m, 2H) |
| 413 | 314.00 | 2.30 | 500MHz DMSO-d6: 12.0(s, 1H), 8.5(t, 1H), 8.45(s, 1H), 8.37(d, 1H), 7.77(d, 1H), 7.71(t, 1H), 7.2(m, 1H), 3.5(dt, 2H), 1.6(sept, 1H), 1.4(dt, 2H), 0.95(d, 6H) |
| 414 | 327.00 | 2.10 | 500MHz DMSO-d6: 12.0(s, 1H), 8.41(d, 1H), 8.38(d, 1H), 7.77(dt, 1H), 7.67(dd, 1H), 7.0(m, 1H), 5.17(quin, 0.5H), 4.7(m, 0.5H0, 4.37(quin, 0.5H), 4.2(m, 0.5H), 2.3(m, 0.5H), 2.15(m, 0.5H), 2.0(m, 0.5H), 1.7(m, 1.5H), 1.55(dd, o.5H), 1.3(br d, 3H), one set of CH3's; 1.2(d, 1.5H), 0.95(d, 1.5H), the other set of CH3's |
| 415 | 297.00 | 1.80 | 500MHz DMSO-d6: 12.0(s, 1H), 8.55(s, 1H), 8.36(d, 1H), 7.7(m, 2H), 7.0(s, 1H), 6.0(m, 2H), 4.8(m, 2H), 4.35(m, 2H) |
| 416 | 327.00 | 2.50 | |
| 417 | 327.00 | 2.50 | |
| 418 | 299.00 | 2.10 | 500MHz DMSO-d6: 12.0(s, 1H), 8.4(s, 1H), 8.35(d, 1H), 7.68(m, 1H), 7.63(d, 1H), 7.0(m, 1H), 3.95(t, 2H), 3.55(t, 2H), 1.9(m, 4H) |
| 419 | 313.00 | 2.40 | 500MHz DMSO-d6: peaksare doubled due to rotomers |
| 420 | 327.00 | 2.50 | 500MHz DMSO-d6: 12.0(s, 1H), 8.35(d, 1H), 8.2(s, 1H), 7.7(m, 1H), 7.65(d, 1H), 7.0(m, 1H), 4.5(br m, 1H), 3.0br m, 1H), 1.6(m, 6H), 1.2(d, 3H) |
| 421 | 341.00 | 2.70 | 500MHz DMSO-d6: 12.0(s, 1H), 8.35(d, 1H), 8.2(s, 1H), 7.7(m, 1H), 7.65(d, 1H), 7.0(m, 1H), 3.3(m, 1H), 1.85(m, 1H), 1.6(m, 4H), 1.45(m, 1H), 1.25(d, 6H) |
| 422 | 385.00 | 2.60 | 500MHz DMSO-d6: peaks doubled due to rotomers |
| 423 | 341.00 | 2.70 | 500MHz DMSO-d6: 12.0(s, 1H), 8.35(d, 1H), 8.2(s, 1H), 7.7(m, 1H), 7.65(d, 1H), 7.0(m, 1H), 4.7–4.0(series of small m, 2H), 1.8(m, 1H), 1.6(m, 7H), 0.8(2m, 3H) |
| 424 | 375.13 | 1.81 | H NMR(500MHz, MeOD) 9.25(s, 1H), 8.98(m, 0.24H), 8.45(m, 2H), 7.74(d, J=3.5Hz, 1H), 7.70(m, 2H), 6.84(d, J=3.5Hz, 1H), 5.25(s, 2H), 4.03–3.96(m, 2H). |
| 425 | 417.20 | 2.50 | H NMR(500MHz, Methanol-d4) d 9.30(s, 1H), 8.57(d, J=6.0Hz, 1H), 8.51(d, J=6.0Hz, 1H), 8.06(d, J=3.7Hz, 1H), 7.86(d, J=3.5Hz, 1H), 7.79(d, J=3.5Hz, 1H), 6.90(d, J=3.7Hz, 1H), 5.45(d, J=10.1Hz, 1H), 4.12(m, 1H), 3.90(m, 1H), 2.75(m, 1H), 1.22(d, J=6.6Hz, 3H), 0.84(d, J=6.7Hz, 3H) |
| 426 | 327.00 | 7.09 | 300MHz 1H NMR(CDCl3): δ 1.85(2H, m), 2.41(2H, m), 2.86(2H, m), 3.68(2H, s), 4.68(1H, m), 5.26(1H, d, J=8.3), 6.53(1H, d, J=3.6), 712(1H, d, J=3.8), 7.30(5H, m), 8.03(1H, s), 10.62(1H, s). |

Example 3

JAK3 Inhibition Assay

Compounds were screened for their ability to inhibit JAK using the assay shown below. Reactions were carried out in a kinase buffer containing 100 mM HEPES (pH 7.4), 1 mM DTT, 10 mM $MgCl_2$, 25 mM NaCl, and 0.01% BSA.

Substrate concentrations in the assay were 5 μM ATP (200 μCi/μmole ATP) and 1 μM poly(Glu)$_4$Tyr. Reactions were carried out at 25° C. and 1 nM JAK3.

To each well of a 96 well polycarbonate plate was added 1.5 μl of a candidate JAK3 inhibitor along with 50/1 of kinase buffer containing 2 μM poly(Glu)$_4$Tyr and 10 μM ATP. This was then mixed and 50 μl of kinase buffer containing 2 nM JAK3 enzyme was added to start the reaction. After 20 minutes at room temperature (25 C), the reaction was stopped with 50 μl of 20% trichloroacetic acid (TCA) that also contained 0.4 mM ATP. The entire contents of each well were then transferred to a 96 well glass fiber filter plate using a TomTek Cell Harvester. After washing, 60 μl of scintillation fluid was added and $^{33}P$ incorporation detected on a Perkin Elmer TopCount.

Example 4

JAK2 Inhibition Assay

The assays were as described above in Example 3 except that JAK-2 enzyme was used, the final poly(Glu)$_4$Tyr concentration was 15 µM, and final ATP concentration was 12 µM.

Example 5

ROCK-I Inhibition Assay

Compounds were screened for their ability to inhibit ROCK using a standard radioactive enzyme assay. Assays were carried out in a solution containing 100 mM HEPES (pH 7.5), 10 mM MgCl$_2$, 25 mM NaCl, 2 mM DTT, and 1.5% DMSO. Final substrate concentrations in the assay were 13 µM [γ-$^{33}$P] ATP (25 mCi $^{33}$P ATP/mmol ATP, Perkin Elmer, Cambridge, Mass./Sigma Chemicals, St Louis, Mo.) and 27 µM Myelin Basic Protein (MBP). Final enzyme concentration in the assay was 5 nM ROCK. Assays were carried out at room temperature. 1.5 µl of DMSO stock containing serial dilutions of the compound of the present invention (concentrations ranging from 10 µM to 2.6 nM) was placed in a 96 well plate. 50 µl of Solution 1 (100 mM HEPES (pH 7.5), 10 mM MgCl$_2$, 26 mM [γ-$^{33}$P] ATP) was added to the plate. The reaction was initiated by addition of 50 µl of Solution 2 (100 mM HEPES (pH 7.5), 10 mM MgCl$_2$, 4 mM DTT, 54 mM MBP and 10 nM ROCK). After 2 hours the reaction was quenched with 50 µL of 30% trichloroacetic acid (TCA, Fisher) containing 9 mM ATP. Transfer of 140 µL of the quenched reaction to a glass fiber filter plate (Corning, Cat. No. 3511) was followed by washing 3 times with 5% TCA. 50 µl of Optima Gold scintillation fluid (Perkin Elmer) was added and the plates were counted on a Top Count (Perkin Elmer). After removing mean background values for all of the data points the data was fit using Prism software to obtain a $K_i$(app).

Table 5 and 6 depict enzyme inhibition data ($K_i$) for certain exemplary compounds. Compound numbers in Table 5 correspond to those compounds depicted in Table 1, while compound numbers in Table 6 correspond to those compounds depicted in Table 2. In Table 5, "A" represents a $K_i$ of less than 0.5 µM, "B" represents a $K_i$ of between 0.5 and 5.0 µM, and "C" represents a $K_i$ greater than 5.0 µM for the indicated enzyme (for Table 6, "C" represents a Ki greater than 4.0 µM for ROCK I).

TABLE 5

| Cmpd # | JAK2 | JAK3 | ROCK I |
|---|---|---|---|
| 1 | | B | |
| 2 | | B | |
| 3 | | A | A |
| 4 | | A | A |
| 5 | | A | A |
| 6 | | A | A |
| 7 | | A | A |
| 8 | | A | A |
| 9 | | A | A |
| 10 | | A | A |
| 11 | | A | A |
| 12 | | B | B |
| 13 | | A | A |
| 14 | | A | A |
| 15 | | A | A |
| 16 | | A | A |
| 17 | | A | A |
| 18 | A | B | B |
| 19 | A | B | B |
| 20 | B | B | B |
| 21 | | A | B |
| 22 | A | A | B |
| 23 | | B | A |
| 24 | B | B | |
| 25 | A | B | A |
| 26 | B | B | B |
| 27 | A | A | A |
| 28 | A | A | B |
| 29 | A | A | B |
| 30 | A | A | A |
| 31 | A | A | A |
| 32 | B | C | B |
| 33 | B | B | B |
| 34 | B | B | B |
| 35 | B | B | A |
| 36 | B | B | B |
| 37 | C | C | B |
| 38 | B | B | B |
| 39 | B | B | B |
| 40 | B | B | B |
| 41 | A | B | A |
| 42 | B | A | A |
| 43 | A | A | A |
| 44 | A | A | A |
| 45 | B | B | A |
| 46 | B | B | B |
| 47 | B | B | B |
| 48 | A | A | B |
| 49 | B | A | A |
| 50 | B | B | B |
| 51 | B | B | B |
| 52 | A | A | A |
| 53 | B | B | A |
| 54 | C | C | B |
| 55 | A | B | A |
| 56 | A | B | B |
| 57 | B | C | B |
| 58 | B | B | B |
| 59 | C | C | B |
| 60 | B | B | B |
| 61 | A | B | B |
| 62 | A | A | A |
| 63 | A | A | A |
| 64 | B | B | B |
| 65 | A | B | A |
| 66 | A | B | A |
| 67 | A | A | B |
| 68 | B | A | B |
| 69 | B | A | B |
| 70 | A | A | B |
| 71 | A | A | A |
| 72 | A | B | B |
| 73 | B | B | B |
| 74 | C | B | B |
| 75 | B | B | B |
| 76 | A | A | B |
| 77 | A | A | B |
| 78 | B | B | B |
| 79 | B | B | B |
| 80 | A | A | B |
| 81 | A | A | B |
| 82 | A | A | B |
| 83 | A | A | B |
| 84 | B | B | A |
| 85 | B | A | A |
| 86 | B | B | A |
| 87 | B | B | B |
| 88 | B | B | B |
| 89 | B | B | B |
| 90 | A | A | B |
| 91 | B | B | B |
| 92 | B | B | B |
| 93 | C | B | B |
| 94 | B | B | B |
| 95 | C | C | B |

TABLE 5-continued

| Cmpd # | JAK2 | JAK3 | ROCK I |
|---|---|---|---|
| 96 | B | B | B |
| 97 | A | A | A |
| 98 | A | B | B |
| 99 | A | C | B |
| 100 | A | B | B |
| 101 | A | A | A |
| 102 | A | A | A |
| 103 | A | A | A |
| 104 | B | B | B |
| 105 | A | A | A |
| 106 | B | A | A |
| 107 | B | B | B |
| 108 | A | A | A |
| 109 | A | A | A |
| 110 | A | A | A |
| 111 | A | A | A |
| 112 | A | B | A |
| 113 | A | B | A |
| 114 | B | B | A |
| 115 | A | A | A |
| 116 | A | A | A |
| 117 | C | C | B |
| 118 | C | C | B |
| 119 | C | C | B |
| 120 | B | A | B |
| 121 | B | A | B |
| 122 | B | A | B |
| 123 | A | A | A |
| 124 | C | B | B |
| 125 | A | A | A |
| 126 | A | A | A |
| 127 | A | A | A |
| 128 | C | C | B |
| 129 | C | C | B |
| 130 | B | B | B |
| 131 | B | A | B |
| 132 | C | B | B |
| 133 | A | B | A |
| 134 | C | B | B |

TABLE 6

| Cmpd # | JAK2 | JAK3 | ROCK I |
|---|---|---|---|
| 135 | A | A | A |
| 136 | A | A | A |
| 137 | A | A | C |
| 138 | A | A | C |
| 139 | A | A | B |
| 140 | A | A | B |
| 141 | A | A | C |
| 142 | A | A | B |
| 143 | B | C | C |
| 144 | A | A | B |
| 145 | A | A | C |
| 146 | C | C | C |
| 147 | C | C | C |
| 148 | B | B | C |
| 149 | A | A | A |
| 150 | A | A | A |
| 151 | B | B | C |
| 152 | A | A | A |
| 153 | A | A | B |
| 154 | A | A | C |
| 155 | A | A | C |
| 156 | A | A | C |
| 157 | A | A | A |
| 158 | A | A | B |
| 159 | A | A | C |
| 160 | B | B | C |
| 161 | A | A | A |
| 162 | A | A | B |
| 163 | A | A | C |
| 164 | A | A | C |
| 165 | A | A | C |

TABLE 6-continued

| Cmpd # | JAK2 | JAK3 | ROCK I |
|---|---|---|---|
| 166 | A | B | C |
| 167 | A | A | C |
| 168 | A | B | C |
| 169 | A | A | B |
| 170 | A | A | B |
| 171 | A | A | B |
| 172 | A | A | B |
| 173 | A | A | B |
| 174 | A | A | B |
| 175 | A | A | C |
| 176 | A | A | B |
| 177 | A | A | B |
| 178 | A | A | C |
| 179 | A | A | C |
| 180 | A | A | C |
| 181 | A | A | B |
| 182 | A | A | B |
| 183 | A | A | C |
| 184 | A | A | B |
| 185 | A | A | C |
| 186 | A | A | B |
| 187 | A | A | B |
| 188 | A | A | B |
| 189 | A | B | C |
| 190 | A | A | B |
| 191 | A | A | C |
| 192 | B | A | C |
| 193 | B | B | C |
| 194 | C | C | C |
| 195 | C | C | C |
| 196 | B | B | C |
| 197 | B | B | C |
| 198 | B | B | C |
| 199 | B | A | C |
| 200 | B | B | C |
| 201 | B | A | C |
| 202 | B | A | C |
| 203 | B | B | C |
| 204 | B | A | B |
| 205 | B | B | B |
| 206 | B | B | C |
| 207 | B | A | B |
| 208 | C | C | B |
| 209 | C | C | A |
| 210 | B | B | A |
| 211 | B | B | A |
| 212 | B | B | B |
| 213 | C | C | C |
| 214 | C | B | B |
| 215 | B | A | C |
| 216 | B | B | B |
| 217 | C | C | C |
| 218 | C | B | A |
| 219 | C | B | B |
| 220 | B | B | B |
| 221 | C | C | B |
| 222 | C | C | C |
| 223 | B | B | B |
| 224 | B | B | A |
| 225 | C | C | C |
| 226 | C | C | C |
| 227 | C | C | C |
| 228 | A | A | C |
| 229 | A | A | B |
| 230 | B | B | C |
| 231 | B | B | B |
| 232 | C | C | C |
| 233 | C | B | B |
| 234 | C | B | C |
| 235 | B | B | B |
| 236 | B | A | A |
| 237 | B | C | B |
| 238 | C | C | C |
| 239 | B | B | B |
| 240 | C | C | C |
| 241 | C | C | C |
| 242 | C | C | C |
| 243 | C | B | B |

TABLE 6-continued

| Cmpd # | JAK2 | JAK3 | ROCK I |
|---|---|---|---|
| 244 | C | B | B |
| 245 | C | C | C |
| 246 | C | C | C |
| 247 | C | C | C |
| 248 | B | B | B |
| 249 | A | A | A |
| 250 | A | A | A |
| 251 | B | A | A |
| 252 | B | A | B |
| 253 | C | C | C |
| 254 | C | C | C |
| 255 | B | B | B |
| 256 | C | B | B |
| 257 | C | C | C |
| 258 | C | C | C |
| 259 | A | A | A |
| 260 | A | A | A |
| 261 | A | A | A |
| 262 | A | A | A |
| 263 | A | A | A |
| 264 | A | A | A |
| 265 | A | A | A |
| 266 | A | B | B |
| 267 | A | A | A |
| 268 | A | A | A |
| 269 | A | A | A |
| 270 | A | B | B |
| 271 | A | A | A |
| 272 | A | A | A |
| 273 | A | B | B |
| 274 | B | A | C |
| 275 | A | A | A |
| 276 | A | A | B |
| 277 | A | A | B |
| 278 | A | A | C |
| 279 | A | A | B |
| 280 | A | A | B |
| 281 | A | A | B |
| 282 | A | A | A |
| 283 | A | A | A |
| 284 | A | A | A |
| 285 | A | A | A |
| 286 | A | A | A |
| 287 | A | A | A |
| 288 | A | A | A |
| 289 | A | A | A |
| 290 | A | B | A |
| 291 | A | A | A |
| 292 | A | A | A |
| 293 | A | A | A |
| 294 | A | A | A |
| 295 | A | A | A |
| 296 | A | A | A |
| 297 | A | A | A |
| 298 | A | A | A |
| 299 | A | A | A |
| 300 | A | A | A |
| 301 | A | A | A |
| 302 | A | A | A |
| 303 | A | A | A |
| 304 | A | A | A |
| 305 | A | A | B |
| 306 | A | A | A |
| 307 | A | A | A |
| 308 | A | A | B |
| 309 | A | A | A |
| 310 | A | A | B |
| 311 | A | A | A |
| 312 | A | A | A |
| 313 | A | A | A |
| 314 | A | A | A |
| 315 | A | A | A |
| 316 | A | A | A |
| 317 | A | A | A |
| 318 | A | A | A |
| 319 | A | A | A |
| 320 | A | A | A |
| 321 | A | A | A |
| 322 | A | A | A |
| 323 | A | A | A |
| 324 | A | A | A |
| 325 | A | A | A |
| 326 | A | A | A |
| 327 | A | B | A |
| 328 | A | A | A |
| 329 | A | A | B |
| 330 | A | A | B |
| 331 | A | A | B |
| 332 | A | A | B |
| 333 | A | A | C |
| 334 | A | A | B |
| 335 | A | A | B |
| 336 | A | A | B |
| 337 | A | A | B |
| 338 | A | A | B |
| 339 | A | A | C |
| 340 | A | A | C |
| 341 | A | A | B |
| 342 | A | A | C |
| 343 | A | A | B |
| 344 | A | A | B |
| 345 | A | A | B |
| 346 | A | A | C |
| 347 | A | A | B |
| 348 | B | B | C |
| 349 | B | B | C |
| 350 | A | A | C |
| 351 | A | A | C |
| 352 | A | A | C |
| 353 | A | A | B |
| 354 | A | A | B |
| 355 | A | B | C |
| 356 | A | A | B |
| 357 | A | A | B |
| 358 | A | A | B |
| 359 | A | A | B |
| 360 | A | A | B |
| 361 | A | A | A |
| 362 | A | B | B |
| 363 | A | B | B |
| 364 | B | B | B |
| 365 | B | B | A |
| 366 | B | B | B |
| 367 | A | A | A |
| 368 | B | A | B |
| 369 | A | A | A |
| 370 | A | A | A |
| 371 | B | B | B |
| 372 | B | B | B |
| 373 | A | A | A |
| 374 | A | A | A |
| 375 | A | A | A |
| 376 | A | A | A |
| 377 | B | B | A |
| 378 | A | A | A |
| 379 | A | A | A |
| 380 | C | C | C |
| 381 | B | B | C |
| 382 | A | A | B |
| 383 | A | A | B |
| 384 | A | A | B |
| 385 | A | A | B |
| 386 | A | A | B |
| 387 | A | A | A |
| 388 | A | A | A |
| 389 | A | A | B |
| 390 | A | A | B |
| 391 | A | A | A |
| 392 | A | A | B |
| 393 | A | A | A |
| 394 | A | A | A |
| 395 | A | A | B |
| 396 | A | A | A |
| 397 | A | A | A |
| 398 | A | A | A |
| 399 | A | A | A |

TABLE 6-continued

| Cmpd # | JAK2 | JAK3 | ROCK I |
|---|---|---|---|
| 400 | A | A | A |
| 401 | A | A | A |
| 402 | A | A | A |
| 403 | A | A | A |
| 404 | A | A | A |
| 405 | A | A | A |
| 406 | A | A | A |
| 407 | A | A | A |
| 408 | A | A | A |
| 409 | A | A | A |
| 410 | A | A | A |
| 411 | B | B | B |
| 412 | A | A | B |
| 413 | A | B | B |
| 414 | A | A | A |
| 415 | A | B | A |
| 416 | A | A | A |
| 417 | A | A | A |
| 418 | A | B | A |
| 419 | A | A | A |
| 420 | A | A | A |
| 421 | A | A | A |
| 422 | B | B | B |
| 423 | A | A | A |
| 424 | A | A | C |
| 425 | A | A | C |
| 426 | A | A | A |

We claim:
1. A compound of formula I

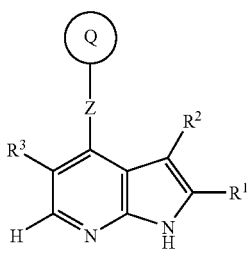

I or a pharmaceutically acceptable salt thereof wherein
Q is

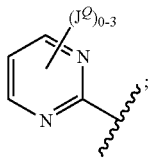

Z is a bond, NH, N($C_{1-3}$aliphatic) or C=$CH_2$;
$R^1$ is —($C_{1-2}$ aliphatic)$_p$-$R^4$ wherein each $R^1$ is optionally substituted with 1-3 occurrences of J;
$R^2$ is —($C_{1-2}$ aliphatic)$_d$-$R^5$ wherein each $R^2$ is optionally substituted with 1-3 occurrences of J;
$R^3$ is halogen, —CN, —$NO_2$ or —(U)$_m$—X, wherein
U is a $C_{1-6}$ aliphatic, wherein up to two methylene units are optionally and independently replaced by $G^U$ and wherein U is optionally substituted with 1-4 $J^U$;
X is H, halogen, CN, $NO_2$, S(O)R, $SO_2R$, $C_{1-4}$ haloaliphatic, or a group selected from $C_{1-6}$ aliphatic, a $C_{3-10}$ cycloaliphatic, $C_{6-10}$ aryl, 5-10 membered heteroaryl, 5-10 membered heterocyclyl; wherein said group is optionally substituted with 1-4 $J^X$;
$G^U$ is —NH—, —NR—, —O—, —S—, —$CO_2$—, —OC(O)—, —C(O)CO—, —C(O)—, —C(O)NH—, —C(O)NR—, —C(=N—CN)—, —NHCO—, —NRCO—, —NHC(O)O—, —NRC(O)O—, —$SO_2$NH—, —$SO_2$NR—, —NH$SO_2$—, —NR$SO_2$—, —NHC(O)NH—, —NRC(O)NH—, —NHC(O)NR—, —NRC(O)NR, —OC(O)NH—, —OC(O)NR—, —NH$SO_2$NH—, —NR$SO_2$NH—, —NH$SO_2$NR—, —NR$SO_2$NR—, —SO—, or —$SO_2$—;
$R^4$ is H, halogen, CN, $NH_2$, $NO_2$, $CF_3$, $C_{1-3}$ aliphatic, cyclopropyl, $NCH_3$, $OCH_3$, —C(=O)$NH_2$, —C(=O)$CH_3$, —NC(=O)$CH_3$, or OH;
$R^5$ is H, halogen, CN, $NH_2$, $NO_2$, $CF_3$, $C_{1-3}$ aliphatic, cyclopropyl, $NCH_3$, $OCH_3$, —C(=O)$NH_2$, —C(=O)$CH_3$, —NC(=O)$CH_3$, or OH;
R is an optionally substituted group selected from $C_{1-6}$ aliphatic, $C_{3-10}$ cycloaliphatic, $C_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of $J^R$;
$J^U$, $J^X$, and $J^R$ are each independently selected from halogen, L, -($L_n$)—R', -($L_n$)—N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-$NO_2$, -($L_n$)-CN, -($L_n$)-OH, -($L_n$)-$CF_3$, —$CO_2$R', —$CO_2$H, —COR', —COH, —OC(O)R', or —NC(O)R';
or two $J^U$, $J^X$, or $J^R$ groups, on the same substituent or different substituents, together with the atom(s) to which each $J^U$, $J^X$, and $J^R$ group is bound, form a 5-7 membered saturated, unsaturated, or partially saturated ring;
$J^Q$ is each independently selected from R", —$CH_2$R", halogen, —CN, —$NO_2$, —N(R')R", —$CH_2$N(R')R", —OR", —$CH_2$OR", —SR", —$CH_2$SR", —COOR", —NR'COR", —NR'COCH$_2$R", —NR'CO(CH$_2$)$_2$R", —NR'COOR", —CON(R')R", —$SO_2$N(R')R", —CONR'(CH$_2$)$_2$N(R')R", —CONR'(CH$_2$)$_3$N(R')R", —CONR'(CH$_2$)$_4$N(R')R", —O(CH$_2$)$_2$OR", O(CH$_2$)$_3$OR", O(CH$_2$)$_4$OR", —O(CH$_2$)$_2$N(R')R", —O(CH$_2$)$_3$N(R)R", —O(CH$_2$)$_4$N(R')R", —NR'CH(CH$_2$OR$^8$)R", —NR'CH(CH$_2$CH$_2$OR$^8$)R", —NR'CH(CH$_3$)R", NR'CH(CF$_3$)R", —NR'CH(CH$_3$)C(O)OR", —NR'CH(CF$_3$)C(O)OR", —NR'(CH$_2$)R", —NR'(CH$_2$)$_2$R", —NR'(CH$_2$)$_3$R", —NR'(CH$_2$)$_4$R", —NR'(CH$_2$)N(R')R", —NR'(CH$_2$)$_2$N(R')R", —NR'(CH$_2$)$_3$N(R')R", —NR'(CH$_2$)$_4$N(R)R", —NR'(CH$_2$)OR", —NR'(CH$_2$)$_2$OR", —NR'(CH$_2$)$_3$OR", —NR'(CH$_2$)$_4$OR", —NR'CH(CH$_2$CH$_3$)R", —NR'CH$_2$C(O)N(R')R", —NR'CH(CH$_3$)C(O)N(R')R", NR'CH(CF$_3$)C(O)N(R)R", —NR'CH(CH$_2$CH$_3$)C(O)N(R')R", —NR'CH(CH$_3$)$_2$C(O)N(R')R", —NR'CH(C(CH$_3$)$_3$)C(O)N(R')R", —NR'CH(CH$_2$CH(CH$_3$)$_2$)C(O)N(R')R", —NR'CH(CH$_2$OR$^8$)C(O)N(R')R" or —NR'CH(CH$_2$CH$_2$N(Me)$_2$)C(O)N(R')R";
$R^8$ is H or $C_{1-6}$ alkyl;
R' is H or $C_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —$NO_2$, —$CF_3$, —CN, —CO$_2$R*, —COR*, OCOR*, NHCOR*, wherein R* is H or C$_{1-6}$ aliphatic;

R" is H, or is an optionally substituted group selected from C$_{1-6}$ aliphatic, C$_{3-10}$ cycloaliphatic, C$_{6-10}$ aryl, 5-10 membered heteroaryl, or 5-10 membered heterocyclyl; or two R" groups, on the same substituent or different substituents, together with the atom(s) to which each R" group is bound, form an optionally substituted 3-8 membered heterocyclyl; wherein each optionally substituted R" group is independently and optionally substituted with 1-6 occurrences of $J^R$;

L is a C$_{1-6}$ aliphatic wherein up to three methylene units are replaced by —NH—, —NR$^6$—, —O—, —S—, —CO$_2$—, —OC(O)—, —C(O)CO—, —C(O)—, —C(O)NH—, —C(O)NR$^6$—, —C(=N—CN), —NHCO—, —NR$^6$CO—, —NHC(O)O—, —NR$^6$C(O)O—, —SO$_2$NH—, —SO$_2$NR$^6$—, —NHSO$_2$—, —NR$^6$SO$_2$—, —NHC(O)NH—, —NR$^6$C(O)NH—, —NHC(O)NR$^6$—, —NR$^6$C(O)NR$^6$, —OC(O)NH—, —OC(O)NR$^6$—, —NHSO$_2$NH—, —NR$^6$SO$_2$NH—, —NHSO$_2$NR$^6$—, —NR$^6$SO$_2$NR$^6$—, —SO—, or —SO$_2$—;

R$^6$ is selected from C$_{1-6}$ aliphatic, C$_{3-10}$ cycloaliphatic, C$_{6-10}$ aryl, 5-10 membered heteroaryl, or 5-10 membered heterocyclyl; or two R$^6$ groups, on the same substituent or different substituents, together with the atom(s) to which each R$^6$ group is bound, form a 3-8 membered heterocyclyl;

J is halogen, OCH$_3$, OH, NO$_2$, NH$_2$, SCH$_3$, NCH$_3$, CN, unsubstituted C$_{1-2}$aliphatic; two J's, together with the carbon to which they are attached, form a cyclopropyl ring or C=O; and m, n, d, and p are each independently 0 or 1.

2. A compound of formula I-a

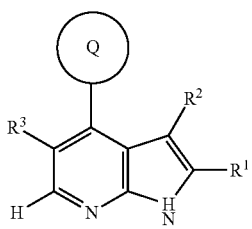

I-a or a pharmaceutically acceptable salt thereof
wherein
Q is

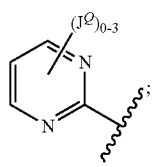

R$^1$ is —(C$_{1-2}$ aliphatic)$_p$-R$^4$ wherein each R$^1$ is optionally substituted with 1-3 occurrences of J;

R$^2$ is —(C$_{1-2}$ aliphatic)$_d$-R$^5$ wherein each R$^2$ is optionally substituted with 1-3 occurrences of J;

R$^3$ is halogen, —CN, —NO$_2$ or —(U)$_m$—X, wherein
U is a C$_{1-6}$ aliphatic, wherein up to two methylene units are optionally and independently replaced by G$^U$ and wherein U is optionally substituted with 1-4 $J^U$;

X is H, halogen, CN, NO$_2$, S(O)R, SO$_2$R, C$_{1-4}$ haloaliphatic, or a group selected from C$_{1-6}$ aliphatic, a C$_{3-10}$ cycloaliphatic, C$_{6-10}$ aryl, 5-10 membered heteroaryl, 5-10 membered heterocyclyl; wherein said group is optionally substituted with 1-4 $J^X$;

G$^U$ is —NH—, —NR—, —O—, —S—, —CO$_2$—, —OC(O)—, —C(O)CO—, —C(O)—, —C(O)NH—, —C(O)NR—, —C(=N—CN)—, —NHCO—, —NRCO—, —NHC(O)O—, —NRC(O)O—, —SO$_2$NH—, —SO$_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO—, or —SO$_2$—;

R$^4$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NC(=O)CH$_3$, or OH;

R$^5$ is H, halogen, CN, NH$_2$, NO$_2$, CF$_3$, C$_{1-3}$ aliphatic, cyclopropyl, NCH$_3$, OCH$_3$, —C(=O)NH$_2$, —C(=O)CH$_3$, —NC(=O)CH$_3$, or OH;

R is an optionally substituted group selected from C$_{1-6}$ aliphatic, C$_{3-10}$ cycloaliphatic, C$_{6-10}$ aryl, 5-10 membered heteroaryl, or 5-10 membered heterocyclyl; or two R groups, on the same substituent or different substituents, together with the atom(s) to which each R group is bound, form an optionally substituted 3-8 membered heterocyclyl; wherein each R group is independently and optionally substituted with 1-4 occurrences of $J^R$;

$J^U$, $J^X$, and $J^R$ are each independently selected from halogen, L, -(L$_n$)-R', -(L$_n$)-N(R')$_2$, -(L$_n$)-SR', -(L$_n$)-OR', -(L$_n$)-(C$_{3-10}$ cycloaliphatic), -(L$_n$)-(C$_{6-10}$ aryl), -(L$_n$)-(5-10 membered heteroaryl), -(L$_n$)-(5-10 membered heterocyclyl), oxo, C$_{1-4}$haloalkoxy, C$_{1-4}$haloalkyl, -(L$_n$)-NO$_2$, -(L$_n$)-CN, -(L$_n$)-OH, -(L$_n$)-CF$_3$, —CO$_2$R', —CO$_2$H, —COR', —COH, —OC(O)R', or —NC(O)R'; or two $J^U$, $J^X$, or $J^R$ groups, on the same substituent or different substituents, together with the atom(s) to which each $J^U$, $J^X$, and $J^R$ group is bound, form a 5-7 membered saturated, unsaturated, or partially saturated ring;

$J^Q$ is each independently selected from R", —CH$_2$R", halogen, —CN, —NO$_2$, —N(R')R", —CH$_2$N(R')R", —OR", —CH$_2$OR", —SR", —CH$_2$SR", —COOR", —NR'COR", —NR'COCH$_2$R", —NR'CO(CH$_2$)$_2$R", —NR'COOR", —CON(R')R", —SO$_2$N(R')R", —CONR'(CH$_2$)$_2$N(R)R", —CONR(CH$_2$)$_3$N(R')R"— CONR'(CH$_2$)$_4$N(R')R", —O(CH$_2$)$_2$OR", O(CH$_2$)$_3$OR", O(CH$_2$)$_4$OR", —O(CH$_2$)$_2$N(R')R", —O(CH$_2$)$_3$N(R)R", —O(CH$_2$)$_4$N(R)R", —NR'CH(CH$_2$OR$^8$)R", —NR'CH(CH$_2$CH$_2$OR$^8$)R", —NR'CH(CH$_3$)R", NR'CH(CF$_3$)R", —NR'CH(CH$_3$)C(O)OR", —NR'CH(CF$_3$)C(O)OR", —NR'(CH$_2$)R", —NR'(CH$_2$)$_2$R", —NR'(CH$_2$)$_3$R", —NR'(CH$_2$)$_4$R", —NR'(CH$_2$)N(R')R", —NR'(CH$_2$)$_2$N(R')R", —NR'(CH$_2$)$_3$N(R')R", —NR'(CH$_2$)$_4$N(R)R", —NR'(CH$_2$)OR", —NR'(CH$_2$)$_2$OR", —NR'(CH$_2$)$_3$OR", —NR'(CH$_2$)$_4$OR", —NR'CH(CH$_2$CH$_3$)R", —NR'CH$_2$C(O)N(R')R", —NR'CH(CH$_3$)C(O)N(R')R", NR'CH(CF$_3$)C(O)N(R')R", —NR'CH(CH$_2$CH$_3$)C(O)N(R')R", —NR'CH(CH(CH$_3$)$_2$)C(O)N(R')R", —NR'CH(C(CH$_3$)$_3$)C(O)N(R')R", —NR'CH(CH$_2$CH(CH$_3$)$_2$)C(O)N(R')R", —NR'CH(CH$_2$OR$^8$)C(O)N(R')R" or —NR'CH(CH$_2$CH$_2$N(Me)$_2$)C(O)N(R')R";

R$^8$ is H or C$_{1-6}$ alkyl;

R' is H or C$_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —NO₂, —CF₃, —CN, —CO₂R*, —COR*, OCOR*, NHCOR*, wherein R* is H or C₁₋₆ aliphatic;

R" is H, or is an optionally substituted group selected from C₁₋₆ aliphatic, C₃₋₁₀ cycloaliphatic, C₆₋₁₀ aryl, 5-10 membered heteroaryl, or 5-10 membered heterocyclyl; or two R" groups, on the same substituent or different substituents, together with the atom(s) to which each R" group is bound, form an optionally substituted 3-8 membered heterocyclyl; wherein each optionally substituted R" group is independently and optionally substituted with 1-6 occurrences of J$^R$;

L is a C₁₋₆ aliphatic wherein up to three methylene units are replaced by —NH—, —NR⁶—, —O—, —S—, —CO₂—, —OC(O)—, —C(O)CO—, —C(O)—, —C(O)NH—, —C(O)NR⁶—, —C(═N—CN), —NHCO—, —NR⁶CO—, —NHC(O)O—, —NR⁶C(O)O—, —SO₂NH—, —SO₂NR⁶—, —NHSO₂—, —NR⁶SO₂—, —NHC(O)NH—, —NR⁶C(O)NH—, —NHC(O)NR⁶—, —NR⁶C(O)NR⁶, —OC(O)NH—, —OC(O)NR⁶—, —NHSO₂NH—, —NR⁶SO₂NH—, —NHSO₂NR⁶—, —NR⁶SO₂NR⁶—, —SO—, or —SO₂—;

R⁶ is selected from C₁₋₆ aliphatic, C₃₋₁₀ cycloaliphatic, C₆₋₁₀ aryl, 5-10 membered heteroaryl, or 5-10 membered heterocyclyl; or two R⁶ groups, on the same substituent or different substituents, together with the atom(s) to which each R⁶ group is bound, form a 3-8 membered heterocyclyl;

J is halogen, OCH₃, OH, NO₂, NH₂, SCH₃, NCH₃, CN, unsubstituted C₁₋₂ aliphatic; two J's, together with the carbon to which they are attached, form a cyclopropyl ring or C═O;

m, n, d, and p are each independently 0 or 1.

3. The compound according to claim 1, wherein R¹ is H, halogen, CN, NH₂, NO₂, CF₃, CH₃, NCH₃, OCH₃, or OH.

4. The compound according to claim 1, wherein R² is H, halogen, CN, NH₂, NO₂, CF₃, CH₃, NCH₃, OCH₃, or OH.

5. The compound according to claim 1, wherein m is 0 and R³ is H, halogen, —CN, —NO₂ or X.

6. The compound according to claim 1, wherein m is 1 and U is an optionally substituted C₁₋₃ aliphatic, wherein up to two methylene units are optionally replaced with 0-2 G$^U$ groups.

7. A compound selected from any one of the following compounds:

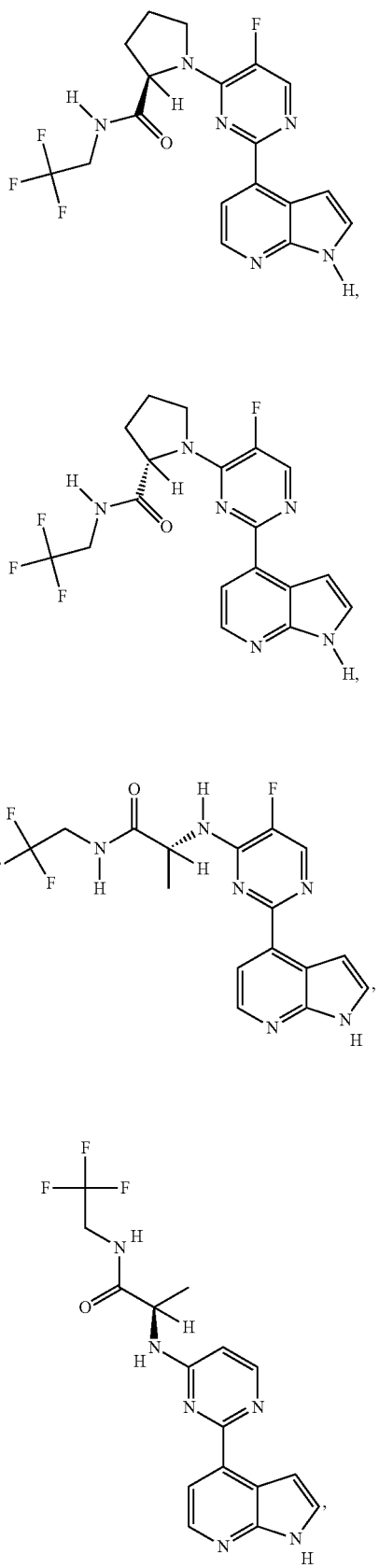

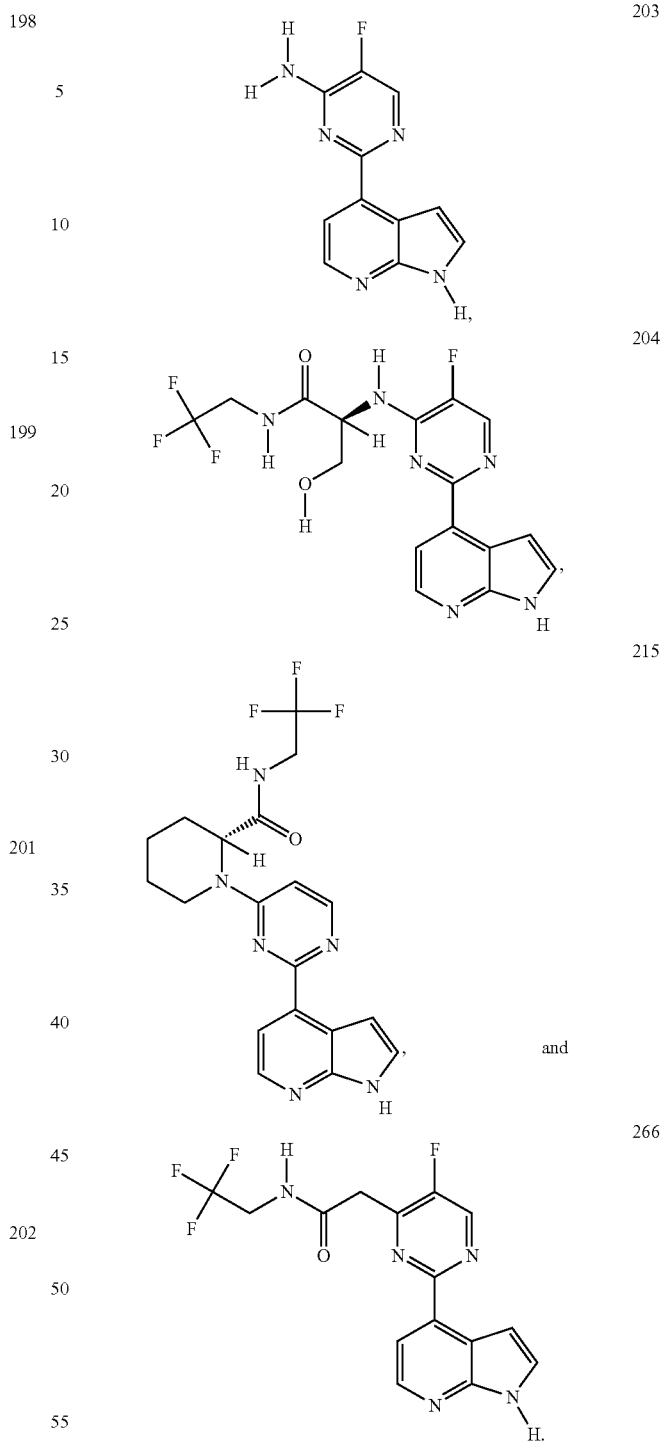

8. A pharmaceutical composition comprising the compound according to claim 1, and a pharmaceutically acceptable carrier, adjuvant, or vehicle.

9. A method of inhibiting ROCK kinase activity or JAK kinase activity in an ex vivo biological sample, comprising contacting said biological sample with a compound according to claim 1, or with a composition comprising said compound.

10. A method of inhibiting ROCK kinase activity or JAK kinase activity in a patient having rheumatoid arthritis, comprising administering to said patient a compound according to claim 1, or with a composition comprising said compound.

11. A method of treating or lessening the severity of rheumatoid arthritis in a patient, comprising the step of administering to said patient a compound according to claim 1, or with a composition comprising said compound.

12. A pharmaceutical composition comprising the compound according to claim 2, and a pharmaceutically acceptable carrier, adjuvant, or vehicle.

13. A method of inhibiting ROCK kinase activity or JAK kinase activity in an ex vivo biological sample, comprising contacting said biological sample with a compound according to claim 2, or with a composition comprising said compound.

14. A method of inhibiting ROCK kinase activity or JAK kinase activity in a patient having rheumatoid arthritis, comprising administering to said patient a compound according to claim 2, or with a composition comprising said compound.

15. A method of treating or lessening the severity of rheumatoid arthritis in a patient, comprising the step of administering to said patient a compound according to claim 2, or with a composition comprising said compound.

16. A pharmaceutical composition comprising the compound according to claim 7, and a pharmaceutically acceptable carrier, adjuvant, or vehicle.

17. A method of inhibiting ROCK kinase activity or JAK kinase activity in an ex vivo biological sample, comprising contacting said biological sample with a compound according to claim 7, or with a composition comprising said compound.

18. A method of inhibiting ROCK kinase activity or JAK kinase activity in a patient having rheumatoid arthritis, comprising administering to said patient a compound according to claim 7, or with a composition comprising said compound.

19. A method of treating or lessening the severity of rheumatoid arthritis in a patient, comprising the step of administering to said patient a compound according to claim 7, or with a composition comprising said compound.

\* \* \* \* \*